(12) United States Patent
Presta

(10) Patent No.: US 8,674,083 B2
(45) Date of Patent: Mar. 18, 2014

(54) POLYPEPTIDE VARIANTS WITH ALTERED EFFECTOR FUNCTION

(75) Inventor: Leonard Presta, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/410,245

(22) Filed: Mar. 1, 2012

(65) Prior Publication Data

US 2012/0202224 A1 Aug. 9, 2012

Related U.S. Application Data

(60) Division of application No. 12/590,801, filed on Nov. 12, 2009, now Pat. No. 8,163,882, which is a continuation of application No. 11/520,121, filed on Sep. 13, 2006, now abandoned, which is a continuation of application No. 09/713,425, filed on Nov. 15, 2000, now Pat. No. 7,183,387, which is a continuation-in-part of application No. 09/483,588, filed on Jan. 14, 2000, now Pat. No. 6,737,056.

(60) Provisional application No. 60/116,023, filed on Jan. 15, 1999.

(51) Int. Cl.
| C07H 21/02 | (2006.01) |
| C12P 21/06 | (2006.01) |
| C12P 21/04 | (2006.01) |
| C12N 5/00 | (2006.01) |
| C12N 5/16 | (2006.01) |
| C12N 1/20 | (2006.01) |
| C12N 15/63 | (2006.01) |
| C07K 16/00 | (2006.01) |

(52) U.S. Cl.
USPC ..... 536/23.53; 435/69.1; 435/69.6; 435/69.7; 435/70.1; 435/325; 435/328; 435/252.3; 435/320.1

(58) Field of Classification Search
None
See application file for complete search history.

(56) References Cited

U.S. PATENT DOCUMENTS

| 4,490,473 A | 12/1984 | Brunhouse |
| 4,752,601 A | 6/1988 | Hahn |
| 5,047,335 A | 9/1991 | Paulson et al. |
| 5,204,244 A | 4/1993 | Fell et al. |
| 5,225,539 A | 7/1993 | Winter et al. |
| 5,278,299 A | 1/1994 | Wong et al. |
| 5,348,876 A | 9/1994 | Michaelsen et al. |
| 5,419,904 A | 5/1995 | Irie |
| 5,510,261 A | 4/1996 | Goochee et al. |
| 5,576,184 A | 11/1996 | Better et al. |
| 5,624,821 A | 4/1997 | Winter et al. |
| 5,648,260 A | 7/1997 | Winter et al. |
| 5,698,449 A | 12/1997 | Baumann et al. |
| 5,730,977 A | 3/1998 | Ooka et al. |
| 5,731,168 A | 3/1998 | Carter et al. |
| 5,736,137 A | 4/1998 | Anderson et al. |
| 5,747,035 A | 5/1998 | Presta et al. |
| 5,834,597 A | 11/1998 | Tso et al. |
| 5,843,398 A | 12/1998 | Kaminski et al. |
| 5,869,046 A | 2/1999 | Presta et al. |
| 5,985,599 A | 11/1999 | McKenzie et al. |
| 6,030,613 A | 2/2000 | Blumberg et al. |
| 6,054,297 A | 4/2000 | Carter et al. |
| 6,086,875 A | 7/2000 | Blumberg et al. |
| 6,136,310 A | 10/2000 | Hanna et al. |
| 6,165,464 A | 12/2000 | Hudziak et al. |
| 6,165,745 A | 12/2000 | Ward et al. |
| 6,172,213 B1 | 1/2001 | Lowman et al. |
| 6,180,377 B1 | 1/2001 | Morgan et al. |
| 6,194,551 B1 | 2/2001 | Idusogie et al. |
| 6,242,195 B1 | 6/2001 | Idusogie et al. |
| 6,277,375 B1 | 8/2001 | Ward |
| 6,323,321 B1 | 11/2001 | Buhring |
| 6,485,726 B1 | 11/2002 | Blumberg et al. |
| 6,491,916 B1 | 12/2002 | Bluestone et al. |
| 6,528,624 B1 | 3/2003 | Idusogie et al. |
| 6,538,124 B1 | 3/2003 | Idusogie et al. |
| 6,582,959 B2 | 6/2003 | Kim |
| 6,676,927 B1 | 1/2004 | Ravetch |
| 6,703,020 B1 | 3/2004 | Thorpe et al. |
| 6,706,265 B1 | 3/2004 | Bolt et al. |
| 6,737,056 B1 | 5/2004 | Presta |
| 6,815,540 B1 | 11/2004 | Pluckthun et al. |
| 6,821,505 B2 | 11/2004 | Ward |
| 6,946,292 B2 | 9/2005 | Kanda et al. |
| 6,982,321 B2 | 1/2006 | Winter |
| 7,060,269 B1 | 6/2006 | Baca et al. |
| 7,083,784 B2 | 8/2006 | Dall'Acqua et al. |

(Continued)

FOREIGN PATENT DOCUMENTS

| CA | 2369292 A | 10/2000 |
| EP | 0 359 096 B1 | 11/1997 |

(Continued)

OTHER PUBLICATIONS

Chappel et al. JBC 1993 268;33:25124-25131.*
Allan and Isliker, "Studies on the complement-binding site of rabbit immunoglobulin G-I. Modification of tryptophan residues and their role in anticomplementary activity of rabbit IgG" *Immunochemistry* 11(4):175-180 (Apr. 1974).
Anderson, D.R. et al. (1997). "Targeting Cytotoxic Immunotherapy: Targeted Anti-Cancer Therapy Using Rituximab, A Chimaeric Anti-CD20 Antibody (IDEC-C2B8) in the Treatment of Non-Hodgkin's B-Cell Lymphoma," *Biochemical Society Transactions* 25:705-708.
Angal et al., "A single amino acid substitution abolishes the heterogeneity of chimeric mouse/human (IgG4) anitbody" *Molecular Immunology* 30(1):105-108 (Jan. 1993).

(Continued)

*Primary Examiner* — Chun Dahle
(74) *Attorney, Agent, or Firm* — Morrison & Foerster LLP

(57) ABSTRACT

The present invention concerns polypeptides comprising a variant Fc region. More particularly, the present invention concerns Fc region-containing polypeptides that have altered effector function as a consequence of one or more amino acid modifications in the Fc region thereof.

13 Claims, 26 Drawing Sheets

(56) References Cited

U.S. PATENT DOCUMENTS

| | | |
|---|---|---|
| 7,122,637 B2 | 10/2006 | Presta |
| 7,183,387 B1 | 2/2007 | Presta |
| 7,214,775 B2 | 5/2007 | Hanai et al. |
| 7,276,585 B2 | 10/2007 | Lazar et al. |
| 7,297,775 B2 | 11/2007 | Idusogie et al. |
| 7,317,091 B2 | 1/2008 | Lazar et al. |
| 7,332,581 B2 | 2/2008 | Presta |
| 7,335,742 B2 | 2/2008 | Presta |
| 7,364,731 B2 | 4/2008 | Idusogie et al. |
| 7,371,826 B2 | 5/2008 | Presta |
| 7,416,727 B2 | 8/2008 | Presta |
| 7,598,055 B2 | 10/2009 | Bobrowicz et al. |
| 7,632,497 B2 | 12/2009 | Stavenhagen |
| 7,691,977 B2 | 4/2010 | Fuh et al. |
| 7,741,072 B2 | 6/2010 | Idusogie et al. |
| 7,785,791 B2 | 8/2010 | Presta |
| 7,790,858 B2 | 9/2010 | Presta |
| 7,923,538 B2 | 4/2011 | Shitara et al. |
| 7,931,895 B2 | 4/2011 | Bellard et al. |
| 7,994,290 B2 | 8/2011 | Shitara et al. |
| 8,088,376 B2 | 1/2012 | Chamberlain et al. |
| 2001/0036459 A1 | 11/2001 | Ravetch |
| 2002/0098193 A1 | 7/2002 | Ward |
| 2002/0197256 A1 | 12/2002 | Grewal |
| 2003/0115614 A1 | 6/2003 | Kanda et al. |
| 2003/0118592 A1 | 6/2003 | Ledbetter et al. |
| 2003/0158389 A1 | 8/2003 | Idusogie et al. |
| 2003/0161826 A1 | 8/2003 | Arnason et al. |
| 2003/0166868 A1 | 9/2003 | Presta et al. |
| 2003/0190311 A1 | 10/2003 | Dall'Acqua et al. |
| 2003/0190317 A1 | 10/2003 | Baca et al. |
| 2003/0203409 A1 | 10/2003 | Kim |
| 2003/0206899 A1 | 11/2003 | Ferrara et al. |
| 2004/0002587 A1 | 1/2004 | Watkins et al. |
| 2004/0093621 A1 | 5/2004 | Shitara et al. |
| 2004/0132101 A1 | 7/2004 | Lazar et al. |
| 2004/0191244 A1 | 9/2004 | Presta |
| 2004/0191256 A1 | 9/2004 | Raju |
| 2004/0191265 A1 | 9/2004 | Schenerman et al. |
| 2004/0228856 A1 | 11/2004 | Presta |
| 2005/0014934 A1 | 1/2005 | Hinton et al. |
| 2005/0031613 A1 | 2/2005 | Nakamura et al. |
| 2005/0031626 A1 | 2/2005 | Stevenson |
| 2005/0032114 A1 | 2/2005 | Hinton et al. |
| 2005/0037000 A1 | 2/2005 | Stavenhagen et al. |
| 2005/0054832 A1 | 3/2005 | Lazar et al. |
| 2005/0079605 A1 | 4/2005 | Umana et al. |
| 2005/0112126 A1 | 5/2005 | Baca et al. |
| 2005/0118174 A1 | 6/2005 | Presta et al. |
| 2005/0136051 A1 | 6/2005 | Scallon |
| 2005/0142133 A1 | 6/2005 | Lazar et al. |
| 2005/0152894 A1 | 7/2005 | Krummen et al. |
| 2005/0186208 A1 | 8/2005 | Fyfe et al. |
| 2005/0227324 A1 | 10/2005 | Huang et al. |
| 2005/0233382 A1 | 10/2005 | Presta et al. |
| 2005/0249723 A1 | 11/2005 | Lazar |
| 2005/0272916 A1 | 12/2005 | Hanai et al. |
| 2005/0276799 A1 | 12/2005 | Hinton et al. |
| 2005/0276805 A1 | 12/2005 | Hanai et al. |
| 2006/0009360 A1 | 1/2006 | Pifer et al. |
| 2006/0018911 A1 | 1/2006 | Ault-Riche et al. |
| 2006/0024292 A1 | 2/2006 | Gerngross et al. |
| 2006/0024298 A1 | 2/2006 | Lazar et al. |
| 2006/0024300 A1 | 2/2006 | Adams et al. |
| 2006/0024304 A1 | 2/2006 | Gerngross et al. |
| 2006/0029604 A1 | 2/2006 | Gerngross et al. |
| 2006/0034828 A1 | 2/2006 | Gerngross et al. |
| 2006/0034829 A1 | 2/2006 | Gerngross et al. |
| 2006/0034830 A1 | 2/2006 | Gerngross et al. |
| 2006/0067930 A1 | 3/2006 | Adams et al. |
| 2006/0074225 A1 | 4/2006 | Chamberlain et al. |
| 2006/0121032 A1 | 6/2006 | Dahiyat et al. |
| 2006/0134709 A1 | 6/2006 | Stavenhagen et al. |
| 2006/0140934 A1 | 6/2006 | Gegg et al. |
| 2006/0153838 A1 | 7/2006 | Watkins et al. |
| 2006/0160996 A9 | 7/2006 | Lazar et al. |
| 2006/0173170 A1 | 8/2006 | Chamberlain et al. |
| 2006/0194290 A1 | 8/2006 | Presta |
| 2006/0194291 A1 | 8/2006 | Presta |
| 2006/0194954 A1 | 8/2006 | Idusogie et al. |
| 2006/0194957 A1 | 8/2006 | Presta |
| 2006/0198840 A1 | 9/2006 | Dall' Acqua et al. |
| 2006/0235208 A1 | 10/2006 | Lazar et al. |
| 2006/0246004 A1 | 11/2006 | Adams et al. |
| 2006/0275282 A1 | 12/2006 | Moore et al. |
| 2006/0275283 A1 | 12/2006 | Van Vlijmen et al. |
| 2007/0009523 A1 | 1/2007 | Presta |
| 2007/0020260 A1 | 1/2007 | Presta |
| 2007/0020267 A1 | 1/2007 | Fuh et al. |
| 2007/0036806 A1 | 2/2007 | Glaesner et al. |
| 2007/0041966 A1 | 2/2007 | Armour et al. |
| 2007/0048300 A1 | 3/2007 | Taylor et al. |
| 2007/0053901 A1 | 3/2007 | Lazar et al. |
| 2007/0122406 A1 | 5/2007 | Chamberlain et al. |
| 2007/0135620 A1 | 6/2007 | Chamberlain et al. |
| 2007/0141065 A1 | 6/2007 | Fuh et al. |
| 2007/0148171 A1 | 6/2007 | Lazar et al. |
| 2007/0160597 A1 | 7/2007 | Lazar et al. |
| 2007/0161783 A1 | 7/2007 | Barbosa et al. |
| 2007/0166309 A1 | 7/2007 | Lazar et al. |
| 2007/0202098 A1 | 8/2007 | Lazar et al. |
| 2007/0219133 A1 | 9/2007 | Lazar et al. |
| 2007/0224189 A1 | 9/2007 | Lazar et al. |
| 2007/0231329 A1 | 10/2007 | Lazar et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0238665 A1 | 10/2007 | Lazar et al. |
| 2007/0243188 A1 | 10/2007 | Lazar et al. |
| 2007/0248602 A1 | 10/2007 | Lazar et al. |
| 2007/0286859 A1 | 12/2007 | Lazar et al. |
| 2008/0051563 A1 | 2/2008 | Lazar et al. |
| 2008/0057056 A1 | 3/2008 | Lazar et al. |
| 2008/0095762 A1 | 4/2008 | Presta |
| 2008/0138338 A1 | 6/2008 | Idusogie et al. |
| 2008/0152649 A1 | 6/2008 | Chamberlain et al. |
| 2008/0154025 A1 | 6/2008 | Lazar et al. |
| 2008/0161541 A1 | 7/2008 | Lazar et al. |
| 2008/0181890 A1 | 7/2008 | Lazar et al. |
| 2008/0206242 A1 | 8/2008 | Lawrence et al. |
| 2008/0274105 A1 | 11/2008 | Presta et al. |
| 2008/0274108 A1 | 11/2008 | Presta |
| 2009/0041770 A1 | 2/2009 | Chamberlain et al. |
| 2009/0060911 A1 | 3/2009 | Ravetch |
| 2009/0148441 A1 | 6/2009 | Gillies |
| 2009/0163699 A1 | 6/2009 | Chamberlain et al. |
| 2010/0098730 A1 | 4/2010 | Lowman |
| 2010/0166749 A1 | 7/2010 | Presta |
| 2010/0255013 A1 | 10/2010 | Presta |
| 2011/0052584 A1 | 3/2011 | Ravetch |
| 2011/0086050 A1 | 4/2011 | Presta |
| 2011/0293632 A1 | 12/2011 | Presta |
| 2012/0201813 A1 | 8/2012 | Presta |

FOREIGN PATENT DOCUMENTS

| | | |
|---|---|---|
| EP | 0 811 691 A1 | 12/1997 |
| EP | 1 176 195 A1 | 1/2002 |
| EP | 1 270 595 A1 | 1/2003 |
| EP | 1 331 266 A1 | 7/2003 |
| EP | 0 904 107 B1 | 10/2004 |
| EP | 1 498 491 A1 | 1/2005 |
| EP | 0 66 868 | 6/2006 |
| WO | WO-88/07089 | 9/1988 |
| WO | WO-93/22332 | 11/1993 |
| WO | 94/08027 | 4/1994 |
| WO | 94/10202 | 5/1994 |
| WO | WO-94/11026 | 5/1994 |
| WO | WO-94/29351 | 12/1994 |
| WO | 96/30046 | 10/1996 |
| WO | 96/32478 | 10/1996 |
| WO | WO-97/28267 | 8/1997 |
| WO | WO-97/30087 A1 | 8/1997 |
| WO | WO-97/34631 | 9/1997 |

(56) References Cited

FOREIGN PATENT DOCUMENTS

| WO | 97/43316 | 11/1997 |
|---|---|---|
| WO | WO-97/44362 | 11/1997 |
| WO | WO-98/23289 | 6/1998 |
| WO | WO-98/33924 A1 | 8/1998 |
| WO | 98/45332 | 10/1998 |
| WO | WO-98/52975 | 11/1998 |
| WO | WO-98/58964 A1 | 12/1998 |
| WO | WO-99/22764 A1 | 5/1999 |
| WO | WO-99/43713 | 9/1999 |
| WO | WO-99/51642 | 10/1999 |
| WO | WO-99/54342 A1 | 10/1999 |
| WO | WO-99/58572 | 11/1999 |
| WO | WO-00/09560 | 2/2000 |
| WO | WO-00/42072 | 7/2000 |
| WO | WO-00/61739 A1 | 10/2000 |
| WO | WO-00/75348 A1 | 12/2000 |
| WO | Wo-00/75348 C1 | 12/2000 |
| WO | WO-01/40309 A2 | 6/2001 |
| WO | WO-01/40309 A3 | 6/2001 |
| WO | WO-01/40309 C1 | 6/2001 |
| WO | WO-01/58957 | 8/2001 |
| WO | WO-01/64754 A1 | 9/2001 |
| WO | WO-01/77181 A2 | 10/2001 |
| WO | WO-01/77181 A3 | 10/2001 |
| WO | WO-02/31140 A1 | 4/2002 |
| WO | WO-02/060919 A2 | 8/2002 |
| WO | WO-02/083854 A2 | 10/2002 |
| WO | WO-03/011878 A2 | 2/2003 |
| WO | WO-03/011878 A3 | 2/2003 |
| WO | WO-03/035835 A2 | 5/2003 |
| WO | WO-03/035835 A3 | 5/2003 |
| WO | WO-03/055993 A1 | 7/2003 |
| WO | WO-03/074679 | 9/2003 |
| WO | WO-2004/004662 | 1/2004 |
| WO | WO-2004/004798 A2 | 1/2004 |
| WO | WO-2004/011611 A2 | 2/2004 |
| WO | WO-2004/029207 A2 | 4/2004 |
| WO | WO-2004/035752 | 4/2004 |
| WO | WO-2004/063351 A2 | 7/2004 |
| WO | WO-2004/092219 | 10/2004 |
| WO | WO-2004/099249 | 11/2004 |
| WO | WO-2004/099249 A2 | 11/2004 |
| WO | WO-2004/099249 A3 | 11/2004 |
| WO | 2005/012359 | 2/2005 |
| WO | 2005/018572 | 3/2005 |
| WO | WO-2005/037867 | 4/2005 |
| WO | 2005/040217 | 5/2005 |
| WO | 2005/044853 | 5/2005 |
| WO | WO-2005/047327 A2 | 5/2005 |
| WO | 2005/123780 | 12/2005 |
| WO | WO-2006/020114 A2 | 2/2006 |
| WO | 2006/031370 | 3/2006 |
| WO | 2006/053301 | 5/2006 |
| WO | WO-2006/076594 A2 | 7/2006 |
| WO | WO-2006/116260 A2 | 11/2006 |
| WO | 2009/058492 | 5/2009 |
| WO | 2009/073160 | 6/2009 |
| WO | 2009/086320 | 7/2009 |
| WO | WO-2010/045193 A1 | 4/2010 |

OTHER PUBLICATIONS

Angata, K. et al. (Oct. 23, 1998). "Differential and Cooperative Polysialylation of the Neural Cell Adhesion Molecule by Two Polysialyltransferases, PST and STX," *The Journal of Biological Chemistry* 273(43):28524-28532.
*Antibodies. A Laboratory Manual*, Harlow and Lane, New York:Cold Spring Harbor Laboratory pp. 321 (1988).
Armour et al., "Recombinant Human IgG Molecules Lacking Fcγ Receptor I binding and monocyte triggering activities," *European Journal of Immunology* 29(8):2613-2624. (Aug. 1999).
Artandi et al., "Monoclonal IgM rheumatoid factors bind IgG at a discontinuous epitope comprised of amino acid loops from heavy-chain constant-region domains 2 and 3" *Proc. Natl. Acad. Sci. USA* 89(1):94-98 (Jan. 1, 1992).

Bloom et al., "Intrachain disulfide bond in the core hinge region of human IgG4," *Protein Science* 6:407-415 (1997).
Bolland et al., "SHIP modulates immune receptor responses by regulating membrane association of Btk," *Immunity* 8(4):509-516 (Apr. 1998).
Boyd, P.N. et al. (1995). "The Effect of the Removal of Sialic Acid, Galactose and Total Carbohydrate on the Functional Activity of Campath-1H," *Molecular Immunology* 32(17/18):1311-1318.
Bredius et al., "Role of neutrophil FcγRIIa (CD32) and FcγRIIIb (CD16) polymorphic forms in phagocytosis of human IgG1- and IgG3-opsonized bacteria and erythrocytes" *Immunology* 83(4):624-630 (Dec. 1994).
Brekke et al., "Human IgG isotype-specific amino acid residues affecting complement-mediated cell lysis and phagocytosis" *European Journal of Immunology* 24(10):2542-2547 (Oct. 1994).
Brekke, O.H. et al. (Jan. 2003). "Therapeutic Antibodies for Human Diseases at the Dawn of the Twenty-First Century," *Nature Reviews Drug Discovery* 2:52-62.
Burmeister et al., "Crystal structure of the complex of rat neonatal Fc receptor with Fc" *Nature* 372(6504):379-383 (Nov. 24, 1994).
Burton and Woof, "Human Antibody Effector Function" *Advances in Immunology* 51:1-84 (1992).
Burton et al., "Molecular recognition of antibody (IgG) by cellular Fc receptor (FcRI)" *Molecular Immunology* 25(11):1175-1181 (1988).
Burton et al., "The C1q receptor site on immunoglobulin G" *Nature* 288(5789):338-344 (Nov. 27, 1980).
Burton, D.R., "Immunoglobulin G: Functional Sites" *Molecular Immunology* 22(3):161-206 (1985).
Byrn, R.A. et al. (Apr. 12, 1990). "Biological Properties of a CD4 Immunoadhesin," *Nature* 344(6267):667-670.
Cameron, D.J. (1985). "Specificity of Macrophage-Mediated Cytotoxicity: Role of Target and Effector Cell Fucose," *Immunol. Lett.* 11:39-44.
Canfield and Morrison, "The binding affinity of human IgG for its high affinity Fc receptor is determined by multiple amino acids in the $C_H 2$ domain and is modulated by the hinge region" Journal of Experimental Medicine 173(6):1483-1491 (Jun. 1, 1991).
Capel et al., "Heterogeneity of Human IgG Fc Receptors" *Immunomethods* 4:25-34 (1994).
Capon et al., "Designing CD4 Immunoadhesins for AIDS Therapy" *Nature* 337:525-531 (Feb. 9, 1989).
Carter et al., "Humanization of an anti-p185$^{HER2}$ antibody for human cancer therapy" *Proc. Natl. Acad. Sci.* 89(10):4285-4289 (May 1992).
Chappel et al., "Identification of Secondary FcγRI Binding Site within a Genetically Engineered Human IgG Antibody" *Journal of Biological Chemistry* 268:25124-25131 (1993).
Chappel et al., "Identification of the Fcγ receptor class I binding site in human IgG through the use of recombinant IgG1/IgG2 hybrid and point-mutated antibodies" *Proc. Natl. Acad. Sci. USA* 88(20):9036-9040 (Oct. 15, 1991).
Clark, M.R. et al. (Sep. 1, 1989). "Molecular Basis for a Polymorphism Involving Fc Receptor II on Human Monocytes," *J. Immunol.* 143(5):1731-1734.
Clark, M.R. (1997). "IgG Effector Mechanisms," *Chem. Immunol.* 65:88-110.
Clynes and Ravetch, "Cytotoxic antibodies trigger inflammation through Fc receptors" *Immunity* 3(1):21-26 (Jul. 1995).
Clynes et al. "Fc receptors are required in passive and active immunity to melanoma," *Proc. Natl. Acad. Sci. USA* 95(2):652-656 (Jan. 20, 1998).
Clynes et al., "Modulation of immune complex-induced inflammation in vivo by the coordinate expression of activation and inhibitory Fc receptors" *Journal of Experimental Medicine* 189(1):179-185 (Jan. 4, 1999).
Clynes et al., "Uncoupling of immune complex formation and kidney damage in autoimmune glomerulonephritis" *Science* 279(5353):1052-1054 (Feb. 13, 1998).
Clynes, R.A. et al. (Apr. 2000). "Inhibitory Fc Receptors Modulate In Vivo Cytoxicity Against Tumor Targets," *Nature Med.* 6(4):443-446.
Cook, J.P.D. et al. (Dec. 1997). "Identification of Contact Residues in the IgE Binding Site of Human FcεRIα," *Biochemistry* 36(50):15579-15588.

(56) References Cited

OTHER PUBLICATIONS

Cosimi, A.B., "Clinical Development of Orthoclone OKT3" *Transplantation Proceedings* (Suppl 1) XIX(2):7-16 (Apr. 1987).
Daeron, M. "Fc Receptor Biology" *Annual Review of Immunology* 15:203-234 (1997).
Dall'Acqua et al., "Increasing the affinity of a human IgG1 for the neonatal Fc receptor: biological consequences" *J Immunol.* 169(9):5171-5180 (Nov. 1, 2002).
Dall'Acqua et al., "Modulation of the effector functions of a human IgG1 through engineering of its hinge region" *J. Immunol.* 177:1129-38 (2006).
Dall'Acqua et al., "Properties of human IgG1s engineered for enhanced binding to the neonatal Fc receptor (FcRn)" *J Biol Chem.* 281(33):23514-24 (Aug. 2006).
Dard, P. et al. (2001). "DNA Sequence Variability of IGHG3 Alleles Associated to The Main G3m Haplotypes in Human Populations," *European Journal of Human Genetics* 9:765-772.
Datta-Mannan et al., "Humanized IgG1 variants with differential binding properties to the neonatal Fc receptor: relationship to pharmacokinetics in mice and primates" *Drug Metab Dispos.* 35(1):86-94 (Jan. 2007).
Datta-Mannan et al., "Monoclonal antibody clearance. Impact of modulating the interaction of IgG with the neonatal Fc receptor" *J Biol Chem.* 282(3):1709-17 (Jan. 19, 2007).
Davies, J. et al. (Aug. 20, 2001, e-pub. Jun. 6, 2001). "Expression of GnTIII in a Recombinant Anti-CD20 CHO Production Cell Line: Expression of Antibodies with Altered Glycoforms Leads to an Increase in ADCC Through Higher Affinity for FcγRIII," *Biotechnol. Bioeng.* 74(4):288-294.
De Haas et al., "Fcγ receptors of phagocytes" *J. of Laboratory Clinical Medicine* 126:330-341 (Oct. 1995).
Deisenhofer, J, "Crystallographic Refinement and Atomic Models of a Human Fc fragment and Its Complex with Fragment B of Protein A from *Staphylococcus aureus* at 2.9- and 2.8-A Resolution" *Biochemistry* 20(9):2361-2370 (1981).
Deng et al., "Pharmacokinetics of Humanized Monoclonal Anti-Tumor Necrosis Factor-α Antibody and Its Neonatal Fc Receptor Variants in Mice and Cynomolgus Monkeys" *Drug Metabolism and Disposition* 38(4):600-605 (2010).
De Vita, S. et al. (Aug. 2002). "Efficacy of Selective B Cell Blockade in the Treatment of Rheumatoid Arthritis," *Arthritis & Rheumatism* 46(8):2029-2033.
Dorai, H. et al. (1991). "Aglycosylated Chimeric Mouse/Human IgG1 Antibody Retains Some Effector Function," *Hybridoma* 10(2):211-217.
Duncan and Winter, "The binding site for C1q on IgG," *Nature* 332(21):738-740 (Apr. 21, 1988).
Duncan et al., "Localization of the binding site for the human high-affinity Fc receptor on IgG," *Nature* 332:563-564 (Apr. 7, 1988).
Eccles et al., "Monoclonal antibodies targeting cancer: 'magic bullets' or just the trigger?" *Breast Cancer Research* 3(2):86-90 (2001).
El-Amine et al., "In vivo induction of tolerance by an Ig peptide is not affected by the deletion of FcR or a mutated IgG Fc fragment" *Int Immunol.* 14(7):761-6 (Jul. 2002).
Elbein, A.D. (Dec. 1991). "Glycosidase Inhibitors: Inhibitors of N-Linked Oligosaccharide Processing," *FASEB J.* 5:3055-3063.
Ellison, J. et al. (Mar. 1982). "Linkage and Sequence Homology of Two Human Immunoglobulin γ Heavy Chain Constant Region Genes," *Proc. Natl. Acad. Sci. USA* 79:1984-1988.
Fridman, W., "Fc receptors and immunoglobulin binding factors" *FASEB Journal* 5(12):2684-2690 (Sep. 1991).
*Fundamental Immunology*, Paul, W. E., 2nd edition, New York:Raven Press pp. 60 and 61 (1989).
Gavin, A. at al. (1998). "Molecular Basis for the Interaction of Fc Receptors with Immunoglobulins," Chapter 2 *in The Immunoglobulin Receptors and their Physiological and Pathological Roles in immunity*, van de Winkel et al. eds., The Netherlands:Kluwer Academic Publishers pp. 11-35.
Gazzano-Santoro et al., "A non-radioactive complement-dependent cytotoxicity assay for anti-CD20 monoclonal antibody" *Journal of Immunological Methods* 202(2):163-171 (Mar. 28, 1997).
Gergely et al., "Fc receptors on lymphocytes and K cells" *Biochemical Society Transactions* 12(5):739-743 (Oct. 1984).
Gessner, J.E. et al. (Jun. 1998). "The IgG Fc Receptor Family," *Ann. Hematol.* 76(6):231-248.
Ghebrehiwet et al., "Isolation, cDNA cloning, and overexpression of a 33-kD cell surface glycoprotein that binds to the globular "heads" of C1q" *Journal of Experimental Medicine* 179(6):1809-1821 (Jun. 1, 1994).
Ghetie and Ward, "FcRn: the MHC class I-related receptor that is more than an IgG transporter" *Immunology Today* 18(12):592-598 (Dec. 1997).
Ghetie and Ward, "Multiple Roles for the Major Histocompatibility Complex Class I-Related Receptor FcRn" *Ann. Rev. Immunol.* 18:739-766 (2000). (39.xx).
Ghetie et al., "Abnormally short serum half lives of IgG in β2-microglobulin-deficient mice" *European Journal of Immunology* 26(3):690-696 (Mar. 1996).
Ghetie et al., "Increasing the serum persistence of an IgG fragment by random mutagenesis" *Nature Biotechnology* 15(7):637-640 (Jul. 1997).
Glennie, M.J. et al. (Aug. 2000)."Clinical Trials of Antibody Therapy," *Immunology Today* 21(8):403-410.
Gorman et al., "Transient Production of Proteins Using an Adenovirus Transformed Cell Line" *DNA Prot. Eng. Tech.* 2(1):3-10 (1990).
Graham et al., "Characteristics of a Human Cell Line Transformed by DNA from Human Adenovirus Type 5" *J. Gen. Virol.* 36:59-72 (1977).
Greenwood et al., "Engineering multiple-domain forms of the therapeutic antibody CAMPATH-1H: effects on complement lysis" *Therapeutic Immunology* 1(5):247-255 (Oct. 1994).
Greenwood et al., "Structural motifs involved in human IgG antibody effector functions" *European Journal of Immunology* 23(5):1098-1104 (May 1993).
Groenink, J. et al. (1996). "On the Interaction Between Agalactosyl IgG and Fcγ Receptors," *European Journal of Immunology* 26:1404-1407.
Guddat et al., "Three-dimensional structure of a human immunoglobulin with a hinge deletion" *PNAS(USA)* 90(9):4271-4275 (1993).
Haagen et al., "Interaction of Human Monocyte Fcγ Receptors with Rat IgG2b: A New Indicator for the FcγRIIa (R-H131) Polymorphism" *J. Immunol.* 154:1852-1860 (1995).
Hadley et al., "The functional activity of FcγRII and FcγRIII on subsets of human lymphocytes" *Immunology* 76(3):446-451 (Jul. 1992).
Hand, P.H. et al. (1992). "Comparative Biological Properties of a Recombinant Chimeric Anti-Carcinoma mAb and a Recombinant Aglycosylated Variant," *Cancer Immunol. Immunother*. 35:165-174.
Harris et al., "Crystallographic Structure of an Intact IgG1 Monoclonal Antibody" *Journal of Molecular Biology* 275:861-872 (1998).
Harris et al., "Refined Structure of an Intact IgG2a Monoclonal Antibody" *Biochemistry* 36:1581-1597 (1997).
Hashim, O.H. et al. (1987)."Role of Processing of N-Linked Oligosaccharides in Control of Immunoglobulin Secretion From Rat Hybridomas," *Molecular Immunology* 24(10):1087-1096.
Hashim, O.H. et al. (1988). "Simultaneous Inhibition of Multiple Steps in the Processing of N-Linked Oligosaccharides Does Not Impair Immunoglobulin Secretion From Rat Hybridoma Cells," *Immunology* 63:383-388.
Hatta et al., "Association of Fcγ receptor IIIB, but not of Fcγ receptor IIA and IIIA, polymorphisms with systemic lupus erythematosus in Japanese" *Genes and Immunity* 1:53-60 (1999).
Heiken et al., "T lymphocyte development in the absence of Fcε receptor 1γ subunit: analysis of thymic-dependent and independent αβ and γδ pathways" *European Journal of Immunology* 26(8):1935-1943 (Aug. 1996).

(56) References Cited

OTHER PUBLICATIONS

Henry et al., "Participation of the N-terminal region of Cε3 in the binding of human IgE to its high-affinity receptor FεRI" *Biochemistry* 36:15568-15578 (1997).

Hills, A.E. et al. (Oct. 20, 2001). "Metabolic Control of Recombinant Monoclonal Antibody N-Glycosylation in GS-NS0 Cells," *Biotechol. Bioeng.* 75(2):239-251.

Hinton et al., "An engineered human IgG1 antibody with longer serum half-life" *J Immunol.* 176(1):346-56 (2006).

Hinton et al., "Engineered human IgG antibodies with longer serum half-lives in primates" *J Biol Chem.* 279(8):6213-6216 (Feb. 20, 2004).

Hobbs, S.M. et al. (1992). "Interaction of Aglycosyl Immunogloblins with the IgG Fc Transport Receptor From Neonatal Rat Gut: Comparison of Deglycosylation by Tunicamycin Treatment and Genetic Engineering," *Molecular Immunology* 29(7/8):949-956.

Hogarth et al., "Characterization of FcR Ig-binding sites and epitope mapping" *Immunomethods* 4(1):17-24 (Feb. 1994).

Hudziak, R.M. et al. (Mar. 1989). "p185$^{HER2}$ Monoclonal Antibody Has Antiproliferative Effects In Vitro and Sensitizes Human Breast Tumor Cells to Tumor Necrosis Factor," *Molecular & Cellular Biology* 9(3):1165-1172.

Huizinga et al., "Binding characteristics of Dimeric IgG Subclass Complexes to Human Neutrophils" *Journal of Immunology* 142:2359-2364 (1989).

Hulett et al., "Chimeric Fc Receptors Identify Functional Domains of the Murine High Affinity Receptors for IgG" *J. Immunol.* 147:1863-1868 (1991).

Idusogie et al., "Engineered Antibodies with Increased Activity to Recruit Complement" *Journal of Immunology* 166(4):2571-2575 (Feb. 15, 2001).

Idusogie et al., "Mapping of the CIq Binding Site on Rituxan, A Chimeric Antibody with a Human IgG1 Fc" *J Immunol.* 164(8):4178-4184 (2000).

International Search Report mailed on Jun. 16, 2003, for PCT Application No. PCT/US02/33739, filed on Oct. 22, 2002, two pages.

Jaakkola et al., "In vivo detector of vascular adhesion protein-1 in experimental inflammation" *American Journal of Pathology* 157(2):463-471 (Aug. 2000).

Janeway et al. "*Immunobiology, The Immune System in Health and Disease*," CB Ltd and Garland Publishing Inc., NY & London pp. 3:29-3:30 (1994).

Jarvis, D.L. et al. (1995). "Biochemical Analysis of the N-Glycosylation Pathway in Baculovirus-Infected Lepidopteran Insect Cells," *Virology* 212:500-511.

Jassal, R. et al. (2001). "Sialylation of Human IgG-Fc Carbohydrate by Transfected Rat α2,6-Sialyltransferase," *Biochem. & Biophys. Res. Comm.* 286(2):243-249.

Jefferis et al., "Molecular Definition of Interaction Sites on Human IgG for Fc Receptors (huFcγR)" *Molecular Immunology* 27(12):1237-1240 (1990).

Jefferis, R. at al. (1990). "A Comparative Study of the *N*-Linked Oligosaccharide Structures of Human IgG Subclass Proteins," *Biochemical Journal* 268:529-537.

Jensen et al., "Rapid tumor lysis in a patient with B-cell chronic lymphocytic leukemia and lymphocytosis treated with an anti-CD20 monoclonal antibody (IDEC-C2B8, rituximab)" *Annals of Hematology* 77(1-2):89-91 (Jul.-Aug. 1998).

Kabat et al., "Introduction" *Sequences of Proteins of Immunological Interest*, US Dept of Health and Human Services, NIH, 5th edition, Bethesda, MD vol. 1:xiii-xcvi (1991).

Kabat et al., *Sequences of Proteins of Immunological Interest* (Table of Contents, Introduction and Constant Region Sequences sections), 5th edition, Bethesda, MD:NIH vol. 1:iii-xcvi and 647-723 (1991).

Kamei et al., "Quantitative methods for developing Fc mutants with extended half-lives" *Biotechnol Bioeng.* 92(6):748-60 (Dec. 2005).

Kaushal, G.P. et al. (1994)."Glycosidase Inhibitors in Study of Glycoconjugates," Chapter 19 in *Methods in Enzymology*, Academic Press, pp. 316-329.

Kilmartin, J.V. et al. (Jun. 1982). "Rat Monoclonal Antitubulin Antibodies Derived by Using a New Nonsecreting Rat Cell Line," *The Journal of Cell Biology* 93:576-582.

Kim et al., "Catabolism of the Murine IgG1 Molecule: Evidence That Both CH2-CH3 Domain Interfaces are Required for Persistence of IgG1 in the Circulation of Mice" *Scandinavian Journal of Immunology* 40(4):457-465 (1994).

Kim et al., "Identifying amino acid residues that influence plasma clearance of murine IgG1 fragments by site-directed mutagenesis" *European Journal of Immunology* 24:542-548 (1994).

Kim et al., "Inhibition of Vascular Endothelial Growth Factor-Induced Angiogenesis Suppresses Tumour Growth in vivo" *Nature* 362:841-844 (Apr. 29, 1993).

Kim et al., "Localization of the site of the murine IgG1 molecule that is involved in binding to the murine intestinal Fc receptor" *European Journal of Immunology* 24:2429-2434 (1994).

Kim et al., "Mapping the site on human IgG for binding of the MHC class I-related receptor, FcRn" *European Journal of Immunology* 29(9):2819-2825 (Sep. 1999).

Kim et al., "The Vascular Endothelial Growth Factor Proteins: Identification of Biologically Relevant Regions by Neutralizing Monoclonal Antibodies" *Growth Factors* 7(1):53-64 (1992).

King, D.J. et al. (1999). "Recombinant Antibodies for the Diagnosis and Therapy of Human Disease," *Curr. Opin. Drug Discovery Develop.* 2(2):110-117.

Koene et al., "FcγRIIIa-158V/F Polymorphism Influences the Binding of the IgG by Natural Killer Cell FcγRIIIa, Independently of the FcγRIIIa-48L/R/H Phenotype" *Blood* 90(3):1109-1114 (1997).

Kojima, N. et al. (Aug. 9, 1996). "Characterization of Mouse ST8Sia II (STX) as a Neural Cell Adhesion Molecule-specific Polysialic Acid Synthase," *The Journal of Biological Chemistry* 271(32):19457-19463.

Kojima, N. et al. (1998). "Alpha 1,6-Linked Fucose Affects the Expression and Stability of Polysialic Acid-Carrying Glycoproteins in Chinese Hamster Ovary Cells," *J. Biochem.* 124(4):726-737.

Kumpel, B.M. et al. (1994)."Galactosylation of Human IgG Monoclonal Anti-D Produced by EBV-transformed B-lymphoblastoid Cell Lines is Dependent on Culture Method and Affects Fc Receptor-mediated Functional Activity," *Hum. Antibod. Hybridomas* 5(3-4):143-151.

Kunkel, T., "Rapid and Efficient Site-Specific Mutagenesis Without Phenotypic Selection" *Proc. Natl. Acad. Sci.* 82(2):488-492 (Jan. 1985).

Lauvrak et al., "Identification and characterisation of CIq-binding phage displayed peptides" *Biological Chemistry* 378(12):1509-1519 (Dec. 1997).

Lazar et al., "Engineered antibody Fc variants with enhanced effector function" *Proc Natl Acad Sci USA.* 103(11):4005-10 (Mar. 2006).

Leatherbarrow, R.J. et al. (1985). "Effector Functions of a Monoclonal Aglycosylated Mouse IgG2a: Binding and Activation of Complement Component CI and Interaction with Human Monocyte Fc Receptor," *Molecular Immunology* 22(4):407-415.

Lehrnbecher et al., "Variant genotypes of FcγRIIIA influence the development of Kaposi's sarcoma in HIV-infected men," *Blood* 95(7):2386-2390 (2000).

Lehrnbecher et al., "Variant genotypes of the low-affinity Fcγ receptors in two control populations and a review of low-affinity Fcγ receptor polymorphisms in control and disease populations" *Blood* 94(12):4220-4232 (Dec. 15, 1999).

Levy, J.A. et al. (Sep. 1968). "Human Lymphoblastoid Lines From Lymph Node and Spleen," *Cancer* 22:517-524.

Li et al., "Reconstitution of human FcγRIII cell type specificity in transgenic mice" *Journal of Experimental Medicine* 183(3):1259-1263 (Mar. 1, 1996).

Lifely et al. "Glycosylation and biological activity of CAMPATH-1H expressed in different cell lines and grown under different culture conditions" *Glycobiology* 5(8):813-822 (Dec. 1995).

Liu, J. at al. (1995). "Characterization of Complex Formation by Humanized Anti-IgE Monoclonal Antibody and Monoclonal Human IgE," *Biochemistry* 34:10474-10482.

Lorenz et al., "Strong association between the responder status of the FcγII receptor and recurrent spontaneous abortion" *European Journal of Immunogenetics* 22(5):397-401 (Oct. 1995).

(56) References Cited

OTHER PUBLICATIONS

Loyet et al., "Technology comparisons for anti-therapeutic antibody and neutralizing antibody assays in the context of an anti-TNF pharmacokinetic study" *Journal of Immunological Methods* 345:17-28 (2009).

Lucas et al., "High-level production of recombinant proteins in CHO cells using a dicistronic DHFR intron expression vector" *Nucleic Acids Research* 24(9):1774-1779 (1996).

Lund et al., "Human FcγRI and Fcγ RII interact with distinct but overlapping sites on human IgG" *Journal of Immunology* 147(8):2657-2662 (Oct. 15, 1991).

Lund et al., "Multiple binding sites on the $C_H 2$ domain of IgG for mouse FcγR11" *Molecular Immunology* 29(1):53-59 (Jan. 1992).

Lund et al., "Multiple Interactions of the IgG with Its Core Oligosaccharide Can Modulate Recognition by Complement and Human Fcγ Receptor I and Influence the Synthesis of Its Oligosaccharide Chains" *J. Immunol.* 157:4963-4969 (1996).

Lund et al., "Oligusaccharide-protein interactions in IgG can modulate recognition by Fcγ receptors" *FASEB Journal* 9:115-119 (1995).

Makrides, S.C. (1998). "Therapeutic Inhibition of the Complement System," *Pharmacol. Rev.* 50(1):59-87.

Malhotra, R. et al. (Mar. 1995). "Glycosylation Changes of IgG Associated with Rheumatoid Arthritis Can Activate Complement Via the Mannose-Binding Protein," *Nat. Med.* 1(3):237-243.

Male, D. Immunology, *An Illustrated Outline*, London:Gower Medical Publishing Ltd. pp. 21 and 23 (1986).

Marionneau, S. et al. (2000). "Susceptibility of Rat Colon Carcinoma Cells to Lymphokine Activated Killer-Mediated Cytotoxicity is Decreased by α1,2-Fucosylation," *Int. J. Cancer* 86:713-717.

Martin et al., "Crystal structure at 2.8 A of an FcRn/heterodimeric Fc complex: mechanism of pH-dependent binding" *Molecular Cell* 7(4):867-877 (Apr. 2001).

Masuda, K. et al. (2007, e-pub. Mar. 26, 2007). "Enhanced Binding Affinity for FcγRIIIa of Fucose-Negative Antibody is Sufficient to Induce Maximal Antibody-Dependent Cellular Cytotoxicity," *Molecular Immunology* 44:3122-3131.

Maxwell et al., "Crystal structure of the human leukocyte Fc receptor, FcγRIIa" *Nature Structural Biology* 6(5):437-442 (May 1999).

Mayo Clinic. (Jan. 8, 2011). "Goiter," located at <http://www.mayoclinic.com/health/goiter/DS00217/METHOD=print&DSECTION=all>, last visited on Sep. 9, 2011, seven pages.

Medesan et al., "Comparative studies of rat IgG to further delineate the Fc:FcRN interaction site" *European Journal of Immunology* 28:2092-2100 (1998).

Medesan et al., "Delineation of the amino acid residues involved in transcytosis and catabolism of mouse IgG1" *Journal of Immunology* 158(5):2211-2217 (Mar. 1, 1997).

Medesan et al., "Localization of the site of the IgG molecule that regulates maternofetal transmission in mice" *European Journal of Immunology* 26(10):2533-2536 (Oct. 1996).

Mellis, S.J. et al. (Oct. 10, 1983). "Structures of the Oligosaccharides Present at the Three Asparagine-Linked Glyosylation Sites of Human IgD," *The Journal of Biological Chemistry* 258(19):11546-11556.

Meng et al., "Green fluorescent protein as a second selectable markerfor selection of high producing clones from transfected CHO cells" *Gene* 242:201-207 (2000).

Michaeli et al., "Optimised Fc variants with enhanced effector function" *Expert Opin. Ther. Patents* 16(10):1449-1452 (2006).

Mikayama et al., "Molecular cloning and functional expression of a cDNA encoding glycosylation-inhibiting factor" *Proc. Natl. Acad. Sci. USA* 90(21):10056-10060 (Nov. 1, 1993).

Miller et al., "A Novel Role for the Fc Receptor γ Subunit: Enhancement of the FcγR Ligand Affinity" *Journal of Experimental Medicine* 183:2227-2233 (1996).

Mimura, Y. et al. (2000). "The Influence of Glycosylation on the Thermal Stability and Effector Function Expression of Human 1gGI-Fc: Properties of a Series of Truncated Glycoforms," *Mol Immunol.* 37(12-13):697-706.

Moore et al., "Engineered Fc variant antibodies with enhanced ability to recruit complement and mediate effector functions" *Landes Bioscience* 2(2):181-189 (2010).

Morgan et al., "The N-terminal end of the $C_H 2$ domain of chimeric human IgG1 anti-HLA-DR is necessary to CIq, FcγRI and FcγRIII binding" *Immunology* 86(2):319-324 (Oct. 1995).

Morrison et al., "Structural Determinants of Human IgG Function" *Immunologist* 2:119-124 (1994).

Nagarajan et al., "Ligand binding and phagocytosis by CD16 (Fcγ receptor III) isoforms. Phagocytic signaling by associated ζ and γ subunits in Chinese hamster ovary cells" *Journal of Biological Chemistry* 270(43):25762-25770 (Oct. 27, 1995).

Newkirk et al., "Rheumatoid factor avidity in patients with rheumatoid arthritis: identification of pathogenic RFs which correlate with disease parameters and with the gaI(0) glycoform of IgG" *Journal of Clinical Immunology* 15(5):250-257 (Sep. 1995).

Ngo et al., "Computational Complexity, Protein Structure Prediction, and the Levinthal Paradox" *The Protein Folding Problem and Tertiary Structure Prediction*, Merz & Le Grand, Boston:Birkhauser pp. 491-495 (1994).

Nieto et al., "Involvement of the Fcγ receptor IIIA genotypes in susceptibility to rheumatoid arthritis" *Arthritis and Rheumatism* 43(4):735-739 (2000).

Niu and Chiu, "FDA perspective on peptide formulation and stability issues" *Journal of Pharmaceutical Sciences* 87(11):1331-1334 (Nov. 1998).

Nose, M. at al. (Nov. 1983). "Biological Significance of Carbohydrate Chains on Monoclonal Antibodies," *Proc. Natl. Acad. Sci. USA* 80:6632-6636.

Ober et al., "Differences in promiscuity for antibody—FcRn interactions across species: implications for therapeutic antibodies" *International Immunology* 13(12):1551-1559 (2001).

Oganesyan et al., "Structural characterization of a human Fc fragment engineered for extended serum half-life" *Molecular Immunology* 46:1750-1755 (2009).

Ohyama, C. et al. (Jun. 5, 1998). "Molecular Cloning and Expression of GDP-D-mannose-4,6-Dehydratase, A Key Enzyme for Fucose Metabolism Defective in Lec13 Cells," *Journal of Biological Chemistry* 273(23):14582-14587.

Okafo, G.N. et al. (1996). "Simple Differentiation Between Core-Fucosylated and Nonfucosylated Glycans by Capillary Electrophoresis," *Analytical Biochemistry* 240:68-74.

Original claims of the Parent Patent US 6,737,056 restricted. Jan. 14, 2000, pp. 1-6.

Okada et al., "Cutting Edge: Role of the inositol phosphatase SHIP in B cell receptor-induced $Ca^{2+}$ oscillatory response" *Journal of Immunology* 161(10):5129-5132 (Nov. 15, 1998).

Olafsen et al., "Tunable pharmacokinetics: modifying the in vivo half-life of antibodies by directed mutagenesis of the Fc fragment" *Nat Protoc.* 1(4):2048-60 (2006).

Ono et al., "Deletion of SHIP or SHP-1 reveals two distinct pathways for inhibitory signaling" *Cell* 90(2):293-301 (Jul. 25, 1997).

Ono et al., "Role of the inositol phosphatase SHIP in negative regulation of the immune system by the receptor FcγRIIB" *Nature* 383(6597):263-266 (Sep. 19, 1996).

Papac et al., "A high-throughput microscale method to release N-linked oligosaccharide from glycoproteins for matrix-assisted laser desorption/ionization time-of-flight mass spectrometric analysis" *Glycobiology* 8(5):463-472 (1998).

Papac et al., "Analysis of Acidic Oligosaccharides and Glycopeptides by Matrix-Assisted Laser Desorption/Ionization Time-of-Flight Mass Spectrometry" *Anal. Chem.* 68:3215-3223 (1996).

Papac, D.I. et al. (1998). "A High-Throughput Microscale Method to Release N-Linked Oligosaccharides From Glycoproteins for Matrix-Assisted Laser Desorption/Ionization Time-of-Flight Mass Spectrometric Analysis," *Glycobiology* 8(5):445-454.

Parekh, R.B. et al. (Aug. 1, 1985). "Association of Rheumatoid Arthritis and Primary Osteoarthritis with Changes in the Glycosylation Pattern of Total Serum IgG," *Nature* 316:452-457.

Penichet, M.L. et al. (2001). "Antibody-Cytokine Fusion Proteins for the Therapy of *Cancer*," *J. Immunol. Meth.* 248:91-101.

(56) References Cited

OTHER PUBLICATIONS

Petkova et al., "Enhanced half-life of genetically engineered human IgG1 antibodies in a humanized FcRn mouse model: potential application in humorally mediated autoimmune disease" *Int Immunol.* 18(12):1759-69 (Dec. 2006).
Popov et al., "The stoichiometry and affinity of the interaction of murine Fc fragments with the MHC class I-related receptor, FcRn" *Molecular Immunology* 33(6):521-530 (Apr. 1996).
Porges et al., "Novel Fcγ Receptor I Family Gene Products in Human Mononuclear Cells" *J. Clin. Invest.* 90:2102-2109 (1992).
Presta et al., "Engineering therapeutic antibodies for improved function" *Biochemical Society* 30:487-490 (2002).
Presta et al., "Humanization of an Anti-Vascular Endothelial Growth Factor Monoclonal Antibody for the Therapy of Solid Tumors and Other Disorders" *Cancer Research* 57(20):4593-4599 (Oct. 15, 1997).
Presta, Leonard, "Antibody engineering for therapeutics" *Current Opinion in Structural Biology* 13:519-525 (2003).
Presta, Leonard, "Engineering of therapeutic antibodies to minimize immunogenicity and optimize function" *Advanced Drug Delivery Reviews* 58:640-656 (2006).
Presta, Leonard, "Molecular engineering and design of therapeutic antibodies" *Current Opinion in Immunology* 20:406-470 (2008).
Presta, Leonard, "Selection, design, and engineering of therapeutic antibodies" *J Allergy Clin Immunol* 116:731-736 (Oct. 2005).
Raghavan and Bjorkman, "Fc Receptors and their Interactions with Immunoglobulins" *Annu. Rev. Cell. Dev. Biol.* 12:181-220 (1996).
Raghavan et al., "Analysis of the pH dependence of the neonatal Fc receptor/immunoglobulin G interaction using antibody and receptor variants" *Biochemistry* 34(45):14649-14657 (Nov. 14, 1995).
Raju, T.S. et al. (2000). "Species-Specific Variation in Glycosylation of IgG: Evidence for the Species-Specific Sialylation and Branch-Specific Galactosylation and Importance for Engineering Recombinant Glycoprotein Therapeutics," *Glycobiology* 10(5):477-486.
Ravetch, J.V. et al. (2001). "IgG Fc Receptors," *Ann. Rev. Immunol.* 19:275-290.
Ravetch and Clynes, "Divergent roles for Fc receptors and complement in vivo" *Annual Review of Immunology* 16:421-432 (1998).
Ravetch and Kinet, "Fc Receptors" *Annual Review of Immunology* 9:457-492 (1991).
Ravetch, J., "Fc receptors: rubor redux" *Cell* 78(4):553-560 (Aug. 26, 1994).
Ravetch, J., "Fc receptors" *Current Opinion in Immunology* 9(1):121-125 (Feb. 1997).
Reff et al., "Depletion of B cells in vivo by a chimeric mouse human monoclonal antibody to CD20" *Blood* 83(2):435-445 (Jan. 15, 1994).
Restriction Requirement for the Parent Patent US 6,737,056. Sep. 25, 2001, pp. 1-8.
Ripka, J. et al. (1986). "Lectin-Resistant CHO Cells: Selection of Four New Pea Lectin-Resistant Phenotypes," *Somatic Cell and Molecular Genetics* 12(1):51-62.
Ripka, J. et al. (Sep. 1986). "Two Chinese Hamster Ovary Glycosylation Mutants Affected in the Conversion of GDP-Mannose to GDP-Fucose," *Archives of Biochemistry & Biophysics* 249(2):533-545.
Rothman, R.J. et al. (1989). "Antibody-Dependent Cytotoxicity Mediated by Natural Killer Cells is Enhanced by Castanospermine-Induced Alterations of IgG Glycosylation," *Molecular Immunology* 26(12):1113-1123.
Roopenian et al., "FcRn: the neonatal Fc receptor comes of age" *Nature Reviews, Immunology* 7:715-725 (2007).
Routier, F.H. et al. (1997). "The Glycosylation Pattern of a Humanized IgGl Antibody (D1.3) Expressed in CHO Cells," *Glycoconjugate Journal* 14:201-207.
Rudd, P.M. et al. (Mar. 23, 2001). "Glycosylation and the Immune System," *Science* 291:2370-2376.
Sampson, J.H. et al. (Jun. 20, 2000). "Unarmed, Tumor-Specific Monoclonal Antibody Effectively Treats Brain Tumors," *Proc. Natl. Acad. Sci. USA* 97(13):7503-7508.

Sarmay et al., "Ligand inhibition studies on the role of Fc receptors in antibody-dependent cell-mediated cytotoxicity" *Molecular Immunology* 21(1):43-51 (Jan. 1984).
Sarmay et al., "Mapping and comparison of the interaction sites on the Fc region of IgG responsible for triggering antibody dependent cellular cytotoxicity (ADCC) through different types of human Fcγ receptor" *Molecular immunology* 29(5):633-639 (May 1992).
Schrama, D. et al. (Feb. 2006, e-pub. Jan. 20, 2006). "Antibody Targeted Drugs as Cancer Therapeutics," *Nature Reviews Drug Discovery* 5:147-159.
Segal, D.M. et al. (2001). "Introduction: Bispecific Antibodies," *J. Immunol. Methods* 248(1-2):1-6.
Sensel et al., "Amino acid differences in the N-terminus of $C_H 2$ influence the relative abilities of IgG2 and IgG3 to activate complement" *Molecular Immunology* 34(14):1019-1029 (Oct. 1997).
Shields et al., "High Resolution Mapping of the Binding Site on Human IgG1 for FcγRI, FcγRII, FcγRIII, and FcRn and Design of IgG1 Variants with Improved Binding to the FcγR" *Journal of Biological Chemistry* 276(9):6591-6604 (2001).
Shields, R.L. et al. (Jul. 26, 2002). "Lack of Fucose on Human IgG1 N-Linked Oligosaccharide Improves Binding to Human FcγRIII and Antibody-dependent Cellular Toxicity," *The Journal of Biological Chemistry* 277(30):26733-26740.
Shinkawa, T. et al. (Jan. 31, 2003, e-pub. Nov. 8, 2002)."The Absence of Fucose but Not the Presence of Galactose or Bisecting N-Acetyglucosamine of Human IgG1 Complex-type Oligosaccharides Shows the Critical Role of Enhancing Antibody-dependent Cellular Cytotoxicity," *Journal of Biological Chemistry* 278(5):3466-3473.
Shitara, K. et al. (1994). "A New Vector for the High Level Expression of Chimeric Antibodies in Myeloma Cells," *Journal of Immunological Methods* 167:271-278.
Shores et al., "T cell development in mice lacking all T cell receptor ζ family members (ζ, η, and FcεRIγ)" *Journal of Experimental Medicine* 187(7):1093-1101 (Apr. 6, 1998).
Sondermann et al., "Crystal structure of the soluble form of the human Fcγ-receptor IIb: a new member of the immunoglobulin superfamily at 1.7 A resolution" *EMBO Journal* 18(5):1095-1103 (1999).
Sonderman et al., "The 3.2-A crystal structure of the human IgG1 Fc Fragment-FcγRIII complex" *Nature* 406(6793):267-273 (2000).
Staňková, J. et al. (Dec. 1985). "Fucose-Activated Killer (FAK) Cells: Anomalous Killers with Augmented Cytotoxic Activity" *J. Immunol.* 135(6):3719-3728.
Steeg, P.S. et al. (May 2011, e-pub. Apr. 7, 2011). "Brain Metastases as Preventive and Theraputic Targets," *Nature Review Cancer* 11:352-363.
Steplewski et al., "Biological activity of human-mouse IgG1, IgG2, IgG3, and IgG4 chimeric monoclonal antibodies with antitumor specificity" *Proc. Natl. Acad. Sci. USA* 85(13):4852-4856 (Jul. 1988).
Strohmeier et al., "Neutrophil functional responses depend on immune complex valency" *Journal of Leukocyte Biology* 58(4):403-414 (Oct. 1995).
Strohmeier et al., "Role of the FcγR subclasses FcγRII and FcγRIII in the activation of human neutrophils by low and high valency immune complexes" *Journal of Leukocyte Biology* 58(4):415-422 (Oct. 1995).
Suzuki et al., "Distinct contribution of Fc receptors and angiotensin II-dependent pathways in anti-GBM glomerulonephritis" *Kidney International* 54(4):1166-1174 (Oct. 1998).
Sylvestre and Ravetch, "A dominant role for mast cell Fc receptors in the Arthus reaction" *Immunity* 5(4):387-390 (Oct. 1996).
Sylvestre and Ravetch, "Fc receptors initiate the Arthus reaction: redefining the inflammatory cascade" *Science* 265(5175):1095-1098 (Aug. 19, 1994).
Sylvestre et al., "Immunoglobulin G-mediated inflammatory responses develop normally in complement-deficient mice" *Journal of Experimental Medicine* 184(6):2385-2392 (Dec. 1, 1996).
Takai et al., "Augmented humoral and anaphylactic responses in FcγRII-deficient mice" *Nature* 379(6563):346-349 (Jan. 25, 1996).
Takai et al., "FcRγ chain deletion results in pleiotrophic effector cell defects" *Cell* 76(3):519-529 (Feb. 11, 1994).

(56) References Cited

OTHER PUBLICATIONS

Takahashi, N. et al. (1987). "Comparative Structural Study of the N-Linked Oligosaccharides of Human Normal and Pathological Immunoglobulin G," *Biochemistry* 26(4):1137-1144.
Tamm et al., "The IgG binding site of human FcγRIIIB receptor involves CC' and FG loops of the membrane-proximal domain" *Journal of Biological Chemistry* 271(7):3659-3666 (Feb. 16, 1996).
Tamura, K. (Jan. 1, 1997). "Human Immunoadhesin: A New Ligand Antagonist," *Pharmaceutical Society of Japan* 33(1):46-50 (English translation.).
Tao and Morrision, "Studies of Aglycosylated Chimeric Mouse-Human IgG: Role of Carbohydrate in the Structure and Effector Functions Mediated by the Human IgG Constant Region." *J. of Immunology* 143(8):2595-2601 (Oct. 15, 1989).
Tao et al., "Structural features of human immunoglobulin G that determine isotype-specific differences in complement activation" *Journal of Experimental Medicine* 178(2):661-667 (Aug. 1, 1993).
Tao et al., "The differential ability of human IgG1 and IgG4 to activate complement is determined by the COOH-terminal sequence of the $C_H2$ domain" *Journal of Experimental Medicine* 173(4):1025-1028 (Apr. 1991).
Tax et al., "Fc receptors for mouse IgG1 on human monocytes: polymorphism and role in antibody-induced T cell proliferation" *Journal of Immunology* 133(3):1185-1189 (Sep. 1984).
Ting et al., "Fcγ receptor activation induces the tyrosine phosphorylation of both phospholipase C (PLC)-γ1 and PCL-γ2 in natural killer cells" *Journal of Experimental Medincine* 176(6):1751-1755 (Dec. 1, 1992).
Tutt et al., "Monoclonal antibody therapy of B cell lymphoma: signaling activity on tumor cells appears more important than recruitment of effectors" *Journal of Immunology* 161(6):3176-3185 (Sep. 15, 1998).
Umana et al., "Engineered glycoforms of an antineuroblastoma IgG1 with optimized antibody-dependent cellular cytotoxic activity" *Nature Biotechnology* 17(2):176-180 (Feb. 1999).
Urfer et al., "High resolution mapping of the binding site of TrkA for nerve growth factor and TrkC for neurotrophin-3 on the second immunoglobulin-like domain of the Trk receptors" *Journal of Biological Chemistry* 273(10):5829-5840 (Mar. 6, 1998).
Van De Winkel and Anderson, "Biology of human immunoglobulin G Fc receptors" *Journal of Leukocyte Biology* 49(5):511-524 (May 1991).
Vance et al., "Binding of monomeric human IgG defines an expression polymorphism of FcγRIII on large granular lymphocyte/natural killer cells" *Journal of Immunology* 151(11):6429-6439 (Dec. 1, 1993).
Vitetta, E.S. et al. (Jul. 21, 2006). "Considering Therapeutic Antibodies," *Science* 313:308-309.
Ward and Ghetie, "The effector functions of immunoglobulins: implications for therapy" *Therapeutic Immunology* 2(2):77-94 (1995).
Warmerdam et al., "A single amino acid in the second Ig-like domain of the human Fcγ receptor II is critical for human IgG2 binding" *Journal of Immunology* 147(4):1338-1343 (Aug. 15, 1991).
Weng et al., "Computational determination of the structure of rat Fc bound to the neonatal Fc receptor" *Journal of Molecular Biology* 282(2):217-225 (Sep. 18, 1998).
Werther et al., "Humanization of an Anti-Lymphocyte Function-Associated Antigen (LFA)-1 Monoclonal Antibody and Reengineering of the Humanized Antibody for Binding to Rhesus LFA-1" *J. of Immunology* 157:4986-4995 (1996).
Williams et al., "Heteroclitic polyclonal and monoclonal anti-Gm(a) and anti-Gm(g) human rheumatoid factors react with epitopes induced in Gm(a–), Gm(g–) IgG by interaction with antigen or by nonspecific aggregation" *Journal of Immunology* 149(5):1817-1824 (Sep. 1, 1992).
Woof et al., "Localisation of the monocyte-binding region on human immunoglobulin G" *Molecular Immunology* 23(3):319-330 (Mar. 1986).

Wright and Morrison, "Effect of altered $C_H2$-associated carbohydrate structure on the functional properties and in vivo fate of chimeric mouse-human immunoglobulin G1" *Journal of Experimental Medicine* 180(3):1087-1096 (Sep. 1, 1994).
Wu et al., "A novel polymorphism of FcγRIIIa (CD16) alters receptor function and predisposes to autoimmune disease" *Journal of Clinical Investigation* 100(5):1059-1070 (Sep. 1, 1997).
Xie, M-H. et al. (Aug. 1997). "Direct Demonstration of MuSK Involvement in Acetylcholine Receptor Clustering Through Identification of Agonist ScFv," *Nature Biotechnology* 15(8):768-771.
Xu et al., "Residue at position 331 in the IgG1 and IgG4 CH2 domains contributes to their differential ability to bind and activate complement" *Journal of Biological Chemistry* 269(5):3469-3474 (Feb. 4, 1994).
Xu et al., "The N-terminal sequence of the $C_H2$ domain controls the differential ability of human IgG1 and IgG2 to activate complement" *Journal of Immunology* (abstract No. 862) 150(8):152A (Apr. 15, 1993).
Yap et al., "Human Fc gamma receptor IIA (FcγRIIA) genotyping and association with systemic lupus erythematosus (SLE) in Chinese and Malays in Malaysia" *Lupus* 8(4):305-310 (1999).
Yeung et al., "A Therapeutic Anti-VEGF Antibody with Increased Potency Independent of Pharmacokinetic Half-life" *Cancer Research* 70(8):3269-3277 (2010).
Yeung, Y.A. et al. (2009). "Engineering Human IgG1 Affinity to Human Neonatal Fc Receptor: Impact of Affinity Improvement on Pharmacokinetics in Primates" *Journal of Immunology* 182:7663-7671.
Yuan et al., "Antibody-mediated modulation of Cryptococcus neoformans infection is dependent on distinct Fc receptor functions and IgG subclasses" *Journal of Experimental Medicine* 187(4):641-648 (Feb. 16, 1998).
Adamis et al., "Inhibition of Vascular Endotherlial growth factor Prevents Retinal Ischemia-Associated Iris Neovascularization in a Nonhuman Primate" Arch. Opthalomogy 114(1):66-71 (1996).
Borgstrom et al., "Complete inhibition of angiogenesis and growth of microtumors by anti-vascular endothelial growth factor neutralizing antibody: novel concepts of angiostatic therapy from intravfital videomicroscopy" Cancer Research 50(17):4032-4039 (Sep. 1, 1996).
Brambell, "The Transmission of Immunity from Mother to young and the Catabolism of Immunoglobulin" Lancet 2:1087-1093 (Nov. 19, 1966).
Brekke et al., "Structure-Function Relationships of Human IgG" The Immunologist 2:125-130 (1994).
International Search Report and Written Opinion for PCT/US2009/060443, pp. 6 (Feb. 23, 2010).
Ferrara and Alitalo, "Clinical appications of angigenic growth factors and their inhibitors" Nat Med. 5(12):1359-1364 (Dec. 1999).
Gillies et al., "MRI of the tumor microenvironment" J Magn Reson Imaging 16(4):430-450 (Oct. 2002).
Gurbaxni and Morrion, "Development of new models for the analysis of Fc-FcRn interactions" Mol. Immunol. 43:1379-1389 (2006).
Guyer et al., "Immunoglobulin Binding by Mouse Intesinal Epithelial Cell Receptors" J. Immunol. 117(2):587-593 (1976).
Hezareh et al., "Effector Function activities of a panel of mutants of a broadly neutralizing antibody against human immunodeficiency virus type 1" J Virol. 75(24);12161-8 (Dec. 2001).
Houck et al., "The vasculaar endothelial growth factor family: identification of a fourth molecular species and characterization of alternative splicing of RNA" Mol. Endocriol. 5(12):1806-1814 (1991).
Israel et al., "Incresed clearance of IgG in mice that lack beta 2-microglobulin: possible protective role of FcRn" Immunology 89(4):573-578 (Dec. 1996).
Jefferis et al., "IgG-Fc-Mediated Effector Functions: Molecular Definition of Interaction Sites for Effector Ligands and the Role of Glycosylation" Immunol. Rev. 163:59-76 (1998).
Jefferis et al., "Recognition Sites of Human IgG for Fcγ Receptors: The Role of Glycosylation" Immunology Letters 44( Suppl 111-117) (1995).
Jones et al., "The Mechanism of intestinal uptake and transcelluarl tranport of IgG in the neonatal rat" Journal of Clinical Investigation 51(11):2916-2927 (Nov. 1972).

(56) References Cited

OTHER PUBLICATIONS

Klagsbrun and D'Amore,, "Regulators of Antiogenesis" Ann. Rev. Physiol. 53:217-239 (1991).

Leung et al., "vascular Endothelial Growth Factor is a Secreted Aangiogenic mitogen" Science 246:1306-1309 (Dec. 8, 1989)

Liang et al., "Crossspecies vascualr endotherlial growth factor (VEGF)-blocking antibodies completely inhibit the growth of human tumor xenografts and measure the contribution of stromal VEGF" J Biol Chem. 281(2):951-961 (Jan. 2006).

McCarthy et al., "Bidirectional transcytosis of IgG by the rat neonatal Fc Receptor expressed in a rat kidney cell line: a system to study proten transport across epithelia" J Cell Sci. 113:1277-1285 (Apr. 2000).

Melnyk et al., "vascular endothelial growth factor promotes tumor dissemination by a mechanism distrinct from its effect on primary tumor growth" Cancer Research 55(4):921-924 (Feb. 15, 1996).

Mizushima et al., "Structural Basis for Improved Efficacy of Therapeutic Antibodies on Defucosylation of Their Fc Glycans" Genes to Cells 16:1071-1080 (2011).

Morris Antigen Absorption by the Gut "2 The Receptor hypothesis of proten ingestion" W.A. Hemmings, Baltimore:University Park Press,:3-22 (1979).

Natsume et al., "Improving Effector Functions of Antibodies for Cancer Treatement: Enhancing ADCC and CDC" Drug Design, Development and Therapy 3:7-16 (2009).

Newman, "Modification of the Fc Region of a primatized IgG Antibody to Human CD4 retains its ability to modulate CD4 receptors but does not deplete CD4(+) T Cells in Chimpanzees" Clin Immuno 98(2):164-174 (Feb. 2001).

Ober et al., "Exocytosis of IgG as mediated by the receptor, FcRn: an Analysis at the Single-Molecule Level" Proc Natl Acad Sci U.S.A. 101(30):11076-11081. (Jul. 2004).

Ober et al., "Visualizing the site and dynamis of IgG Salvage by the MHC Class I-related receptor, FcRn" J Immuno. 172(4):20221-20229 (Feb. 2004).

Okazaki et al., "Fucose Depletion From Human IgG1 Oligosaccharide Enhances Binding Enthalpy and Associateion Rate Between IgG1 and FcγRIIIa" J. Mol. Bio. 336(5):1239-1249 (Mar. 5, 2004).

Popov et al., "Human/mouse cross-reactive anit-BEGF receptor 2 recombinant antibodies selected from an immune b9 allotype rabbit antibdoy library" J Immunol Methods 288(1-2):149-164 (May 2004).

Prabhat et al., "Elucidation of intracelluar recycling pathways leading to exocytosis of the Fc receptor, FcRn, by using multifocal plane microscopy" Proc Natl Aca Sci U.S.A. 104(14):5889-5894 (Apr. 2007).

Praetor et al., "Intracelluarl traffic of the MHC Class I-Like IgG Fc receptor, FcRn, expressed in epithelial MdCK Cells" J Cell Sci. 112:2291-2299 (Jul. 1999).

Radaev et al., "The Structure of a Human Type III Fey Receptor in Complex with Fc" Journal of Biological Chemistry 276:16469-16477 (2001).

Raghavan and Bjorkman, "Fe Receptors and their Interactions with Immunoglobulins" Annu. Rev. Cell. Dev. Biol. 12:181-220 (1996).

Repp et al., "Combined Fc-Protein- and Fc Glyco-Engineering of scFv-Fc Fusion Proteins Synergistically Enhances CD16a Binding but Does not Further Enhance NK-Cell Mediated ADCC" J. Immunol. Methods 373(1-2):67-78 (Oct. 28, 2011).

Rodewald, "ph-dependent binding of immunoglobulins to intestinal cells of the neonatal rat" J Cell Biol 71(2):666-669 (Nov. 1976).

Roopenian et al., "The MHC Class I-like IgG receptor controls perinatal IgG transport, IgG homestasis, and fate of IgG fc-copled drugs" J Immuno. 170(7):3528-3533 (Apr. 2003).

Sato, "Molecular diagnosis of tumor angiogenesis and antiangiogenic cancer therapy" Int J Clin Oncol. 8(5):200-206 (Aug. 2003).

Simon et al., "Consolidation treatement with chimeric anti-GD2-antibody ch14.18 in children older thatn 1 year with metastatic neuroblastoma" J Clin Oncol. 22(17):3549-3557 (Sep. 2004).

Song et al. Cancer Drug Discovery and Development: Cancer Drug Reistance "Influence of TUmor pH on Therapeutic Response" B. Teicher, Totowa, New Jersey:Humana Press, Inc., vol. Chapter 2:21-42 (2007).

Streit and Detmar, "Angiogenesis, lymphang iogenesis, and melanoma Metastasis" Oncogene 22:3172-3179 (2003).

Taylor et al., "n vitro and in vivo activities of OX40 (D134)—IgG fusion protein isoforms with different levels of immune-effector functions" J Leukoc Biol. 7293:522-529 (Sep. 2002).

Tejada et al., "Tumor-driven paracrine platelt-derived growth factor receptor alpha signaling is a key dterminant of stromal cell recruitment in a model of human lung carcionma" Clin Cancer Res. 12(9):2676-2688 (May 2006).

Tesar et al., "Ligand valency affects transcytosis, recycling and intracellular trafficking mediated by the neontal Fc receptor" Traffic 7(9):1127-1142 (Sep. 2006).

Thommesen et al., "Lysine 322 in the juman IgG3 C(h) 2 Domain is crucial for antibody dependent complement activation" Mol. Immuno. 37(16):995-1004 (Spring 2000).

Tonini et al., "Molecular basis of angiogenesis and cancer" Oncogene(22 Suppl 42):6549-6556 (Sep. 29, 2003).

Vaswani and Hamilton, "Humanized Antibodies as Potential Therapeutic Drugs" Ann. Allergy Asthma Immunol. 81:105-119 (Aug. 1998).

Walker et al., "Aglycosylation of Human IgGI and IgG3 Monoclonal Antibodies Can Eliminate Recognition by Human Cells Expressing FcγRI and/or FcγRII Receptors" Biochemical Journal 259:347-353 (1989).

Warren et al., "Regulation by vascular endotheial growth factor of human colon cancer tumorigenesis in a mouse model of experimental liver metastasis" J. Clin. Invest. 95(4):1789-1797 (Apr. 1995).

Watt et al., "Site-specific glycosylation of an aglycosylated human IgG1-Fc antibody protein generated neoglycoproteins with enhanced function" Chem. Biol. 10(9):807-814 (Sep. 2003).

Wawrzynczak et al., "Blood Clearance in the Mouse of an Aglycosyl Recombinant Monoclonal Antibody" Biochemical Society Transactions 17:1061-1062 ( 1989).

Wawrzynczak et al., "Blood Clearance in the Rat of a Recombinant Mouse Monoclonal Antibody Lacking the N-Linked Oligosaccharide Side Chains of the CH2 Domains" Molecular Immunology 29(2):213-220 ( 1992).

Wawrzynczak et al., "Recombinant Mouse Monoclonal Antibodies with single Amino Acid Substitutions Affecting C1q and High Affinity Fc Receptor bidning Have Identical serum half-lives in the BALB/c Mouse" Molecular Immunolgy 29(2):221-227 ( 1992).

Weis et al., "The C-Type Lectin Superfamily in the Immune System" Immunol. Rev. 163:19-34 (1998).

Wright and Morrison, "Effect of C2-Associated Carbohydrate Structure on Ig Effector Function: Studi es with Chimeric Mouse-Human IgGI Antibodies in Glycosylation Mutants of Chinese Hamster Ovary Cells" J. Immunol 160:3393-3402 (1998).

Wright and Morrison, "Effect of Glycosylation on Antibody Function; Implications for Genetic Engineering" Trends in Biotechnology 15:26-32 ( 1997).

Xu et al., "In vitro characterization of five humanized OKT3 Effector Function Variant Antibodies" Cellualr Immunology 200(1):16-26 ( 2000).

Zheng et al., "Adminstration of noncytolytic I1-10/Fc in murine models of lipopolysaccharide-induced septic shock and allogeneic islet transplantion" J Immunol. 154(10):5590-5600 (May 1995).

Schlaeth et al., "Fc-engineered EGF-R antibodies mediate inproved antibody-dependent cellular cytotoxicity (ADCC) against KRAS-mutated tumor cells" Cancer Science 101(5):1080-1088 (May 2010).

Shim et al., "One Target, different effects: a comparison of distinct therapeutic antibodies against the same targets" Experimental and Molecualr Medicine 43(10):539-549 (Oct. 2011).

\* cited by examiner (E27) - Light Chain

DIQLTQSPSS LSASVGDRVT ITCRASKPVD GEGDSYLNWY QQKPGKAPKL LIYAASYLES GVPSRFSGSG
SGTDFTLTIS SLQPEDFATY YCQQSHEDPY TFGQGTKVEI KRTVAAPSVF IFPPSDEQLK SGTASVVCLL
NNFYPREAKV QWKVDNALQS GNSQESVTEQ DSKDSTYSLS STLTLSKADY EKHKVYACEV THQGLSSPVT
KSFNRGEC

*FIG. 4A*

(E27) - Heavy Chain

EVQLVESGGG LVQPGGSLRL SCAVSGYSIT SGYSWNWIRQ APGKGLEWVA SIKYSGETKY NPSVKGRITI
SRDDSKNTFY LQMNSLRAED TAVYYCARGS HYFGHWHFAV WGQGTLVTVS SASTKGPSVF PLAPSSKSTS
GGTAALGCLV KDYFPEPVTV SWNSGALTSG VHTFPAVLQS SGLYSLSSVV TVPSSSLGTQ TYICNVNHKP
SNTKVDKKVE PKSCDKTHTC PPCPAPELLG GPSVFLFPPK PKDTLMISRT PEVTCVVVDV SHEDPEVKFN
WYVDGVEVHN AKTKPREEQY NSTYRVVSVL TVLHQDWLNG KEYKCKVSNK ALPAPIEKTI SKAKGQPREP
QVYTLPPSRE EMTKNQVSLT CLVKGFYPSD IAVEWESNGQ PENNYKTTPP VLDSDGSFFL YSKLTVDKSR
WQQGNVFSCS VMHEALHNHY TQKSLSLSPG K

*FIG. 4B*

```
              230        240        250        260        270
humIgG1    PAPELLGGPSVFLFPPKPKDTLMISRTPEVTCVVVDVSHEDPEVKFNWYV
humIgG2    PAP-PVAGPSVFLFPPKPKDTLMISRTPEVTCVVVDVSHEDPEVQFNWYV
humIgG3    PAPELLGGPSVFLFPPKPKDTLMISRTPEVTCVVVDVSHEDPEVQFKWYV
humIgG4    PAPEFLGGPSVFLFPPKPKDTLMISRTPEVTCVVVDVSQEDPEVQFNWYV
murIgG1    ---TVPEVSSVFIFPPKPKDVLTITLTPKVTCVVVDISKDDPEVQFSWFV
murIgG2A   PAPNLLGGPSVFIFPPKIKDVLMISLSPIVTCVVVDVSEDDPDVQISWFV
murIgG2B   PAPNLEGGPSVFIFPPNIKDVLMISLTPKVTCVVVDVSEDDPDVQISWFV
murIgG3    PPGNILGGPSVFIFPPKPKDALMISLTPKVTCVVVDVSEDDPDVHVSWFV 280        290        300        310        320
humIgG1    DGVEVHNAKTKPREEQYNSTYRVVSVLTVLHQDWLNGKEYKCKVSNKALP
humIgG2    DGVEVHNAKTKPREEQFNSTFRVVSVLTVVHQDWLNGKEYKCKVSNKGLP
humIgG3    DGVEVHNAKTKPREEQFNSTFRVVSVLTVLHQDWLNGKEYKCKVSNKALP
humIgG4    DGVEVHNAKTKPREEQFNSTYRVVSVLTVLHQDWLNGKEYKCKVSNKGLP
murIgG1    DDVEVHTAQTQPREEQFNSTFRSVSELPIMHQDCLNGKEFKCRVNSAAFP
murIgG2A   NNVEVHTAQTQTHREDYNSTLRVVSALPIQHQDWMSGKEFKCKVNNKDLP
murIgG2B   NNVEVHTAQTQTHREDYNSTIRVVSHLPIQHQDWMSGKEFKCKVNNKDLP
murIgG3    DNKEVHTAWTQPREAQYNSTFRVVSALPIQHQDWMRGKEFKCKVNNKALP 330        340        350        360        370
humIgG1    APIEKTISKAKGQPREPQVYTLPPSREEMTKNQVSLTCLVKGFYPSDIAV
                            D  L
humIgG2    APIEKTISKTKGQPREPQVYTLPPSREEMTKNQVSLTCLVKGFYPSDIAV
humIgG3    APIEKTISKTKGQPREPQVYTLPPSREEMTKNQVSLTCLVKGFYPSDIAV
humIgG4    SSIEKTISKAKGQPREPQVYTLPPSQEEMTKNQVSLTCLVKGFYPSDIAV
murIgG1    APIEKTISKTKGRPKAPQVYTIPPPKEQMAKDKVSLTCMITDFFPEDITV
murIgG2A   APIERTISKPKGSVRAPQVYVLPPPEEEMTKKQVTLTCMVTDFMPEDIYV
murIgG2B   SPIERTISKPKGLVRAPQVYTLPPPAEQLSRKDVSLTCLVVGFNPGDISV
murIgG3    APIERTISKPKGRAQTPQVYTIPPPREQMSKKKVSLTCLVTNFFSEAISV 380        390        400        410        420
humIgG1    EWESNGQPENNYKTTPPVLDSDGSFFLYSKLTVDKSRWQQGNVFSCSVMH
humIgG2    EWESNGQPENNYKTTPPMLDSDGSFFLYSKLTVDKSRWQQGNVFSCSVMH
humIgG3    EWESSGQPENNYNTTPPMLDSDGSFFLYSKLTVDKSRWQQGNIFSCSVMH
humIgG4    EWESNGQPENNYKTTPPVLDSDGSFFLYSRLTVDKSRWQEGNVFSCSVMH
murIgG1    EWQWNGQPAENYKNTQPIMDTDGSYFVYSKLNVQKSNWEAGNTFTCSVLH
murIgG2A   EWTNNGKTELNYKNTEPVLDSDGSYFMYSKLRVEKKNWVERNSYSCSVVH
murIgG2B   EWTSNGHTEENYKDTAPVLDSDGSYFIYSKLNMKTSKWEKTDSFSCNVRH
murIgG3    EWERNGELEQDYKNTPPILDSDGTYFLYSKLTVDTDSWLQGEIFTCSVVH 430        440
humIgG1    EALHNHYTQKSLSLSPGK
humIgG2    EALHNHYTQKSLSLSPGK
humIgG3    EALHNRFTQKSLSLSPGK
humIgG4    EALHNHYTQKSLSLSLGK
murIgG1    EGLHNHHTEKSLSHSPGK
murIgG2A   EGLHNHHTTKSFSRTPGK
murIgG2B   EGLKNYYLKKTISRSPGK
murIgG3    EALHNHHTQKNLSRSPGK
```

*FIG. 22A*

Percent Identity Among Fc Sequences

```
              1    2    3    4    5    6    7    8
1. humIgG1    -   94   94   94   64   66   63   68
2. humIgG2         -   93   92   65   63   60   67
3. humIgG3              -   91   64   64   61   67
4. humIgG4                   -   62   64   61   64
5. murIgG1                        -   65   61   67
6. murIgG2A                            -   77   70
7. murIgG2B                                 -   68
8. murIgG3                                       -
```

FIG. 22B

```
          230        240        250        260        270
humIgG1   PAPELLGGPSVFLFPPKPKDTLMISRTPEVTCVVVDVSHEDPEVKFNWYV
humIgG2   PAP-PVAGPSVFLFPPKPKDTLMISRTPEVTCVVVDVSHEDPEVQFNWYV
humIgG3   PAPELLGGPSVFLFPPKPKDTLMISRTPEVTCVVVDVSHEDPEVQFKWYV
humIgG4   PAPEFLGGPSVFLFPPKPKDTLMISRTPEVTCVVVDVSQEDPEVQFNWYV
              ****                            *    *  *

280        290        300        310        320
humIgG1   DGVEVHNAKTKPREEQYNSTYRVVSVLTVLHQDWLNGKEYKCKVSNKALP
humIgG2   DGVEVHNAKTKPREEQFNSTFRVVSVLTVVHQDWLNGKEYKCKVSNKGLP
humIgG3   DGVEVHNAKTKPREEQFNSTFRVVSVLTVLHQDWLNGKEYKCKVSNKALP
humIgG4   DGVEVHNAKTKPREEQFNSTYRVVSVLTVLHQDWLNGKEYKCKVSNKGLP
                          *   *       *                 *

330        340        350        360        370
humIgG1   APIEKTISKAKGQPREPQVYTLPPSREEMTKNQVSLTCLVKGFYPSDIAV
                              D L
humIgG2   APIEKTISKTKGQPREPQVYTLPPSREEMTKNQVSLTCLVKGFYPSDIAV
humIgG3   APIEKTISKTKGQPREPQVYTLPPSREEMTKNQVSLTCLVKGFYPSDIAV
humIgG4   SSIEKTISKAKGQPREPQVYTLPPSQEEMTKNQVSLTCLVKGFYPSDIAV
          **       *              *

380        390        400        410        420
humIgG1   EWESNGQPENNYKTTPPVLDSDGSFFLYSKLTVDKSRWQQGNVFSCSVMH
humIgG2   EWESNGQPENNYKTTPPMLDSDGSFFLYSKLTVDKSRWQQGNIFSCSVMH
humIgG3   EWESSGQPENNYNTTPPMLDSDGSFFLYSKLTVDKSRWQQEGNVFSCSVMH
humIgG4   EWESNGQPENNYKTTPPVLDSDGSFFLYSRLTVDKSRWQEGNVFSCSVMH
              *          *    *              *      *  *

430        440
humIgG1   EALHNHYTQKSLSLSPGK
humIgG2   EALHNHYTQKSLSLSPGK
humIgG3   EALHNRFTQKSLSLSPGK
humIgG4   EALHNHYTQKSLSLSLGK
               **           *
```

FIG. 23

POLYPEPTIDE VARIANTS WITH ALTERED EFFECTOR FUNCTION

This is a divisional of U.S. application Ser. No. 12/590,801, filed Nov. 12, 2009, which is a continuation of U.S. application Ser. No. 11/520,121, filed Sep. 13, 2006, now abandoned, which is a continuation to continuation-in-part application Ser. No. 09/713,425 filed Nov. 15, 2000, now U.S. Pat. No. 7,183,387 issued Feb. 27, 2007, which claims priority to non-provisional application Ser. No. 09/483,588, filed Jan. 14, 2000 (now U.S. Pat. No. 6,737,056 issued May 18, 2004), which claims priority under 35 USC §119 to provisional application No. 60/116,023 filed Jan. 15, 1999, the entire disclosures of which are incorporated herein by reference.

BACKGROUND OF THE INVENTION

1. Field of the Invention

The present invention concerns polypeptides comprising a variant Fc region. More particularly, the present invention concerns Fc region-containing polypeptides that have altered effector function as a consequence of one or more amino acid modifications in the Fc region thereof.

2. Description of Related Art

Antibodies are proteins which exhibit binding specificity to a specific antigen. Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in three segments called complementarity determining regions (CDRs) both in the light chain and the heavy chain variable domains. The more highly conserved portions of the variable domains are called the framework regions (FRs). The variable domains of native heavy and light chains each comprise four FRs, largely adopting a β-sheet configuration, connected by three CDRs, which form loops connecting, and in some cases forming part of, the β-sheet structure. The CDRs in each chain are held together in close proximity by the FRs and, with the CDRs from the other chain, contribute to the formation of the antigen binding site of antibodies (see Kabat et al., Sequences of Proteins of Immunological Interest, 5th Ed. Public Health Service, National Institutes of Health, Bethesda, Md. (1991)).

The constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and several of these may be further divided into subclasses (isotypes), e.g. IgG1, IgG2, IgG3, and IgG4; IgA1 and IgA2. The heavy chain constant regions that correspond to the different classes of immunoglobulins are called α, δ, ε, γ, and μ, respectively. Of the various human immunoglobulin classes, only human IgG1, IgG2, IgG3 and IgM are known to activate complement; and human IgG1 and IgG3 mediate ADCC more effectively than IgG2 and IgG4.

A schematic representation of the native IgG1 structure is shown in FIG. 1, where the various portions of the native antibody molecule are indicated. Papain digestion of antibodies produces two identical antigen binding fragments, called Fab fragments, each with a single antigen binding site, and a residual "Fc" fragment, whose name reflects its ability to crystallize readily. The crystal structure of the human IgG Fc region has been determined (Deisenhofer, *Biochemistry* 20:2361-2370 (1981)). In human IgG molecules, the Fc region is generated by papain cleavage N-terminal to Cys 226. The Fc region is central to the effector functions of antibodies.

The effector functions mediated by the antibody Fc region can be divided into two categories: (1) effector functions that operate after the binding of antibody to an antigen (these functions involve the participation of the complement cascade or Fc receptor (FcR)-bearing cells); and (2) effector functions that operate independently of antigen binding (these functions confer persistence in the circulation and the ability to be transferred across cellular barriers by transcytosis). Ward and Ghetie, *Therapeutic Immunology* 2:77-94 (1995).

While binding of an antibody to the requisite antigen has a neutralizing effect that might prevent the binding of a foreign antigen to its endogenous target (e.g. receptor or ligand), binding alone may not remove the foreign antigen. To be efficient in removing and/or destructing foreign antigens, an antibody should be endowed with both high affinity binding to its antigen, and efficient effector functions.

Fc Receptor (FcR) Binding

The interaction of antibodies and antibody-antigen complexes with cells of the immune system effects a variety of responses, including antibody-dependent cell-mediated cytotoxicity (ADCC) and complement dependent cytotoxicity (CDC) (reviewed in Daëron, *Annu. Rev. Immunol.* 15:203-234 (1997); Ward and Ghetie, *Therapeutic Immunol.* 2:77-94 (1995); as well as Ravetch and Kinet, *Annu. Rev. Immunol.* 9:457-492 (1991)).

Several antibody effector functions are mediated by Fc receptors (FcRs), which bind the Fc region of an antibody. FcRs are defined by their specificity for immunoglobulin isotypes; Fc receptors for IgG antibodies are referred to as FcγR, for IgE as FcεR, for IgA as FcαR and so on. Three subclasses of FcγR have been identified: FcγRI (CD64), FcγRII (CD32) and FcγRIII (CD16). Because each FcγR subclass is encoded by two or three genes, and alternative RNA splicing leads to multiple transcripts, a broad diversity in FcγR isoforms exists. The three genes encoding the FcγRI subclass (FcγRIA, FcγRIB and FcγRIC) are clustered in region 1q21.1 of the long arm of chromosome 1; the genes encoding FcγRII isoforms (FcγRIIA, FcγRIIB and FcγRIIC) and the two genes encoding FcγRIII (FcγRIIIA and FcγRIIIB) are all clustered in region 1q22. These different FcR subtypes are expressed on different cell types (reviewed in Ravetch and Kinet, *Annu. Rev. Immunol.* 9:457-492 (1991)). For example, in humans, FcγRIIIB is found only on neutrophils, whereas FcγRIIIA is found on macrophages, monocytes, natural killer (NK) cells, and a subpopulation of T-cells. Notably, FcγRIIIA is the only FcR present on NK cells, one of the cell types implicated in ADCC.

FcγRI, FcγRII and FcγRIII are immunoglobulin superfamily (IgSF) receptors; FcγRI has three IgSF domains in its extracellular domain, while FcγRII and FcγRIII have only two IgSF domains in their extracellular domains.

Another type of Fc receptor is the neonatal Fc receptor (FcRn). FcRn is structurally similar to major histocompatibility complex (MHC) and consists of an α-chain noncovalently bound to β2-microglobulin.

The binding site on human and murine antibodies for FcγR have been previously mapped to the so-called "lower hinge region" consisting of residues 233-239 (EU index numbering as in Kabat et al., Sequences of Proteins of Immunological Interest, 5th Ed. Public Health Service, National Institutes of Health, Bethesda, Md. (1991)). Woof et al. Molec. Immunol. 23:319-330 (1986); Duncan et al. Nature 332:563 (1988); Canfield and Morrison, J. Exp. Med. 173:1483-1491 (1991); Chappel et al., Proc. Natl. Acad. Sci USA 88:9036-9040 (1991). Of residues 233-239, P238 and S239 have been cited as possibly being involved in binding, but these two residues have never been evaluated by substitution or deletion.

Other previously cited areas possibly involved in binding to FcγR are: G316-K338 (human IgG) for human FcγRI (by sequence comparison only; no substitution mutants were evaluated) (Woof et al. Molec. Immunol. 23:319-330 (1986)); K274-R301 (human IgG1) for human FcγRIII (based on peptides) (Sarmay et al. Molec. Immunol. 21:43-51 (1984)); Y407-R416 (human IgG) for human FcγRIII (based on peptides) (Gergely et al. Biochem. Soc. Trans. 12:739-743 (1984)); as well as N297 and E318 (murine IgG2b) for murine FcγRII (Lund et al., Molec. Immunol., 29:53-59 (1992)).

Pro331 in IgG3 was changed to Ser, and the affinity of this variant to target cells analyzed. The affinity was found to be six-fold lower than that of unmutated IgG3, indicating the involvement of Pro331 in FcγRI binding. Morrison et al., Immunologist, 2:119-124 (1994); and Canfield and Morrison, J. Exp. Med. 173:1483-91 (1991).

C1q Binding

C1q and two serine proteases, C1r and C1s, form the complex C1, the first component of the complement dependent cytotoxicity (CDC) pathway. C1q is a hexavalent molecule with a molecular weight of approximately 460,000 and a structure likened to a bouquet of tulips in which six collagenous "stalks" are connected to six globular head regions. Burton and Woof, Advances in Immunol. 51:1-84 (1992). To activate the complement cascade, it is necessary for C1q to bind to at least two molecules of IgG1, IgG2, or IgG3 (the consensus is that IgG4 does not activate complement), but only one molecule of IgM, attached to the antigenic target. Ward and Ghetie, Therapeutic Immunology 2:77-94 (1995) at page 80.

Based upon the results of chemical modifications and crystallographic studies, Burton et al. (Nature, 288:338-344 (1980)) proposed that the binding site for the complement subcomponent C1q on IgG involves the last two (C-terminal) β-strands of the CH2 domain. Burton later suggested (Molec. Immunol., 22(3):161-206 (1985)) that the region comprising amino acid residues 318 to 337 might be involved in complement fixation.

Duncan and Winter (Nature 332:738-40 (1988)), using site directed mutagenesis, reported that Glu318, Lys320 and Lys322 form the binding site to C1q. The data of Duncan and Winter were generated by testing the binding of a mouse IgG2b isotype to guinea pig C1q. The role of Glu318, Lys320 and Lys322 residues in the binding of C1q was confirmed by the ability of a short synthetic peptide containing these residues to inhibit complement mediated lysis. Similar results are disclosed in U.S. Pat. No. 5,648,260 issued on Jul. 15, 1997, and U.S. Pat. No. 5,624,821 issued on Apr. 29, 1997.

The residue Pro331 has been implicated in C1q binding by analysis of the ability of human IgG subclasses to carry out complement mediated cell lysis. Mutation of Ser331 to Pro331 in IgG4 conferred the ability to activate complement. (Tao et al., J. Exp. Med., 178:661-667 (1993); Brekke et al., Eur. J. Immunol., 24:2542-47 (1994)).

From the comparison of the data of the Winter group, and the Tao et al. and Brekke et al. papers, Ward and Ghetie concluded in their review article that there are at least two different regions involved in the binding of C1q: one on the β-strand of the CH2 domain bearing the Glu318, Lys320 and Lys322 residues, and the other on a turn located in close proximity to the same β-strand, and containing a key amino acid residue at position 331.

Other reports suggested that human IgG1 residues Leu235, and Gly237, located in the lower hinge region, play a critical role in complement fixation and activation. Xu et al., Immunol. 150:152A (Abstract) (1993). WO94/29351 published Dec. 22, 1994 reports that amino acid residues necessary for C1q and FcR binding of human IgG1 are located in the N-terminal region of the CH2 domain, i.e. residues 231 to 238.

It has further been proposed that the ability of IgG to bind C1q and activate the complement cascade also depends on the presence, absence, or modification of the carbohydrate moiety positioned between the two CH2 domains (which is normally anchored at Asn297). Ward and Ghetie, Therapeutic Immunology 2:77-94 (1995) at page 81.

SUMMARY OF THE INVENTION

The present invention provides a variant of a parent polypeptide comprising an Fc region, which variant mediates antibody-dependent cell-mediated cytotoxicity (ADCC) in the presence of human effector cells more effectively, or binds an Fc gamma receptor (FcγR) with better affinity, than the parent polypeptide and comprises at least one amino acid modification in the Fc region. The polypeptide variant may, for example, comprise an antibody or an immunoadhesin. The Fc region of the parent polypeptide preferably comprises a human Fc region; e.g., a human IgG1, IgG2, IgG3 or IgG4 Fc region. The polypeptide variant preferably comprises an amino acid modification (e.g. a substitution) at any one or more of amino acid positions 256, 290, 298, 312, 326, 330, 333, 334, 360, 378 or 430 of the Fc region, wherein the numbering of the residues in the Fc region is that of the EU index as in Kabat.

In addition, the invention provides a polypeptide comprising a variant Fc region with altered Fc gamma receptor (FcγR) binding affinity, which polypeptide comprises an amino acid modification at any one or more of amino acid positions 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439 of the Fc region, wherein the numbering of the residues in the Fc region is that of the EU index as in Kabat. The variant Fc region preferably comprises a variant human IgG Fc region, e.g., a variant human IgG1, IgG2, IgG3 or IgG4 Fc region. In this respect, it is noted that, in the work in the above-cited art where the parent polypeptide had a non-human murine Fc region, different residues from those identified herein were thought to impact FcR binding. For example, in the murine IgG2b/murine FcγRII system, IgG E318 was found to be important for binding (Lund et al. *Molec. Immunol.* 27(1):53-59 (1992)), whereas E318A had no effect in the human IgG/human FcγRII system (Table 6 below).

In one embodiment, the polypeptide variant with altered FcγR binding activity displays reduced binding to an FcγR and comprises an amino acid modification at any one or more of amino acid positions 238, 239, 248, 249, 252, 254, 265, 268, 269, 270, 272, 278, 289, 292, 293, 294, 295, 296, 298, 301, 303, 322, 324, 327, 329, 333, 335, 338, 340, 373, 376, 382, 388, 389, 414, 416, 419, 434, 435, 437, 438 or 439 of the Fc region, wherein the numbering of the residues in the Fc region is that of the EU index as in Kabat.

For example, the polypeptide variant may display reduced binding to an FcγRI and comprise an amino acid modification at any one or more of amino acid positions 238, 265, 269, 270, 327 or 329 of the Fc region, wherein the numbering of the residues in the Fc region is that of the EU index as in Kabat.

The polypeptide variant may display reduced binding to an FcγRII and comprise an amino acid modification at any one or more of amino acid positions 238, 265, 269, 270, 292, 294, 295, 298, 303, 324, 327, 329, 333, 335, 338, 373, 376, 414, 416, 419, 435, 438 or 439 of the Fc region, wherein the numbering of the residues in the Fc region is that of the EU index as in Kabat.

The polypeptide variant of interest may display reduced binding to an FcγRIII and comprise an amino acid modification at one or more of amino acid positions 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 of the Fc region, wherein the numbering of the residues in the Fc region is that of the EU index as in Kabat.

In another embodiment, the polypeptide variant with altered FcγR binding affinity displays improved binding to the FcγR and comprises an amino acid modification at any one or more of amino acid positions 255, 256, 258, 267, 268, 272, 276, 280, 283, 285, 286, 290, 298, 301, 305, 307, 309, 312, 315, 320, 322, 326, 330, 331, 333, 334, 337, 340, 360, 378, 398 or 430 of the Fc region, wherein the numbering of the residues in the Fc region is that of the EU index as in Kabat.

For example, the polypeptide variant may display increased binding to an FcγRIII and, optionally, may further display decreased binding to an FcγRII. An exemplary such variant comprises amino acid modification(s) at position(s) 298 and/or 333 of the Fc region, wherein the numbering of the residues in the Fc region is that of the EU index as in Kabat.

The polypeptide variant may display increased binding to an FcγRII and comprise an amino acid modification at any one or more of amino acid positions 255, 256, 258, 267, 268, 272, 276, 280, 283, 285, 286, 290, 301, 305, 307, 309, 312, 315, 320, 322, 326, 330, 331, 337, 340, 378, 398 or 430 of the Fc region, wherein the numbering of the residues in the Fc region is that of the EU index as in Kabat. Such polypeptide variants with increased binding to an FcγRII may optionally further display decreased binding to an FcγRIII and may, for example, comprise an amino acid modification at any one or more of amino acid positions 268, 272, 298, 301, 322 or 340 of the Fc region, wherein the numbering of the residues in the Fc region is that of the EU index as in Kabat.

The invention further provides a polypeptide comprising a variant Fc region with altered neonatal Fc receptor (FcRn) binding affinity, which polypeptide comprises an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439 or 447 of the Fc region, wherein the numbering of the residues in the Fc region is that of the EU index as in Kabat. Such polypeptide variants with reduced binding to an FcRn may comprise an amino acid modification at any one or more of amino acid positions 252, 253, 254, 255, 288, 309, 386, 388, 400, 415, 433, 435, 436, 439 or 447 (and preferably one or more of amino acid positions 253, 254, 435 or 436) of the Fc region, wherein the numbering of the residues in the Fc region is that of the EU index as in Kabat. The above mentioned polypeptide variants may, alternatively, display increased binding to FcRn and comprise an amino acid modification at any one or more of amino acid positions 238, 256, 265, 272, 286, 303, 305, 307, 311, 312, 317, 340, 356, 360, 362, 376, 378, 380, 382, 413, 424 or 434 (and preferably one or more of amino acid positions 238, 256, 307, 311, 312, 380, 382 or 434) of the Fc region, wherein the numbering of the residues in the Fc region is that of the EU index as in Kabat.

The polypeptide variant may be in one of the following classes of variants as shown in Table 6 herein (with increased, reduced or unchanged binding to a receptor being calculated as described with respect to that table):

1. A polypeptide variant which displays reduced binding to FcγRI, FcγRIIA, FcγRIIB and FcγRIIIA comprising an amino acid modification at any one or more of amino acid positions 238, 265, 327 or 329 of the Fc region, wherein the numbering of the residues in the Fc region is that of the EU index as in Kabat.

2. A polypeptide variant with reduced binding to FcγRII and FcγRIIIA comprising an amino acid modification at any one or more of amino acid positions 270, 295 or 327 of the Fc region, wherein the numbering of the residues in the Fc region is that of the EU index as in Kabat.

3. A polypeptide variant which displays increased binding to FcγRII and FcγRIIIA comprising an amino acid modification at any one or more of amino acid positions 256 or 290 of the Fc region, wherein the numbering of the residues in the Fc region is that of the EU index as in Kabat.

4. A polypeptide variant which displays increased binding to FcγRII but unchanged binding to FcγRIIIA and comprises an amino acid modification at any one or more of amino acid positions 255, 258, 267, 272, 276, 280, 285, 286, 307, 309, 315, 326, 331, 337, 378 or 430 of the Fc region, wherein the numbering of the residues in the Fc region is that of the EU index as in Kabat.

5. A polypeptide variant which displays increased binding to FcγRII and reduced binding to FcγRIIIA comprising an amino acid modification at any one or more of amino acid positions 268, 301 or 322 of the Fc region, wherein the numbering of the residues in the Fc region is that of the EU index as in Kabat.

6. A polypeptide variant which displays reduced binding to FcγRII but unchanged FcγRIIIA binding and comprises an amino acid modification at any one or more of amino acid positions 292 or 414 of the Fc region, wherein the numbering of the residues in the Fc region is that of the EU index as in Kabat.

7. A polypeptide variant which displays reduced binding to FcγRII and improved binding to FcγRIIIA comprising an amino acid modification at amino acid position 298 of the Fc region, wherein the numbering of the residues in the Fc region is that of the EU index as in Kabat.

8. A polypeptide variant which displays reduced binding to FcγRIIIA but unchanged FcRII binding comprising an amino acid modification at any one or more of amino acid positions 239, 269, 293, 296, 303, 327, 338 or 376 of the Fc region, wherein the numbering of the residues in the Fc region is that of the EU index as in Kabat.

9. A polypeptide variant which displays improved binding to FcγRIIIA but unchanged FcRII binding comprising an amino acid modification at any one or more of amino acid positions 333 or 334 of the Fc region, wherein the numbering of the residues in the Fc region is that of the EU index as in Kabat.

10. A polypeptide variant which displays altered binding to FcRn but unchanged FcγR binding and comprises an amino acid modification at any one or more of amino acid positions 253, 254, 288, 305, 311, 312, 317, 360, 362, 380, 382, 415, 424, 433, 434, 435 or 436 of the Fc region, wherein the numbering of the residues in the Fc region is that of the EU index as in Kabat.

The polypeptide variant herein with improved ADCC activity is preferably selected from:

1. A polypeptide variant which comprises an amino acid modification at any one or more of amino acid positions 298, 333 or 334 of the Fc region, wherein the numbering of the residues in the Fc region is that of the EU index as in Kabat.

2. A polypeptide variant which comprises amino acid modifications at two or more of amino acid positions 298, 333, 334 or 339 of the FC region, wherein the numbering of the residues in the Fc region is that of the EU index as in Kabat.

3. A polypeptide variant which comprises an amino acid modification at amino acid position 298 of the Fc region, wherein the numbering of the residues in the Fc region is that of the EU index as in Kabat.

4. A polypeptide variant which comprises amino acid modifications at amino acid positions 298 and 334 of the Fc region, wherein the numbering of the residues in the Fc region is that of the EU index as in Kabat.

5. A polypeptide variant which comprises amino acid modifications at three or more of amino acid positions 298, 333, 334 or 339 of the Fc region, wherein the numbering of the residues in the Fc region is that of the EU index as in Kabat.

6. A polypeptide variant which comprises amino acid modifications at amino acid positions 298, 333 and 334 of the Fc region, wherein the numbering of the residues in the Fc region is that of the EU index as in Kabat.

The invention provides a polypeptide variant selected from:

1. A polypeptide comprising a variant Fc region which comprises amino acid modifications at amino acid positions 298, 333 and 334 of the Fc region, wherein the numbering of the residues in the Fc region is that of the EU index as in Kabat.

2. A polypeptide comprising a variant Fc region which comprises amino acid modifications at amino acid positions 298 and 334 of the Fc region, wherein the numbering of the residues in the Fc region is that of the EU index as in Kabat.

3. A polypeptide comprising a variant Fc region which comprises an amino acid modification at amino acid position 298 of the Fc region, wherein the numbering of the residues in the Fc region is that of the EU index as in Kabat.

4. A polypeptide comprising a variant Fc region which comprises amino acid modifications at two or all of amino acid positions 307, 380 and 434 of the Fc region, wherein the numbering of the residues is that of the EU index as in Kabat.

In a further embodiment, the invention provides a polypeptide comprising a variant Fc region with altered affinity for an FcγR allotype (e.g. an FcγRIIIA-Phe158, FcγRIIIA-Val158, FcγRIIA-R131 or FcγRIIA-H131 allotype), which polypeptide comprises an amino acid modification at any one or more of amino acid positions 265, 267, 268, 270, 290, 298, 305, 307, 315, 317, 320, 331, 333 or 334 of the Fc region, wherein the numbering of the residues in the Fc region is that of the EU index as in Kabat. Preferably, the polypeptide displays increased binding to FcγRIIIA-Phe158 and hence has improved therapeutic effectiveness, particularly in patients who express FcγRIIIA-Phe158. Polypeptide variants with increased binding to FcγRIIIA-Phe158 preferably comprise an amino acid modification at anyone or more of amino acid positions 290, 298, 333 or 334 of the Fc region, wherein the numbering of the residues in the Fc region is that of the EU index as in Kabat.

The invention also provides a composition comprising the polypeptide variant and a physiologically or pharmaceutically acceptable carrier or diluent. This composition for potential therapeutic use is sterile and may be lyophilized.

Diagnostic and therapeutic uses for the polypeptide variants disclosed herein are contemplated. In one diagnostic application, the invention provides a method for determining the presence of an antigen of interest comprising exposing a sample suspected of containing the antigen to the polypeptide variant and determining binding of the polypeptide variant to the sample. In one therapeutic application, the invention provides a method of treating a mammal suffering from or predisposed to a disease or disorder, comprising administering to the mammal a therapeutically effective amount of a polypeptide variant as disclosed herein, or of a composition comprising the polypeptide variant and a pharmaceutically acceptable carrier.

The invention further provides: isolated nucleic acid encoding the polypeptide variant; a vector comprising the nucleic acid, optionally, operably linked to control sequences recognized by a host cell transformed with the vector; a host cell containing the vector; a method for producing the polypeptide variant comprising culturing this host cell so that the nucleic acid is expressed and, optionally, recovering the polypeptide variant from the host cell culture (e.g. from the host cell culture medium).

The invention further provides a method for making a variant Fc region with altered Fc receptor (FcR) binding affinity, or altered antibody-dependent cell-mediated cytotoxicity (ADCC) activity, comprising:

(a) introducing one or more amino acid modifications into an Fc region of a parent polypeptide in order to generate a variant Fc region;

(b) determining binding of the variant Fc region to an FcR, or determining ADCC activity of the variant Fc region.

Step (b) of the method may comprise determining binding of the variant Fc region to one or more FcRs in vitro. Moreover, the method may result in the identification of a variant Fc region with improved FcR binding affinity, or with improved ADCC activity, in step (b) thereof. Where step (b) comprises determining binding of the Fc region to an FcR, the FcR may, for example, be human Fc gamma receptor III (FcγRIII). Where step (b) comprises determining binding of the variant Fc region to at least two different FcRs, the FcRs tested preferably include human Fc gamma receptor II (FcγRII) and human Fc gamma receptor III (FcγRIII).

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIGS. 4A and 4B depict the amino acid sequences of E27 anti-IgE antibody light chain (FIG. 4A; SEQ ID NO:1) and heavy chain (FIG. 4B; SEQ ID NO:2).

FIG. 15A shows the binding pattern for the humanized anti-IgE E27 IgG1 as a monomer (open circles), hexamer (closed squares), and immune complex consisting of multiple hexamers (closed triangles) to a recombinant GST fusion protein of the human FcγRIIB (CD32) receptor α subunit. The hexameric complex (closed squares) was formed by the mixture of equal molar concentrations of E27 (which binds to the Fc region of human IgE) and a human myeloma IgE. The hexamer is a stable 1.1 kD complex consisting of 3 IgG molecules (150 kD each) and 3 IgE molecules (200 kD each). The immune complex (closed triangles) was formed sequentially by first mixing equal molar concentrations of E27 and recombinant anti-VEGF IgE (human IgE with Fab variable domains that bind human VEGF) to form the hexamer. Hexamers were then linked to form an immune complex by the addition of 2× molar concentration of human VEGF, a 44 kD homodimer which has two binding sites for the anti-VEGF IgE per mole of VEGF.

FIG. 15B shows the binding pattern to a recombinant GST fusion protein of the human FcγRIIIA (CD16) receptor α subunit.

FIG. 18A illustrates binding of selected alanine variants to FcγRIIIA-GST fusion protein. S317A (298 in EU numbering) and S317A/K353A (298 and 334 in EU numbering) bind better than E27 wildtype, while D278A (265 in EU numbering) almost completely abrogates binding. FIG. 18B illustrates that a similar pattern of binding is found on CHO cells expressing a recombinant GPI-linked form of FcγRIIIA.

FIG. 19A illustrates binding of selected alanine variants to FcγRIIB-GST fusion protein. H281A (268 in EU numbering) binds better than E27 wildtype while S317A (298 in EU numbering) shows reduced binding. FIG. 19B illustrates that a similar pattern of binding is found on CHO cells expressing a recombinant membrane bound form of FcγRIIB.

FIG. 22A depicts alignments of native sequence IgG Fc regions. Native sequence human IgG Fc region sequences, humIgG1 (non-A and A allotypes) (SEQ ID NOs: 3 and 4, respectively), humIgG2 (SEQ ID NO:5), humIgG3 (SEQ ID NO:6) and humIgG4 (SEQ ID NO:7), are shown. The human IgG1 sequence is the non-A allotype, and differences between this sequence and the A allotype (at positions 356 and 358; EU numbering system) are shown below the human IgG1 sequence. Native sequence murine IgG Fc region sequences, murIgG1 (SEQ ID NO:8), murIgG2A (SEQ ID NO:9), murIgG2B (SEQ ID NO:10) and murIgG3 (SEQ ID NO:11), are also shown. FIG. 22B shows percent identity among the Fc region sequences of FIG. 22A.

FIG. 23 depicts alignments of native sequence human IgG Fc region sequences, humIgG1 (non-A and A allotypes; SEQ ID NOs:3 and 4, respectively), humIgG2 (SEQ ID NO:5), humIgG3 (SEQ ID NO:6) and humIgG4 (SEQ ID NO:7) with differences between the sequences marked with asterisks.

FIG. 25A shows binding of E27 monomers (solid circles), dimeric (solid squares), and hexameric (open squares) complexes to FcγRIIA-R131. FIG. 25B shows binding of E27 monomers (solid circles), dimeric (solid squares), and hexameric (open squares) complexes to FcγRIIIA-F158. Dimers were formed by mixing E27 IgG1 and a F(ab')$_2$ fragment of goat anti-human k light chain at 1:0.5 molar ratio at 25° C. for 1 hr (Huizinga et al. *J. Immunol.* 142: 2359-2364 (1989)). Hexameric complexes (i.e. trimeric in E27 IgG1) were formed by mixing E27 IgG1 with human IgE in a 1:1 molar ratio at 25° C. for 1 hr (Liu et al. *Biochem.* 34:10474-10482 (1995)).

FIG. 26A depicts IgG1 residues comprising the binding site for FcγRI and FcγRII. The two Fc heavy chains are in light and medium gray; carbohydrate is in dark gray. Residues that affected binding to all FcγR are in red; the FcγRI binding site is comprised only of red residues. Residues that showed improved binding to FcγRII and FcγRIIIA are in magenta. Residues that showed reduced binding only to FcγRII are in yellow. Residues that showed ≥50% improved binding only to FcγRII are in green. FIG. 26B depicts IgG1 residues comprising the binding site for FcγRI and FcγRIIIA. The two Fc heavy chains are in light and medium gray; carbohydrate is in dark gray. Residues that affected binding to all FcγR are in red; the FcγRI binding site is comprised only of red residues. Residues that showed improved binding to FcγRII and FcγRIIIA are in magenta. Residues that showed reduced binding only to FcγRIIIA are in yellow. Residues that showed ≥25% improved binding only to FcγRIIIA are in green. Glu430, involved in a salt-bridge with Lys338, is shown in blue.

FIG. 27A shows representative ADCC assay for IgG1 variants using NK cells from an FcγRIIIA-Val158/Val158 donor. Native anti-p$^{185}$HER2 IgG1 (solid circles), Ser298Ala (solid squares), Lys334Ala (solid triangles), Ser298Ala/Lys334Ala (open circles), Ser298Ala/Glu333Ala/Lys334Ala (open squares), AICC (open triangles). FIG. 27B shows representative ADCC assay for IgG1 variants using NK cells from an FcγRIIIA-Phe158/Phe158 donor. Native anti-p$^{185}$HER2 IgG1 (solid circles), Ser298Ala (solid squares), Lys334Ala (solid triangles), Ser298Ala/Lys334Ala (open circles), Ser298Ala/Glu333Ala/Lys334Ala (open squares), AICC (open triangles). FIG. 27C shows a bar plot of mean % increase in ADCC of variants compared to native anti-p$^{185}$HER2 IgG1. Percent increase was calculated as (% cytotoxicity$_{variant}$-% cytotoxicity$_{native\ IgG1}$)/% cytotoxicity$_{native\ IgG1}$. For each variant, the mean and standard deviation are for 13 data points using three different donors. For all variants the FcγRIIIA-Phe158/Phe158 donors showed a significant increase in ADCC over the increase seen for FcγRIIIA-Val158/Val158 donors (P<0.0001 for all variants using paired t-test).

DETAILED DESCRIPTION OF THE PREFERRED EMBODIMENTS

I. Definitions

Throughout the present specification and claims, the numbering of the residues in an immunoglobulin heavy chain is that of the EU index as in Kabat et al., *Sequences of Proteins of Immunological Interest,* 5th Ed. Public Health Service, National Institutes of Health, Bethesda, Md. (1991), expressly incorporated herein by reference. The "EU index as in Kabat" refers to the residue numbering of the human IgG1 EU antibody.

A "parent polypeptide" is a polypeptide comprising an amino acid sequence which lacks one or more of the Fc region modifications disclosed herein and which differs in effector function compared to a polypeptide variant as herein disclosed. The parent polypeptide may comprise a native sequence Fc region or an Fc region with pre-existing amino acid sequence modifications (such as additions, deletions and/or substitutions).

Figure 1:
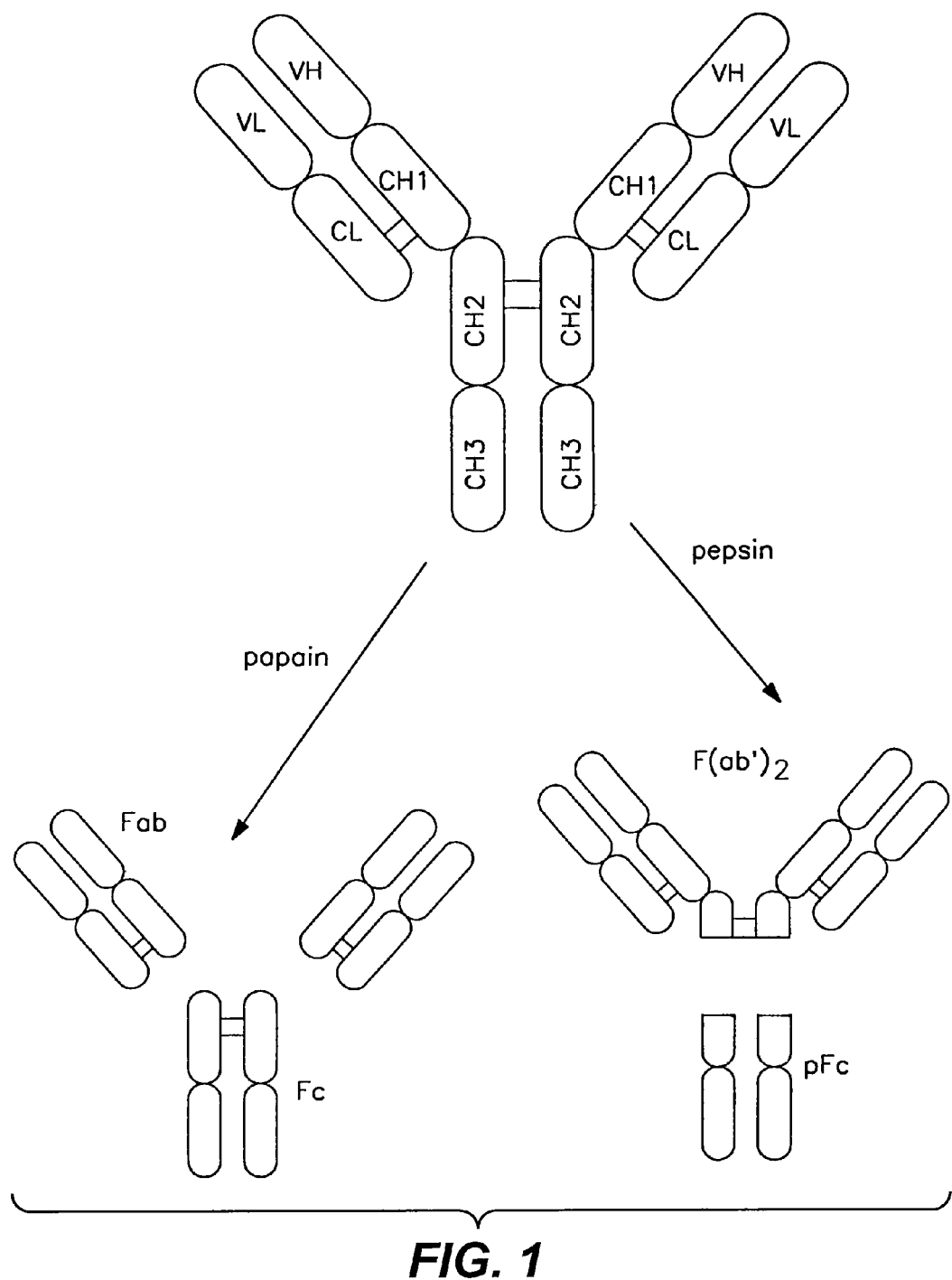
FIG. 1 is a schematic representation of a native IgG. Disulfide bonds are represented by heavy lines between CH1 and CL domains and the two CH2 domains. V is variable domain; C is constant domain; L stands for light chain and H stands for heavy chain.

The term "Fc region" is used to define a C-terminal region of an immunoglobulin heavy chain, e.g., as shown in FIG. 1. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The Fc region of an immunoglobulin generally comprises two constant domains, CH2 and CH3, as shown, for example, in FIG. 1.

The "CH2 domain" of a human IgG FC region (also referred to as "Cγ2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec. Immunol.* 22:161-206 (1985).

The "CH3 domain" comprises the stretch of residues C-terminal to a CH2 domain in an Fc region (i.e. from about amino acid residue 341 to about amino acid residue 447 of an IgG)

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays as herein disclosed, for example.

A "native sequence Fc region" comprises an amino acid sequence identical to the amino acid sequence of an Fc region found in nature. Native sequence human Fc regions are shown in FIG. 23 and include a native sequence human IgG1 Fc region (non-A and A allotypes); native sequence human IgG2 Fc region; native sequence human IgG3 Fc region; and native sequence human IgG4 Fc region as well as naturally occurring variants thereof. Native sequence murine Fc regions are shown in FIG. 22A.

A "variant Fc region" comprises an amino acid sequence which differs from that of a native sequence Fc region by virtue of at least one "amino acid modification" as herein defined. Preferably, the variant Fc region has at least one amino acid substitution compared to a native Sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at east about 95% homology therewith.

"Homology" is defined as the percentage of residues in the amino acid sequence variant that are identical after aligning the sequences and introducing gaps, if necessary, to achieve the maximum percent homology. Methods and computer programs for the alignment are well known in the art. One such computer program is "Align 2", authored by Genentech, Inc., which was filed with user documentation in the United States Copyright Office, Washington, D.C. 20559, on Dec. 10, 1991.

The term "Fc region-containing polypeptide" refers to a polypeptide, such as an antibody or immunoadhesin (see definitions below), which comprises an Fc region.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)). The term includes allotypes, such as FcγRIIIA allotypes: FcγRIIIA-Phe158, FcγRIIIA-Val158, FcγRIIA-R131 and/or FcγRIIA-H131.

Antibody-dependent cell-mediated cytotoxicity" and "ADCC" refer to a cell-mediated reaction in which nonspecific cytotoxic cells that express FcRs (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

A polypeptide variant with "altered" FcR binding affinity or ADCC activity is one which has either enhanced or diminished FcR binding activity and/or ADCC activity compared to a parent polypeptide or to a polypeptide comprising a native sequence Fc region. The polypeptide variant which "displays increased binding" to an FcR binds at least one FcR with better affinity than the parent polypeptide. The improvement in binding compared to a parent polypeptide may be about 25% or better improvement, e.g. up to about 200% or about 1000% improvement in binding. The polypeptide variant which "displays decreased binding" to an FcR, binds at least one FcR with worse affinity than a parent polypeptide. The decrease in binding compared to a parent polypeptide may be about 40% or more decrease in binding, e.g. down to a variant which possess little or no appreciable binding to the FcR. Such variants which display decreased binding to an FcR may possess little or no appreciable binding to an FcR, e.g., 0-20% binding to the FcR compared to a native sequence IgG Fc region, e.g. as determined in the Examples herein.

The polypeptide variant which binds an FcR with "better affinity" than a parent polypeptide, is one which binds any one or more of the above identified FcRs with substantially better binding affinity than the parent antibody, when the amounts of polypeptide variant and parent polypeptide in the binding assay are essentially the same. For example, the polypeptide variant with improved FcR binding affinity may display from about 1.15 fold to about 100 fold, e.g. from about 1.2 fold to about 50 fold improvement in FcR binding affinity compared to the parent polypeptide, where FcR binding affinity is determined, for example, as disclosed in the Examples herein.

The polypeptide variant which "mediates antibody-dependent cell-mediated cytotoxicity (ADCC) in the presence of human effector cells more effectively" than a parent antibody is one which in vitro or in vivo is substantially more effective at mediating ADCC, when the amounts of polypeptide variant and parent antibody used in the assay are essentially the same. Generally, such variants will be identified using the in vitro ADCC assay as herein disclosed, but other assays or methods for determining ADCC activity, e.g. in an animal model etc, are contemplated. The preferred variant is from about 1.5 fold to about 100 fold, e.g. from about two fold to about fifty fold, more effective at mediating ADCC than the parent, e.g. in the in vitro assay disclosed herein.

An "amino acid modification" refers to a change in the amino acid sequence of a predetermined amino acid sequence. Exemplary modifications include an amino acid substitution, insertion and/or deletion. The preferred amino acid modification herein is a substitution.

An "amino acid modification at" a specified position, e.g. of the Fc region, refers to the substitution or deletion of the specified residue, or the insertion of at least one amino acid residue adjacent the specified residue. By insertion "adjacent" a specified residue is meant insertion within one to two residues thereof. The insertion may be N-terminal or C-terminal to the specified residue.

An "amino acid substitution" refers to the replacement of at least one existing amino acid residue in a predetermined amino acid sequence with another different "replacement" amino acid residue. The replacement residue or residues may be "naturally occurring amino acid residues" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). Preferably, the replacement residue is not cysteine. Substitution with one or more non-naturally occurring amino acid residues is also encompassed by the definition of an amino acid substitution herein. A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. *Meth. Enzym.* 202:301-336 (1991). To generate such non-naturally occurring amino acid residues, the procedures of Noren et al. *Science* 244:182 (1989) and Ellman et al., supra, can be used. Briefly, these procedures involve chemically activating a suppressor tRNA with a non-naturally occurring amino acid residue followed by in vitro transcription and translation of the RNA.

An "amino acid insertion" refers to the incorporation of at least one amino acid into a predetermined amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as disclosed above.

An "amino acid deletion" refers to the removal of at least one amino acid residue from a predetermined amino acid sequence.

"Hinge region" is generally defined as stretching from Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e. residues 233 to 239 of the Fc region. Prior to the present invention, FcγR binding was generally attributed to amino acid residues in the lower hinge region of an IgG Fc region.

"C1q" is a polypeptide that includes a binding site for the Fc region of an immunoglobulin. C1q together with two serine proteases, C1r and C1s, forms the complex C1, the first component of the complement dependent cytotoxicity (CDC) pathway. Human C1q can be purchased commercially from, e.g. Quidel, San Diego, Calif.

The term "binding domain" refers to the region of a polypeptide that binds to another molecule. In the case of an FcR, the binding domain can comprise a portion of a polypeptide chain thereof (e.g. the a chain thereof) which is responsible for binding an Fc region. One useful binding domain is the extracellular domain of an FcR α chain.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

"Antibody fragments", as defined for the purpose of the present invention, comprise a portion of an intact antibody, generally including the antigen binding or variable region of the intact antibody or the Fc region of an antibody which retains FcR binding capability. Examples of antibody fragments include linear antibodies; single-chain antibody molecules; and multispecific antibodies formed from antibody fragments. The antibody fragments preferably retain at least part of the hinge and optionally the CH1 region of an IgG heavy chain. More preferably, the antibody fragments retain the entire constant region of an IgG heavy chain, and include an IgG light chain.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of immunological Interest*, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196: 901-917 (1987)). "Framework" or "FR" residues are those variable domain residues other than the hypervariable region residues as herein defined.

As used herein, the term "immunoadhesin" designates antibody-like molecules which combine the "binding domain" of a heterologous "adhesin" protein (e.g. a receptor, ligand or enzyme) with an immunoglobulin constant domain. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence.

The term "ligand binding domain" as used herein refers to any native cell-surface receptor or any region or derivative thereof retaining at least a qualitative ligand binding ability of a corresponding native receptor. In a specific embodiment, the receptor is from a cell-surface polypeptide having an extracellular domain that is homologous to a member of the immunoglobulin supergenefamily. Other receptors, which are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules, e.g. (E-, L- and P-) selectins.

The term "receptor binding domain" is used to designate any native ligand for a receptor, including cell adhesion molecules, or any region or derivative of such native ligand retaining at least a qualitative receptor binding ability of a corresponding native ligand. This definition, among others, specifically includes binding sequences from ligands for the above-mentioned receptors.

An "antibody-immunoadhesin chimera" comprises a molecule that combines at least one binding domain of an antibody (as herein defined) with at least one immunoadhesin (as defined in this application). Exemplary antibody-immunoadhesin chimeras are the bispecific CD4-IgG chimeras described in Berg et al., *PNAS (USA)* 88:4723-4727 (1991) and Chamow et al., *J. Immunol.* 153:4268 (1994).

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

"Treatment" refers to both therapeutic treatment and prophylactic or preventative measures. Those in need of treatment include those already with the disorder as well as those in which the disorder is to be prevented.

A "disorder" is any condition that would benefit from treatment with the polypeptide variant. This includes chronic and acute disorders or diseases including those pathological conditions which predispose the mammal to the disorder in question. In one embodiment, the disorder is cancer.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

A "HER2-expressing cancer" is one comprising cells which have HER2 receptor protein (Semba et al., *PNAS* (*USA*) 82:6497-6501 (1985) and Yamamoto et al. *Nature* 319:230-234 (1986) (Genebank accession number X03363)) present at their cell surface, such that an anti-HER2 antibody is able to bind to the cancer.

The word "label" when used herein refers to a detectable compound or composition which is conjugated directly or indirectly to the polypeptide. The label may be itself be detectable (e.g., radioisotope labels or fluorescent labels) or, in the case of an enzymatic label, may catalyze chemical alteration of a substrate compound or composition which is detectable.

An "isolated" nucleic acid molecule is a nucleic acid molecule that is identified and separated from at least one contaminant nucleic acid molecule with which it is ordinarily associated in the natural source of the polypeptide nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the polypeptide where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "molecular complex" when used herein refers to the relatively stable structure which forms when two or more heterologous molecules (e.g. polypeptides) bind (preferably noncovalently) to one another. The preferred molecular complex herein is an immune complex.

"Immune complex" refers to the relatively stable structure which forms when at least one target molecule and at least one heterologous Fc region-containing polypeptide bind to one another forming a larger molecular weight complex. Examples of immune complexes are antigen-antibody aggregates and target molecule-immunoadhesin aggregates. The term "immune complex" as used herein, unless indicated otherwise, refers to an ex vivo complex (i.e. other than the form or setting in which it may be found in nature). However, the immune complex may be administered to a mammal, e.g. to evaluate clearance of the immune complex in the mammal.

The term "target molecule" refers to a molecule, usually a polypeptide, which is capable of being bound by a heterologous molecule and has one or more binding sites for the heterologous molecule. The term "binding site" refers to a region of a molecule to which another molecule can bind. The "first target molecule" herein comprises at least two distinct binding sites (for example, two to five separate binding sites) for an analyte (e.g. an Fc region-containing polypeptide) such that at least two analyte molecules can bind to the first target molecule. In the preferred embodiment of the invention, the two or more binding sites are identical (e.g. having the same amino acid sequence, where the target molecule is a polypeptide). In Example 1 below, the first target molecule was IgE and had two separate binding sites in the Fc region thereof to which the Fc region-containing polypeptide (an anti-IgE antibody, E27) could bind. Other first target molecules include dimers of substantially identical monomers (e.g. neurotrophins, IL8 and VEGF) or are polypeptides comprising two or more substantially identical polypeptide chains (e.g. antibodies or immunoadhesins). The "second target molecule" comprises at least two distinct binding sites (for example, two to five separate binding sites) for the first target molecule such that at least two first target molecules can bind to the second target molecule. Preferably, the two or more binding sites are identical (e.g. having the same amino acid sequence, where the target molecule is a polypeptide). In Example 2, the second target molecule was VEGF, which has a pair of distinct binding sites to which the variable domain of the IgE antibody could bind. Other second target molecules are contemplated, e.g. other dimers of substantially identical monomers (e.g. neurotrophins or IL8) or polypeptides comprising two or more substantially identical domains (e.g. antibodies or immunoadhesins).

An "analyte" is a substance that is to be analyzed. The preferred analyte is an Fc region-containing polypeptide that is to be analyzed for its ability to bind to an Fc receptor.

A "receptor" is a polypeptide capable of binding at least one ligand. The preferred receptor is a cell-surface receptor having an extracellular ligand-binding domain and, optionally, other domains (e.g. transmembrane domain, intracellular domain and/or membrane anchor). The receptor to be evaluated in the assay described herein may be an intact receptor or a fragment or derivative thereof (e.g. a fusion protein comprising the binding domain of the receptor fused to one or more heterologous polypeptides). Moreover, the receptor to be evaluated for its binding properties may be present in a cell or isolated and optionally coated on an assay plate or some other solid phase.

The phrase "low affinity receptor" denotes a receptor that has a weak binding affinity for a ligand of interest, e.g. having a binding constant of about 50 nM or worse affinity. Exemplary low affinity receptors include FcγRII and FcγRIII.

II. Modes for Carrying Out the Invention

The invention herein relates to a method for making a polypeptide variant. The "parent", "starting" or "nonvariant"

polypeptide is prepared using techniques available in the art for generating polypeptides comprising an Fc region. In the preferred embodiment of the invention, the parent polypeptide is an antibody and exemplary methods for generating antibodies are described in more detail in the following sections. The parent polypeptide may, however, be any other polypeptide comprising an Fc region, e.g. an immunoadhesin. Methods for making immunoadhesins are elaborated in more detail hereinbelow.

In an alternative embodiment, a variant Fc region may be generated according to the methods herein disclosed and this "variant Fc region" can be fused to a heterologous polypeptide of choice, such as an antibody variable domain or binding domain of a receptor or ligand.

The parent polypeptide comprises an Fc region. Generally the Fc region of the parent polypeptide will comprise a native sequence Fc region, and preferably a human native sequence Fc region. However, the Fc region of the parent polypeptide may have one or more pre-existing amino acid sequence alterations or modifications from a native sequence Fc region. For example, the C1q binding activity of the Fc region may have been previously altered (other types of Fc region modifications are described in more detail below). In a further embodiment the parent polypeptide Fc region is "conceptual" and, while it does not physically exist, the antibody engineer may decide upon a desired variant Fc region amino acid sequence and generate a polypeptide comprising that sequence or a DNA encoding the desired variant Fc region amino acid sequence.

In the preferred embodiment of the invention, however, a nucleic acid encoding an Fc region of a parent polypeptide is available and this nucleic acid sequence is altered to generate a variant nucleic acid sequence encoding the Fc region variant.

DNA encoding an amino acid sequence variant of the starting polypeptide is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide Site-directed mutagenesis is a preferred method for preparing substitution variants. This technique is well known in the art (see, e.g., Carter et al. *Nucleic Acids Res.* 13:4431-4443 (1985) and Kunkel et al., *Proc. Natl. Acad. Sci. USA* 82:488 (1987)). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the starting polypeptide. See Higuchi, in *PCR Protocols*, pp. 177-183 (Academic Press, 1990); and Vallette et al., *Nuc. Acids Res.* 17:723-733 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., *Gene* 34:315-323 (1985). The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding a polypeptide variant can be determined, and a nucleic acid sequence encoding such amino acid sequence variant can be generated synthetically.

The amino acid sequence of the parent polypeptide is modified in order to generate a variant Fc region with altered Fc receptor binding affinity or activity in vitro and/or in vivo and/or altered antibody-dependent cell-mediated cytotoxicity (ADCC) activity in vitro and/or in vivo.

Generally, the modification entails one or more amino acid substitutions. In one embodiment, the replacement residue does not correspond to a residue present in the same position in any of the native sequence Fc regions in FIG. 22A. For example, according to this embodiment of the invention, Pro331 of a human IgG3 or IgG1 Fc region is replaced with a residue other than Ser (the corresponding aligned residue found in native sequence human IgG4). In one embodiment, the residue in the parent polypeptide which is substituted with a replacement residue is not an alanine and/or is not residue Ala339 of an Fc region. In the case of an amino acid substitution, preferably the residue in the parent polypeptide is replaced with an alanine residue. However, the present invention contemplates replacement of the residue of the parent polypeptide with any other amino acid residue. The substitution may, for example, be a "conservative substitution". Such conservative substitutions are shown in Table 1 under the heading of "preferred substitution". More substantial changes may be achieved by making one or more "exemplary substitutions" which are not the preferred substitution in Table 1.

TABLE 1

| Original Residue | Exemplary Substitutions | Preferred Substitution |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |

TABLE 1-continued

| Original Residue | Exemplary Substitutions | Preferred Substitution |
|---|---|---|
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the Fc region may be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for a member of another class. Conservative and non-conservative amino acid substitutions are exemplified in Table 7 hereinbelow.

As is demonstrated in Example 4 herein, one can engineer an Fc region variant with altered binding affinity for one or more FcRs. As was shown in that Example, different classes of Fc region variants can be made e.g., as summarized in the following table. Where the variant Fc region has more than one amino acid substitution, generally, but not necessarily, amino acid substitutions in the same class are combined to achieve the desired result.

TABLE 2

CLASSES OF Fc REGION VARIANTS

| Class | FcR binding property | Position of Fc region substitution(s) |
|---|---|---|
| 1 | reduced binding to all FcγR | 233-236#, 238, 265#, 297#*, 327 Gln, 329 |
| 2 | reduced binding to both FcγRII and FcγRIII | 270, 295, 327Ser |
| 3 | improved binding to both FcγRII and FcγRIII | 256, 290 |
| 4 | improved binding to FcγRII and no effect on FcγRIII binding | 255, 258, 267, 272, 276, 280, 285, 286, 307, 309, 315, 326, 331, 337, 378, 430 |
| 5 | improved binding to FcγRII and reduced binding to FcγRIII | 268, 301, 322 |
| 6 | reduced binding to FcγRII and no effect on FcγyRIII binding | 292, 414 |
| 7 | reduced binding to FcγRII and improved binding to FcγRIII | 298 |
| 8 | no effect on FcγRII binding and reduced binding to FcγRIII | 239, 269, 293, 296, 303, 327Gly, 338, 376 |
| 9 | no effect on FcγRII binding and improved binding to FcγRIII | 333, 334, 339# |
| 10 | effect only FcRn | 253, 254, 288, 305, 311, 312, 317, 360, 362, 380, 382, 415, 424, 433, 434, 435, 436 |

*deglycosylated version
Preferably combined with other Fc modification(s), (e.g. as disclosed herein)

Aside from amino acid substitutions, the present invention contemplates other modifications of the parent Fc region amino acid sequence in order to generate an Fc region variant with altered effector function.

One may, for example, delete one or more amino acid residues of the Fc region in order to reduce binding to an FcR. Generally, one will delete one or more of the Fc region residues identified herein as effecting FcR binding (see Example 4 below) in order to generate such an Fc region variant. Generally, no more than one to about ten Fc region residues will be deleted according to this embodiment of the invention. The Fc region herein comprising one or more amino acid deletions will preferably retain at least about 80%, and preferably at least about 90%, and most preferably at least about 95%, of the parent Fc region or of a native sequence human Fc region.

One may also make amino acid insertion Fc region variants, which variants have altered effector function. For example, one may introduce at least one amino acid residue (e.g. one to two amino acid residues and generally no more than ten residues) adjacent to one or more of the Fc region positions identified herein as impacting FcR binding. By "adjacent" is meant within one to two amino acid residues of a Fc region residue identified herein. Such Fc region variants may display enhanced or diminished FcR binding and/or ADCC activity. In order to generate such insertion variants, one may evaluate a co-crystal structure of a polypeptide comprising a binding region of an FcR (e.g. the extracellular domain of the FcR of interest) and the Fc region into which the amino acid residue(s) are to be inserted (see, for example, Deisenhofer, *Biochemistry* 20(9):2361-2370 (1981); and Burmeister et al., *Nature* 372:379-383, (1994)) in order to rationally design an Fc region variant with, e.g., improved FcR binding ability. Such insertion(s) will generally be made in an Fc region loop, but not in the secondary structure (i.e. in a β-strand) of the Fc region.

By introducing the appropriate amino acid sequence modifications in a parent Fc region, one can generate a variant Fc region which (a) mediates antibody-dependent cell-mediated cytotoxicity (ADCC) in the presence of human effector cells more effectively and/or (b) binds an Fc gamma receptor (FcγR) with better affinity than the parent polypeptide. Such Fc region variants will generally comprise at least one amino acid modification in the Fc region. Combining amino acid modifications is thought to be particularly desirable. For example, the variant Fc region may include two, three, four, five, etc substitutions therein, e.g. of the specific Fc region positions identified herein.

Preferably, the parent polypeptide Fc region is a human Fc region, e.g. a native sequence human Fc region human IgG1 (A and non-A allotypes), IgG2, IgG3 or IgG4 Fc region. Such sequences are shown in FIG. 23.

To generate an Fc region with improved ADCC activity, the parent polypeptide preferably has pre-existing ADCC activity, e.g., it comprises a human IgG1 or human IgG3 Fc region. In one embodiment, the variant with improved ADCC mediates ADCC substantially more effectively than an antibody with a native sequence IgG1 or IgG3 Fc region and the antigen-binding region of the variant. Preferably, the variant comprises, or consists essentially of, substitutions of two or three or all of the residues at positions 298, 333, 334 and 339 of the Fc region. Most preferably, residues at positions 298, 333, 334 and 339 are substituted, (e.g. with alanine residues). At position 298, the preferred replacement residue is an ala or gly, and most preferably ala. The preferred replacement residue at position 333 is ala or asp, and most preferably ala. The residue at position 334 is preferably replaced by one of the following amino acids: ala, gln, glu, met, tyr, his, val, leu, asn, ser, trp, with ala or glu being the most preferred replacement residues at this position. The preferred replacement residue at position 339 is a thr. Moreover, in order to generate the Fc region variant with improved ADCC activity, one will generally engineer an Fc region variant with improved binding affinity for FcγRIII, which is thought to be an important FcR for mediating ADCC. For example, one may introduce an amino acid modification (e.g. a substitution) into the parent Fc region at any one or more of amino acid positions 256, 290, 298, 312, 326, 330, 333, 334, 360, 378 or 430 to generate such a variant. The variant with improved binding affinity for FcγRIII may further have reduced binding affinity for FcγRII, especially reduced affinity for the inhibiting FcγRIIB receptor.

The amino acid modification(s) are preferably introduced into the CH2 domain of a Fc region, since the experiments herein indicate that the CH2 domain is important for FcR binding activity. Moreover, unlike the teachings of the above-cited art, the instant application contemplates the introduction of a modification into a part of the Fc region other than in the lower hinge region thereof.

Useful amino acid positions for modification in order to generate a variant IgG Fc region with altered Fc gamma receptor (FcγR) binding affinity or activity include any one or more of amino acid positions 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439 of the Fc region. Preferably, the parent Fc region used as the template to generate such variants comprises a human IgG Fc region. Where residue 331 is substituted, the parent Fc region is preferably not human native sequence IgG3, or the variant Fc region comprising a substitution at position 331 preferably displays increased FcR binding, e.g. to FcγRII.

To generate an Fc region variant with reduced binding to the FcγR one may introduce an amino acid modification at any one or more of amino acid positions 238, 239, 248, 249, 252, 254, 265, 268, 269, 270, 272, 278, 289, 292, 293, 294, 295, 296, 298, 301, 303, 322, 324, 327, 329, 333, 335, 338, 340, 373, 376, 382, 388, 389, 414, 416, 419, 434, 435, 437, 438 or 439 of the Fc region.

Variants which display reduced binding to FcγRI, include those comprising an Fc region amino acid modification at any one or more of amino acid positions 238, 265, 269, 270, 327 or 329.

Variants which display reduced binding to FcγRII include those comprising an Fc region amino acid modification at any one or more of amino acid positions 238, 265, 269, 270, 292, 294, 295, 298, 303, 324, 327, 329, 333, 335, 338, 373, 376, 414, 416, 419, 435, 438 or 439.

Fc region variants which display reduced binding to FcγRIII include those comprising an Fc region amino acid modification at any one or more of amino acid positions 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437.

Variants with improved binding to one or more FcγRs may also be made. Such Fc region variants may comprise an amino acid modification at any one or more of amino acid positions 255, 256, 258, 267, 268, 272, 276, 280, 283, 285, 286, 290, 298, 301, 305, 307, 309, 312, 315, 320, 322, 326, 330, 331, 333; 334, 337, 340, 360, 378, 398 or 430 of the Fc region.

For example, the variant with improved FcγR binding activity may display increased binding to FcγRIII, and optionally may further display decreased binding to FcγRII; e.g. the variant may comprise an amino acid modification at position 298 and/or 333 of an Fc region.

Variants with increased binding to FcγRII include those comprising an amino acid modification at any one or more of amino acid positions 255, 256, 258, 267, 268, 272, 276, 280, 283, 285, 286, 290, 301, 305, 307, 309, 312, 315, 320, 322, 326, 330, 331, 337, 340, 378, 398 or 430 of an Fc region. Such variants may further display decreased binding to FcγRIII. For example, they may include an Fc region amino acid modification at any one or more of amino acid positions 268, 272, 298, 301, 322 or 340.

While it is preferred to alter binding to a FcγR, Fc region variants with altered binding affinity for the neonatal receptor (FcRn) are also contemplated herein. Fc region variants with improved affinity for FcRn are anticipated to have longer serum half-lives, and such molecules will have useful applications in methods of treating mammals where long half-life of the administered polypeptide is desired, e.g., to treat a chronic disease or disorder. Fc region variants with decreased FcRn binding affinity, on the contrary, are expected to have shorter half-lives, and such molecules may, for example, be administered to a mammal where a shortened circulation time may be advantageous, e.g. for in vivo diagnostic imaging or for polypeptides which have toxic side effects when left circulating in the blood stream for extended periods, etc. Fc region variants with decreased FcRn binding affinity are anticipated to be less likely to cross the placenta, and thus may be utilized in the treatment of diseases or disorders in pregnant women.

Fc region variants with altered binding affinity for FcRn include those comprising an Fc region amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439 or 447. Those which display reduced binding to FcRn will generally comprise an Fc region amino acid modification at any one or more of amino acid positions 252, 253, 254, 255, 288, 309, 386, 388, 400, 415, 433, 435, 436, 439, or 447; and those with increased binding to FcRn will usually comprise an Fc region amino acid modification at any one or more of amino acid positions 238, 256, 265, 272, 286, 303, 305, 307, 311, 312, 317, 340, 356, 360, 362, 376, 378, 380, 382, 413, 424 or 434.

The polypeptide variant(s) prepared as described above may be subjected to further modifications, oftentimes depending on the intended use of the polypeptide. Such modifications may involve further alteration of the amino acid sequence (substitution, insertion and/or deletion of amino acid residues), fusion to heterologous polypeptide(s) and/or covalent modifications. Such "further modifications" may be made prior to, simultaneously with, or following, the amino acid modification(s) disclosed above which result in an alteration of Fc receptor binding and/or ADCC activity. In one embodiment, one may combine the Fc region modification herein with Fc region substitutions disclosed in the references cited in the "Related Art" section of this application.

Alternatively or additionally, it may be useful to combine the above amino acid modifications with one or more further amino acid modifications that alter FcRn binding and/or half-life of the antibody and/or C1q binding and/or complement dependent cytotoxicity function of the Fc region.

The starting polypeptide of particular interest herein is usually one that binds to C1q and displays complement dependent cytotoxicity (CDC). The further amino acid substitutions described herein will generally serve to alter the ability of the starting polypeptide to bind to C1q and/or modify its complement dependent cytotoxicity function, e.g. to reduce and preferably abolish these effector functions. However, polypeptides comprising substitutions at one or more of the described positions with improved C1q binding and/or complement dependent cytotoxicity (CDC) function are contemplated herein. For example, the starting polypeptide may be unable to bind C1q and/or mediate CDC and may be modified according to the teachings herein such that it acquires these further effector functions. Moreover, polypeptides with pre-existing C1q binding activity, optionally further having the ability to mediate CDC may be modified such that one or both of these activities are enhanced.

To generate an Fc region with altered C1q binding and/or complement dependent cytotoxicity (CDC) function, the amino acid positions to be modified are generally selected from heavy chain positions 270, 322, 326, 327, 329, 331, 333, and 334, where the numbering of the residues in an IgG heavy chain is that of the EU index as in Kabat et al., *Sequences of Proteins of Immunological Interest,* 5th Ed. Public Health Service, National Institutes of Health, Bethesda, Md. (1991). In one embodiment, only one of the eight above-identified positions is altered in order to generate the polypeptide variant region with altered C1q binding and/or complement dependent cytotoxicity (CDC) function. Preferably only residue 270, 329 or 322 is altered if this is the case. Alternatively, two or more of the above-identified positions are modified. If substitutions are to be combined, generally substitutions which enhance human C1q binding (e.g. at residue positions 326, 327, 333 and 334) or those which diminish human C1q binding (e.g., at residue positions 270, 322, 329 and 331) are combined. In the latter embodiment, all four positions (i.e., 270, 322, 329 and 331) may be substituted. Preferably, further substitutions at two, three or all of positions 326, 327, 333 or 334 are combined, optionally with other Fc region substitutions, to generate a polypeptide with improved human C1q binding and preferably improved CDC activity in vitro or in vivo.

Proline is conserved at position 329 in human IgG's. This residue is preferably replaced with alanine, however substitution with any other amino acid is contemplated, e.g., serine, threonine, asparagine, glycine or valine.

Proline is conserved at position 331 in human IgG1, IgG2 and IgG3, but not IgG4 (which has a serine residue at position 331). Residue 331 is preferably replaced by alanine or another amino acid, e.g. serine (for IgG regions other than IgG4), glycine or valine.

Lysine 322 is conserved in human IgGs, and this residue is preferably replaced by an alanine residue, but substitution with any other amino acid residue is contemplated, e.g. serine, threonine, glycine or valine.

D270 is conserved in human IgGs, and this residue may be replaced by another amino acid residue, e.g. alanine, serine, threonine, glycine, valine, or lysine.

K326 is also conserved in human IgGs. This residue may be substituted with another residue including, but not limited to, valine, glutamic acid, alanine, glycine, aspartic acid, methionine or tryptophan, with tryptophan being preferred.

Likewise, E333 is also conserved in human IgGs. E333 is preferably replaced by an amino acid residue with a smaller side chain volume, such as valine, glycine, alanine or serine, with serine being preferred.

K334 is conserved in human IgGs and may be substituted with another residue such as alanine or other residue.

In human IgG1 and IgG3, residue 327 is an alanine. In order to generate a variant with improved C1q binding, this alanine may be substituted with another residue such as glycine. In IgG2 and IgG4, residue 327 is a glycine and this may be replaced by alanine (or another residue) to diminish C1q binding.

As disclosed above, one can design an Fc region with altered effector function, e.g., by modifying C1q binding and/or FcR binding and thereby changing CDC activity and/or ADCC activity. For example, one can generate a variant Fc region with improved C1q binding and improved FcγRIII binding; e.g. having both improved ADCC activity and improved CDC activity. Alternatively, where one desires that effector function be reduced or ablated, one may engineer a variant Fc region with reduced CDC activity and/or reduced ADCC activity. In other embodiments, one may increase only one of these activities, and optionally also reduce the other activity, e.g. to generate an Fc region variant with improved ADCC activity, but reduced CDC activity and vice versa.

With respect to further amino acid sequence alterations, any cysteine residue not involved in maintaining the proper conformation of the polypeptide variant also may be substituted, generally with serine, to improve the oxidative stability of the molecule and prevent aberrant cross linking.

Another type of amino acid substitution serves to alter the glycosylation pattern of the polypeptide. This may be achieved by deleting one or more carbohydrate moieties found in the polypeptide, and/or adding one or more glycosylation sites that are not present in the polypeptide. Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original polypeptide (for O-linked glycosylation sites). An exemplary glycosylation variant has an amino acid substitution of residue Asn 297 of the heavy chain.

Moreover, the class, subclass or allotype of the Fc region may be altered by one or more further amino acid substitutions to generate an Fc region with an amino acid sequence more homologous to a different class, subclass or allotype as desired. For example, a murine Fc region may be altered to generate an amino acid sequence more homologous to a human Fc region; a human non-A allotype IgG1 Fc region may be modified to achieve a human A allotype IgG1 Fc region etc. In one embodiment, the amino modification(s) herein which alter FcR binding and/or ADCC activity are made in the CH2 domain of the Fc region and the CH3 domain is deleted or replaced with another dimerization domain. Preferably, however, the CH3 domain is retained (aside from amino acid modifications therein which alter effector function as herein disclosed).

The polypeptide variant may be subjected to one or more assays to evaluate any change in biological activity compared to the starting polypeptide.

Preferably the polypeptide variant essentially retains the ability to bind antigen compared to the nonvariant polypeptide, i.e. the binding capability is no worse than about 20 fold, e.g. no worse than about 5 fold of that of the nonvariant polypeptide. The binding capability of the polypeptide variant may be determined using techniques such as fluorescence activated cell sorting (FACS) analysis or radioimmunoprecipitation (RIA), for example.

The ability of the polypeptide variant to bind an FcR may be evaluated. Where the FcR is a high affinity Fc receptor, such as FcγRI, FcRn or FcγRIIIA-V158, binding can be measured by titrating monomeric polypeptide variant and measuring bound polypeptide variant using an antibody which specifically binds to the polypeptide variant in a standard ELISA format (see Example 2 below). Another FcR binding assay for low affinity FcRs is described in Examples 1 and 4.

To assess ADCC activity of the polypeptide variant, an in vitro ADCC assay, such as that described in Example 4 may be performed using varying effector:target ratios. Useful "effector cells" for such assays include peripheral blood mononuclear cells (PBMC) and Natural Killer (NK) cells. Alternatively, or additionally, ADCC activity of the polypeptide variant may be assessed in vivo, e.g., in a animal model such as that disclosed in Clynes et al. *PNAS (USA)* 95:652-656 (1998).

The ability of the variant to bind C1q and mediate complement dependent cytotoxicity (CDC) may be assessed.

To determine C1q binding, a C1q binding ELISA may be performed. Briefly, assay plates may be coated overnight at 4° C. with polypeptide variant or starting polypeptide (control) in coating buffer. The plates may then be washed and blocked. Following washing, an aliquot of human C1q may be added to each well and incubated for 2 hrs at room temperature. Following a further wash, 100 µl of a sheep anti-complement C1q peroxidase conjugated antibody may be added to each well and incubated for 1 hour at room temperature. The plate may again be washed with wash buffer and 100 µl of substrate buffer containing OPD (O-phenylenediamine dihydrochloride (Sigma)) may be added to each well. The oxidation reaction, observed by the appearance of a yellow color, may be allowed to proceed for 30 minutes and stopped by the addition of 100 µl of 4.5 N $H_2SO_4$. The absorbance may then read at (492-405) nm.

An exemplary polypeptide variant is one that displays a "significant reduction in C1q binding" in this assay. This means that about 100 µg/ml of the polypeptide variant displays about 50 fold or more reduction in C1q binding compared to 100 µg/ml of a control antibody having a nonmutated IgG1 Fc region. In the most preferred embodiment, the polypeptide variant "does not bind C1q", i.e. 100 µg/ml of the polypeptide variant displays about 100 fold or more reduction in C1q binding compared to 100 µg/ml of the control antibody.

Another exemplary variant is one which "has a better binding affinity for human C1q than the parent polypeptide". Such a molecule may display, for example, about two-fold or more, and preferably about five-fold or more, improvement in human C1q binding compared to the parent polypeptide (e.g. at the $IC_{50}$ values for these two molecules). For example, human C1q binding may be about two-fold to about 500-fold, and preferably from about two-fold or from about five-fold to about 1000-fold improved compared to the parent polypeptide.

To assess complement activation, a complement dependent cytotoxicity (CDC) assay may be performed, e.g. as described in Gazzano-Santoro et al., *J. Immunol. Methods* 202:163 (1996). Briefly, various concentrations of the polypeptide variant and human complement may be diluted with buffer. Cells which express the antigen to which the polypeptide variant binds may be diluted to a density of ~1×10⁶ cells/ml. Mixtures of polypeptide variant, diluted human, complement and cells expressing the antigen may be added to a flat bottom tissue culture 96 well plate and allowed to incubate for 2 hrs at 37° C. and 5% $CO_2$ to facilitate complement mediated cell lysis. 50 µl of alamar blue (Accumed International) may then be added to each well and incubated overnight at 37° C. The absorbance is measured using a 96-well fluorometer with excitation at 530 nm and emission at 590 nm. The results may be expressed in relative fluorescence units (RFU). The sample concentrations may be computed from a standard curve and the percent activity as compared to nonvariant polypeptide is reported for the polypeptide variant of interest.

Yet another exemplary variant "does not activate complement". For example, 0.6 µg/ml of the polypeptide variant displays about 0-10% CDC activity in this assay compared to a 0.6 µg/ml of a control antibody having a nonmutated IgG1 Fc region. Preferably the variant does not appear to have any CDC activity in the above CDC assay.

The invention also pertains to a polypeptide variant with enhanced CDC compared to a parent polypeptide, e.g., displaying about two-fold to about 100-fold improvement in CDC activity in vitro or in vivo (e.g. at the $IC_{50}$ values for each molecule being compared).

A. Receptor Binding Assay and Immune Complex

A receptor binding assay has been developed herein which is particularly useful for determining binding of an analyte of interest to a receptor where the affinity of the analyte for the receptor is relatively weak, e.g. in the micromolar range as is the case for FcγRIIA, FcγRIIB, FcγRIIIA and FcγRIIIB. The method involves the formation of a molecular complex that has an improved avidity for the receptor of interest compared to the noncomplexed analyte. The preferred molecular complex is an immune complex comprising: (a) an Fc region-containing polypeptide (such as an antibody or an immunoadhesin); (b) a first target molecule which comprises at least two binding sites for the Fc region-containing polypeptide; and (c) a second target molecule which comprises at least two binding sites for the first target molecule.

Figure 5:
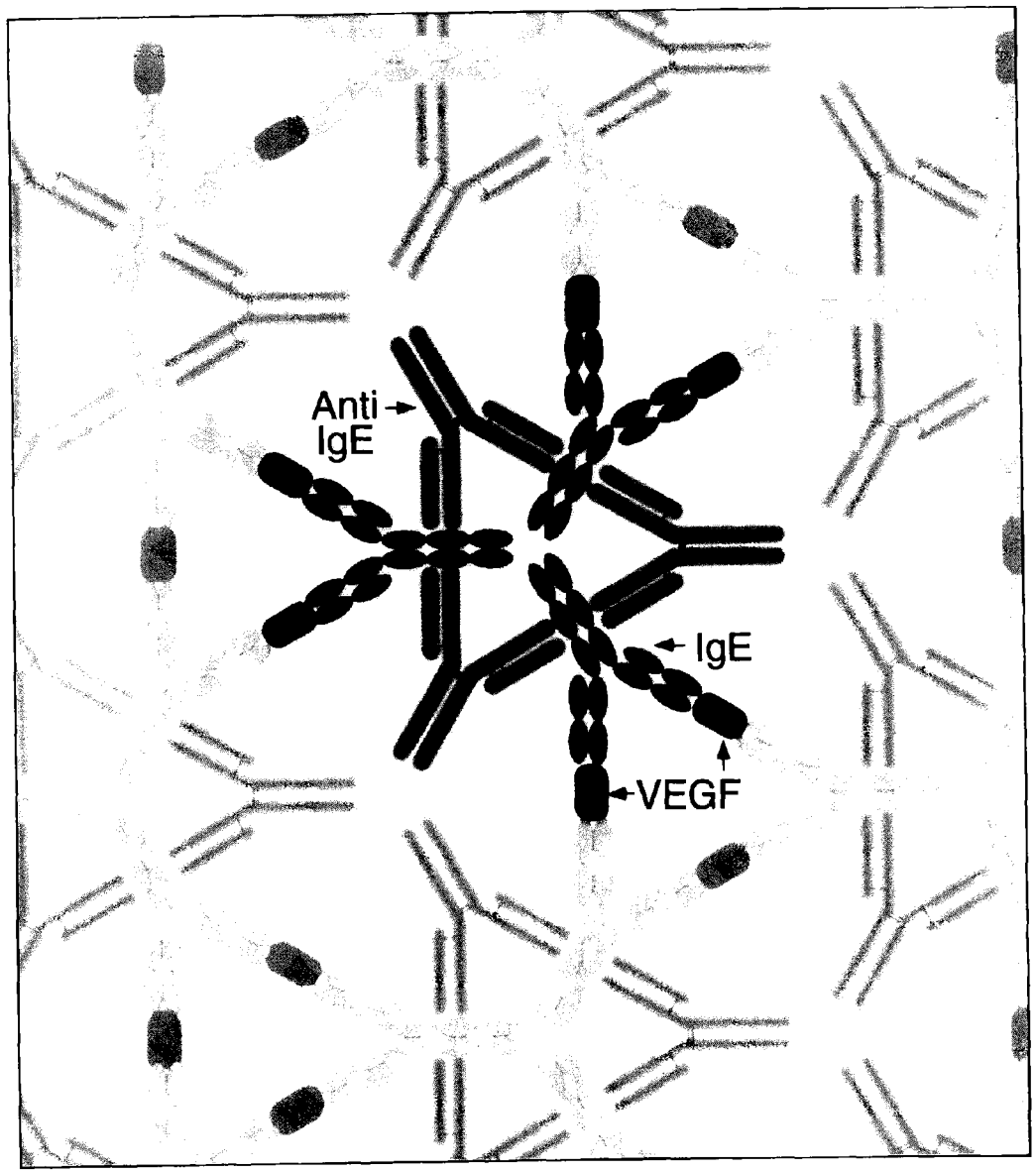
FIG. 5 is a schematic diagram of the "immune complex" prepared for use in the FcR assay described in Example 1. The hexamer comprising three anti-IgE antibody molecules (the "Fc region-containing polypeptide") and three IgE molecules (the "first target molecule") is shown. IgE has two "binding sites" for the anti-IgE antibody (E27) in the Fc region thereof. Each IgE molecule in the complex is further able to bind two VEGF molecules ("the second target polypeptide"). VEGF has two "binding sites" for IgE.

In Example 1 below, the Fc region-containing polypeptide is an anti-IgE antibody, such as the E27 antibody (FIGS. 4A-4B). E27, when mixed with human IgE at an 1:1 molar ratio, forms a stable hexamer consisting of three E27 molecules and three IgE molecules. In Example 1 below, the "first target molecule" is a chimeric form of IgE in which the Fab portion of an anti-VEGF antibody is fused to the human IgE Fc portion and the "second target molecule" is the antigen to which the Fab binds (i.e. VEGF). Each molecule of IgE binds two molecules of VEGF. VEGF also binds two molecules of IgE per molecule of VEGF. When recombinant human VEGF was added at a 2:1 molar ratio to IgE:E27 hexamers, the hexamers were linked into larger molecular weight complexes via the IgE:VEGF interaction (FIG. 5). The Fc region of the anti-IgE antibody of the resultant immune complex binds to FcR with higher avidity than either uncomplexed anti-IgE or anti-IgE:IgE hexamers.

Other forms of molecular complexes for use in the receptor assay are contemplated. Examples comprising only an Fc region-containing polypeptide:first target molecule combination include an immunoadhesin:ligand combination such as VEGF receptor (KDR)-immunoadhesin:VEGF and a full-length bispecific antibody (bsAb):first target molecule. A further example of an Fc region-containing polypeptide:first target molecule:second target molecule combination include a nonblocking antibody:soluble receptor:ligand combination such as anti-Trk antibody:soluble Trk receptor:neurotrophin (Urfer et al. *J. Biol. Chem.* 273(10):5829-5840 (1998)).

Aside from use in a receptor binding assay, the immune complexes described above have further uses including evaluation of Fc region-containing polypeptide function and immune complex clearance in vivo. Hence, the immune complex may be administered to a mammal (e.g. in a pre-clinical animal study) and evaluated for its half-life etc.

To determine receptor binding, a polypeptide comprising at least the binding domain of the receptor of interest (e.g. the extracellular domain of an α subunit of an FcR) may be coated on solid phase, such as an assay plate. The binding domain of the receptor alone or a receptor-fusion protein may be coated on the plate using standard procedures. Examples of receptor-fusion proteins include receptor-glutathione S-transferase (GST) fusion protein, receptor-chitin binding domain fusion protein, receptor-hexaHis tag fusion protein (coated on glutathione, chitin, and nickel coated plates, respectively). Alternatively, a capture molecule may be coated on the assay plate and used to bind the receptor-fusion protein via the non-receptor portion of the fusion protein. Examples include anti-hexaHis F(ab')$_2$ coated on the assay plate used to capture receptor-hexaHis tail fusion or anti-GST antibody coated on the assay plate used to capture a receptor-GST fusion. In other embodiments, binding to cells expressing at least the binding domain of the receptor may be evaluated. The cells may be naturally occurring hematopoietic cells that express the FcR of interest or may be transformed with nucleic acid encoding the FcR or a binding domain thereof such that the binding domain is expressed at the surface of the cell to be tested.

The immune complex described hereinabove is added to the receptor-coated plates and incubated for a sufficient period of time such that the analyte binds to the receptor. Plates may then be washed to remove unbound complexes, and binding of the analyte may be detected according to known methods. For example, binding may be detected using a reagent (e.g. an antibody or fragment thereof) which binds specifically to the analyte, and which is optionally conjugated with a detectable label (detectable labels and methods for conjugating them to polypeptides are described below in the section entitled "Non-Therapeutic Uses for the Polypeptide Variant").

As a matter of convenience, the reagents can be provided in an assay kit, i.e., a packaged combination of reagents, for combination with the analyte in assaying the ability of the analyte to bind to a receptor of interest. The components of the kit will generally be provided in predetermined ratios. The kit may provide the first target molecule and/or the second target molecule, optionally complexed together. The kit may further include assay plates coated with the receptor or a binding domain thereof (e.g. the extracellular domain of the α subunit of an FcR). Usually, other reagents, such as an antibody that binds specifically to the analyte to be assayed, labeled directly or indirectly with an enzymatic label, will also be provided in the kit. Where the detectable label is an enzyme, the kit will include substrates and cofactors required by the enzyme (e.g. a substrate precursor which provides the detectable chromophore or fluorophore). In addition, other additives may be included such as stabilizers, buffers (e.g. assay and/or wash lysis buffer) and the like. The relative amounts of the various reagents may be varied widely to provide for concentrations in solution of the reagents that substantially optimize the sensitivity of the assay. Particularly, the reagents may be provided as dry powders, usually lyophilized, including excipients that on dissolution will provide a reagent solution having the appropriate concentration. The kit also suitably includes instructions for carrying out the assay.

B. Antibody Preparation

In the preferred embodiment of the invention, the Fc region-containing polypeptide which is modified according to the teachings herein is an antibody. Techniques for producing antibodies follow:

(i) Antigen Selection and Preparation

Where the polypeptide is an antibody, it is directed against an antigen of interest. Preferably, the antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated.

Where the antigen is a polypeptide, it may be a transmembrane molecule (e.g. receptor) or ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

Preferred molecular targets for antibodies encompassed by the present invention include CD proteins such as CD3, CD4, CD8, CD19, CD20 and CD34; members of the ErbB receptor family such as the EGF receptor, HER2, HER3 or HER4 receptor; cell adhesion molecules such as LFA-1, Mac1, p150.95, VLA-4, ICAM-1, VCAM, α4/β7 integrin, and αv/β3 integrin including either α or β subunits thereof (e.g. anti-CD11a, anti-CD18 or anti-CD11b antibodies); growth factors such as VEGF; tissue factor (TF); alpha interferon (α-IFN); an interleukin; such as IL-8; IgE; blood group antigens; flk2/flt3 receptor; obesity (OB) receptor; mpl receptor; CTLA-4; protein C etc.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

(ii) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described in McCafferty et al., *Nature*, 348: 552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iv) Humanized and Human Antibodies

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239: 1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and Duchosal et al. *Nature* 355:258 (1992). Human antibodies can also be derived from phage-display libraries (Hoogenboom et al., *J. Mol. Biol.*, 227:381 (1991); Marks et al., *J. Mol. Biol.*, 222:581-597 (1991); Vaughan et al. *Nature Biotech* 14:309 (1996)).

(v) Multispecific Antibodies

Multispecific antibodies have binding specificities for at least two different antigens. While such, molecules normally will only bind two antigens (i.e. bispecific antibodies, BsAbs), antibodies with additional specificities such as trispecific antibodies are encompassed by this expression when used herein. Examples of BsAbs include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA); BsAbs for targeting immune complexes to cell surface receptors such as anti-low density lipoprotein (LDL)/anti-Fc receptor (e.g. FcγRI, FcγRII or FcγRIII); BsAbs for use in therapy of infectious diseases such as anti-CD3/anti-herpes simplex virus (HSV), anti-T-cell receptor:CD3 complex/anti-influenza, anti-FcγR/anti-HIV; BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase. Examples of trispecific antibodies include anti-CD3/anti-CD4/anti-CD37, anti-CD3/anti-CD5/anti-CD37 and anti-CD3/anti-CD8/anti-CD37. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different-antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986). According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Antibodies with more than two valencies are contemplated. For example, trispecific antibodies can be prepared. Tutt et al. *J. Immunol.* 147: 60 (1991).

While the polypeptide of interest herein is preferably an antibody, other Fc region-containing polypeptides which can be modified according to the methods described herein are contemplated. An example of such a molecule is an immunoadhesin.

C. Immunoadhesin Preparation

The simplest and most straightforward immunoadhesin design combines the binding domain(s) of the adhesin (e.g. the extracellular domain (ECD) of a receptor) with the Fc region of an immunoglobulin heavy chain. Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain. The precise site at which the fusion is made is not critical; particular sites are well known and may be selected in order to optimize the biological activity, secretion, or binding characteristics of the immunoadhesin.

In a preferred embodiment, the adhesin sequence is fused to the N-terminus of the Fc region of immunoglobulin $G_1$ (IgG$_1$). It is possible to fuse the entire heavy chain constant region to the adhesin sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the adhesin amino acid sequence is fused to (a) the hinge region and $C_H2$ and $C_H3$ or (b) the $C_H1$, hinge, $C_H2$ and $C_H3$ domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagrammed below:

(a) $AC_L\text{-}AC_L$;
(b) $AC_H\text{-}(AC_H, AC_L\text{-}AC_H, AC_L\text{-}V_HC_H,$ or $V_LC_L\text{-}AC_H)$;
(c) $AC_L\text{-}AC_H\text{-}(AC_L\text{-}AC_H, AC_L\text{-}V_HC_H, V_LC_L\text{-}AC_H,$ or $V_LC_L\text{-}V_HC_H)$
(d) $AC_L\text{-}V_HC_H\text{-}(AC_H,$ or $AC_L\text{-}V_HC_H,$ or $V_LC_L\text{-}AC_H)$;
(e) $V_LC_L\text{-}AC_H\text{-}(AC_L\text{-}V_HC_H,$ or $V_LC_L\text{-}AC_H)$; and
(f) $(A\text{-}Y)_n\text{-}(V_LC_L\text{-}V_HC_H)_2$, wherein each A represents identical or different adhesin amino acid sequences;

$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H2$ domain, or between the $C_H2$ and $C_H3$ domains. Similar constructs have been reported by Hoogenboom, et al., *Mol. Immunol.* 28:1027-1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued 28 Mar. 1989.

Immunoadhesins are most conveniently constructed by fusing the cDNA sequence encoding the adhesin portion in-frame to an immunoglobulin cDNA sequence. However, fusion to genomic immunoglobulin fragments can also be used (see, e.g. Aruffo et al., *Cell* 61:1303-1313 (1990); and Stamenkovic et al., Cell 66:1133-1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells.

D. Vectors, Host Cells and Recombinant Methods

The invention also provides isolated nucleic acid encoding a polypeptide variant as disclosed herein, vectors and host cells comprising the nucleic acid, and recombinant techniques for the production of the polypeptide variant.

For recombinant production of the polypeptide variant, the nucleic acid encoding it is isolated and inserted into a replicable vector for further cloning (amplification of the DNA) or for expression. DNA encoding the polypeptide variant is readily isolated and sequenced using conventional procedures (e.g., by using oligonucleotide probes that are capable of binding specifically to genes encoding the polypeptide variant). Many vectors are available. The vector components generally include, but are not limited to, one or more of the following: a signal sequence, an origin of replication, one or more marker genes, an enhancer element, a promoter, and a transcription termination sequence.

(i) Signal Sequence Component

The polypeptide variant of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native polypeptide variant signal sequence, the signal sequence is substituted by a prokaryotic signal sequence selected, for example, from the group of the alkaline phosphatase, penicillinase, Ipp, or heat-stable enterotoxin II leaders. For yeast secretion the native signal sequence may be substituted by, e.g., the yeast invertase leader, α factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the polypeptide variant.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding β-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the polypeptide variant nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding polypeptide variant, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

(iv) Promoter Component

Expression and cloning vectors usually contain a promoter that is recognized by the host organism and is operably linked to the polypeptide variant nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the polypeptide variant.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Polypeptide variant transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human β-interferon cDNA in mouse cells under the control of a thymidine kinase promoter from herpes simplex virus. Alternatively, the rous sarcoma virus long terminal repeat can be used as the promoter.

(v) Enhancer Element Component

Transcription of a DNA encoding the polypeptide variant of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the polypeptide variant-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide variant. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide variant-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated polypeptide variant are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol*. 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for polypeptide variant production and cultured in conventional nutrient media modified as appropriate for inducing promoters, selecting transformants, or amplifying the genes encoding the desired sequences.

(viii) Culturing the Host Cells

The host cells used to produce the polypeptide variant of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. No. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Polypeptide Variant Purification

When using recombinant techniques, the polypeptide variant can be produced intracellularly, in the periplasmic space, or directly secreted into the medium. If the polypeptide variant is produced intracellularly, as a first step, the particulate debris, either host cells or lysed fragments, is removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the polypeptide variant is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The polypeptide variant composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc region that is present in the polypeptide variant. Protein A can be used to purify polypeptide variants that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the polypeptide variant comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the polypeptide variant to be recovered.

Following any preliminary purification step(s), the mixture comprising the polypeptide variant of interest and contaminants may be subjected to low pH hydrophobic interaction chromatography using an elution buffer at a pH between about 2.5-4.5, preferably performed at low salt concentrations (e.g., from about 0-0.25M salt).

E. Pharmaceutical Formulations

Therapeutic formulations of the polypeptide variant are prepared for storage by mixing the polypeptide variant having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the polypeptide variant, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

F. Non-Therapeutic Uses for the Polypeptide Variant

The polypeptide variant of the invention may be used as an affinity purification agent. In this process, the polypeptide variant is immobilized on a solid phase such a Sephadex resin or filter paper, using methods well known in the art. The immobilized polypeptide variant is contacted with a sample containing the antigen to be purified, and thereafter the support is washed with a suitable solvent that will remove substantially all the material in the sample except the antigen to be purified, which is bound to the immobilized polypeptide variant. Finally, the support is washed with another suitable solvent, such as glycine buffer, pH 5.0, that will release the antigen from the polypeptide variant.

The polypeptide variant may also be useful in diagnostic assays, e.g., for detecting expression of an antigen of interest in specific cells, tissues, or serum.

For diagnostic applications, the polypeptide variant typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The polypeptide variant can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the polypeptide variant using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the polypeptide variant. The skilled artisan will be aware of various techniques for achieving this. For example, the polypeptide variant can be conjugated with biotin and any of the three broad categories of labels mentioned above can be conjugated with avidin, or vice versa. Biotin binds selectively to avidin and thus, the label can be conjugated with the polypeptide variant in this indirect manner. Alternatively, to achieve indirect conjugation of the label with the polypeptide variant, the polypeptide variant is conjugated with a small hapten (e.g., digoxin) and one of the different types of labels mentioned above is conjugated with an anti-hapten polypeptide variant (e.g., anti-digoxin antibody). Thus, indirect conjugation of the label with the polypeptide variant can be achieved.

In another embodiment of the invention, the polypeptide variant need not be labeled, and the presence thereof can be detected using a labeled antibody which binds to the polypeptide variant.

The polypeptide variant of the present invention may be employed in any known assay method, such as competitive binding assays, direct and indirect sandwich assays, and immunoprecipitation assays. Zola, *Monoclonal Antibodies: A Manual of Techniques*, pp. 147-158 (CRC Press, Inc. 1987).

The polypeptide variant may also be used for in vivo diagnostic assays. Generally, the polypeptide variant is labeled with a radionuclide (such as $^{111}$In, $^{99}$Tc, $^{14}$C, $^{131}$I, $^{125}$I, $^{3}$H, $^{32}$P or $^{35}$S) so that the antigen or cells expressing it can be localized using immunoscintiography.

G. In Vivo Uses for the Polypeptide Variant

It is contemplated that the polypeptide variant of the present invention may be used to treat a mammal e.g. a patient suffering from, or predisposed to, a disease or disorder who could benefit from administration of the polypeptide variant. The conditions which can be treated with the polypeptide variant are many and include cancer (e.g. where the polypeptide variant binds the HER2 receptor, CD20 or vascular endothelial growth factor (VEGF)); allergic conditions such as asthma (with an anti-IgE antibody); and LFA-1-mediated disorders (e.g. where the polypeptide variant is an anti-LFA-1 or anti-ICAM-1 antibody) etc.

Where the antibody binds the HER2 receptor, the disorder preferably is HER2-expressing cancer, e.g. a benign or malignant tumor characterized by overexpression of the HER2 receptor. Such cancers include, but are not limited to, breast cancer, squamous cell cancer, small-cell lung cancer, non-small cell lung cancer, gastrointestinal cancer, pancreatic cancer, glioblastoma, cervical cancer, ovarian cancer, bladder cancer, hepatoma, colon cancer, colorectal cancer, endometrial carcinoma, salivary gland carcinoma, kidney cancer, liver cancer, prostate cancer, vulval cancer, thyroid cancer, hepatic carcinoma and various types of head and neck cancer. According to the teachings herein, one may prepare a polypeptide with a variant Fc region which has improved, or diminished, ADCC activity. Such molecules will find applications in the treatment of different disorders.

For example, the polypeptide variant with improved ADCC activity may be employed in the treatment of diseases or disorders where destruction or elimination of tissue or foreign micro-organisms is desired. For example, the polypeptide may be used to treat cancer; inflammatory disorders; infections (e.g. bacterial, viral, fungal or yeast infections); and other conditions (such as goiter) where removal of tissue is desired, etc.

Where the polypeptide variant has diminished ADCC activity, such variants may be used to treat diseases or disorders where a Fc region-containing polypeptide with long half-life is desired, but the polypeptide preferably does not have undesirable effector function(s). For example, the Fc region-containing polypeptide may be an anti-tissue factor (TF) antibody; anti-IgE antibody; and anti-integrin antibody (e.g. an anti-α4β7 antibody). The desired mechanism of action of such Fc region-containing polypeptides may be to block ligand-receptor binding pairs. Moreover, the Fc-region containing polypeptide with diminished ADCC activity may be an agonist antibody.

The polypeptide variant is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration.

In addition, the polypeptide variant is suitably administered by pulse infusion, particularly with declining doses of the polypeptide variant. Preferably the dosing is given by injections, most preferably intravenous or subcutaneous injections, depending in part on whether the administration is brief or chronic.

For the prevention or treatment of disease, the appropriate dosage of polypeptide variant will depend on the type of disease to be treated, the severity and course of the disease, whether the polypeptide variant is administered for preventive or therapeutic purposes, previous therapy, the patient's clinical history and response to the polypeptide variant, and the discretion of the attending physician. The polypeptide variant is suitably administered to the patient at one time or over a series of treatments.

Depending on the type and severity of the disease, about 1 µg/kg to 15 mg/kg (e.g., 0.1-20 mg/kg) of polypeptide variant is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

The polypeptide variant composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the polypeptide variant to be administered will be governed by such considerations, and is the minimum amount necessary to prevent, ameliorate, or treat a disease or disorder. The polypeptide variant need not be, but is optionally formulated with one or more agents currently used to prevent or treat the disorder in question. The effective amount of such other agents depends on the amount of polypeptide variant present in the formulation, the type of disorder or treatment, and other factors discussed above. These are generally used in the same dosages and with administration routes as used hereinbefore or about from 1 to 99% of the heretofore employed dosages.

The invention will be more fully understood by reference to the following examples. They should not, however, be construed as limiting the scope of this invention. All literature and patent citations mentioned herein are expressly incorporated by reference.

EXAMPLE 1

Low Affinity Receptor Binding Assay

This assay determines binding of an IgG Fc region to recombinant FcγRIIA, FcγRIIB and FcγRIIIA α subunits expressed as His6-glutathione S transferase (GST)-tagged fusion proteins. Since the affinity of the Fc region of IgG1 for the FcγRI is in the nanomolar range, the binding of IgG1 Fc variants can be measured by titrating monomeric IgG and measuring bound IgG with a polyclonal anti-IgG in a standard ELISA format (Example 2 below). The affinity of the other members of the FcγR family, i.e. FcγRIIA, FcγRIIB and FcγRIIIA for IgG is however in the micromolar range and binding of monomeric IgG1 for these receptors can not be reliably measured in an ELISA format.

The following assay utilizes Fc variants of recombinant anti-IgE E27 (FIGS. 4A and 4B) which, when mixed with human IgE at a 1:1 molar ratio, forms a stable hexamer consisting of three anti-IgE molecules and three IgE molecules. A recombinant chimeric form of IgE (chimeric IgE) was engineered and consists of a human IgE Fc region and the Fab of an anti-VEGF antibody (Presta et al. *Cancer Research* 57:4593-4599 (1997)) which binds two VEGF molecules per mole of anti-VEGF. When recombinant human VEGF is added at a 2:1 molar ratio to chimeric IgE:E27 hexamers, the hexamers are linked into larger molecular weight complexes via the chimeric IgE Fab:VEGF interaction. The E27 component of this complex binds to the FcγRIIA, FcγRIIB and FcγRIIIA α subunits with higher avidity to permit detection in an ELISA format.

Materials and Methods

Receptor Coat:

Fcγreceptor α subunits were expressed as GST fusions of His6 tagged extracellular domains (ECDs) in 293 cells resulting in an ECD-6His-GST fusion protein (Graham et al. *J. Gen. Virol.* 36:59-74 (1977) and Gorman et al. *DNA Prot. Eng. Tech.* 2:3-10 (1990)) and purified by Ni-NTA column chromatography (Qiagen, Australia) and buffer exchanged into phosphate buffered saline (PBS). Concentrations were determined by absorption at 280 nm using extinction coefficients derived by amino acid composition analysis. Receptors were coated onto Nunc F96 maxisorb plates (cat no: 439454) at 100 ng per well by adding 100 µl of receptor-GST fusion at 1 µg/ml in PBS and incubated for 48 hours at 4° C. Prior to assay, plates are washed 3× with 250 µl of wash buffer (PBS pH 7.4 containing 0.5% TWEEN 20™) and blocked with 250 µl of assay buffer (50 mM Tris buffered saline, 0.05% TWEEN 20™, 0.5% RIA grade bovine albumin (Sigma A7888), and 2 mM EDTA pH 7.4).

Immune Complex Formation:

Equal molar amounts (1:1) of E27 and recombinant chimeric IgE which binds two moles recombinant human VEGF per mole of chimeric IgE are added to a 12×75 mm polypropylene tube in PBS and mixed by rotation for 30 minutes at 25° C. E27 (anti-IgE)/chimeric IgE (IgE) hexamers are formed during this incubation. Recombinant human VEGF (165 form, MW 44,000) is added at a 2:1 molar ratio to the IgE concentration and mixed by rotation an additional 30 minutes at 25° C. VEGF-chimeric IgE binding links E27:chimeric IgE hexamers into larger molecular weight complexes which bind FcγR α subunit ECD coated plates via the Fc region of the E27 antibody.

E27:Chimeric IgE:VEGF:

(1:1:2 molar ratio) complexes are added to FcγR α subunit coated plates at E27 concentrations of 5 µg and 1 µg total IgG in quadruplicate in assay buffer and incubated for 120 minutes at 25° C. on an orbital shaker.

Complex Detection:

Plates are washed 5× with wash buffer to remove unbound complexes and IgG binding is detected by adding 100 µl horse radish peroxidase (HRP) conjugated goat anti-human IgG (γ) heavy chain specific (Boehringer Mannheim 1814249) at 1:10,000 in assay buffer and incubated for 90 min at 25° C. on an orbital shaker. Plates are washed 5× with wash buffer to remove unbound HRP goat anti-human IgG and bound anti-IgG is detected by adding 100 µl of substrate solution (0.4 mg/ml o-phenylenediamine dihydrochloride, Sigma P6912, 6 mM $H_2O_2$ in PBS) and incubating for 8 min at 25° C.

Enzymatic reaction is stopped by the addition of 100 µl 4.5N $H_2SO_4$ and colorimetric product is measured at 490 nm on a 96 well plate densitometer (Molecular Devices). Binding of E27 variant complexes is expressed as a percent of the wild type E27 containing complex.

EXAMPLE 2

Identification of Unique C1q Binding Sites in a Human IgG Antibody

In the present study, mutations were identified in the CH2 domain of a human IgG1 antibody, "C2B8" (Reff et al., *Blood* 83:435 (1994)), that ablated binding of the antibody to C1q but did not alter the conformation of the antibody nor affect binding to each of the FcγRs. By alanine scanning mutagenesis, five variants in human IgG1 were identified, D270K, D270V, K322A P329A, and P331, that were non-lytic and had decreased binding to C1q. The data suggested that the core C1q binding sites in human IgG1 is different from that of murine IgG2b. In addition, K322A, P329A and P331A were found to bind normally to the CD20 antigen, and to four Fc receptors, FcγRI, FcγRII, FcγRIII and FcRn.

Materials and Methods

Construction of C2B8 Variants:

The chimeric light and heavy chains of anti-CD20-antibody C2B8 (Reff et al., *Blood* 83:435 (1994)) subcloned separately into previously described PRK vectors (Gorman et al., *DNA Protein Eng. Tech.* 2:3 (1990)) were used. By site directed mutagenesis (Kunkel et al., *Proc. Natl. Acad. Sci. USA* 82:488 (1987)), alanine scan variants of the Fc region in the heavy chain were constructed. The heavy and light chain plasmids were co-transfected into an adenovirus transformed human embryonic kidney cell line as previously described (Werther et al., *J. Immunol.* 157:4986 (1996)). The media was changed to serum-free 24 hours after transfection and the secreted antibody was harvested after five days. The antibodies were purified using Protein A-SEPHAROSE CL4B™ (Pharmacia), buffer exchanged and concentrated to 0.5 ml with PBS using a Centricon-30 (Amicon), and stored at 4° C. The concentration of the antibody was determined using total Ig-binding ELISA.

C1q Binding ELISA:

Costar 96 well plates were coated overnight at 4° C. with the indicated concentrations of C2B8 in coating buffer (0.05 M sodium carbonate buffer), pH 9. The plates were then washed 3× with PBS/0.05% TWEEN 20™, pH 7.4 and blocked with 200 µl of ELISA diluent without thimerosal (0.1M NaPO4/0.1M NaCl/0.1% gelatin/0.05% TWEEN 20™/0.05% ProClin300) for 1 hr at room temperature. The plate was washed 3× with wash buffer, an aliquot of 100 µl of 2 µg/ml C1q (Quidel, San Diego, Calif.) was added to each well and incubated for 2 hrs at room temperature. The plate was then washed 6× with wash buffer. 100 µl of a 1:1000 dilution of sheep anti-complement C1q peroxidase conjugated antibody (Biodesign) was added to each well and incubated for 1 hour at room temperature. The plate was again washed 6× with wash buffer and 100 µl of substrate buffer (PBS/0.012% $H_2O_2$) containing OPD (O-phenylenediamine dihydrochloride (Sigma)) was added to each well. The oxidation reaction, observed by the appearance of a yellow color, was allowed to proceed for 30 minutes and stopped by the addition of 100 µl of 4.5 N $H_2SO_4$. The absorbance was then read at (492-405) nm using a microplate reader (SPECTRA MAX 250™, Molecular Devices Corp.). The appropriate controls were run in parallel (i.e. the ELISA was performed without C1q for each concentration of C2B8 used and also the ELISA was performed without C2B8). For each variant, C1q binding was measured by plotting the absorbance (492-405) nm versus concentration of C2B8 in µg/ml using a 4-parameter curve fitting program (KALEIDAGRAPH™) and comparing $EC_{50}$ values.

Complement Dependent Cytotoxicity (CDC) Assay:

This assay was performed essentially as previously described (Gazzano-Santoro et al., *J. Immunol. Methods* 202: 163 (1996)). Various concentrations of C2B8 (0.08-20 µg/ml) were diluted with RHB buffer (RPMI 1640/20 mM HEPES (pH 7.2)/2 mM Glutamine/0.1% BSA/100 µg/ml Gentamicin). Human complement (Quidel) was diluted 1:3 in RHB buffer and WIL2-S cells (available from the ATCC, Manassas, Va.) which express the CD20 antigen were diluted to a density of 1×10⁶ cells/ml with RHB buffer. Mixtures of 150 µl containing equal volumes of C2B8, diluted human complement and WIL2-S cells were added to a flat bottom tissue culture 96 well plate and allowed to incubate for 2 hrs at 37° C. and 5% $CO_2$ to facilitate complement mediated cell lysis. 50 µl of alamar blue (Accumed International) was then added to each well and incubated overnight at 37° C. The absorbance was measured using a 96-well fluorometer with excitation at 530 nm and emission at 590 nm. As described by Gazzano-Santoro et al., the results are expressed in relative fluorescence units (RFU). The sample concentrations were computed from a C2B8 standard curve and the percent activity as compared to wild type C2B8 is reported for each variant.

CD20 Binding Potency of the C2B8 Variants:

The binding of C2B8 and variants to the CD20 antigen were assessed by a method previously described (Reff et al., (1994), supra; reviewed in Gazzano-Santoro et al., (1996), supra). WIL2-S cells were grown for 3-4 days to a cell density of 1×10⁶ cells/ml. The cells were washed and spun twice in FACS buffer (PBS/0.1% BSA/0.02% $NaN_3$) and resuspended to a cell density of 5×10⁶ cells/ml. 200 µl of cells (5×10⁶ cells/ml) and 20 µl of diluted C2B8 samples were added to a 5 ml tube and incubated at room temperature for 30 minutes with agitation. The mixture was then washed with 2 ml of cold FACS buffer, spun down and resuspended in 200 µl of cold FACS buffer. To the suspension, 10 µl of goat anti-human IgG-FITC (American Qualex Labs.) was added and the mixture was incubated in the dark at room temperature for 30 minutes with agitation. After incubation, the mixture was washed with 2 ml of FACS buffer, spun down and resuspended in 1 ml of cold fixative buffer (1% formaldehyde in PBS). The samples were analyzed by flow cytometry and the results expressed as relative fluorescence units (RFU) were plotted against antibody concentrations using a 4-parameter curve fitting program (KALEIDAGRAPH™). The $EC_{50}$ values are reported as a percentage of that of the C2B8 reference material.

FcγR Binding ELISAs:

FcγRI α subunit-GST fusion was coated onto Nunc F96 maxisorb plates (cat no. 439454) by adding 100 µl of receptor-GST fusion at 1 µg/ml in PBS and incubated for 48 hours at 4° C. Prior to assay, plates are washed 3× with 250 µl of wash buffer (PBS pH 7.4 containing 0.5% TWEEN 20™) and blocked with 250 µl of assay buffer (50 mM Tris buffered saline, 0.05% TWEEN 20™, 0.5% RIA grade bovine albumin (Sigma A7888), and 2 mM EDTA pH 7.4). Samples diluted to 10 µg/ml in 1 ml of assay buffer are added to FcγRI α subunit coated plates and incubated for 120 minutes at 25° C. on an orbital shaker. Plates are washed 5× with wash buffer to remove unbound complexes and IgG binding is detected by adding 100 µl horse radish peroxidase (HRP) conjugated goat anti-human IgG (γ) heavy chain specific (Boehringer Mannheim 1814249) at 1:10,000 in assay buffer and incubated for 90 min at 25° C. on an orbital shaker. Plates are washed 5× with wash buffer to remove unbound HRP goat anti-human IgG and bound anti-IgG Is detected by adding 100 µl of substrate solution (0.4 mg/ml o-phenylenediamine dihydrochloride, Sigma P6912, 6 mM $H_2O_2$ in PBS) and incubating for 8 min at 25° C. Enzymatic reaction is stopped by the addition of 100 µl 4.5N $H_2SO_4$ and colorimetric product is measured at 490 nm on a 96 well plate densitometer (Molecular Devices). Binding of variant is expressed as a percent of the wild type molecule.

FcγRII and III binding ELISAs were performed as described in Example 1 above.

For measuring FcRn binding activity of IgG variants, ELISA plates were coated with 2 µg/ml streptavidin (Zymed, South San Francisco) in 50 mM carbonate buffer, pH 9.6, at 4° C. overnight and blocked with PBS-0.5% BSA, pH 7.2 at room temperature for one hour. Biotinylated FcRn (prepared using biotin-X-NHS from Research Organics, Cleveland, Ohio and used at 1-2 µg/ml) in PBS-0.5% BSA, 0.05% polysorbate 20, pH 7.2, was added to the plate and incubated for one hour. Two fold serial dilutions of IgG standard (1.6-100 ng/ml) or variants in PBS-0.5% BSA, 0.05% polysorbate 20, pH 6.0, were added to the plate and incubated for two hours. Bound IgG was detected using peroxidase labeled goat $F(ab')_2$ anti-human IgG $F(ab')_2$ in the above pH 6.0 buffer (Jackson ImmunoResearch, West Grove, Pa.) followed by 3,3',5,5'-tetramethyl benzidine (Kirgaard & Perry Laboratories) as the substrate. Plates were washed between steps with PBS-0.05% polysorbate 20 at either pH 7.2 or 6.0. Absorbance was read at 450 nm on a Vmax plate reader (Molecular Devices, Menlo Park, Calif.). Titration curves were fit with a four-parameter nonlinear regression curve-fitting program (KaleidaGraph, Synergy software, Reading, Pa.). Concentrations of IgG variants corresponding to the mid-point absorbance of the titration curve of the standard were calculated and then divided by the concentration of the standard corresponding to the mid-point absorbance of the standard titration curve.

Results and Discussion

By alanine scanning mutagenesis, several single point mutations were constructed in the CH2 domain of C2B8 beginning with E318A, K320A and K322A. All the variants constructed bound normally to the CD20 antigen (Table 3).

TABLE 3

|        | wt  | E318A | K320A | K322A | P329A | P331A |
|--------|-----|-------|-------|-------|-------|-------|
| FcRn   | +   | +     | +     | +     |       |       |
| CD20   | +   | +     | +     | +     | +     | +     |
| FcγRI  | +   | +     | +     | +     | +     | +     |
| FcγRII | +   | +     | +     | +     | +     | +     |
| FcγRIII| +   | +     | +     | +     | +     | +     |
| *C1q   | +++ | ++    | +++   | −     | −     | −     |
| CDC    | +   | +     | +     | −     | −     | −     |

Figure 2:
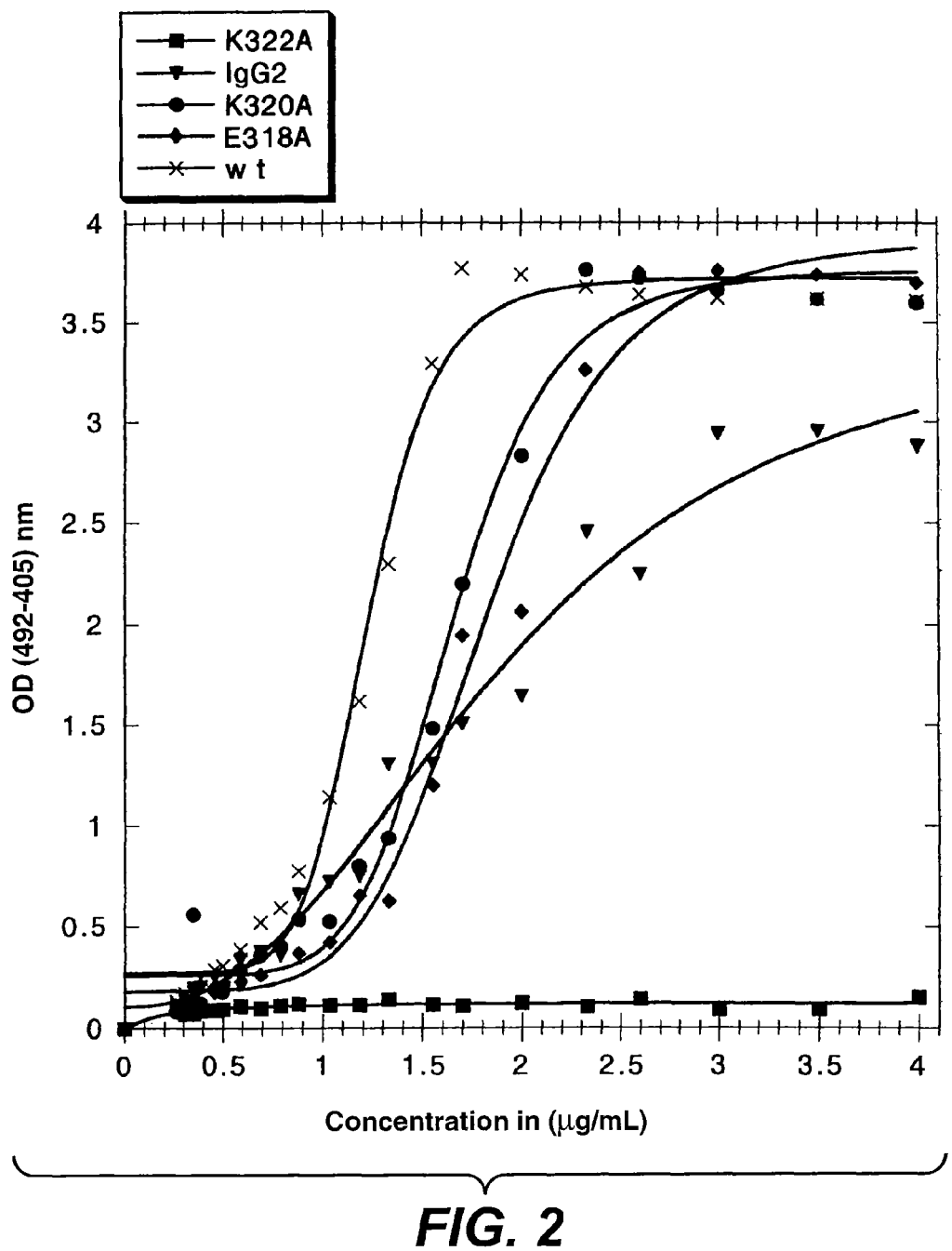
FIG. 2 shows C1q binding of wild type (wt) C2B8 antibody; C2B8 antibody with a human IgG2 constant region (IgG2); and variants K322A, K320A and E318A.

(+) indicates binding and (−) signifies binding abolished
*With respect to C1q binding, each + sign is equivalent to approximately 33% binding.

Where binding of human complement to an antibody with a human Fc was analyzed, the ability of E318A and K320A to activate complement was essentially identical to that of wild type C2B8 (Table 3). When compared to wild type C2B8, there appears to be little difference in the binding of E318A and K320A to C1q. There is only a 10% decrease in the binding of K320A and about a 30% decrease in the binding of E318A to C1q (FIG. 2). The results indicate that the effect of the E318A and the K320A substitution on complement activation and C1q binding is minimal. Also, the human IgG1 of C2B8 was substituted for human IgG2 and used as a negative control in the C1q binding studies. The IgG2 variant appears to have a much lower affinity for C1q than the E318A and K320A variants (FIG. 2). Thus, the results demonstrate that E318 and K320 do not constitute the core C1q binding sites for human IgG1. Conversely, the K322A substitution had a significant effect on both complement activity and C1q binding. The K322A variant did not have CDC activity when tested in the above CDC assay and was more than a 100 fold lower than wild type C2B8 in binding to C1q (FIG. 2). In the human system, K322 is the only residue of the proposed core C1q binding sites that appeared to have a significant effect on complement activation and C1q binding.

Figure 3:
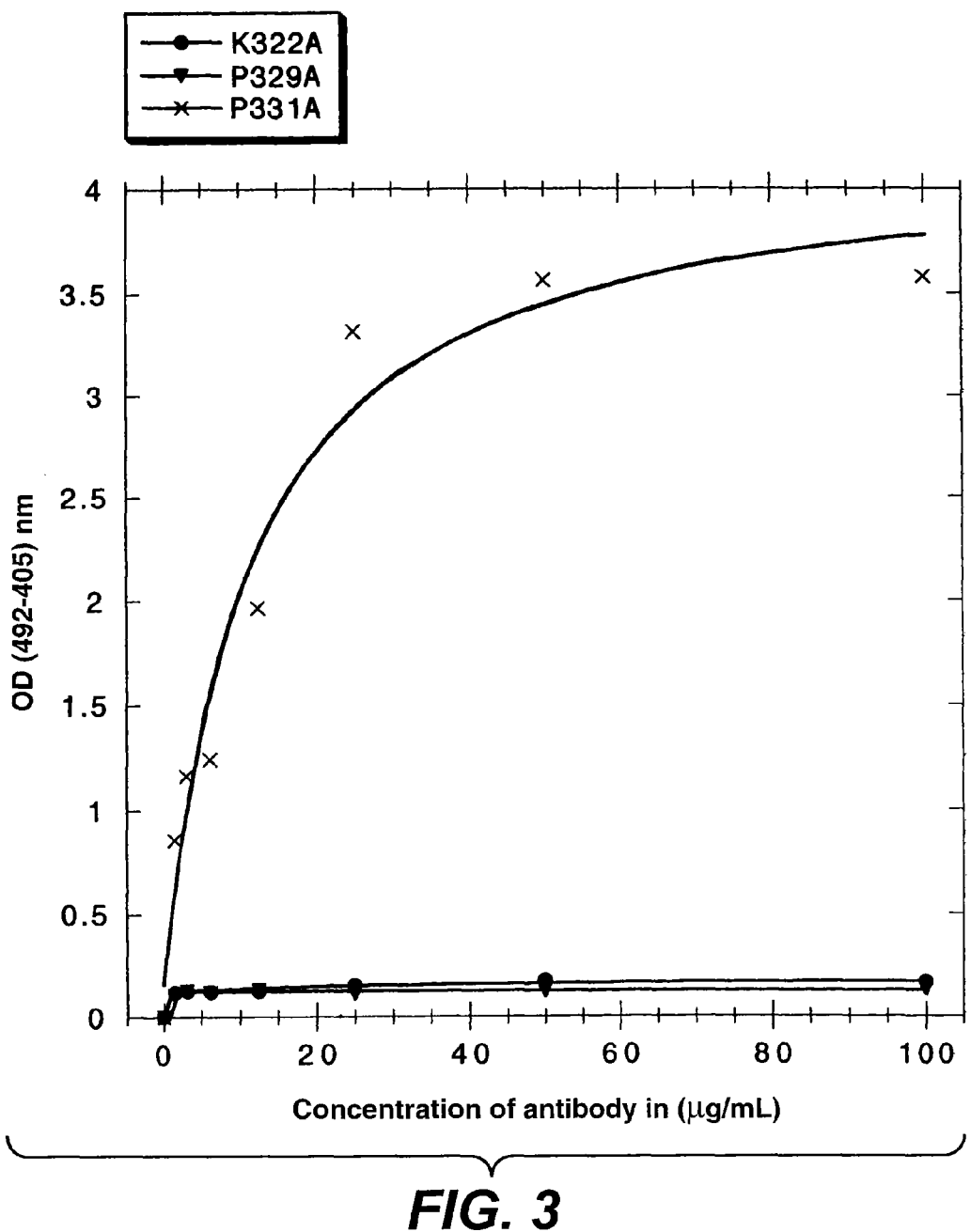
FIG. 3 depicts C1q binding of variants P331A, P329A and K322A.

Since the Duncan and Winter study was performed using mouse IgG2b and the above results reveal that K320 and E318 in human IgG1 are not involved in C1q binding, and without being bound to any one theory, the above data suggest that the C1q binding region in murine IgGs is different from that of the human. To investigate this further and also to identify additional variants that do not bind to C1q and hence do not activate complement, several more point mutations in the vicinity of K322 were constructed as assessed from the three dimensional structure of the C2B8 Fc. Variants constructed, K274A, N276A, Y278A, S324A, P329A, P331A, K334A, and T335A, were assessed for their ability to bind C1q and also to activate complement. Many of these substitutions had little or no effect on C1q binding or complement activation. In the above assays, the P329A and the P331A variants did not activate complement and had decreased binding to C1q. The P331A variant did not activate complement and was 60 fold lower in binding to C1q (FIG. 3) when compared to wild type C2B8 (FIG. 2). The concentration range of the antibody variants used in FIG. 3 is expanded to 100 µg/ml in order to observe saturation of C1q binding to the P331A variant. The mutation P329A results in an antibody that does not activate complement and is more than a 100 fold lower in binding to C1q (FIG. 3) when compared to wild type C2B8 (FIG. 2).

Variants that did not bind to C1q and hence did not activate complement were examined for their ability to bind to the Fc receptors: FcγRI, FcγRIIA, FcγRIIB, FcγRIIIA and FcRn. This particular study was performed using a humanized anti-IgE antibody, an IgG1 antibody with these mutations (see Example 1 above). The results revealed the variants, K322A and P329A, bind to all the Fc receptors to the same extent as the wild type protein (Table 4). However, there was a slight decrease in the binding of P331A to FcγRIIB.

In conclusion, two amino acid substitutions in the COOH terminal region of the CH2 domain of human IgG1, K322A and P329A were identified that result in more than 100 fold decrease in C1q binding and do not activate the CDC pathway. These two variants, K322A and P329A, bind to all Fc receptors with the same affinity as the wild type antibody. Based on the results, summarized in Table 4, and without being bound to any one theory, it is proposed that the C1q binding epicenter of human IgG1 is centered around K322, P329 and P331 and is different from the murine IgG2b epicenter which constitutes E318, K320 and K322.

TABLE 4

|  | wt | E318A | K320A | K322A | P329A | P331A |
|---|---|---|---|---|---|---|
| CD20 | 100 | 89 | 102 | 86 | 112 | 103 |
| ᵃFcγRI | 100 | 93 | 102 | 90 | 104 | 74 |
| ᵃFcγRIIA | 100 | 113 | 94 | 109 | 111 | 86 |
| ᵃFcγRIIB | 100 | 106 | 83 | 101 | 96 | 58 |
| ᵃFcγRIII | 100 | 104 | 72 | 90 | 85 | 73 |
| CDC | 100 | 108 | 108 | none | none | none |

ᵃFor binding to the FcγRs the variants were made in the E27 background (anti-IgE). The results are presented as a percentage of the wild type.

Figure 6:
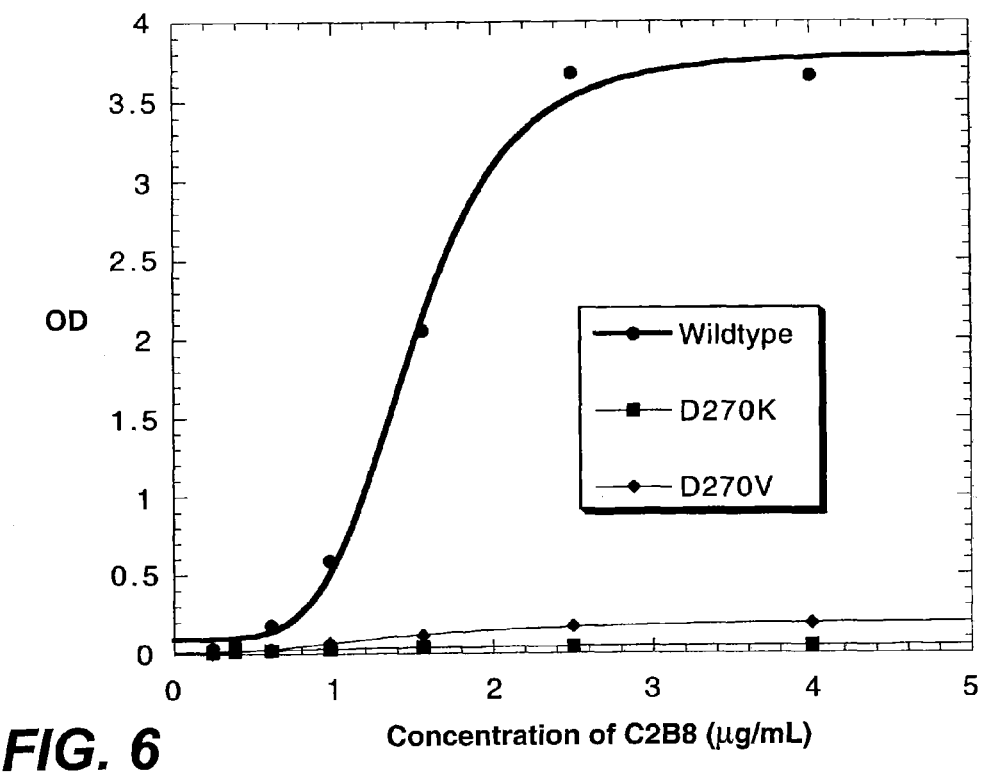
FIG. 6 shows C1q binding results obtained for variants D270K and D270V compared to wild type C2B8.
Figure 7:
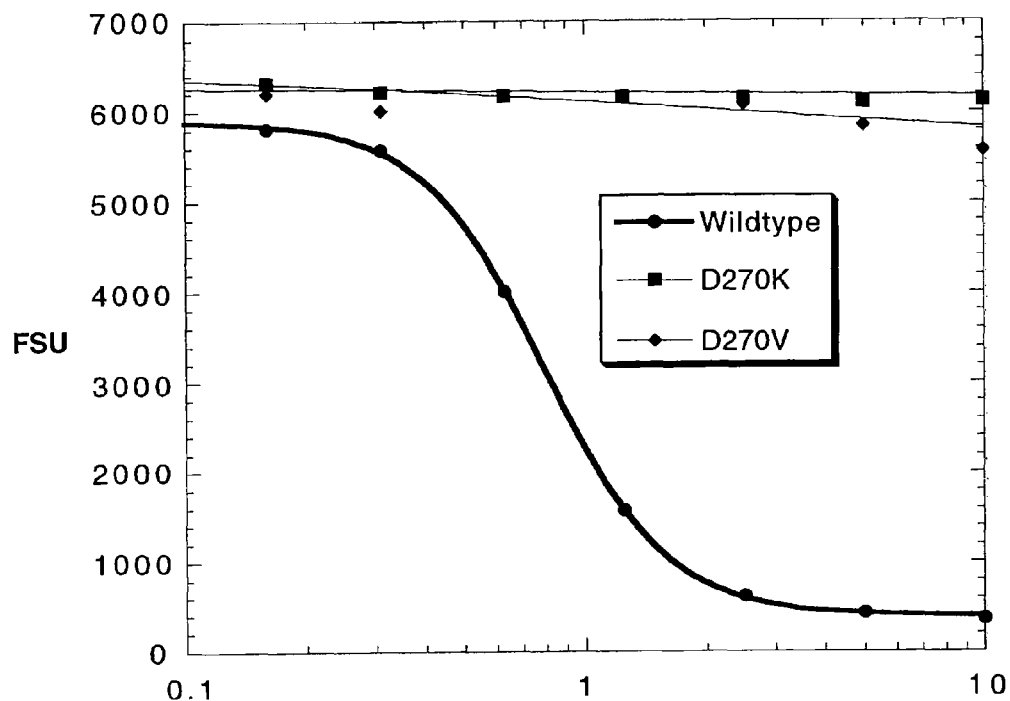
FIG. 7 depicts complement dependent cytotoxicity (CDC) of variants D270K and D270V, compared to wild type C2B8.

A further residue involved in binding human C1q was identified using the methods described in the present example. The residue D270 was replaced with lysine and valine to generate variants D270K and D270V, respectively. These variants both showed decreased binding to human C1q (FIG. 6) and were non-lytic (FIG. 7). The two variants bound the CD20 antigen normally and recruited ADCC.

EXAMPLE 3

Variants with Improved C1q Binding

The following study shows that substitution of residues at positions K326, A327, E333 and K334 resulted in variants with at least about a 30% increase in binding to C1q when compared to the wild type antibody. This indicated K326, A327, E333 and K334 are potential sites for improving the efficacy of antibodies by way of the CDC pathway. The aim of this study was to improve CDC activity of an antibody by increasing binding to C1q. By site directed mutagenesis at K326 and E333, several variants with increased binding to C1q were constructed. The residues in order of increased binding at K326 are K<V<E<A<G<D<M<W, and the residues in order of increased binding at E333 are E<Q<D<V<G<A<S. Four variants, K326M, K326D, K326E and E333S were constructed with at least a two-fold increase in binding to C1q when compared to wild type. Variant K326W displayed about a five-fold increase in binding to C1q.

Variants of the wild type C2B8 antibody were prepared as described above in Example 2. A further control antibody, wild type C2B8 produced in Chinese hamster ovary (CHO) cells essentially as described in U.S. Pat. No. 5,736,137, was included in a C1q binding ELISA to confirm that wt C2B8 produced in the 293 kidney cell line had the same C1q binding activity as the CHO-produced antibody (see "CHO-wt-C2B8" in FIG. 8). The C1q binding ELISA, CDC assay, and CD20 binding potency assay in this example were performed as described in Example 2 above.

Figure 8:
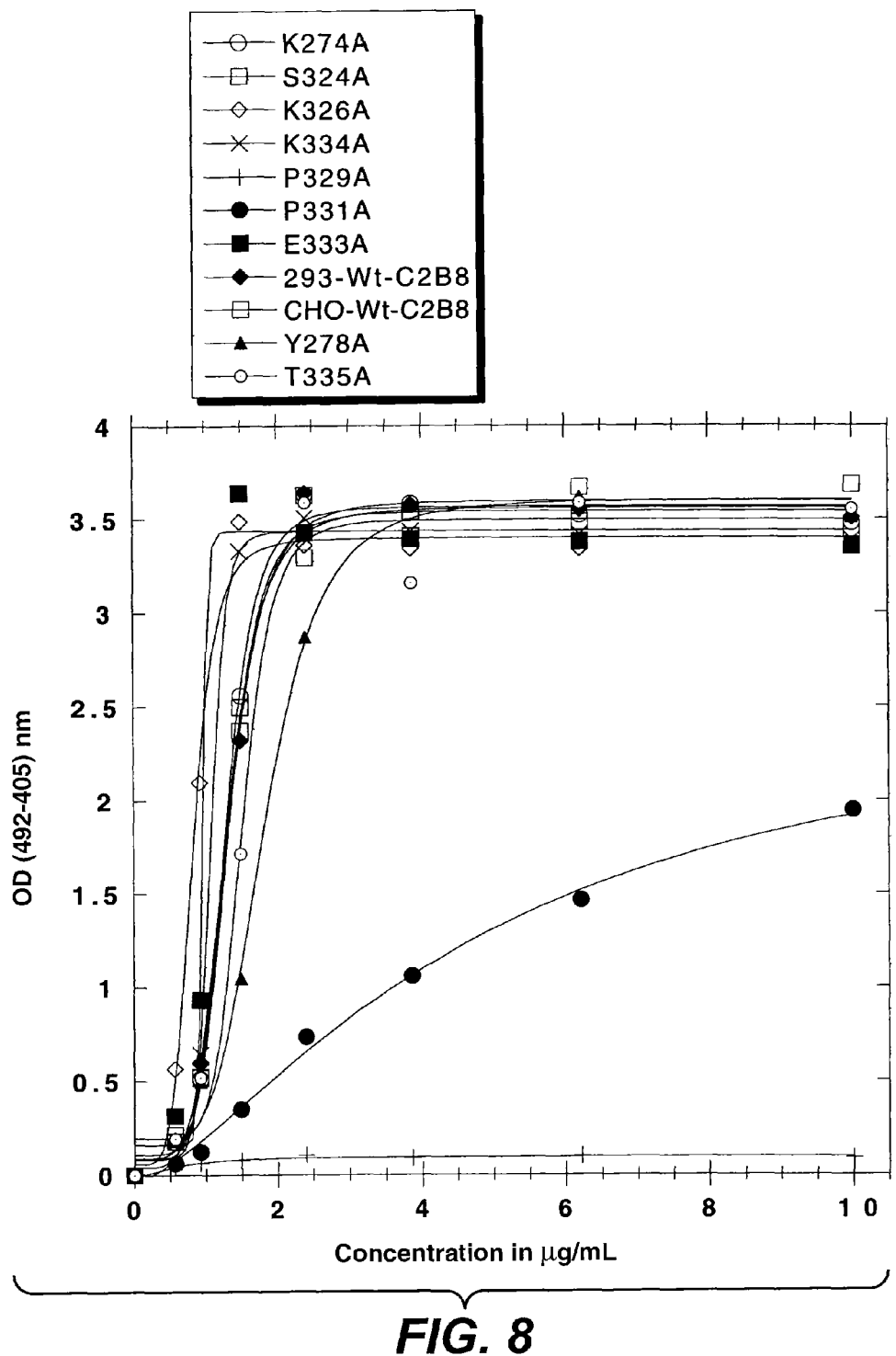
FIG. 8 shows C1q binding ELISA results for 293 cell-produced wild type C2B8 antibody (293-Wt-C2B8), CHO-produced wild type C2B8 antibody (CHO-Wt-C2B8) and various variant antibodies.

As shown in FIG. 8, alanine substitution at K326 and E333 in C2B8 resulted in variants with about a 30% increase in binding to C1q.

Several other single point variants at K326 and E333 were constructed and assessed for their ability to bind C1q and activate complement. All the variants constructed bound normally to the CD20 antigen.

Figure 9:
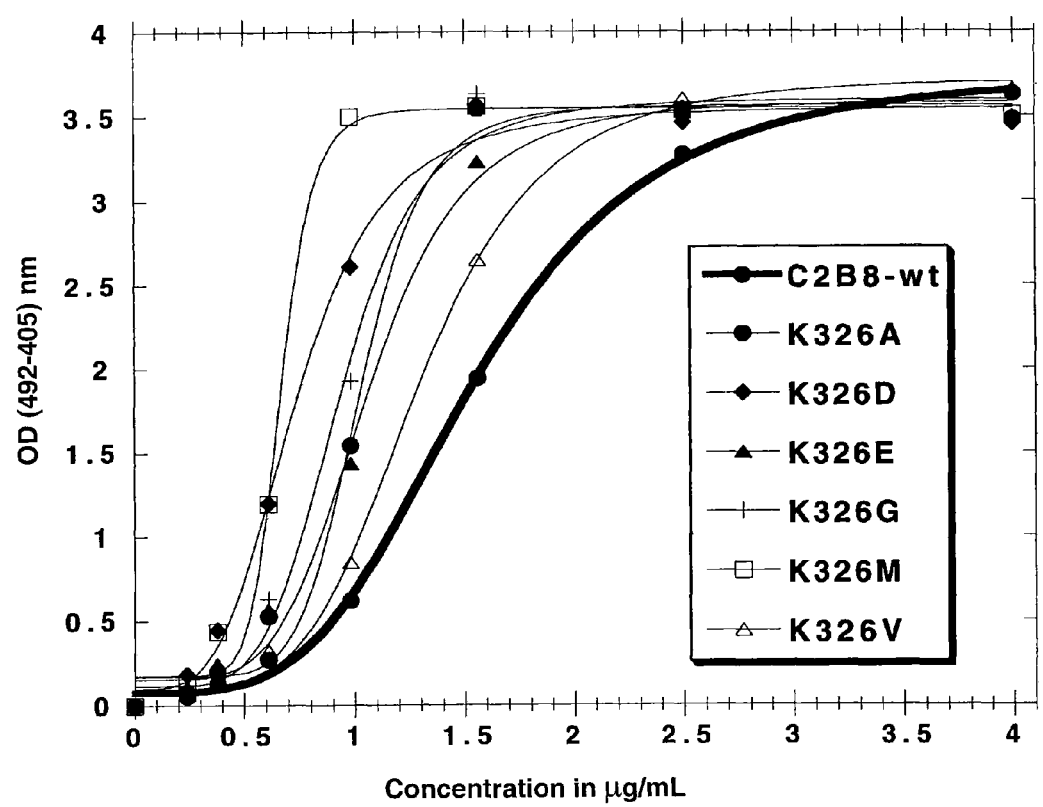
FIG. 9 shows C1q binding ELISA results obtained for wild type (wt) C2B8 and various variant antibodies as determined in Example 3.

With respect to K326, the other single point variants constructed were K326A, K326D, K326E, K326G, K326V, K326M and K326W. As shown in FIG. 9, these variants all bound to C1q with a better affinity than the wild type antibody. K326W, K326M, K326D and K326E showed at least a two-fold increase in binding to C1q (Table 5). Among the K326 variants, K326W had the best affinity for C1q.

TABLE 5

| Variant | EC$_{50}$ value |
|---|---|
| Wild type | 1.53 |
| K326V | 1.30 |
| K326A | 1.03 |
| K326E | 1.08 |
| K326G | 0.95 |
| K326D | 0.76 |
| K326M | 0.67 |
| K326W | 0.47 |
| E333S | 0.81 |
| E333A | 0.98 |
| E333G | 1.14 |
| E333V | 1.18 |
| E333D | 1.22 |
| E333Q | 1.52 |
| K334A | 1.07 |

Figure 10:
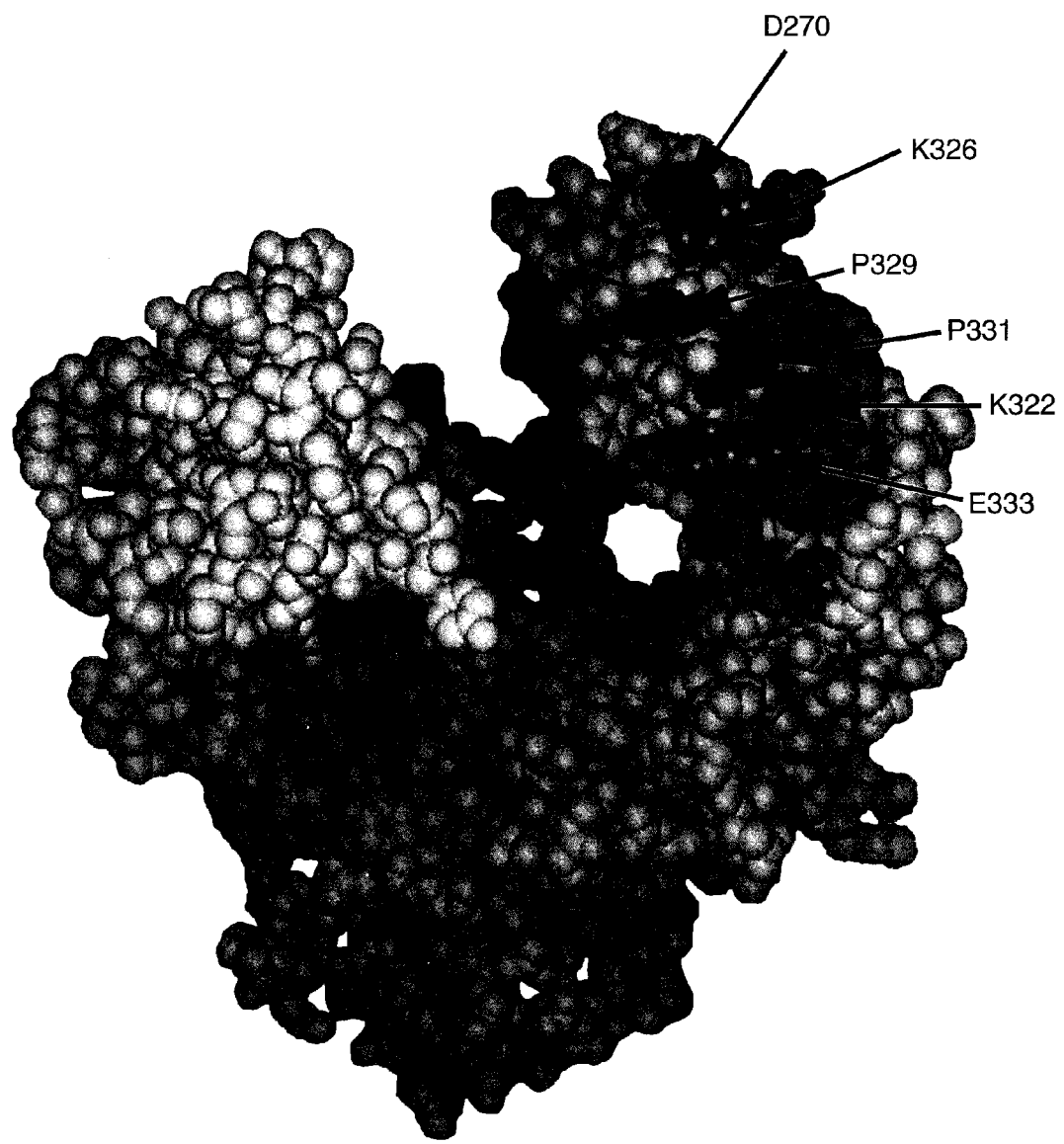
FIG. 10 depicts the three-dimensional structure of a human IgG Fc region, highlighting residues: Asp270, Lys326, Pro329, Pro331, Lys322 and Glu333.

Substitutions with hydrophobic as well as charged residues resulted in variants with increased binding to C1q. Even substitution with glycine which is known to impart flexibility to a chain and is well conserved in nature, resulted in a variant with higher affinity for C1q when compared to the wild type. It would appear that any amino acid substitution at this site would result in a variant with higher affinity for C1q. As assessed from the three-dimensional structure, K326 and E333 are in the vicinity of the core C1q binding sites (FIG. 10).

Figure 11:
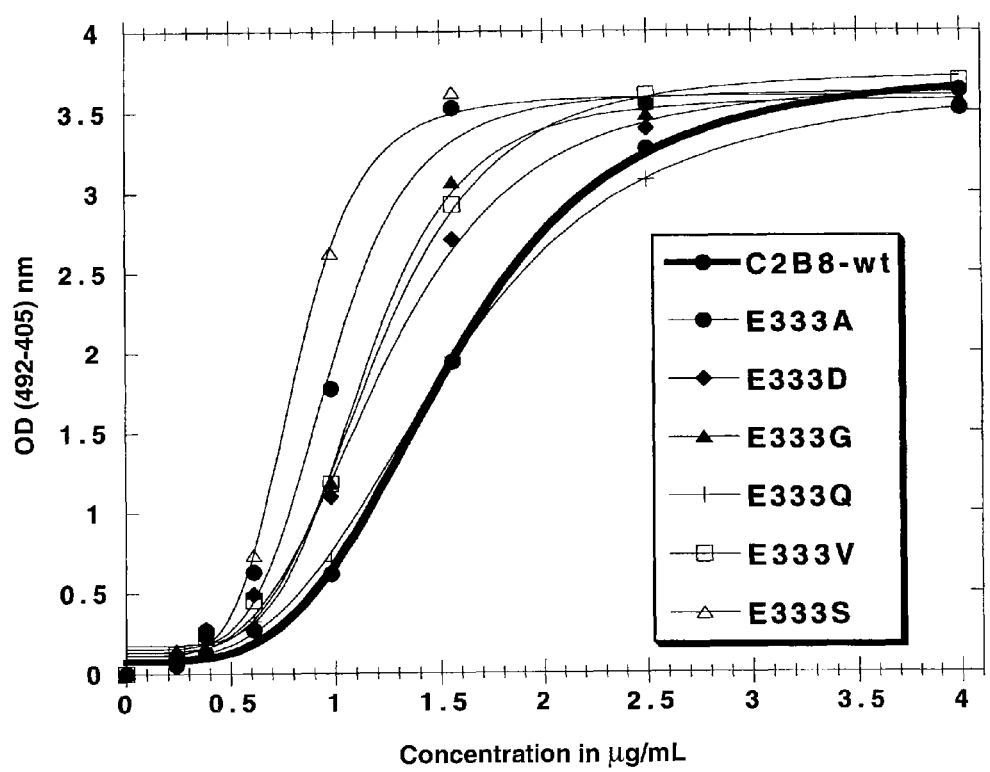
FIG. 11 shows C1q binding ELISA results obtained for wild type C2B8 and various variant antibodies as determined in Example 3.

In addition to alanine, E333 was also substituted with other amino acid residues. These variants, E333S, E333G, E333V, E333D, and E333Q, all had increased binding to C1q when compared to the wild type (FIG. 11). As shown in Table 5, the order of binding affinity for C1q was as follows: E333S>E333A>E333G>E333V>E333D>E333Q. Substitutions with amino acid residues with small side chain volumes, i.e. serine, alanine and glycine, resulted in variants with higher affinity for C1q in comparison to the other variants, E333V, E333D and E333Q, with larger side chain volumes. The variant E333S had the highest affinity for C1q, showing a two-fold increase in binding when compared to the wild type. Without being bound to any one theory, this indicates the effect on C1q binding at 333 may also be due in part to the polarity of the residue.

Figure 12:
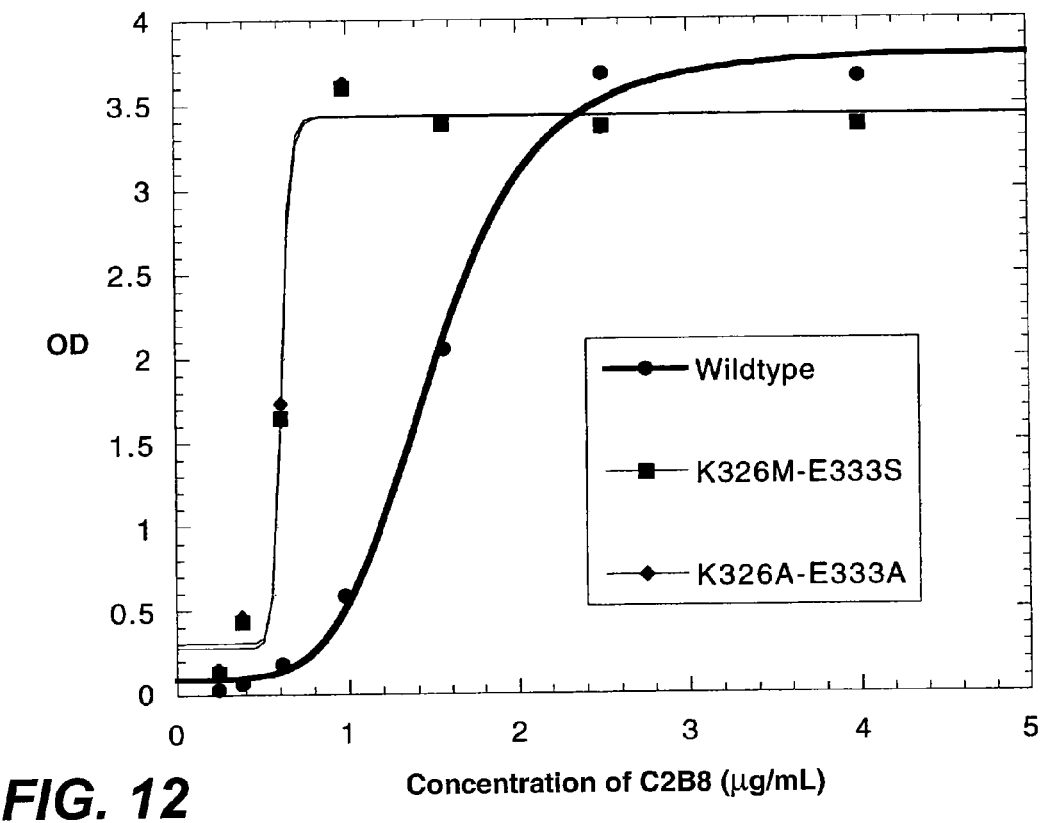
FIG. 12 shows C1q binding ELISA results obtained for wild type C2B8 and double variants, K326M-E333S and K326A-E333A.
Figure 13:
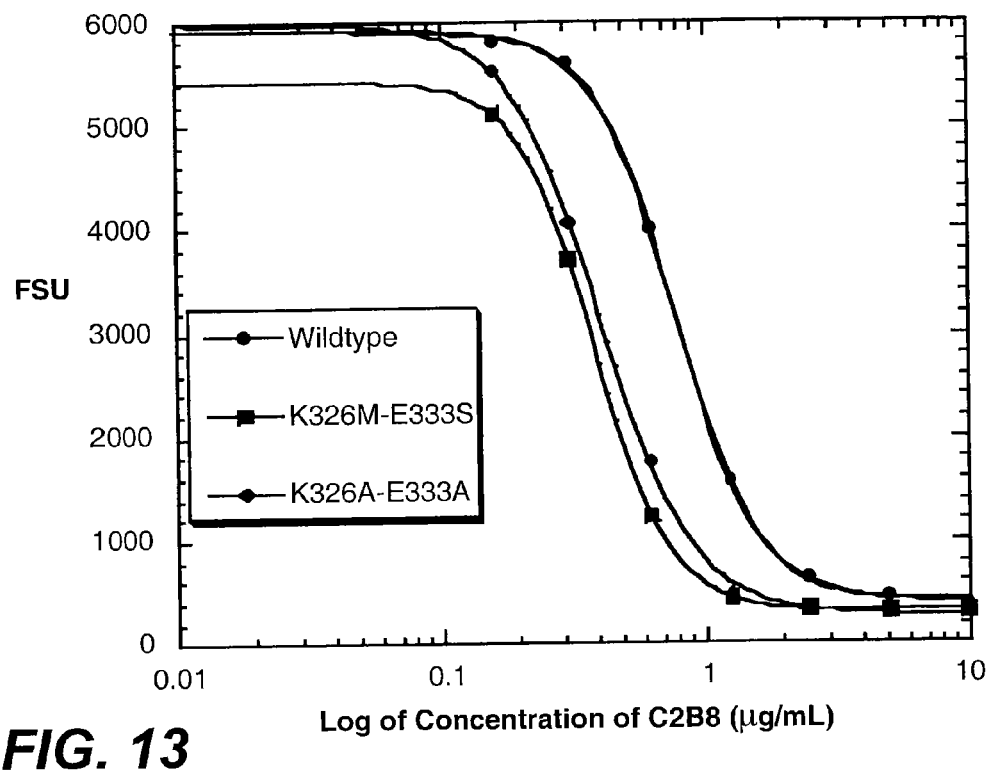
FIG. 13 shows CDC of wild type C2B8 and double variants, K326M-E333S and K326A-E333A.

Double variants were also generated. As shown in FIGS. 12 and 13, double variants K326M-E333S and K326A-E333A were at least three-fold better at binding human C1q than wild type C2B8 (FIG. 12) and at least two-fold better at mediating CDC compared to wild type C2B8 (FIG. 13). Additivity indicates these are independently acting variants.

Figure 14:
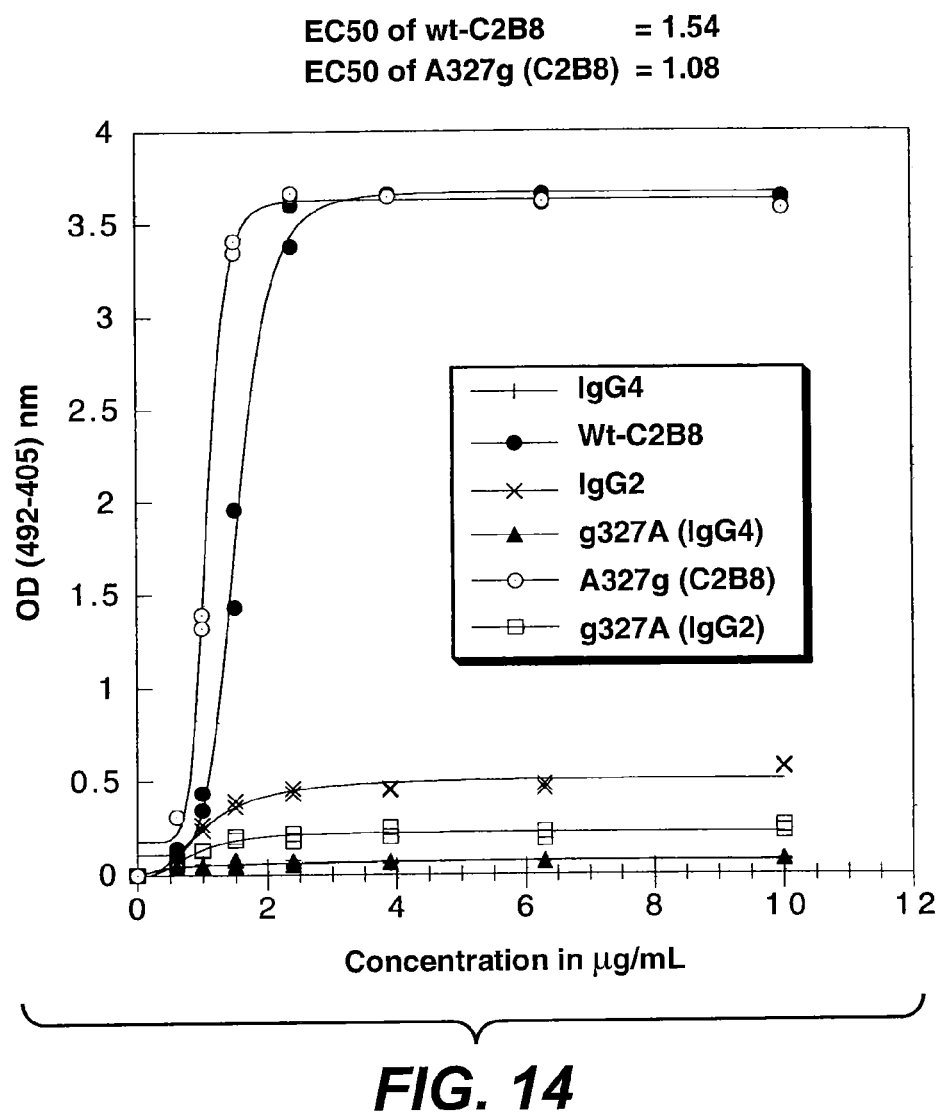
FIG. 14 depicts C1q binding ELISA results obtained for C2B8 with a human IgG4 (IgG4), wild type C2B8 (Wt-C2B8), C2B8 with a human IgG2 constant region (IgG2), and variant antibodies as described in Example 3.

As shown in FIG. 14, a further variant with improved C1q binding (50% increase) was made by changing A327 in a human IgG1 constant region to glycine. Conversely, in a human IgG2 constant region, changing G327 to alanine reduced C1q binding of the IgG2 antibody.

EXAMPLE 4

Identification of FcR Binding Sites in Human IgG Antibodies

In the present study, the effect of mutating various Fc region residues of an IgG1 antibody with respect to binding FcγRI, FcγRIIA, FcγRIIB and FcγRIIIA as well as FcRn was evaluated. Antibody variants with improved as well as diminished FcR binding were identified.

Materials and Methods

Construction of IgG1 Variants:

Recombinant anti-IgE E27 having the light chain and heavy chain sequences in FIGS. 4A and 4B, respectively, was used as the parent antibody in the following experiments. This antibody binds the antigen IgE and has a non-A allotype IgG1 Fc region. By site directed mutagenesis (Kunkel et al., *Proc. Natl. Acad. Sci. USA* 82:488 (1987)), variants of the Fc region in the heavy chain of the above parent antibody were constructed. The heavy and light chain plasmids were co-transfected into an adenovirus transformed human embryonic kidney cell line as previously described (Werther et al., *J. Immunol.* 157:4986 (1996)). The media was changed to serum-free 24 hours after transfection and the secreted antibody was harvested after five days. The antibodies were purified by Protein G SEPHAROSE® (Pharmacia), buffer exchanged and concentrated to 0.5 ml with PBS using a Centricon-30 (Amicon), and stored at 4° C. Concentration was determined by adsorption at 280 nm using extinction coefficients derived by amino acid composition analysis.

High Affinity FcγRIA Binding ELISA:

FcγRIA was expressed as a GST fusion of His6 tagged extracellular domain in 293 cells and purified by Ni-NTA column chromatography.

To purify FcγRIA, supernatant from transfected 293 cells was removed after three days. Protease inhibitors were added; 50 μL Aprotinin (Sigma)/50 mL supernatant, and PMSF (1 mM). Supernatants were concentrated to 10 mL in a stirred cell (Amicon), and dialyzed overnight at 4° C. against 1 liter column buffer (50 mM Tris pH 8.0, 20 mM Imidazole, 300 mM NaCl). Additional dialysis was done the following morning against fresh column buffer for 4 hours at 4° C. The solution was loaded on to a 1 mL $Ni^{++}$ column (NTA super flow resin, Qiagen) previously equilibrated with 10 mL column buffer. Columns were washed with 10 mL column buffer, and protein was eluted with 2.5 mL elution buffer (50 mM Tris pH 8.0, 250 mM Imidazole, 300 mM NaCl). Protein was concentrated to 0.5 mL and buffer exchanged into PBS. Concentrations were determined by adsorption at 280 nm using an extinction coefficient derived by amino acid composition analysis.

Purified receptors were coated onto Nunc F96 maxisorb plates (cat no. 439545) at approximately 150 ng per well by adding 100 μL of receptor at 1.5 μg/mL in PBS and incubated for 24 hours at 4° C. Prior to assay, plates were washed 3× with 250 μL of wash buffer (phosphate buffered saline pH 7.4 containing 0.5% TWEEN 20®) and blocked with 250 μL of assay buffer (50 mM tris buffered saline, 0.05% TWEEN 20®, 0.5% RIA grade bovine albumin (Sigma A7888), and 2 mM EDTA pH 7.4).

100 μL of E27 was added to the first four wells of the FcγRIA subunit coated plated at a concentration of 10 μg/mL. 80 μL of assay buffer was added to the next four well followed by 20 μL of the 10 μg/mL E27 IgG to give a final concentration of 2 μg/mL. Plates were incubated at 25° C. for 2 hours on an orbital shaker.

For detection, plates were washed 5× with wash buffer to remove unbound antibody. IgG binding to GST-FcγRIA was detected by adding 100 μL horse radish peroxidase (HRP) conjugated protein G (BIORAD) at 1:5000. HRP conjugates were incubated for 1.5 hours at 25° C. on an orbital shaker. Plates were washed ×5 with wash buffer to remove unbound HRP conjugate. Binding was detected by adding 100 μL of substrate solution (0.4 mg/mL o-phenylenediamine dihydrochloride, Sigma P6912, 6 mM $H_2O_2$ in PBS) and incubating for 10 minutes at 25° C. Enzymatic reaction was stopped by the addition of 100 μL of 4.5 N $H_2SO_4$ and colorimetric product was measured at 490 nm on a 96 well plate densitometer (Molecular Devices).

Binding of E27 variants at IgG concentration of 2 μg/mL was expressed as a ratio of wild type E27.

FcγRIA THP-1 Assay:

100 μL of E27 was added to the first three wells of a serocluster plate (Costar) at a concentration of 20 μg/mL in assay buffer (1×PBS, 0.1% BSA, 0.01% $NaN_3$). 92.5 μL of assay buffer was added to the next three wells followed by 7.5 μL of the 20 μg/mL E27 IgG to give a final concentration of 1.5 μg/mL. To each well, 100 μL of THP-1 cells were added at a concentration of 5 million cells/mL in FACS assay buffer. The plate is incubated on ice for 30 minutes For detection, cells were washed 2× with assay buffer to remove unbound antibody. IgG binding FcγRIA was detected by adding 100 μL FITC conjugated F(ab')$_2$ fragment of goat anti-human IgG heavy chain specific. (Jackson Immunoresearch) at 1:200. FITC conjugates were incubated with cells for 30 minutes on ice. Cells were washed ×3 with assay buffer to remove unbound FITC conjugate. Cells were stained with P.I. (SIGMA) at 2.5 μg/mL and analyzed by flow cytometry.

Binding of E27 variants at IgG concentration of 1.5 μg/mL was expressed as a ratio of wild type E27.

Data from the plate assay (FcγRIA ELISA) and cell-based assay (FcγRIA THP-1 assay) was averaged to arrive at an FcγRIA-binding activity.

Low Affinity FcγR Binding ELISAs:

FcγRIIA, FcγRIIB and FcγRIIIA binding ELISAs were performed as described in Example 1 above, with detection of the stable hexamer (consisting of three anti-IgE molecules and three IgE molecules).

Binding Values:

For all FcγR, binding values reported in Table 6 are the binding of each E27 variant relative to native E27, taken as ($A_{490\ nm\ variant}/A_{490\ nm\ native\ IgG1}$) at 0.33 or 1 μg/ml for FcγRII and FcγRIIIA and 2 μg/ml for FcγRI. A value greater than 1 denotes binding of the variant was improved compared to native IgG1 while a ratio less than 1 denotes reduced binding compared to native IgG1. Reduced binding to any given receptor was defined as a reduction of ≥40% compared to native IgG; better binding was defined as an improvement of ≥25% compared to native IgG 1. The latter was chosen based on the observation that variants with ≥25% improved binding in the ELISA-format assay, such as Glu333Ala, Lys334Ala and Ser298Ala, also showed improved efficacy in the cell-based binding and ADCC assays.

FcRn Binding ELISA:

For measuring FcRn binding activity of IgG variants, ELISA plates were coated with 2 μg/ml streptavidin (Zymed, South San Francisco) in 50 mM carbonate buffer, pH 9.6, at 4° C. overnight and blocked with PBS-0.5% BSA, pH 7.2 at room temperature for one hour. Biotinylated FcRn (prepared using biotin-X—NHS from Research Organics, Cleveland, Ohio and used at 1-2 μg/ml) in PBS-0.5% BSA, 0.05% polysorbate 20, pH 7.2, was added to the plate and incubated for one hour. Two fold serial dilutions of IgG standard (1.6-100 ng/ml) or variants in PBS-0.5% BSA, 0.05% polysorbate 20, pH 6.0, were added to the plate and Incubated for two hours. Bound IgG was detected using peroxidase labeled goat F(ab')$_2$ anti-human IgG F(ab')$_2$ in the above pH 6.0 buffer (Jackson ImmunoResearch, West Grove, Pa.) followed by 3,3',5,5'-tetramethyl benzidine (Kirgaard & Perry Laboratories) as the substrate. Plates were washed between steps with PBS-0.05% TWEEN 20® at either pH 7.2 or 6.0. Absorbance was read at 450 nm on a Vmax plate reader (Molecular Devices, Menlo Park, Calif.). Titration curves were fit with a four-parameter nonlinear regression curve-fitting program (KaleidaGraph, Synergy software, Reading, Pa.). Concentrations of IgG variants corresponding to the mid-point absorbance of the titration curve of the standard were calculated and then divided by the concentration of the standard corresponding to the mid-point absorbance of the standard titration curve.

In Vitro ADCC Assay:

To prepare chromium 51-labeled target cells, tumor cell lines were grown in tissue culture plates and harvested using sterile 10 mM EDTA in PBS. SK-BR-3 cells, a 3+ HER2-overexpressing human breast cancer cell line, were used as targets in all assays. The detached cells were washed twice with cell culture medium. Cells ($5 \times 10^6$) were labeled with 200 µCi of chromium51 (New England Nuclear/DuPont) at 37° C. for one hour with occasional mixing. Labeled cells were washed three times with cell culture medium, then were resuspended to a concentration of $1 \times 10^5$ cells/mL. Cells were used either without opsonization, or were opsonized prior to the assay by incubation with rhuMAb HER2 wildtype (HERCEPTIN®) or seven Fc mutants (G14 D265A; G18 D270A; G17 E269A; G36 S298A; G30 K290A; G31 R292A; and G34 Q295A) at 100 ng/mL and 1.25 ng/mL in PBMC assay or 20 ng/mL and 1 ng/mL in NK assay.

Peripheral blood mononuclear cells (PBMCs) were prepared by collecting blood on heparin from normal healthy donors and dilution with an equal volume of phosphate buffered saline (PBS). The blood was then layered over LYMPHOCYTE SEPARATION MEDIUM® (LSM: Organon Teknika) and centrifuged according to the manufacturer's instructions. Mononuclear cells were collected from the LSM-plasma interface and were washed three times with PBS. Effector cells were suspended in cell culture medium to a final concentration of $1 \times 10^7$ cells/mL.

After purification through LSM, natural killer (NK) cells were isolated from PBMCs by negative selection using an NK cell isolation kit and a magnetic column (Miltenyi Biotech) according to the manufacturer's instructions. Isolated NK cells were collected, washed and resuspended in cell culture medium to a concentration of $2 \times 10^6$ cells/mL. The identity of the NK cells was confirmed by flow cytometric analysis.

Varying effector:target ratios were prepared by serially diluting the effector (either PBMC or NK) cells two-fold along the rows of a microtiter plate (100 µL final volume) in cell culture medium. The concentration of effector cells ranged from $1.0 \times 10^7$/mL to $2.0 \times 10^4$/mL for PBMC and from $2.0 \times 10^6$/mL to $3.9 \times 10^3$/mL for NK. After titration of effector cells, 100 µL of chromium 51-labeled target cells (opsonized or nonoponsonized) at $1 \times 10^5$ cells/mL were added to each well of the plate. This resulted in an initial effector:target ratio of 100:1 for PBMC and 20:1 for NK cells. All assays were run in duplicate, and each plate contained controls for both spontaneous lysis (no effector cells) and total lysis (target cells plus 100 µL) 1% sodium dodecyl sulfate, 1 N sodium hydroxide). The plates were incubated at 37° C. for 18 hours, after which the cell culture supernatants were harvested using a supernatant collection system (Skatron Instrument, Inc.) and counted in a Minaxi auto-gamma 5000 series gamma counter (Packard) for one minute. Results were then expressed as percent cytotoxicity using the formula: % Cytotoxicity= (sample cpm-spontaneous lysis)/(total lysis-spontaneous lysis)×100. Four-parameter curve-fitting was then used to evaluate the data (KaleidaGraph 3.0.5).

RESULTS

A variety of antibody variants were generated which had FcR binding activity that differed from the parent antibody. The FcR binding data for the variants generated is shown in Tables 6 and 7 below. An additional variant, T307Q, also displayed improved FcRn binding compared to E27 parent antibody.

TABLE 6

Binding of Human IgG1 Variants to Human FcRn and FcγR

| Variant[a] | FcRn[b] | | | FcγRI | | | FcγRIIA | | FcγRIIB | | FcγRIIIA | | |
|---|---|---|---|---|---|---|---|---|---|---|---|---|---|
| | mean | (sd) | N | mean | (sd) | N | mean | (sd) | mean | (sd) | mean | sd | N[c] |
| Class 1 = Reduced binding to all FcγR | | | | | | | | | | | | | |
| Glu233Pro Leu234Val Leu235Ala Gly236deleted | 0.54 | (0.20) | 3 | 0.12 | (0.06) | 6 | 0.08 | (0.01) | 0.12 | (0.01) | 0.04 | (0.02) | 2 |
| Pro238Ala | 1.49 | (0.17) | 3 | 0.60 | (0.05) | 5 | 0.38 | (0.14) | 0.36 | (0.15) | 0.07 | (0.05) | 4 |
| Asp265Ala | 1.23 | (0.14) | 4 | 0.16 | (0.05) | 9 | 0.07 | (0.01) | 0.13 | (0.05) | 0.09 | (0.06) | 4 |
| Asn297Ala | 0.80 | (0.18) | 8 | 0.15 | (0.06) | 7 | 0.05 | (0.00) | 0.10 | (0.02) | 0.03 | (0.01) | 3 |
| Ala327Gln | 0.97 | | | 0.60 | (0.12) | 9 | 0.13 | (0.03) | 0.14 | (0.03) | 0.06 | (0.01) | 4 |
| Pro329Ala | 0.80 | | | 0.48 | (0.10) | 6 | 0.08 | (0.02) | 0.12 | (0.08) | 0.21 | (0.03) | 4 |
| Class 2 = Reduced binding to FcγRII and FcγRIIIA | | | | | | | | | | | | | |
| Asp270Ala | 1.05 | | | 0.76 | (0.12) | 6 | 0.06 | (0.02) | 0.10 | (0.06) | 0.14 | (0.04) | 6 |
| Gln295Ala | 0.79 | | | 1.00 | (0.11) | 4 | 0.62 | (0.20) | 0.50 | (0.24) | 0.25 | (0.09) | 5 |
| Ala327Ser | | | | 0.86 | (0.03) | 4 | 0.23 | (0.06) | 0.22 | (0.05) | 0.06 | (0.01) | 4 |
| Class 3 = Improved binding to FcγRII and FcγRIIIA | | | | | | | | | | | | | |
| Thr256Ala | 1.91 | (0.43) | 6 | 1.01 | (0.07) | 5 | 1.41 | (0.27) | 2.06 | (0.66) | 1.32 | (0.18) | 9 |
| Lys290Ala | 0.79 | (0.14) | 3 | 1.01 | (0.06) | 11 | 1.30 | (0.21) | 1.38 | (0.17) | 1.31 | (0.19) | 9 |
| Class 4 = Improved binding to FcγRII and no effect on FcγRIIIA | | | | | | | | | | | | | |
| Arg255Ala | 0.59 | (0.19) | 4 | 0.99 | (0.12) | 7 | 1.30 | (0.20) | 1.59 | (0.42) | 0.98 | (0.18) | 5 |
| Glu258Ala | 1.18 | | | 1.18 | (0.13) | 4 | 1.33 | (0.22) | 1.65 | (0.38) | 1.12 | (0.12) | 5 |
| Ser267Ala | 1.08 | | | 1.09 | (0.08) | 10 | 1.52 | (0.22) | 1.84 | (0.43) | 1.05 | (0.24) | 11 |
| Glu272Ala | 1.34 | (0.24) | 4 | 1.05 | (0.06) | 7 | 1.23 | (0.12) | 1.53 | (0.22) | 0.80 | (0.18) | 6 |
| Asn276Ala | 1.15 | (0.21) | 3 | 1.05 | (0.14) | 4 | 1.29 | (0.20) | 1.34 | (0.40) | 0.95 | (0.04) | 4 |

TABLE 6-continued

Binding of Human IgG1 Variants to Human FcRn and FcγR

| Variant[a] | FcRn[b] mean | (sd) | N | FcγRI mean | (sd) | N | FcγRIIA mean | (sd) | FcγRIIB mean | (sd) | FcγRIIIA mean | sd | N[c] |
|---|---|---|---|---|---|---|---|---|---|---|---|---|---|
| Asp280Ala | 0.82 | | | 1.04 | (0.08) | 10 | 1.34 | (0.14) | 1.60 | (0.31) | 1.09 | (0.20) | 10 |
| His285Ala | 0.85 | | | 0.96 | (0.07) | 4 | 1.26 | (0.12) | 1.23 | (0.15) | 0.87 | (0.04) | 4 |
| Asn286Ala | 1.24 | (0.04) | 2 | 0.95 | (0.18) | 16 | 1.24 | (0.23) | 1.36 | (0.15) | 1.05 | (0.04) | 6 |
| Thr307Ala | 1.81 | (0.32) | 6 | 0.99 | (0.14) | 4 | 1.07 | (0.15) | 1.27 | (0.24) | 1.09 | (0.18) | 10 |
| Leu309Ala | 0.63 | (0.18) | 4 | 0.93 | (0.18) | 6 | 1.13 | (0.08) | 1.26 | (0.12) | 1.07 | (0.20) | 3 |
| Asn315Ala | 0.76 | (0.14) | 3 | 0.99 | (0.16) | 6 | 1.15 | (0.06) | 1.30 | (0.17) | 1.07 | (0.21) | 5 |
| Lys326Ala | 1.03 | | | 1.03 | (0.05) | 10 | 1.23 | (0.09) | 1.41 | (0.27) | 1.23 | (0.23) | 7 |
| Pro331Ala | 0.85 | | | 1.01 | (0.09) | 7 | 1.29 | (0.14) | 1.34 | (0.35) | 1.08 | (0.19) | 4 |
| Ser337Ala | 1.03 | | | 1.17 | (0.23) | 3 | 1.22 | (0.30) | 1.26 | (0.06) | 0.94 | (0.18) | 4 |
| Ala378Gln | 1.32 | (0.13) | 3 | 1.06 | (0.05) | 3 | 1.40 | (0.17) | 1.45 | (0.17) | 1.19 | (0.17) | 5 |
| Glu430Ala | 0.93 | (0.03) | 2 | 1.05 | (0.02) | 3 | 1.24 | (0.11) | 1.28 | (0.10) | 1.20 | (0.18) | 5 |
| Class 5 = Improved binding to FcγRII and reduced binding to FcγRIIIA | | | | | | | | | | | | | |
| His268Ala | 1.02 | (0.22) | 3 | 1.09 | (0.11) | 8 | 1.21 | (0.14) | 1.44 | (0.22) | 0.54 | (0.12) | 13 |
| Arg301Ala | 0.86 | | | 1.06 | (0.10) | 4 | 1.14 | (0.13) | 1.29 | (0.16) | 0.22 | (0.08) | 7 |
| Lys322Ala | 0.98 | | | 0.94 | (0.04) | 9 | 1.17 | (0.11) | 1.28 | (0.21) | 0.62 | (0.12) | 6 |
| Class 6 = Reduced binding to FcγRII and no effect on FcγRIIIA | | | | | | | | | | | | | |
| Arg292Ala | 0.81 | (0.18) | 4 | 0.95 | (0.05) | 8 | 0.27 | (0.13) | 0.17 | (0.07) | 0.89 | (0.17) | 10 |
| Lys414Ala | 1.02 | | | 1.00 | (0.04) | 3 | 0.64 | (0.15) | 0.58 | (0.18) | 0.82 | (0.27) | 3 |
| Class 7 = Reduced binding to FcγRII and improved binding to FcγRIIIA | | | | | | | | | | | | | |
| Ser298Ala | 0.80 | | | 1.11 | (0.03) | 9 | 0.40 | (0.15) | 0.23 | (0.13) | 1.34 | (0.20) | 16 |
| Class 8 = No effect on FcγRII and reduced binding to FcγRIIIA | | | | | | | | | | | | | |
| Ser239Ala | 1.06 | | | 0.81 | (0.09) | 7 | 0.73 | (0.25) | 0.76 | (0.36) | 0.26 | (0.08) | 3 |
| Glu269Ala | 1.05 | | | 0.61 | (0.14) | 9 | 0.65 | (0.18) | 0.75 | (0.29) | 0.45 | (0.13) | 5 |
| Glu293Ala | 0.85 | | | 1.11 | (0.07) | 4 | 1.08 | (0.19) | 1.07 | (0.20) | 0.31 | (0.13) | 6 |
| Tyr296Phe | 0.79 | | | 1.03 | (0.09) | 8 | 0.97 | (0.23) | 0.86 | (0.17) | 0.55 | (0.12) | 6 |
| Val303Ala | 1.26 | (0.21) | 3 | 0.91 | (0.11) | 5 | 0.86 | (0.10) | 0.65 | (0.17) | 0.33 | (0.09) | 8 |
| Ala327Gly | | | | 0.96 | (0.01) | 3 | 0.92 | (0.09) | 0.83 | (0.10) | 0.36 | (0.05) | 3 |
| Lys338Ala | 1.14 | | | 0.90 | (0.05) | 3 | 0.78 | (0.09) | 0.63 | (0.08) | 0.15 | (0.01) | 2 |
| Asp376Ala | 1.45 | (0.36) | 4 | 1.00 | (0.05) | 3 | 0.80 | (0.16) | 0.68 | (0.14) | 0.55 | (0.10) | 5 |
| Class 9 = No effect on FcγRII and improved binding to FcγRIIIA | | | | | | | | | | | | | |
| Glu333Ala | 1.03 | (0.01) | 2 | 0.98 | (0.15) | 5 | 0.92 | (0.12) | 0.76 | (0.11) | 1.27 | (0.17) | 10 |
| Lys334Ala | 1.05 | (0.03) | 2 | 1.06 | (0.06) | 11 | 1.01 | (0.15) | 0.90 | (0.12) | 1.39 | (0.19) | 16 |
| Ala339Thr | | | | 1.06 | (0.04) | 6 | 1.09 | (0.03) | 1.20 | (0.03) | 1.34 | (0.09) | 2 |
| Class 10 = Effect only FcRn | | | | | | | | | | | | | |
| Ile253Ala | 0.10 | | | 0.96 | (0.05) | 4 | 1.14 | (0.02) | 1.18 | (0.06) | 1.08 | (0.14) | 3 |
| Ser254Ala | <0.10 | | | 0.96 | (0.08) | 4 | 0.97 | (0.24) | 1.15 | (0.38) | 0.73 | (0.14) | 3 |
| Lys288Ala | 0.38 | (0.12) | 5 | 0.88 | (0.15) | 15 | 1.15 | (0.26) | 1.14 | (0.20) | 1.06 | (0.04) | 4 |
| Val305Ala | 1.46 | (0.48) | 6 | 1.04 | (0.19) | 10 | 1.12 | (0.12) | 1.23 | (0.22) | 0.84 | (0.15) | 4 |
| Gln311Ala | 1.62 | (0.25) | 4 | 0.93 | (0.05) | 4 | 1.11 | (0.06) | 1.19 | (0.13) | 0.93 | (0.17) | 3 |
| Asp312Ala | 1.50 | (0.06) | 4 | 1.01 | (0.12) | 5 | 1.20 | (0.24) | 1.19 | (0.07) | 1.23 | (0.14) | 3 |
| Lys317Ala | 1.44 | (0.18) | 4 | 0.92 | (0.17) | 6 | 1.13 | (0.05) | 1.18 | (0.27) | 1.10 | (0.23) | 4 |
| Lys360Ala | 1.30 | (0.08) | 4 | 1.02 | (0.04) | 3 | 1.12 | (0.10) | 1.12 | (0.08) | 1.23 | (0.16) | 6 |
| Gln362Ala | 1.25 | (0.24) | 3 | 1.00 | (0.04) | 3 | 1.03 | (0.10) | 1.02 | (0.03) | 1.03 | (0.16) | 4 |
| Glu380Ala | 2.19 | (0.29) | 6 | 1.04 | (0.06) | 3 | 1.18 | (0.01) | 1.07 | (0.05) | 0.92 | (0.12) | 2 |
| Glu382Ala | 1.51 | (0.18) | 4 | 1.06 | (0.03) | 3 | 0.95 | (0.11) | 0.84 | (0.04) | 0.76 | (0.17) | 3 |
| Ser415Ala | 0.44 | | | 1.04 | (0.03) | 3 | 0.90 | (0.11) | 0.88 | (0.05) | 0.86 | (0.18) | 2 |
| Ser424Ala | 1.41 | (0.14) | 3 | 0.98 | (0.03) | 3 | 1.04 | (0.06) | 1.02 | (0.02) | 0.88 | (0.09) | 2 |
| His433Ala | 0.41 | (0.14) | 2 | 0.98 | (0.03) | 3 | 0.92 | (0.18) | 0.79 | (0.18) | 1.02 | (0.15) | 3 |
| Asn434Ala | 3.46 | (0.37) | 7 | 1.00 | (0.04) | 3 | 0.96 | (0.06) | 0.97 | (0.12) | 0.77 | (0.13) | 6 |
| His435Ala | <0.10 | | 4 | 1.25 | (0.09) | 3 | 0.77 | (0.05) | 0.72 | (0.05) | 0.78 | (0.03) | 3 |
| Tyr436Ala | <0.10 | | 2 | 0.99 | (0.02) | 2 | 0.93 | (0.05) | 0.91 | (0.06) | 0.91 | (0.15) | 3 |

[a]Residue numbers are according to the Eu numbering system (Kabat et al. (1991)). Variants that had no effect on binding (i.e. did not reduce binding by more than 60% or improve binding by more than 20%) to FcγR or FcRn were: Lys246, Lys248, Asp249, Met252, Thr260, Lys274, Tyr278, Val282, Glu283, Thr289, Glu294, Tyr300Phe, Glu318, Lys320, Ser324, Ala330Gln, Thr335, Lys340, Gln342, Arg344, Glu345, Gln347, Arg355, Glu356, Met358, Thr359, Lys360, Asn361, Tyr373, Ser375, Ser383, Asn384, Gln386, Glu388, Asn389, Asn390, Tyr391Phe, Lys392, Leu398, Ser400, Asp401, Asp413, Arg416, Gln418, Gln419, Asn421, Val422, Thr437, Gln438, Lys439, Ser440, Ser442, Ser444, Lys447.
[b]Values are the ratio of binding of the variant to that of native IgG1 at 0.33 or 1 μg/ml. A value greater than 1 denotes binding of the variant was improved compared to native IgG1 while a ratio less than 1 denotes reduced binding compared to native IgG1. Reduced binding to any given receptor was defined as a reduction of ≥40% compared to native IgG; better binding was defined as an improvement of ≥25% compared to native IgG1.
[c]Number of independent assays for FcγRIIA, FcγRIIB and FcγRIIIA. At least two separately expressed and purified lots of each variant were assayed.

Aside from alanine variants, various non-alanine substitution variants were made, and the FcR binding activity of those variants is summarized in the following table.

TABLE 7

| | | FcRn | | | FcγRI | | | FcγRIIA[a] | | FcγRIIB | | FcγRIIIA | | |
|---|---|---|---|---|---|---|---|---|---|---|---|---|---|---|
| IG2 | Res#EU (Kabat) | mean | sd | n | mean | sd | n | mean | sd | mean | sd | mean | sd | |
| 222 | D249(262)E | | | | | | | 0.97 | | 0.99 | | 0.84 | | n = 1[b] |
| 176 | T256(269)G | | | | | | | 1.10 | (0.03) | 1.06 | (0.07) | 0.96 | (0.27) | n = 2 |
| 254 | T256(269)N | | | | | | | 1.03 | | 0.89 | | 1.13 | | n = 1 |
| 157 | D265(278)N | | | | | | | 0.02 | (0.01) | 0.03 | (0.01) | 0.02 | (0.01) | n = 3 |
| 158 | D265(278)E | | | | | | | 0.11 | (0.04) | 0.03 | (0.01) | 0.02 | (0.01) | n = 3 |
| 189 | S267(280)G | | | | | | R131 | 1.18 | (0.10) | 0.95 | (0.16) | 0.08 | (0.02) | n = 4 |
| | | | | | | | H131 | 0.59 | (0.09) | | | | | n = 3 |
| 84 | H268(281)N | | | | | | | 1.33 | | 1.41 | | 0.56 | | n = 1 |
| 85 | H268(281)S | | | | | | | 1.35 | | 1.38 | | 0.81 | | n = 1 |
| 87 | H268(281)Y | | | | | | | 1.19 | | 1.29 | | 0.76 | | n = 1 |
| 168 | E269(282)D | | | | | | | 0.89 | (0.10) | 0.73 | (0.07) | 1.13 | (0.21) | n = 2 |
| 169 | E269(282)Q | | | | | | | 0.08 | (0.01) | 0.16 | (0.00) | 0.28 | (0.03) | n = 2 |
| 92 | D270(283)N | | | | | | | 0.03 | (0.02) | 0.05 | (0.05) | 0.04 | (0.03) | n = 5 |
| 93 | D270(283)E | | | | | | | 0.08 | (0.01) | 0.06 | (0.01) | 0.90 | (0.17) | n = 3 |
| 223 | E272(285)Q | | | | | | | 1.93 | | 1.81 | | 0.82 | | n = 1 |
| 224 | E272(285)N | | | | | | | 0.43 | | 0.23 | | 0.50 | | n = 1 |
| 167 | K274(287)Q | | | | | | | 0.86 | | 0.94 | | 0.62 | | n = 1 |
| 165 | N276(289)K | | | | | | | 0.81 | | 0.77 | | 0.61 | | n = 1 |
| 233 | N276(289)Q | | | | | | | 1.09 | | 0.79 | | 0.91 | | n = 1 |
| 79 | D280(295)N | | | | | | | 1.07 | (0.18) | 1.22 | (0.19) | 1.16 | (0.21) | n = 6 |
| 149 | D280(295)S | | | | | | | 1.07 | (0.06) | 1.04 | (0.08) | 1.09 | (0.06) | n = 2 |
| 226 | E283(300)Q | | | | | | | 1.12 | | 1.24 | | 1.19 | | n = 1 |
| 227 | E283(300)S | | | | | | | 1.03 | | 1.07 | | 0.85 | | n = 1 |
| 228 | E283(300)N | | | | | | | 1.18 | | 1.28 | | 0.94 | | n = 1 |
| 229 | E283(300)D | | | | | | | 1.14 | | 1.23 | | 0.95 | | n = 1 |
| 23 | N286(303)Q | | | | | | | 1.52 | | 1.13 | | 0.96 | | n = 1 |
| 237 | N286(303)S | | | | | | | 1.72 | | 1.38 | | 1.32 | | n = 1 |
| 238 | N286(303)D | | | | | | | 1.41 | | 1.23 | | 0.98 | | n = 1 |
| 73 | K290(307)Q | | | | | | | 1.17 | | 1.26 | | 1.40 | | n = 1 |
| 75 | K290(307)S | | | | | | | 1.27 | | 1.34 | | 1.26 | | n = 1 |
| 77 | K290(307)E | | | | 1.14 | | | 1.10 | | 1.20 | | 1.30 | | n = 1 |
| 78 | K290(307)R | | | | 1.25 | | | 1.05 | | 1.15 | | 1.08 | | n = 1 |
| 177 | K290(307)G | | | | | | | 1.07 | | 1.21 | | 1.23 | | n = 1 |
| 80 | R292(309)K | | | | | | | 0.71 | (0.17) | 0.75 | (0.10) | 1.15 | (0.18) | n = 3 |
| 81 | R292(309)H | | | | | | | 0.21 | (0.09) | 0.12 | (0.01) | 0.92 | (0.08) | n = 2 |
| 82 | R292(309)Q | | | | | | | 0.47 | (0.12) | 0.25 | (0.06) | 0.45 | (0.09) | n = 3 |
| 83 | R292(309)N | | | | | | | 0.54 | (0.16) | 0.29 | (0.07) | 0.88 | (0.02) | n = 3 |
| 144 | E293(310)Q | | | | | | | 0.85 | (0.03) | 0.77 | (0.13) | 0.99 | (0.04) | n = 2 |
| 145 | E293(310)D | | | | | | | 0.90 | (0.02) | 0.88 | (0.07) | 0.37 | (0.07) | n = 3 |
| 147 | E293(310)K | | | | | | | 1.13 | (0.04) | 1.31 | (0.17) | 0.72 | (0.08) | n = 4 |
| 173 | E294(311)Q | | | | | | | 1.01 | | 0.95 | | 0.84 | | n = 1 |
| 174 | E294(311)D | | | | | | | 0.37 | | 0.26 | | 0.14 | | n = 1 |
| 185 | Y296(313)H | | | | | | | 0.90 | | 0.81 | | 0.92 | | n = 1 |
| 186 | Y296(313)W | | | | | | | 0.96 | | 0.93 | | | | n = 1 |
| 70 | S298(317)G | | | | | | | 0.87 | (0.17) | 0.63 | (0.33) | 0.46 | (0.09) | n = 4 |
| 71 | S298(317)T | | | | | | | 0.29 | (0.19) | 0.27 | (0.19) | 0.73 | (0.21) | n = 6 |
| 72 | S298(317)N | | | | | | | 0.05 | (0.03) | 0.08 | (0.08) | 0.06 | (0.03) | n = 5 |
| 218 | S298(317)V | | | | | | | 0.11 | (0.06) | 0.17 | (0.01) | 0.33 | (0.19) | n = 3 |
| 219 | S298(317)L | | | | | | | 1.14 | (0.12) | 1.42 | (0.31) | 0.34 | (0.04) | n = 3 |
| 150 | V303(322)L | | | | | | | 0.89 | (0.05) | 0.73 | (0.10) | 0.76 | (0.09) | n = 4 |
| 151 | V303(322)T | | | | | | | 0.64 | (0.11) | 0.34 | (0.05) | 0.20 | (0.05) | n = 4 |
| 217 | E318(337)K | | | | | | | 1.03 | | 1.08 | | 0.72 | | n = 1 |
| 172 | K320(339)R | | | | | | | 0.71 | | 0.66 | | 0.68 | | n = 1 |
| 202 | K320(339)M | | | | | | | 1.34 | | 1.40 | | 1.27 | | n = 1 |
| 204 | K320(339)Q | | | | | | | 1.23 | | 1.12 | | 1.17 | | n = 1 |
| 205 | K320(339)E | | | | | | | 1.29 | | 1.34 | | 1.12 | | n = 1 |
| 235 | K320(339)R | | | | | | | 1.24 | | 0.95 | | 0.86 | | n = 1 |
| 155 | K322(341)R | | | | | | | 0.87 | (0.07) | 0.87 | (0.21) | 0.92 | (0.15) | n = 3 |
| 156 | K322(341)Q | | | | | | | 0.87 | (0.02) | 0.92 | (0.23) | 0.78 | (0.18) | n = 3 |
| 206 | K322(341)E | | | | | | | 1.38 | | 1.34 | | 0.81 | | n = 1 |
| 207 | K322(341)N | | | | | | | 0.57 | | 0.36 | | 0.04 | | n = 1 |
| 213 | S324(343)N | | | | | | | 1.15 | | 1.09 | | 0.97 | | n = 1 |
| 214 | S324(343)Q | | | | | | | 0.82 | | 0.83 | | 0.78 | | n = 1 |
| 215 | S324(343)K | | | | | | | 0.66 | | 0.37 | | 0.77 | | n = 1 |
| 216 | S324(343)E | | | | | | | 0.82 | | 0.73 | | 0.81 | | n = 1 |
| 208 | K326(345)S | | | | | | | 1.44 | | 1.62 | | 1.37 | | n = 1 |
| 209 | K326(345)N | | | | | | | 1.04 | | 1.00 | | 1.27 | | n = 1 |
| 210 | K326(345)Q | | | | | | | 1.36 | | 1.41 | | 1.15 | | n = 1 |
| 211 | K326(345)D | | | | | | | 1.68 | | 2.01 | | 1.36 | | n = 1 |
| 212 | K326(345)E | | | | | | | 1.34 | (0.27) | 1.47 | (0.33) | 1.26 | (0.04) | n = 2 |
| 131 | A327(346)S | | | | | | | 0.23 | (0.06) | 0.22 | (0.05) | 0.06 | (0.01) | n = 4 |
| 159 | A327(346)G | | | | | | | 0.92 | (0.09) | 0.83 | (0.10) | 0.36 | (0.05) | n = 3 |
| 196 | A330(349)D | | | | | | | 0.18 | | 0.08 | | 0.07 | | n = 1 |
| 197 | A330(349)K | | | | | | | 1.28 | | 1.25 | | 1.28 | | n = 1 |

TABLE 7-continued

NON-ALANINE VARIANTS

| Res#EU | | FcRn | | | FcγRI | | | FcγRIIA[a] | | FcγRIIB | | FcγRIIIA | | |
|---|---|---|---|---|---|---|---|---|---|---|---|---|---|---|
| IG2 | (Kabat) | mean | sd | n | mean | sd | n | mean | sd | mean | sd | mean | sd | |
| 198 | P331(350)S | | | | | | | 0.91 | (0.08) | 0.78 | (0.07) | 0.58 | (0.19) | n = 4 |
| 199 | P331(350)N | | | | | | | 0.86 | | 0.65 | | 0.23 | | n = 1 |
| 200 | P331(350)E | | | | | | | 1.06 | | 0.91 | | 0.42 | | n = 1 |
| 203 | P331(350)K | | | | | | | 0.94 | | 0.71 | | 0.33 | | n = 1 |
| 141 | E333(352)Q | | | | | | | 0.70 | (0.05) | 0.64 | (0.09) | 1.05 | (0.09) | n = 3 |
| 142 | E333(352)N | | | | | | | 0.59 | (0.04) | 0.52 | (0.07) | 0.56 | (0.10) | n = 4 |
| 143 | E333(352)S | | | | | | | | | | | 0.94 | | n = 1 |
| 152 | E333(352)K | | | | | | | | | | | 0.85 | (0.14) | n = 3 |
| 153 | E333(352)R | | | | | | | 0.75 | (0.04) | 0.66 | (0.03) | 0.84 | (0.05) | n = 2 |
| 154 | E333(352)D | | | | | | | | | | | 1.26 | (0.04) | n = 3 |
| 178 | E333(352)G | | | | | | | 0.87 | | 0.76 | | 1.05 | | n = 1 |
| 179 | K334(353)G | | | | | | | 0.76 | (0.08) | 0.60 | (0.13) | 0.88 | (0.22) | n = 5 |
| 135 | K334(353)R | | | | | | | 1.15 | (0.09) | 1.33 | (0.18) | 0.68 | (0.07) | n = 5 |
| 136 | K334(353)Q | | | | | | | 1.08 | (0.11) | 1.10 | (0.21) | 1.23 | (0.08) | n = 7 |
| 137 | K334(353)N | | | | | | | 1.16 | (0.11) | 1.29 | (0.30) | 1.11 | (0.12) | n = 8 |
| 138 | K334(353)S | | | | | | | 1.01 | (0.11) | 1.03 | (0.05) | 1.19 | (0.08) | n = 3 |
| 139 | K334(353)E | | | | | | | 0.74 | (0.15) | 0.72 | (0.12) | 1.30 | (0.09) | n = 6 |
| 140 | K334(353)D | | | | | | | 0.51 | (0.09) | 0.40 | (0.03) | 1.13 | (0.09) | n = 4 |
| 190 | K334(353)M | | | | 1.18 | | | 0.99 | (0.13) | 0.93 | (0.15) | 0.49 | (0.04) | n = 2 |
| 191 | K334(353)Y | | | | 1.15 | | | 1.08 | | 1.05 | | 1.31 | | n = 1 |
| 192 | K334(353)W | | | | 1.16 | | | 0.94 | | 0.91 | | 1.07 | | n = 1 |
| 193 | K334(353)H | | | | 1.11 | | | 1.09 | | 1.07 | | 1.26 | | n = 1 |
| 220 | K334(353)V | | | | | | | 1.13 | (0.11) | 1.09 | (0.15) | 1.34 | (0.18) | n = 3 |
| 221 | K334(353)L | | | | | | | 1.05 | | 1.09 | | 1.38 | | n = 1 |
| 171 | T335(354)Q | | | | | | | 0.86 | | 0.79 | | 0.84 | | n = 1 |
| 194 | T335(354)E | | | | | | | 1.24 | | 1.30 | | 1.19 | | n = 1 |
| 195 | T335(354)K | | | | | | | 1.19 | | 1.14 | | 1.30 | | n = 1 |
| 273 | A339(359)T | | | | 1.23 | | | 1.11 | | 1.23 | | 1.42 | | n = 1 |
| | S267(280)T | | | | | | | 0.42 | (0.10) | 0.45 | (0.01) | 0.05 | (0.05) | n = 3 |
| | R301(320)M | | | | 1.29 | (0.17) | | 1.56 | (0.12) | 0.48 | (0.21) | n = 4 | | |
| | K338(358)M | | | | 0.99 | (0.13) | | 0.93 | (0.15) | 0.49 | (0.04) | n = 2 | | |

[a]Values are the ratio of binding of the variant to that of native IgG1 at 0.33 or 1 μg/ml. A value greater than 1 denotes binding of the variant was improved compared to native IgG1 while a ratio less than 1 denotes reduced binding compared to native IgG1.
[b]Number of independent assays for FcγRIIA, FcγRIIB and FcγRIIIA. At least two separately expressed and purified lots of each variant were assayed.

The following table summarizes the FcR binding activity of various combination variants.

TABLE 8

COMBINATION VARIANTS

| Res#EU | | FcRn[a] | | | FcγRI | | | FcγRIIA[b] | | FcγRIIB | | FcγRIIIA | | |
|---|---|---|---|---|---|---|---|---|---|---|---|---|---|---|
| IG2 | (Kabat) | mean | sd | n | mean | sd | n | mean | sd | mean | sd | mean | sd | |
| 96 | S267(280)A H268(281)A | | | | | | | 1.41 | (0.00) | 1.56 | (0.16) | 0.96 | (0.12) | n = 2 |
| 134 | E333(352)A K334(353)A | | | | | | | 0.72 | (0.08) | 0.63 | (0.13) | 1.30 | (0.12) | n = 5 |
| 1059 | T256(269)A S298(317)A | | | | | | | 0.44 | (0.03) | 0.22 | (0.04) | 1.41 | (0.06) | n = 2 |
| 1051 | T256(269)A D280(295)A S298(317)A T307(326)A | | | | | | | 0.47 | (0.01) | 0.30 | (0.03) | 1.21 | (0.26) | n = 2 |
| 106 | T256(269)A D280(295)A R292(309)A S298(317)A T307(326)A | | | | | | | 0.11 | | 0.08 | | 0.90 | | n = 1 |
| 107 | S298(317)A E333(352)A | | | | | | | 0.34 | (0.05) | 0.16 | (0.08) | 1.53 | (0.24) | n = 5 |
| 109 | S298(317)A K334(353)A | | | | | | | 0.41 | (0.07) | 0.19 | (0.08) | 1.62 | (0.34) | n = 6 |
| 110 | S298(317)A E333(352)A K334(353)A | | | | | | | 0.34 | (0.15) | 0.15 | (0.06) | 1.51 | (0.31) | n = 10 |
| 246 | S267(280)A E258(271)A | | | | | | | 1.62 | (0.15) | 2.01 | (0.45) | 1.04 | (0.12) | n = 2 |

TABLE 8-continued

COMBINATION VARIANTS

| IG2 | Res#EU (Kabat) | FcRn[a] mean | sd | n | FcγRI mean | sd | n | FcγRIIA[b] mean | sd | FcγRIIB mean | sd | FcγRIIIA mean | sd | |
|---|---|---|---|---|---|---|---|---|---|---|---|---|---|---|
| 247 | S267(280)A R255(268)A | | | | | | | 1.60 | (0.18) | 1.72 | (0.13) | 0.88 | (0.07) | n = 3 |
| 248 | S267(280)A D280(295)A | | | | | | | 1.54 | (0.08) | 1.96 | (0.37) | 1.13 | (0.07) | n = 2 |
| 250 | S267(280)A E272(285)A | | | | | | | 1.51 | (0.13) | 1.82 | (0.32) | 0.95 | (0.05) | n = 3 |
| 251 | S267(280)A E293(310)A | | | | | | | 1.67 | (0.11) | 1.85 | (0.10) | 0.92 | (0.09) | n = 3 |
| 264 | S267(280)A E258(271)A D280(295)A R255(268)A | | | | | | | 1.48 | (0.12) | 2.03 | (0.30) | 0.89 | (0.04) | n = 2 |
| 269 | E380(405)A N434(465)A | 8.0 | (1.0) | 6 | | | | 1.02 | (0.07) | 1.05 | (0.11) | 1.02 | | n = 2 |
| 270 | E380(405)A N434(465)A T307(326)A | 11.8 | (1.5) | 5 | | | | 0.99 | (0.06) | 0.99 | (0.11) | 0.96 | | n = 2 |
| 271 | E380(405)A L309(328)A | 0.9 | (0.1) | 4 | | | | 0.98 | | 1.04 | | 0.92 | | n = 1 |
| 272 | N434(465)A K288(305)A | 2.9 | (0.4) | 4 | | | | 0.94 | (0.11) | 0.96 | (0.17) | 0.88 | | n = 2 |

[a]Values are the ratio of binding of the variant to that of native IgG1 at pH 6.0.
[b]Values are the ratio of binding of the variant to that of native IgG1 at 0.33 or 1 μg/ml. A value greater than 1 denotes binding of the variant was improved compared to native IgG1 while a ratio less than 1 denotes reduced binding compared to native IgG1.

DISCUSSION

Figure 15A:
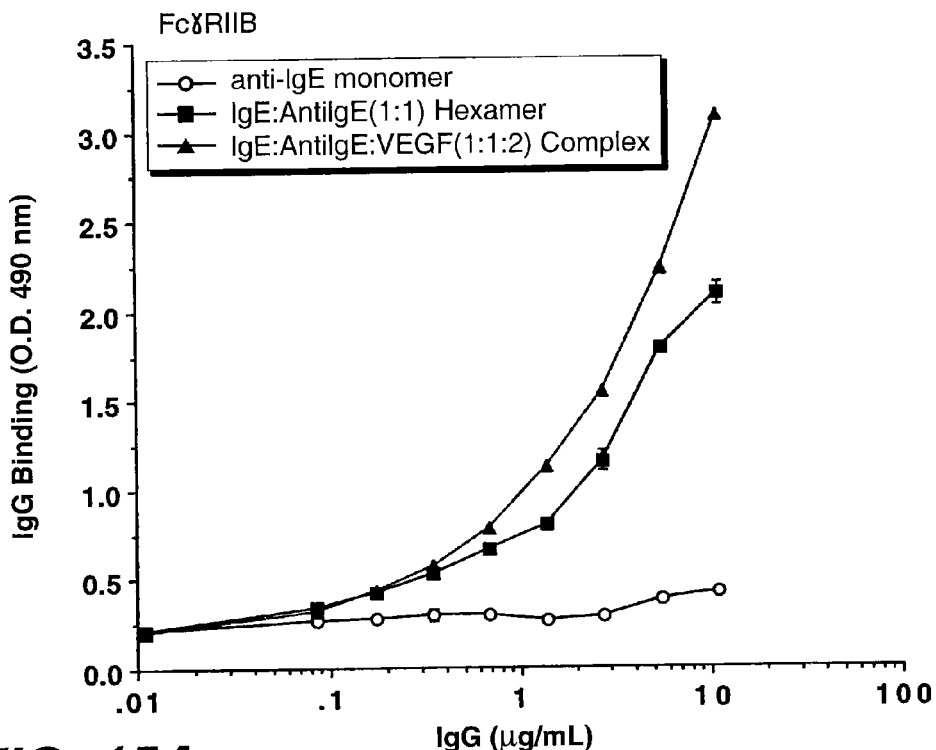
FIGS. 15A and 15B show binding patterns for parent antibody (E27) to FcγRIIB and FcγRIIIA.
Figure 15B:
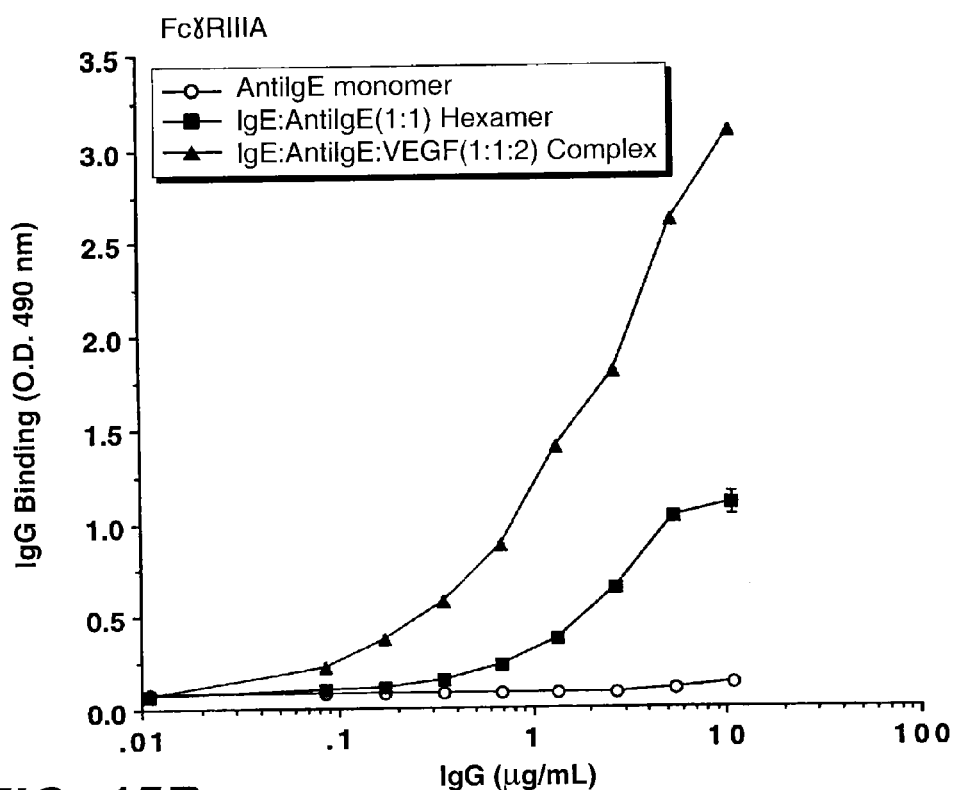
Figure 16A:
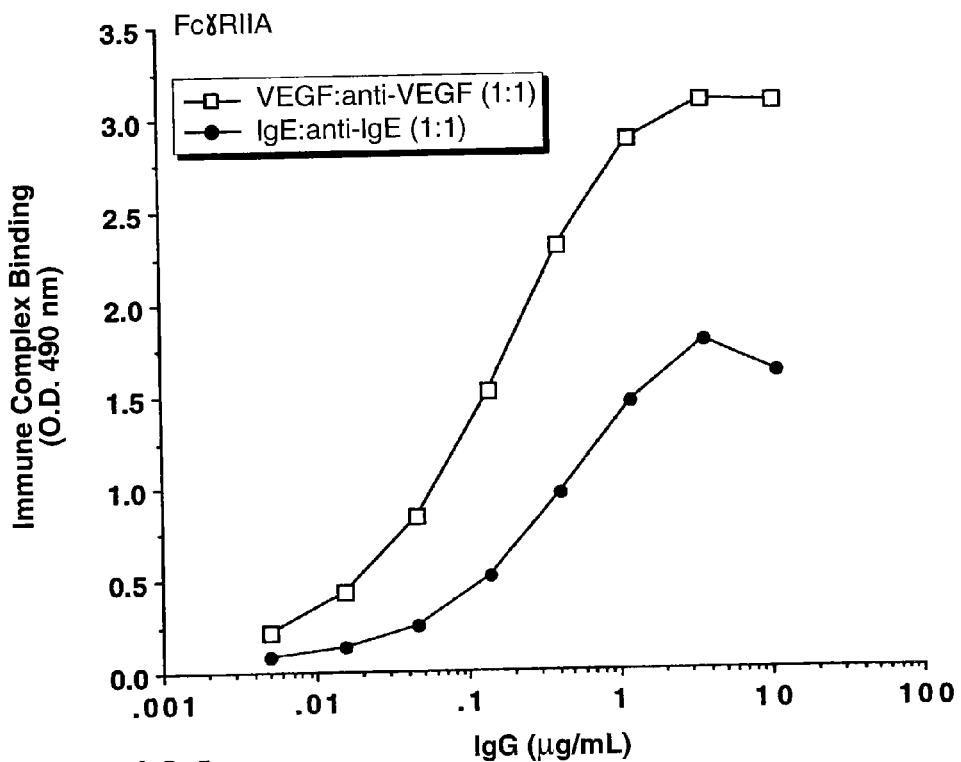
FIG. 16A shows the binding of immune complexes using different antigen-antibody pairs to recombinant GST fusion protein of the FcγRIIA receptor α subunit.
Figure 16B:
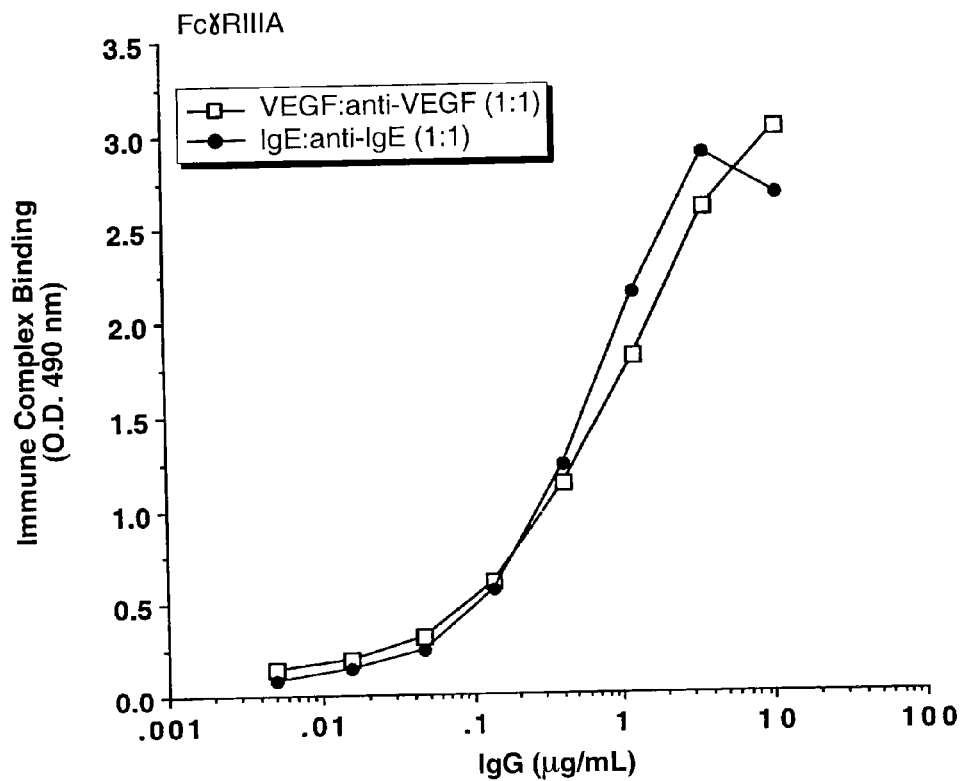
FIG. 16B shows the binding of the same antigen-antibody pairs to the GST fusion protein of the FcγRIIIA receptor α subunit. Closed circles represent binding of human IgE:anti-IgE E27 IgG1; open circles represent binding of human VEGF:humanized anti-VEGF IgG1.

This study includes a complete mapping of human IgG1 for human FcγRI, FcγRIIA, FcγRIIB, FcγRIIIA, and FcRn. An alanine-scan of all amino acids in human IgG1 Fc (CH2 and CH3 domains) exposed to solvent, based on the crystal structure of human Fc (Deisenhofer, *Biochemistry* 20:2361-2370 (1981)), was performed. Each exposed amino acid in CH2 and CH3 was individually changed to alanine and the variant IgG assayed against all five human receptors; all variants were evaluated using humanized anti-IgE E27 IgG1 as the parent polypeptide. FcγRI and FcRn are high affinity receptors and monomeric IgG could be evaluated in the assays for these two receptors. FcγRIIA, FcγRIIB and FcγRIIIA are low affinity receptors and required use of an immune complex. Hence, an ELISA-type assay was used for FcγRIIA, FcγRIIB, and FcγRIIIA, in which pre-formed hexamers, consisting of three anti-IgE E27 and three IgE molecules were bound to the FcγR and either anti-human IgG Fc-HRP or protein G-HRP used as detection reagent. In order to increase binding, these hexamers could be linked into multimers by addition of human VEGF (using anti-VEGF IgE). The hexamers bound to the low affinity FcγR significantly better than the IgG monomers; the multimers bound better than the hexamers (FIGS. 15A and 15B). The hexameric complexes were used since these provided sufficient binding and required less IgG. Complexes formed using other antibody:antigen combinations are also possible reagents, as long as the antigen contains at least two identical binding sites per molecule for the antibody. As an example, VEGF contains two binding sites per VEGF dimer for anti-VEGF A.4.6.1 (Kim et al., *Growth Factors* 7:53 (1992) and Kim et al. *Nature* 362:841 (1993)). VEGF:anti-VEGF multimers also bound to the low affinity FcγRIIA and FcγRIIIA (FIGS. 16A and 16B).

Classes of Fc Region Variants

Figure 17:
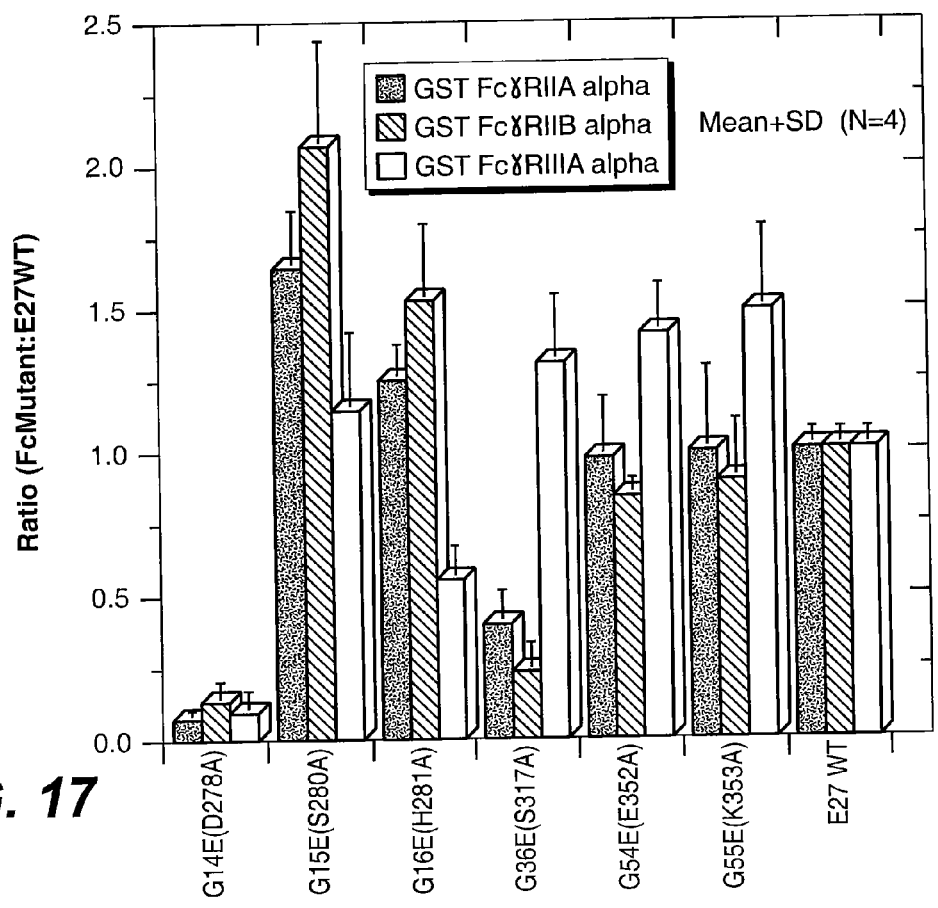
FIG. 17 summarizes differences in binding selectivity of some alanine variants between the different FcγRs. Binding of alanine variants at residues in the CH2 domain of anti-IgE E27 IgG1 are shown to FcγRIIA, FcγRIIB, and FcγRIIIA. Type 1 abrogates binding to all three receptors: D278A (265 in EU numbering). Type 2 improves binding to FcγRIIA and FcγRIIB, while binding to FcγRIIIA is unaffected: S280A (267 in EU numbering). Type 3 improves binding to FcγRIIA and FcγRIIB, but reduces binding to FcγRIIIA: H281A (268 in EU numbering). Type 4 reduces binding to FcγRIIA and FcγRIIB, while improving binding to FcγRIIIA: S317A (298 in EU numbering). Type 5 Improves binding to FcγRIIIA, but does not affect binding to FcγRIIA and FcγRIIB: E352A, K353A (333 and 334 in EU numbering).
Figure 18A:
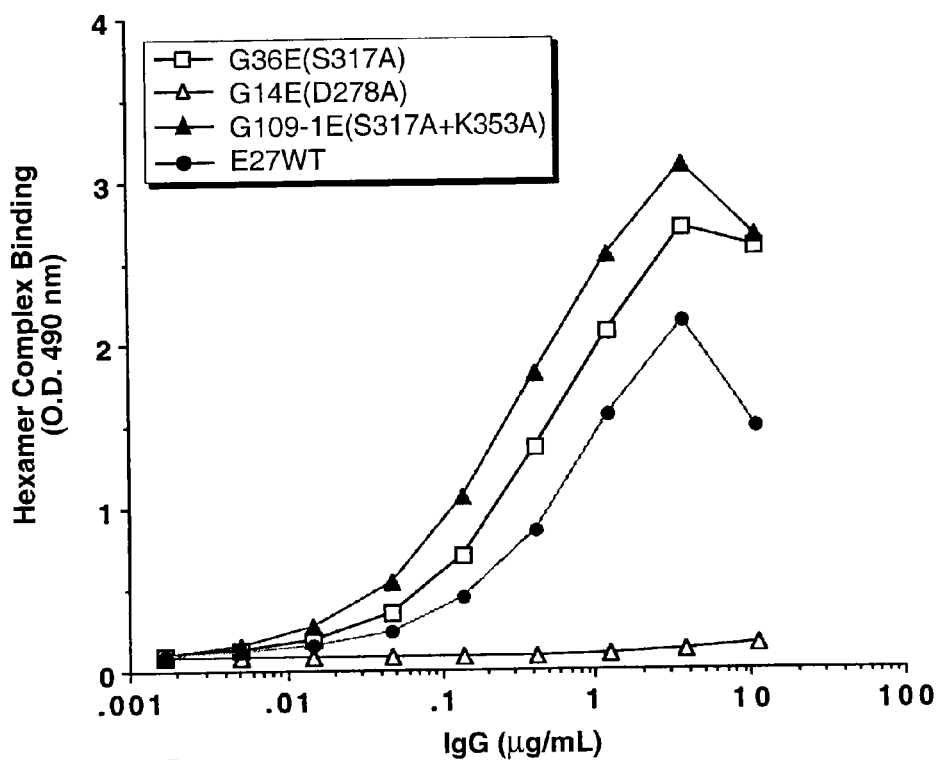
FIGS. 18A and 18B compare the FcγRIIIA protein/protein assay and CHO GPI-FcγRIIIA cell based assay, respectively.
Figure 18B:
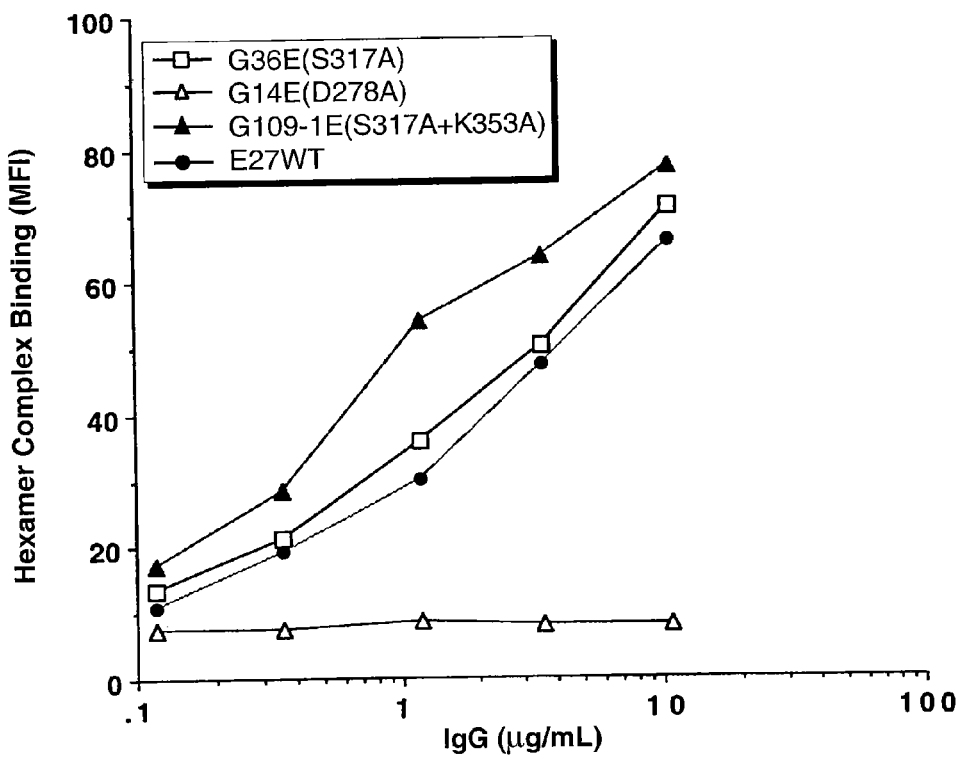
Figure 19A:
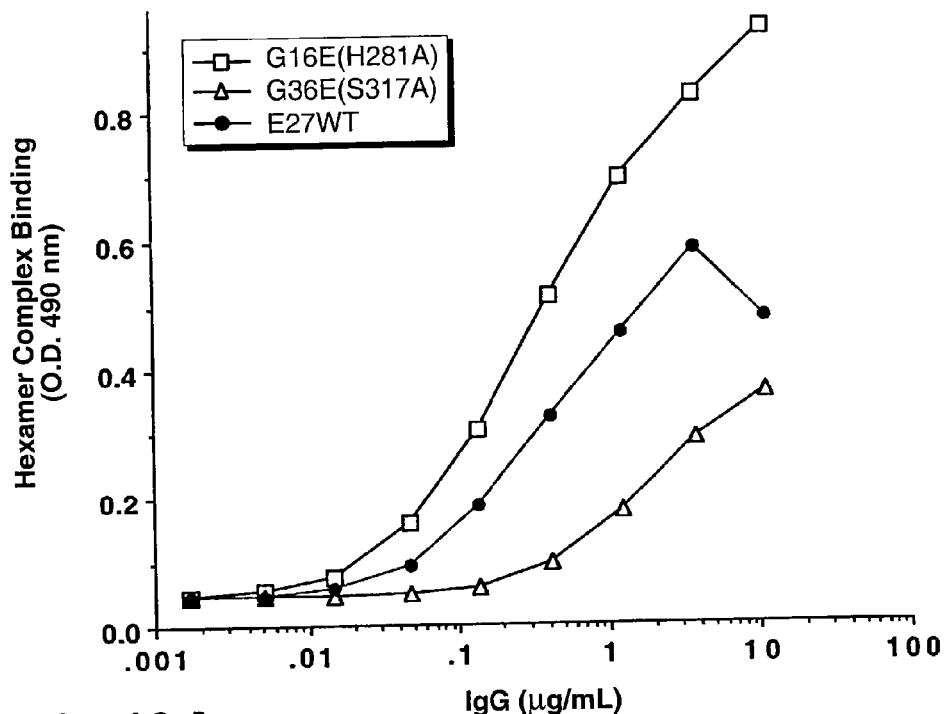
FIGS. 19A and 19B compare the FcγRIIB protein/protein assay and CHO GPI-FcγRIIB cell based assay, respectively.
Figure 19B:
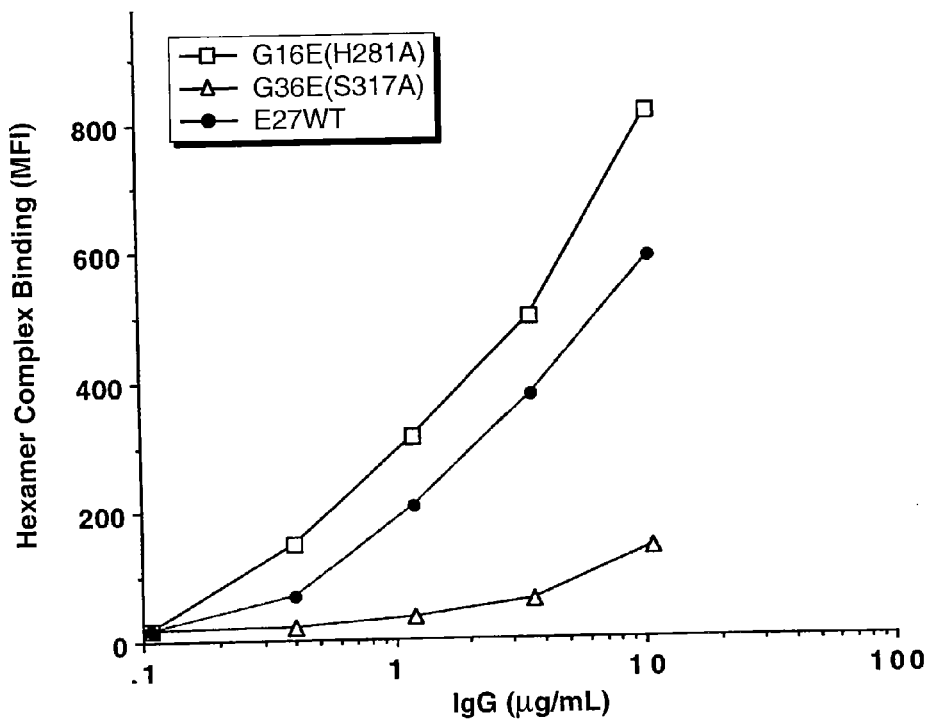
Figure 20:
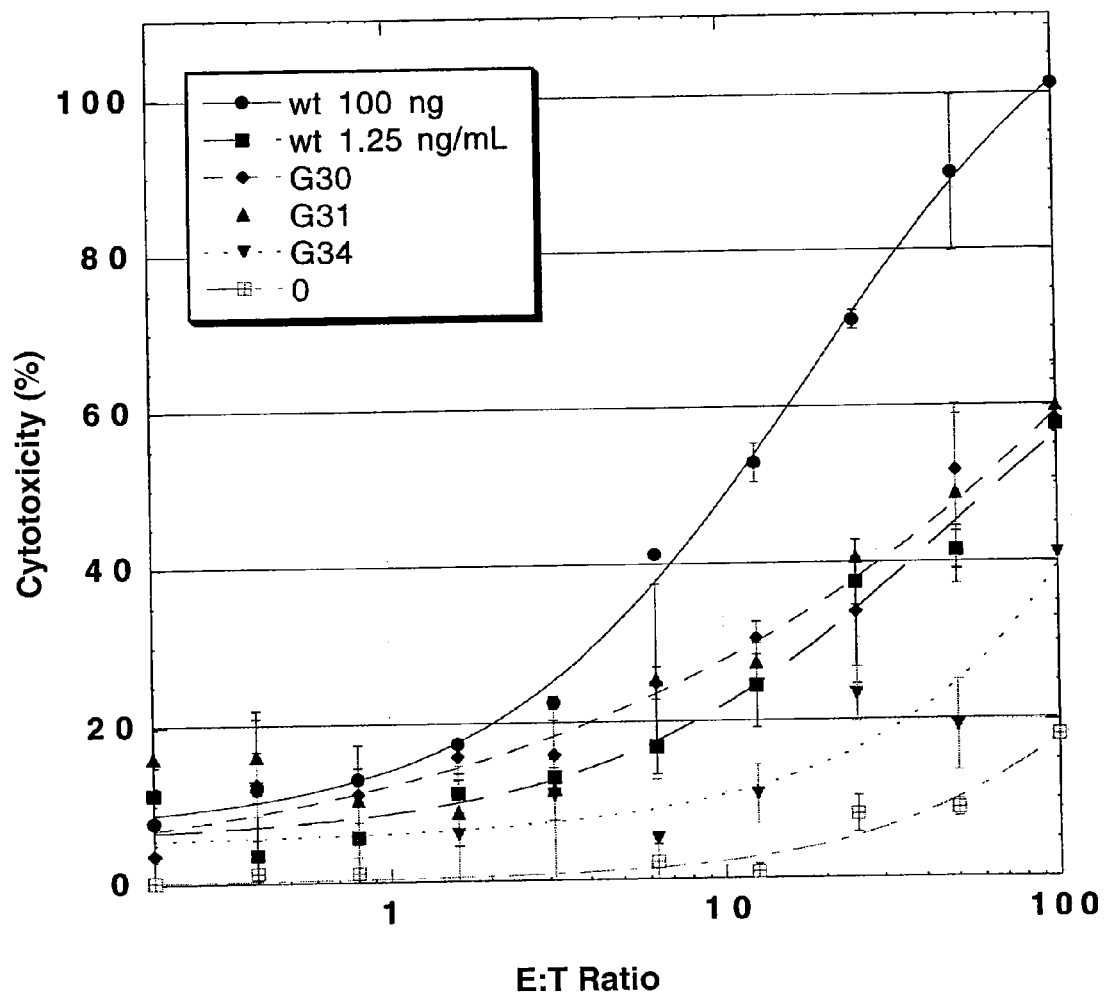
FIG. 20 shows single alanine substitutions in the CH2 domain of anti-HER2 IgG1 (HERCEPTIN®) that influence FcγRIIIA binding in both the protein-protein and cell-based assays alter the ability to bind to FcγRIIIA on peripheral blood mononuclear cell (PBMC) effector cells. Recombinant humanized anti-HER2 (HERCEPTIN®), which binds to HER2-expressing SK-BR-3 breast tumor cells, was preincubated with $^{51}$Cr-labeled SK-BR-3 cells for 30 minutes (opsonization) at 100 ng/ml (filled circles) and 1.25 ng/ml (filled squares). Keeping the SK-BR-3 tumor target cell concentration constant, the ratio of effector cells was increased from 0 to 100. The spontaneous cytotoxicity in the absence of antibody (hatched squares) was 20% at an effector:target (E:T) ratio of 100:1. A single alanine mutation that did not affect FcγRIIIA binding, variant G31=R309A (292 in EU numbering), did not effect ADCC (filled triangles). A single alanine mutation that only slightly increased binding to FcγRIIIA, variant G30=K307A (290 in EU numbering), also showed slightly improved ADCC (i.e., a 1.1 fold improvement in ADCC activity, calculated as area under the curve) at 1.25 ng/ml at all E:T ratios (filled diamonds) compared to wildtype antibody at 1.25 ng/ml (filled square). A single alanine mutation that decreased binding to FcγRIIIA, variant G34=Q312A (295 in EU numbering), also showed decreased ADCC activity (filled inverted triangles).
Figure 21:
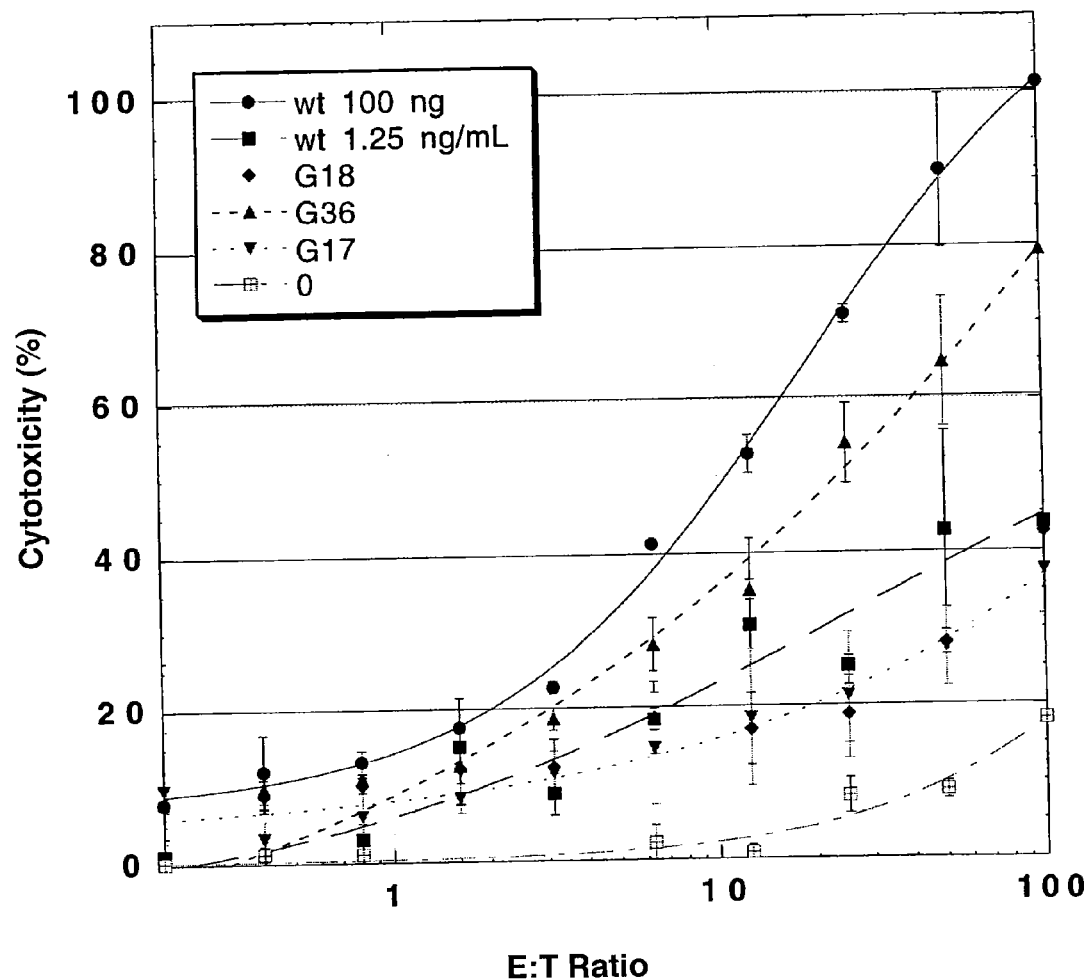
FIG. 21 illustrates that a single alanine mutation which had the most improved binding to FcγRIIIA, variant G36=S317A (298 in EU numbering), in the protein-protein and cell-based assays also showed the most improvement in ADCC (filled triangles) among the variants compared to wildtype (closed squares) at 1.25 ng/ml. G36 displayed a 1.7 fold improvement in ADCC activity, calculated as area under the curve. Variants G17=E282A (269 in EU numbering) and G18=D283A (270 in EU numbering) both showed reduced binding to FcγRIIIA as well as reduced efficacy in ADCC. The effector cells were PBMCs.
Figure 24:
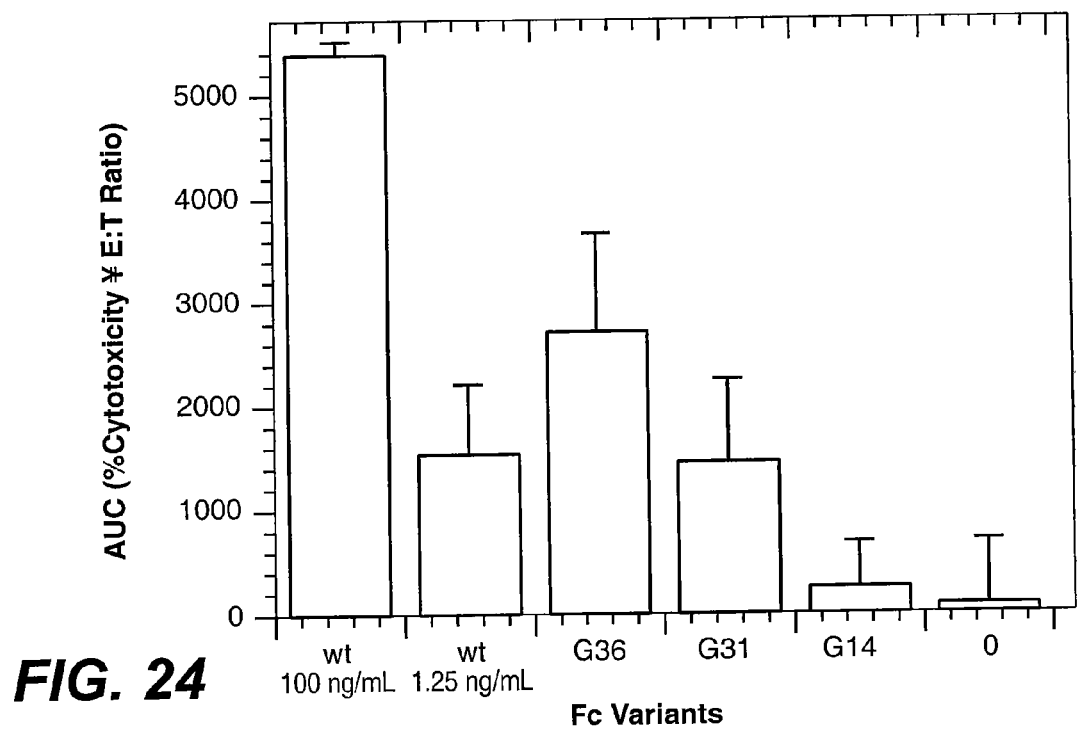
FIG. 24 shows area under curve (AUC) for selected variants compared to anti-HER2 IgG1 (HERCEPTIN®) in a 4 hour ADCC assay. The effector cells were PBMCs (N=5). Variant G36 (S317A; 298 in Eu numbering) with improved binding to FcγRIIIA showed improved ADCC activity; variant G31 (R309A; 292 in Eu numbering) which did not display altered FcγRIIIA binding, also had unaltered ADCC activity; and G14 (D265A; 278 in Eu numbering) which had reduced FcγRIIIA binding, also had reduced ADCC activity.
Figure 25A:
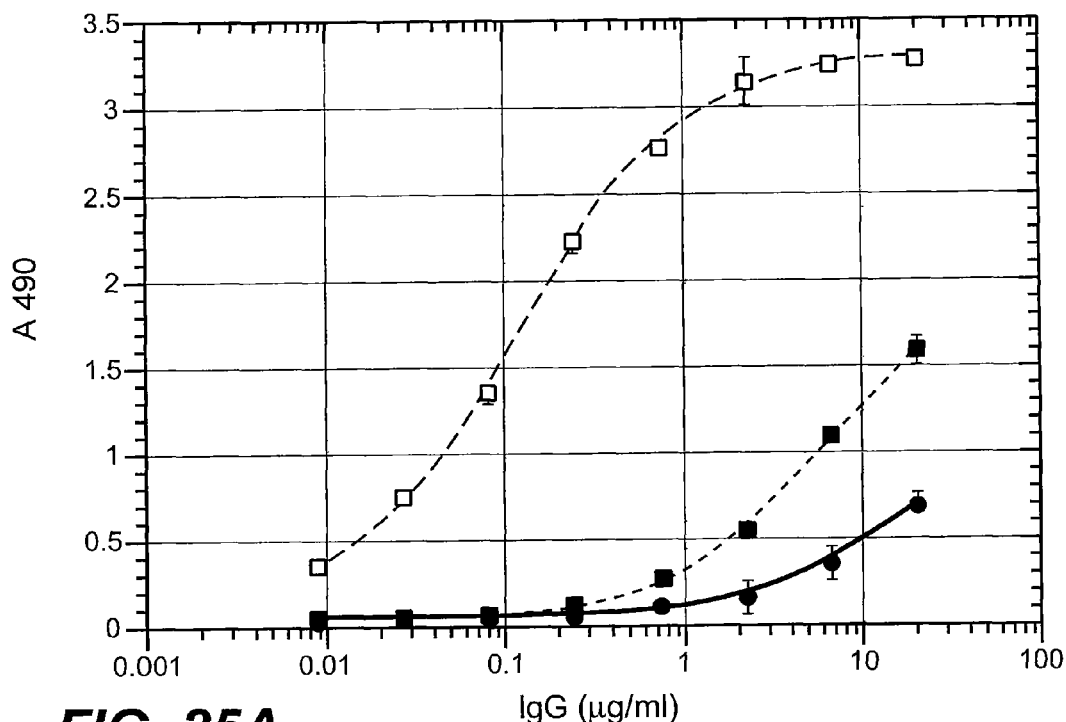
FIGS. 25A and 25B depict binding of anti-IgE E27 IgG1 to human FcγR.
Figure 25B:
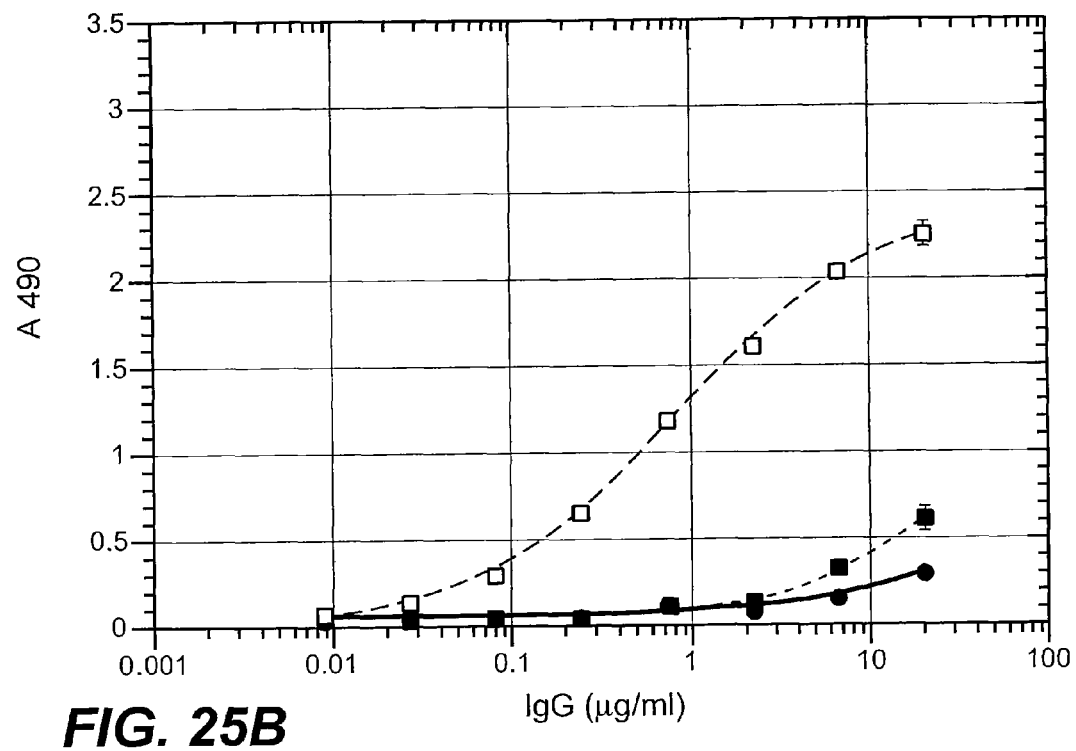

Once the complete alanine-scan was performed, several classes of alanine variants were found. Some variants exhibited reduced binding to all FcγR (G14 D265A; FIG. 17), while other variants showed reduced binding only to one FcγR (G16 H268A; FIG. 17), improved binding only to one FcγR (G15 S267A; G54 E333A; G55 K334A; FIG. 17), or simultaneous reduction to one FcγR with improvement to another (G36 S298A; FIG. 17).

Figure 26B:
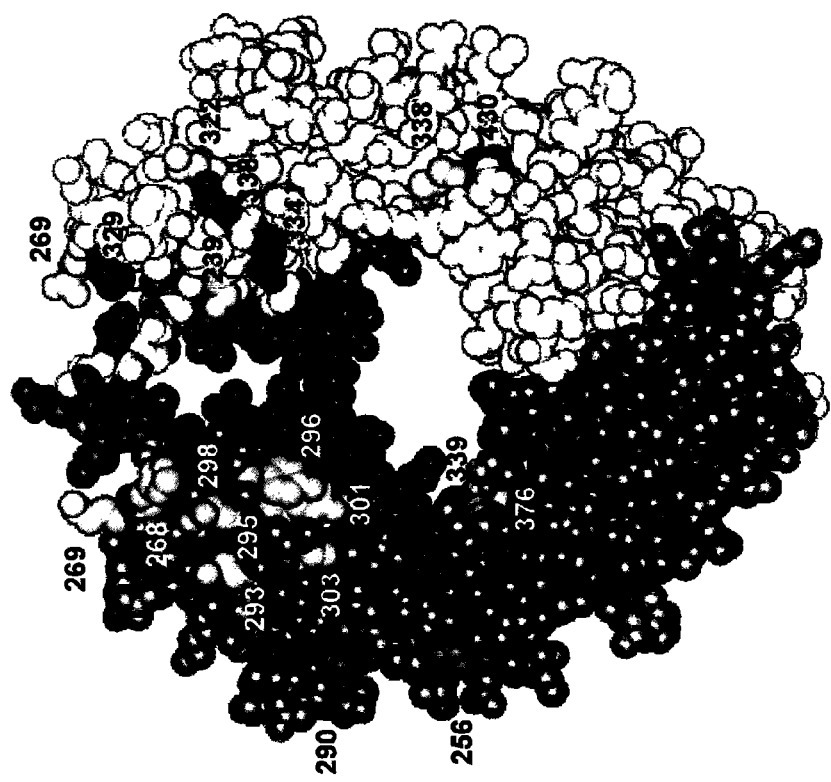
FIGS. 26A and 26B show binding sites of human IgG1 for FcγR.
Figure 26A:
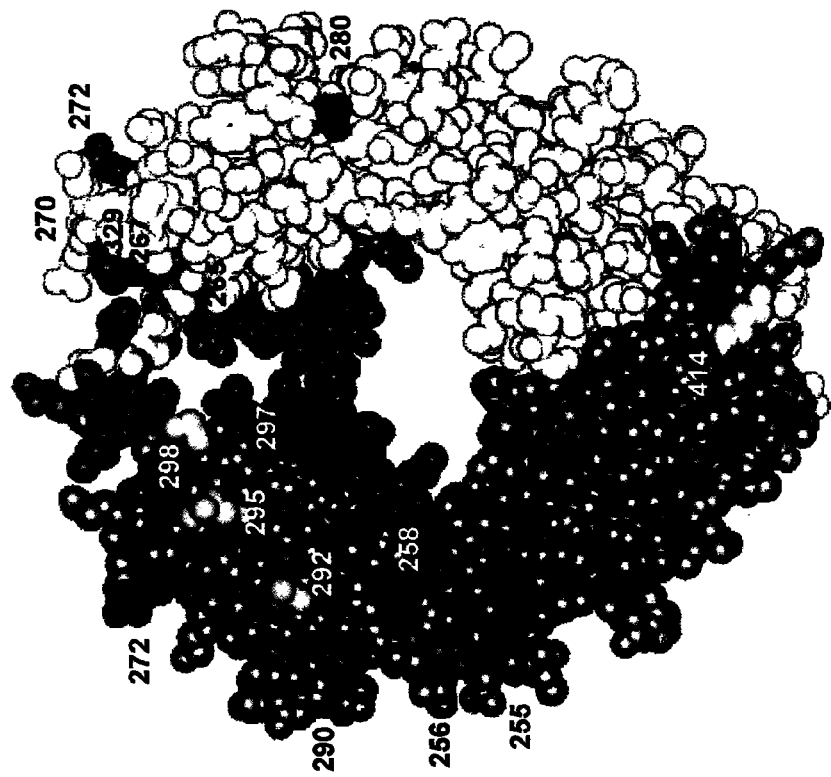

The IgG1 variants can be separated into distinct classes based on their effects on binding to the various receptors. Class 1 consists of variants which showed reduced binding to all FcγR (Table 6) and are clustered near the region of the CH2 domain where the hinge joins CH2 (FIG. 26A). In the Glu233Pro/Leu234Val/Leu235Ala/Gly236 deleted variant, part of the so-called lower hinge region (residues 233-239) of human IgG1 was exchanged with that of human IgG2. The reduction in binding to all FcγR is in agreement with previous studies; this variant also showed impaired binding to FcRn. Two other residues in the lower hinge region were individually changed to Ala; Pro238Ala (Class 1) had a more pronounced effect than Ser239Ala (Class 8). If the Pro238Ala effect is due to a conformation change, this change was beneficial for binding to FcRn. In contrast, Pro329Ala showed a relatively modest reduction in binding to FcRn compared to the significant reduction in binding to the FcγR. In the IgG1 Fc:FcγRIIIA crystal structure (Sondermann et al. *Nature* 406: 267-273 (2000)), Pro329 intimately interacts with two Trp sidechains of the receptor and the loss of these interactions by Pro329Ala may account for the severe reduction in binding. Pro329 is also involved in binding of human IgG1 to human C1q (Example 2 herein).

Removal of the conserved Asn-linked glycosylation site in the CH2 domain, Asn297Ala, abolished binding, in agreement with earlier studies (Lund et al. *J. Immunol.* 157: 4963-4969 (1996); and Lund et al. *FASEB J.* 9: 115-119 (1995)). Another residue which interacts with carbohydrate, Asp265, has also been previously found to be important in human IgG3 binding to human FcγRI (Lund et al. *J. Immunol.* 157: 4963-4969 (1996); and Lund et al. *FASEB J.* 9: 115-119 (1995)). In human IgG1, changing Asp265 to Ala, Asn or Glu nullified binding (Tables 6 and 7), suggesting that both the charge and size are important. The results of the Ala327Gln (Class 1) and Ala327Ser (Class 2) variants imply that the region around Ala327 involved in binding to the FcγR may require a close fit between receptor and IgG1, as enlarging this sidechain diminished binding. This position is an Asp in mouse IgG2a and IgG2b and therefore changing the human IgG1 Ala to a larger sidechain is unlikely to have affected the conformation. The Ala327Gly (Class 8) variant reduced binding only to FcγRIIIA suggesting that this receptor requires the presence of a small amino acid sidechain at this position whereas the other receptors do not.

Class 1 variants (in addition to the hinge residues, which were not investigated in this study) comprise the entire binding site on IgG1 for FcγRI. Residues in the F(ab) portions of the IgG1 do not contribute to FcγRI binding as evidenced by both a CD4-immunoadhesin (Capon et al. *Nature* 337:525-531 (1989)) and an Fc fragment binding to FcγRI as effectively as did intact IgG1. Notably, no variants were found which reduced binding only to FcγRI.

Class 2 consists of three variants with reduced binding to FcγRII and FcγRIII but not FcγRI. Like the residues in Class 1, Asp270 and Gln295 are located near the hinge (FIG. 26A). In crystal structures of human IgG1 Fc (Deisenhofer J., *Biochemistry* 20: 2361-2370 (1981); Guddat et al., *PNAS(USA)* 90: 4271-4275 (1993)), Gln295 is completely solvent exposed whereas Asp270, though exposed, forms hydrogen bonds from its sidechain OS atom to the backbone nitrogens of Lys326 and Ala327 and to the sidechain N6 of Asn325. Disruption of these interactions by Asp270Ala could cause a local conformational perturbation that effected the severe reduction in binding to FcγRII and FcγRIIIA. However, Asp270Ala did not affect binding to FcγRI or FcRn. Furthermore, Asp270Asn, which could maintain the aforementioned hydrogen bonds, also abolished binding to FcγRII and FcγRIIIA, and Asp270Glu bound to FcγRIIIA as effectively as did native IgG1 (Table 7). Taken together, these data suggest that the sidechain charge of Asp270 is important for interaction with FcγRII and FcγRIIIA.

Class 3 consists of two variants with improved binding to FcγRIIA, FcγRIIB, and FcγRIIIA. Thr256 and Lys290 are located near one another in the CH2 domain (FIG. 26). Thr256Ala also exhibited improved binding to FcRn.

Class 4 variants were characterized by improved binding only to FcγRIIA and FcγRIIB. Those that improved binding to FcγRII the most—Arg255Ala, Glu258Ala, Ser267Ala, Glu272Ala, and Asp280Ala—are distant from one another in the CH2 domain (FIG. 26). Of these, only Ser267 was cited as an interacting residue in the Fc:FcγRIIA crystal structure (Sondermann et al. *Nature* 406:267-273 (2000)). Ser267Ala improved binding only to FcγRII, Ser267Gly abolished binding only to FcγRIIIA and Ser267Thr reduced binding to FcγRII and FcγRIIIA (Tables 6 and 7). Asp280Asn (Table 7), like Asp280Ala (Table 6), improved binding only to FcγRII. Three of the Class 4 residues also exhibited improved binding to FcRn (Glu272Ala, Thr307Ala, Ala378Gln) while Arg255Ala exhibited reduced binding. Ala378 interacts with CH2 domain loop AB, which contains residues that interact directly with FcRn, and hence may influence binding to FcRn indirectly.

Class 5 variants exhibited improved binding to FcγRIIA and FcγRIIB but, in contrast to Class 4, also showed reduced binding to FcγRIIIA. Of these, Lys322 has also been implicated in human C1q binding (Example 2 above). The aliphatic portion of the Arg301 sidechain is buried and interacts with the Tyr296 sidechain, at least in some crystal structures, while the Arg301 guanidinium group may interact with the Asn297-linked carbohydrate (Deisenhofer, J. *Biochemistry* 20: 2361-2370 (1981); Guddat et al. *Proc. Natl. Acad. Sci. USA* 90: 4271-4275 (1993); and Harris et al. *J. Mol. Biol.* 275: 861-872 (1998)). The Arg301Ala variant effected a modest improvement in binding to FcγRIIB and a pronounced reduction in binding to FcγRIIIA (Table 6); the Arg301Met variant, which may maintain the aliphatic interaction of the Arg301 sidechain, showed improved binding to FcγRIIA and FcγRIIB and a less pronounced reduction of binding to FcγRIIIA compared to Arg301Ala (Table 7).

Class 6 residues show diminished binding to FcγRII only. Arg292Ala is located in the CH2 domain distant from the hinge. Lys414 is at the "bottom" of the IgG1, spatially removed from all other residues having an effect on FcγRII binding, suggesting that it may play only a minor role in binding (discussed below).

Class 7 is comprised of Ser298Ala which reduced binding to FcγRII, but improved binding to FcγRIIIA. Situated among the Class 1 residues near the hinge (FIG. 26), Ser298 is also part of the Asn-linked glycosylation sequence Asn297-Ser298-Thr299. Ser298Thr followed the pattern of Ser298Ala, whereas Ser298Asn abolished binding to FcγRIIIA as well as FcγRII (Table 7).

Reduced binding only to FcγRIIIA characterizes Class 8 and includes five residues in the CH2 domain and two in the CH3 domain (Ala327Gln is in Class 1). Ser239 has been previously identified as playing a minor role in murine IgG2b binding to murine FcγRII (Lund et al. *Mol. Immunol.* 29: 53-59 (1992)) and in the IgG1 Fc:FcγRIIIA crystal structure (Sondermann et al. *Nature* 406:267-273 (2000)), the Ser239 in one of the two heavy chains forms a hydrogen-bond to the Lys117 sidechain of FcγRIIIA. In contrast, Glu293Ala (Table 6) and Glu293Asp (Table 7) reduced binding as much as did Ser239Ala even thought Glu293 is not located near the Fc:FcγRIIIA interface in the crystal structure. In some crystal structures (Deisenhofer, J. *Biochemistry* 20: 2361-2370 (1981); Guddat et al. *Proc. Natl. Acad. Sci. USA* 90: 4271-4275 (1993); and Harris et al. *J. Mol. Biol.* 275: 861-872 (1998)), the Tyr296 sidechain interacts intimately with the aliphatic portion of Arg301 (Class 5); altering either of these reduced binding to FcγRIIIA. Note, however, that Tyr296 was changed to Phe (not Ala) and the 50% reduction in binding to FcγRIIIA is believed to be due to removal of the sidechain hydroxyl group.

At position Lys338, altering the sidechain to Ala or Met effected reduction in binding to FcγRIIIA, suggesting that both the sidechain charge and aliphatic portions are required. The Lys338 sidechain forms part of the interface between the CH2 and CH3 domains and participates in a salt-bridge with Glu430 in several crystal structures (Deisenhofer, J. *Biochemistry* 20: 2361-2370 (1981); Harris et al. *J. Mol. Biol.* 275: 861-872 (1998); Harris et al. *Biochemistry* 36: 1581-1597 (1997)) (FIG. 26B). While it is possible that altering Lys338 may disrupt the CH2:CH3 interface and thereby influence binding, Lys338Ala (Table 6) and Lys338Met (Table 7) did not disrupt binding to FcγRI, FcγRII or FcRn. Since it is known that binding of IgG1 to FcRn involves residues in both CH2 and CH3 (Raghavan and Bjorkman *Annu. Rev. Cell Dev. Biol.* 12: 181-220 (1996); Ward and Ghetie *Ther. Immunol.* 2: 77-94 (1995); and Burmeister et al. *Nature* 372: 379-383 (1994)), this suggests that any conformational effect of Lys338Ala must be local and minimal. Note also that while Lys338Ala and Lys338Met reduced binding to FcγRIIIA, Glu430Ala (Class 4) improved binding, suggesting that the Lys338:Glu430 salt-bridge is not essential in maintaining binding. Another CH3 residue affecting FcγRIIIA is Asp376 that interacts with the CH2 domain.

Class 9 is characterized by improved binding only to FcγRIIIA and includes Glu333Ala, Lys334Ala and Ala339Thr. A previous study found that Ala339Thr improved binding to FcγRI (Chappel et al. *J. Biol. Chem.* 268: 25124-25131 (1993)); in this study the Ala339Thr variant bound better than native IgG1 to FcγRIIIA but not FcγRI (Table 6). Several non-Ala variants were tested at Glu333 and Lys334. Glu333Asp also improved binding to FcγRIIIA while Glu333Asn reduced binding to FcγRII as well as FcγRIIIA (Table 7). At position 334, changing Lys to Gln, Glu or Val maintained the improved binding to FcγRIIIA (Table 7). Surprisingly, the Lys334Arg variant reversed the receptor preference, i.e. this variant bound better to FcγRIIB, not FcγRIIIA as for the Lys334Ala variant. Taken together these data suggest that FcγRIIIA interacts with Lys334 even though this residue is not among the IgG1 residues found to interact with FcγRIIIA in the co-crystal structure (Sondermann et al. *Nature* 406:267-273 (2000)).

Class 10 residues influenced binding only to FcRn. Note that residues in other classes may also have affected binding to FcRn, but were classified according to their effect on FcγR. Positions which effectively abrogated binding to FcRn when changed to alanine include Ile253, Ser254, His435, and Tyr436. Other positions showed a less pronounced reduction in binding: Glu233-Gly236 (Class 1), Arg255 (Class 4), Lys288, Ser415, and His433. Several amino acid positions exhibited an improvement in FcRn binding when changed to alanine; notable among these are Pro238 (Class 1), Thr256 (Class 3), Thr307 (Class 4), Gln311, Asp312, Glu380, Glu382 and Asn434. The pattern of binding was the same when a second assay format was used, e.g. with IgE-coated plates rather than FcRn-coated plates.

The set of IgG1 residues involved in binding to all human FcγR are represented by Class 1 (Table 6). Indeed, this set comprises the entire binding site on IgG1 for FcγRI. Class 1 residues are located in the CH2 domain proximal to the hinge and fall into two categories: (1) positions that may interact directly with all FcγR include Leu234-Pro238, Ala327, and Pro329 (and possibly Asp265); (2) positions that influence carbohydrate nature or position include Asp265 and Asn297.

Previous studies mapping the binding residues in mouse or human IgG have concentrated primarily on the lower hinge region, i.e. residues Leu234-Ser239, revealing Leu234 and Leu235 as the two most important for FcγRI (Duncan et al. *Nature* 332, 563-564 (1988); Canfield and Morrison *J. Exp. Med.* 173:1483-1491 (1991)) and Leu234 and Gly237 as the two most important for FcγRII (Lund et al. *Mol. Immunol.* 29:53-59 (1992); Sondermann et al. *Nature* 406: 267-273 (2000)). Of the two residues in the lower hinge investigated in this study, Pro238Ala affected binding to all FcγR while Ser239Ala affected binding only to FcγRIIIA.

In the co-crystal structure of IgG1 Fc:FcγRIIIA (Sondermann et al. *Nature* 406: 267-273 (2000)), Pro329 interacts with two Trp sidechains from the receptor and a similar interaction may occur with the other FcγR. However, removal of the Pro sidechain, as in Pro329Ala, might cause a localized conformational change which perturbs adjacent binding residues, supported by the above report that Pro329Ala also effects C1q binding (Example 2). Ala327Gln could be causing steric hindrance to binding due to introduction of a large sidechain at this position, though altering Ala327 to Ser did not affect binding to FcγRI. Inspection of the IgG1 Fc:FcγRIIIA crystal structure shows that Ala327 is near the IgG1:FcγRIIIA interface and forms a van der Waals' interaction with the Trp87 sidechain; however, it is not obvious why introduction of a larger sidechain such as Ser or Gln should so severely reduce binding. For Asn297 and Asp265, earlier studies evaluated the requirement for carbohydrate attached at Asn297 as well as the influence of Asp265 on the nature of the carbohydrate (Lifely et al. *Glycobiology* 5:813-822 (1995); Lund et al. *J. Immunol.* 157: 4963-4969 (1996); and Lund et al. *FASEB J.* 9: 115-119 (1995)); these will be discussed below.

For FcγRI the IgG segment Gly316-Ala339 has also been previously implicated based on sequence comparison and binding of IgG subclasses from different species (Woof et al. *Mol. Immunol.* 23: 319-330 (1986); Burton et al. *Mol. Immunol.* 25: 1175-1181 (1988)) and mutagenesis (Canfield and Morrison *J. Exp. Med.* 173: 1483-1491 (1991); Chappel et al. *J. Biol. Chem.* 268: 25124-25131 (1993)). Within the segment Gly316-Ala339, however, only Ala327Gln and Pro329Ala affected binding to FcγRI (Class 1). All other exposed residues in the 316-339 segment had no effect. In contrast to a previous study in which changing residue 331 from Pro to Ser in human IgG3 reduced binding by 10-fold (Canfield and Morrison *J. Exp. Med.* 173: 1483-1491 (1991)), in human IgG1 the Pro331Ala (Table 6) and Pro331Ser (Table 7) variants had no effect. Another previous report showed that an Ala339Thr substitution could improve binding to FcγRI by 3-fold (Chappel et al. *J. Biol. Chem.* 268: 25124-25131 (1993)); in this study the Ala339Thr variant was only equivalent in binding to native IgG1 (Class 3).

It has been noted that the presence of the γ-chain may augment the binding affinity of the FcγRI α-chain (Miller et al. *J. Exp. Med.* 183: 2227-2233 (1996)). Since it is conceivable that some residues in the human IgG1 might interact directly with the γ-chain, binding of the IgG1 variants to FcγRI on THP-1 cells was tested as well to the FcγRI α-chain coated on a plate. The results of the two assay formats were the same for the entire panel of variants, suggesting that the γ-chain augments binding by the α-chain through a mechanism other than direct interaction with the IgG1.

Since FcγRI binds monomeric IgG1 about 100-fold more strongly than do FcγRII and FcγRIII, one might expect that FcγRI would utilize either different or additional IgG1 residues to effect the tighter binding. However, the set of IgG1 residues that control binding to FcγRI are a subset of those effecting binding to FcγRII and FcγRIII (Class 1). This suggests that the comparatively strong binding of IgG1 to FcgRI results from either (1) utilization of only two Ig-like domains of FcγRI (analogous to the two Ig-like domains of FcγRII and FcγRIII) but with interaction of different amino acids in FcγRI than are used by FcγRII and FcγRIII, (2) utilization of the same amino acids on all three receptors but with additional direct interaction of amino acids in the third FcγRI domain, or (3) the third domain of FcγRI effects a conformational change in the other two Ig-like domains which results in more efficacious interaction of these domains with the common set of binding residues on IgG1. In both human and murine FcγRI, removal of the third domain reduces affinity for monomeric IgG and alters specificity for IgG subclasses (Hulett et al. *J. Immunol.* 147: 1863-1868 (1991); Porges et al. *J. Clin. Invest.* 90: 2102-2109 (1992)). This would support, but does not discriminate between, possibilities 2 and 3.

In contrast to FcγRI, FcγRII requires the presence of two identical IgG heavy chains (Haagen et al. *J. Immunol.* 154: 1852-1860 (1995)), suggesting that residues from both heavy chains may form the FcγRII binding site in IgG. The set of IgG1 residues, in addition to the common Class 1 residues, which affect binding to FcγRII are: (largest effect) Arg255, Thr256, Glu258, Ser267, Asp270, Glu272, Asp280, Arg292, Ser298 and (less effect) His268, Asn276, His 285, Asn286, Lys290, Gln295, Arg301, Thr307, Leu309, Asn315, Lys322, Lys326, Pro331, Ser337, Ala339, Ala378, Lys414.

A previous study elucidated the residues in murine IgG2b involved in binding to murine FcγRII (Lund et al. *Mol. Immunol.* 29: 53-59 (1992)). Of the residues investigated in that study, only Asn297Ala and Glu318Ala showed a complete abrogation of binding. Several other murine IgG2b residues exhibited more modest reduction in binding to FcγRII: Ser239Ala, Lys248Ala, Ser267Ala, Lys322Ala, Glu333Ala, Thr335Ala, Ser337Ala, and Lys340Ala (Lund et al. *Mol. Immunol.* 29: 53-59 (1992)). Several of these residues also exhibited modest reduction in binding in the human system (e.g. Ser239Ala, Thr335Ala) or modest improvement in binding (e.g. Lys340Ala) but fell outside of the cutoff used in this study. Noteworthy differences between the two systems are: Asp270Ala affecting only the human system, Glu318Ala affecting only the murine system, and Lys322Ala, Ser267Ala, and Ser337Ala exhibiting improved binding in the human system but slightly reduced binding in the murine.

In contrast to FcγRI, several variants exhibited improved binding to FcγRIIA and FcγRIIB (Classes 3, 4 and 5). Of special interest are Class 4 containing residues which, when changed to Ala, improved binding only to FcγRII and Class 5 containing residues which, when changed to Ala, simultaneously improved binding to FcγRII and reduced binding to FcγRIIIA. These can be used to make IgG1 with improved specificity for FcγRII over FcγRIIIA.

Recently the crystal structures of human FcγRIIA (Maxwell et al. *Nature Struct. Biol.* 6: 437-442 (1999)) and FcγRIIB (Sondermann et al. *EMBO J.* 18: 1095-1103 (1999)) have been solved. In the FcγRIIA report, it was suggested that in addition to the lower hinge (Leu234-Gly237), residues in IgG CH2 domain loops FG (residues 326-330) and BC (residues 265-271) might play a role in binding, though it was noted that these had yet to be demonstrated by mutagenesis. Of the four exposed residues in loop FG, Ala330Gln had no effect, Ala327Gln, Ala327Ser and Pro329Ala reduced binding, while Lys326Ala improved binding. Of the five exposed residues in loop BC, two reduced binding when altered to Ala (Asp265Ala and Asp270Ala) and two improved binding (Ser267Ala and His268Ala). Several of the residues found to influence binding to FcγRII lie outside of the residues at the Fc:FcγRIIIA interface in the co-crystal structure (Sondermann et al. *EMBO J.* 18: 1095-1103 (1999)). One of these, Asp280, is not only distant from the Fc:FcγRIIIA interface but is distant from other FcγRII-influencing residues (FIG. 26A). However, both Asp280Ala and Asp280Asn improved binding to FcγRII, suggesting that this residue does indeed interact with FcγRII.

In addition to the Class 1 residues, positions which reduced binding to FcγRIIIA by 40% or more (when changed to Ala) are: Ser239, Ser267 (Gly only), His268, Glu293, Gln295, Tyr296, Arg301, Val303, Lys338, Asp376. In the Fc crystal structure, these residues separate into two groups. Lys338 and Asp376 are at the CH2-CH3 interface and may affect the spatial relationship of these two domains, thereby affecting FcγRIIIA binding; note, though, that changing these two residues did not significantly reduce binding to FcγRI, FcγRII or FcRn. The other eight positions are clustered together near the Class 1 residues at the hinge-proximal end of the CH2 domain; of these, only Ser239, Ser267, and His268 were cited as part of the binding site in the Fc:FcγRIIIA crystal structure report (Sondermann et al. *EMBO J.* 18: 1095-1103 (1999)). Of the remaining seven, a few might conceivably exert their effect by conformational change, e.g. Tyr296, Arg301, Val303, Lys338, and Asp376 (FIG. 26B). However, the Glu293 and Gln295 sidechains are quite solvent exposed, based on Fc crystal structures (Deisenhofer, J. *Biochemistry* 20: 2361-2370 (1981); Guddat et al. *Proc. Natl. Acad. Sci. USA* 90:4271-4275 (1993)), and are not involved in interactions which would hint at a conformational role. In addition to Glu293Ala reducing binding by 70% (Class 8), the more conservative change of Glu293Asp also showed a similar reduction (Table 7) implying that Glu293 can indeed interact with FcγRIIIA.

Figure 27A:
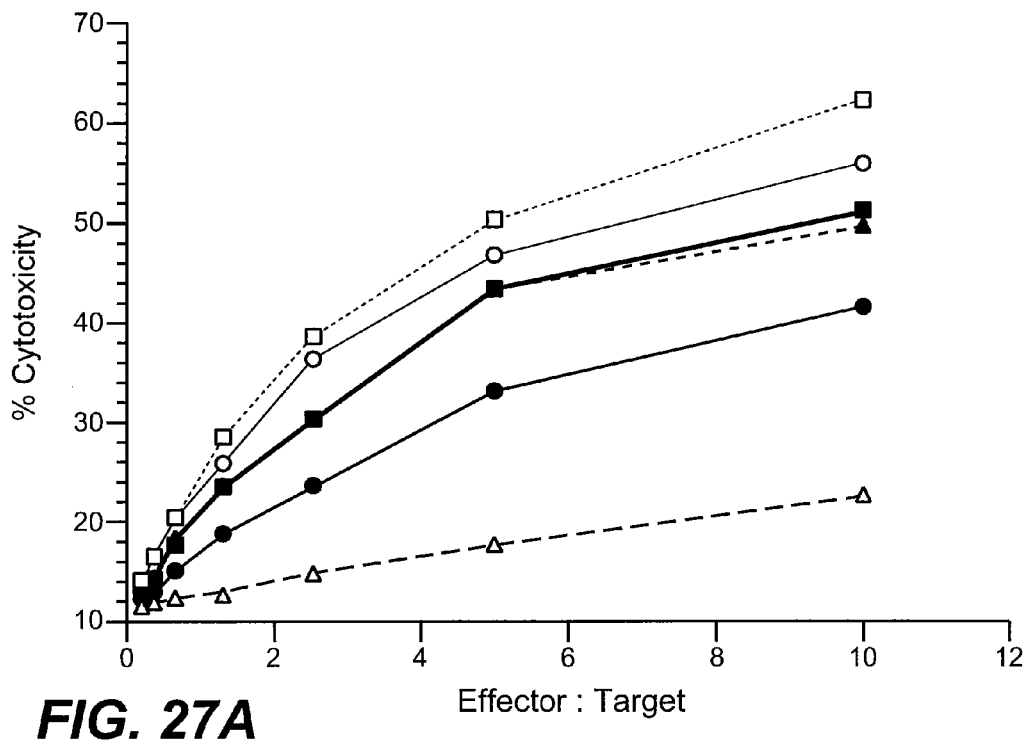
FIGS. 27A, 27B and 27C show ADCC of anti-p$^{185}$HER2 IgG1 variants for FcγRIIIA-F158 and FcγRIIA-V158 allotypes. ADCC was performed using p$^{185}$HER2-expressing SK-BR-3 cells as target and Natural Killer cells (NKs) isolated from three FcγRIIIA-Val158/Val158 donors or three FcγRIIIA-Phe158/Phe158 donors were used as effector cells. Cytotoxicity was detected by LDH release. Antibody-independent cell cytotoxicity (AICC) was measured using target and effector cells together (i.e. no antibody). Maximal release (MR) was measured by adding 1% Triton-100™ to target cells. Percent cytotoxicity was calculated as (LDH release$_{sample}$/MR$_{target}$)×100. The Effector:Target ratio was plotted versus % cytotoxicity.
Figure 27B:
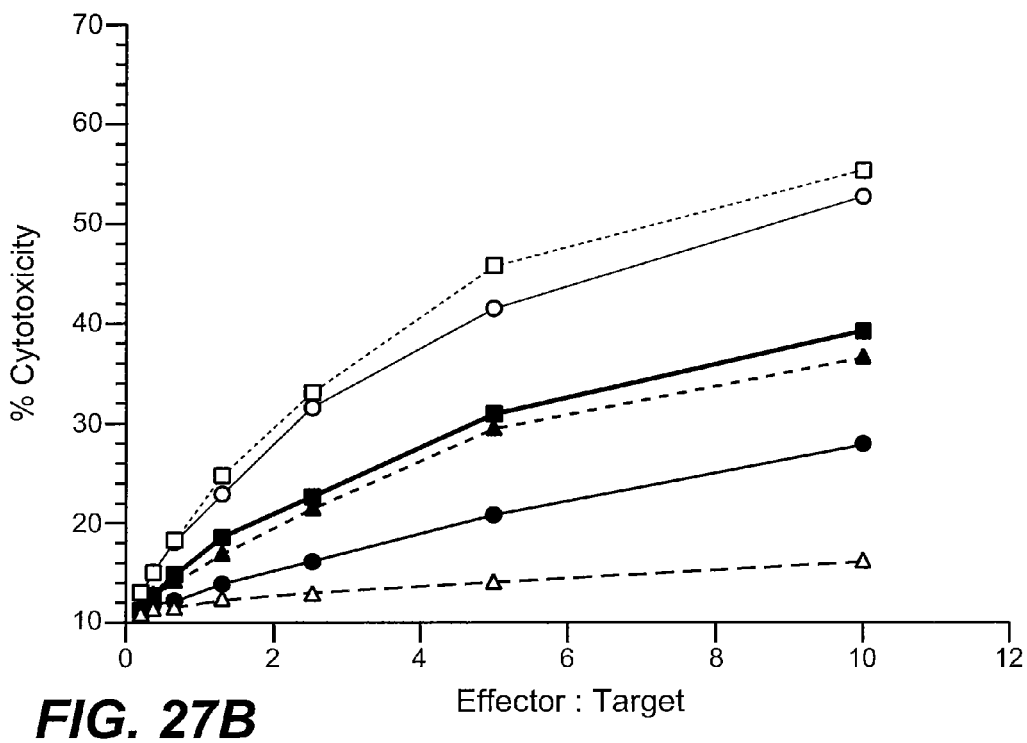

Variants which improved binding to FcγRIIIA (Classes 3, 7 and 9) include Thr256Ala, Lys290Ala, Ser298Ala, Glu333Ala, Lys334Ala and Ala339Thr. Of these, only Ser298 was cited as part of the binding site in the Fc:FcγRIIIA crystal structure report (Sondermann et al. *EMBO J.* 18: 1095-1103 (1999)). Though Glu333 and Lys334 do not interact with FcγRIIIA in the co-crystal structure, their interaction with FcγRIIIA is supported by four lines of evidence. First, murine IgG2b Glu333Ala exhibited a modest reduction in binding to murine FcγRII (Lund et al. *Mol. Immunol.* 29:53-59 (1992)). Though the same might not occur for murine FcγRIII, this shows that residues distant from the hinge region can influence binding to FcγR. Second, several non-Ala variants at Glu333 and Lys334 either improved or reduced binding to FcγRIIIA (Table 7). Third, binding of Glu333Ala and Lys334Ala to FcγRIIIA-expressing CHO cells improved even more than seen in ELISA-based assays (Table 11). Finally, Lys334Ala exhibited a significant increase in ADCC. This increase in ADCC was additive when Lys334Ala was present with Ser298Ala and was further enhanced when Glu333Ala was present (FIG. 27).

Several residues which influenced binding, albeit modestly, to FcγRIIIA, FcγRIIA and FcγRIIB, are located at the "bottom" of the CH3 domain distant from the larger set of residues in the CH2 domain which exhibited a more pronounced effect on binding. Lys414 (FIG. 26A) showed a 40% reduction in binding for FcγRIIA and FcγRIIB (Class 6), Arg416 a 30% reduction for FcγRIIA and FcγRIIIA, Gln419 a 30% reduction to FcγRIIA and a 40% reduction to FcγRIIB, and Lys360 a 23% improvement to FcγRIIIA (Class 10). Taken together, their effect on binding of IgG1 to FcγRIIA, FcγRIIB and FcγRIIIA suggests that the "bottom" of IgG1 may indeed be involved in the IgG1:FcγR interaction, though it may play only a minor role.

Previous studies have mapped the binding site of murine IgG for murine FcRn (Ghetie et al. *Nature Biotech.* 15: 637-640 (1997); Kim et al. *Eur. J. Immunol.* 24: 542-548 (1994); Kim et al. *Eur. J. Immunol.* 24: 2429-2434 (1994); Kim et al. *Scand. J. Immunol.* 40: 457-465 (1994); Medesan et al. *J. Immunol.* 158: 2211-2217 (1997)). These studies have implicated murine IgG residues Ile253, His310, Gln311, His433, Asn434, His435, and His436 as contacts for one FcRn molecule and Glu272 and His285 as contacts for a second FcRn molecule. In addition, the pH dependence of the IgG:FcRn interaction has been ascribed to His310 and His433 on IgG (as well as His250 and His251 on FcRn) (Raghavan et al. *Biochemistry* 34: 14649-14657 (1995)).

In the current study of the human system, a larger number of residues were found which affected binding of IgG1 to human FcRn. Comparison of the human IgG1 sequence with the crystal structure of rat Fc bound to murine FcRn (Burmeister et al. *Nature* 372: 379-383 (1994)) shows that in the human Fc some of these residues could interact directly with human FcRn: Ile253, Ser254, Lys288, Thr307, Gln311, Asn434, and His435. Near the Fc:FcRn interface in the crystal structure but not interacting directly are: Arg255, Thr256, Asp312, Glu380, Glu382, His 433, and Tyr436. In the murine system it was found that altering Asn434 to Ala or Gln did not affect binding to murine FcRn (Ghetie and Ward *Immunol. Today* 18:592-598 (1997); Medesan et al. *J. Immunol.* 158: 2211-2217 (1997)). However, in the human system Asn434Ala exhibited the largest improvement in binding seen for any single Ala substitution (Class 10) as well as showing additivity in combination variants (Table 8). Note that while improvement in binding of the variants to FcRn occurred at pH 7.2 as well as at pH 6.0 (Table 8), none of the variants bound well at pH 7.2. Hence, these single or combination variants may be useful in extending the half-life of human IgG1 in therapeutic antibodies, as previously found for murine IgG (Ghetie et al. *Nature Biotech.* 15: 637-640 (1997)), and fulfill the requirement for binding at pH 6.0 and dissociating at pH 7.2.

Selected IgG variants were also tested for their binding to FcγR transfected into mammalian cells. The α-chain extracellular portion of human FcγRIIIA was transfected into CHO cells using a GPI-link, whereas for human FcγRIIB the full-length receptor was transfected into CHO cells. For the variants tested, the pattern of binding to the cells was the same as the pattern of binding in the protein:protein (ELISA) assay (FIGS. 18A-B and 19A-B).

Combination Variants

A number of combination variants were tested in which two or more residues were simultaneously altered to Ala. Some of these combinations showed additive effects. An example is the Glu258Ala/Ser267Ala variant which exhibited binding to FcγRIIA and FcγRIIB that was better than the Glu258Ala (Class 4) and Ser267Ala (Class 4) variants (Tables 6 and 8). A similar outcome was found for the Ser298Ala/Glu333Ala and Ser298Ala/Lys334Ala variants in which the binding to FcγRIIIA improved over the parental variants (Table 8). In other combinations, one residue dominated the other, e.g. the Thr256Ala/Ser298Ala variant showed reduced binding to FcγRIIA and FcγRIIB similar to the Ser298Ala variant even though the Thr256Ala change effected better binding to both these receptors (Class 3).

The most pronounced additivity was found for combination variants with improved binding to FcRn. At pH 6.0, the Glu380Ala/Asn343Ala variant showed over 8-fold better binding to FcRn, relative to native IgG1, compared to 2-fold for Glu380Ala and 3.5-fold for Asn434Ala (Tables 6 and 8). Adding Thr307Ala to this effected a 13-fold improvement in binding relative to native IgG1. Likewise, combining Glu380Ala and Leu309Ala, the latter being deleterious to FcRn binding, resulted in a variant which was intermediate between the two parental variants (Table 8). As with the FcγR, some combinations showed dominance of one residue over the other; for the Lys288Ala/Asn434Ala variant, the better binding due to Asn434Ala clearly overcame the reduction in binding from Lys288Ala (Table 8). At pH 7.2 none of variants bound well.

Combining S298(317)A with K334(353)A improved binding to FcγRIIIA more than either S298(317)A or K334(353)A alone (FIGS. 18A and B; and compare the variants in Tables 6 and 8) (residue numbers in parentheses are those of the EU index as in Kabat). Similarly, combining S298(317)A with E333(352)A improved binding to FcγRIIIA more than either S298(317)A or E333(352)A alone (compare the variants in Tables 6 and 8).

ADCC Activity of the Variants

One application of these variants is to improve the ADCC effector function of an antibody. This can be achieved by modifying Fc region amino acids at one or more residues which would lead to improved binding to FcγRIIIA. Improved FcγRIIIA binding would lead to improved binding by NK cells, which carry only FcγRIIIA and can mediate ADCC. Selected alanine variants which were either reduced in binding to FcγRIIIA (variants D265(278)A, E269(282)A, D270(283)A, Q295(312)A; Table 6), had no effect on FcγRIIIA binding (R292(309)A; Table 6), or had improved binding to FcγRIIIA (variants K290(307)A, S298(317)A; Table 6) were tested in an in vitro ADCC assay using human PBMCs as effector cells. Since the target cells were HER2-overexpressing SKBR3 cells, the IgG Fc variants used in this assay were generated by substituting the $V_H$/$V_L$ domains of anti-IgE E27 with those from anti-HER2 antibody; HERCEPTIN® (humAb4D5-8 in Table 1 of Carter et al. *PNAS* (*USA*) 89:4285-4289 (1992)). The pattern of ADCC exhibited by the variants correlated well with the pattern of binding to FcγRIIIA (FIGS. 20 and 21). Notably the variant which showed the best improvement in binding to FcγRIIIA in protein:protein assays, variant S298(317)A, also showed improvement in ADCC compared to wildtype HERCEPTIN® at 1.25 ng/ml (FIG. 21).

One set of ADCC assays with PBMCs compared the effect of Asp265Ala (Class 1), Arg292Ala (Class 6), and Ser298Ala (Class 7). The assay was repeated using four different donors. FIG. 24 shows that the ADCC pattern of the variants reiterated that seen in the ELISA binding assay for FcγRIIIA: Asp265Ala prevented ADCC ($P<0.01$; paired t-test), Arg292Ala had no effect, and Ser298Ala statistically improved ADCC ($P<0.01$; paired t-test).

A second set of assays were performed in which the FcγRIIIA allotype of the donors were determined. Using three FcγRIIIA-Val158/Val158 and three FcγRIIIA-Phe158/Phe158 donors, ADCC assays using only NK cells were repeated 3-4 times for each donor. Representative ADCC plots are shown in FIGS. 27A and 27B and the summary of all assays is shown in FIG. 27C. The variants tested were: Ser298Ala (Class 7), Lys334Ala (Class 9), Ser298Ala/Lys334Ala (Table 8), and Ser298Ala/Glu333Ala/Lys334Ala (Table 8). In agreement with the binding exhibited in the ELISA-format assay (Tables 6, 8 and 11), the pattern of improved ADCC was Ser298Ala/Glu333Ala/Lys334Ala>Ser298Ala/Lys334Ala>Ser298Ala=Lys334Ala. This pattern was seen with both the FcγRIIIA-Phe158/Phe158 and FcγRIIIA-Val158/Val158 donors, though improvement in ADCC was less pronounced for the latter. Comparing the improvement in binding to receptor for these variants in the ELISA-format assay (Tables 6, 8 and 11) with that in the cell-based (Table 11) and ADCC assays (FIGS. 24 and 27) shows that the improvement in binding for any specific variant is enhanced when the receptor is expressed on cells.

EXAMPLE 5

Bind of Fc Variants to Polymorphic Fc Receptors

Allelic variants of several of the human FcγR have been found in the human population. These allelic variant forms have been shown to exhibit differences in binding of human and murine IgG and a number of association studies have correlated clinical outcomes with the presence of specific allelic forms (reviewed in Lehrnbecher et al. *Blood* 94(12): 4220-4232 (1999)). Several studies have investigated two forms of FcγRIIA, R131 and H131, and their association with clinical outcomes (Hatta et al. *Genes and Immunity* 1:53-60 (1999); Yap et al. *Lupus* 8:305-310 (1999); and Lorenz et al. European *J. Immunogenetics* 22:397-401 (1995)). Two allelic forms of FcγRIIIA, F158 and V158, are only now being investigated (Lehrnbecher et al., supra; and Wu et al. *J. Clin.*

*Invest.* 100(5):1059-1070 (1997)). In this example, selected IgG variants were tested against both allelic forms of FcγRIIA or FcγRIIIA. Fc receptor binding assays were performed essentially as described in the above examples. However, for FcγRIIIA-V158, both (a) the low affinity receptor binding assay of Example 1 (which analyzes binding of the IgG complex to FcγRIIIA-V158); and (b) the high affinity FcγR binding assay of Example 4 (which analyzes binding of IgG monomer to FcγRIIIA-V158) were carried out. The CHO stable cell lines expressing FcγRIIIA-Phe158 and FcγRIIIA-Val158 with human γ-chain were generated by subcloning the α-chain and γ-chains into a previously described vector which includes DNA encoding a green fluorescent protein (GFP) (Lucas et al. *Nucl. Acids Res.* 24: 1774-1779 (1996)). CHO cell transfection was carried out using Superfect (Qiagen) according to the manufacturer's instructions. FACS sorting was done based on GFP expression as described previously (Meng et al. *Gene* 242: 201-207 (2000)). Receptor expression levels were determined by staining with anti-FcγRIII monoclonal antibody 3G8 (Medarex). Binding of IgG1 variants was performed by adding monomeric IgG in staining buffer to $5\times10^5$ cells and incubating in 96 well round-bottom tissue culture plates (Costar, Cambridge, Mass.) at 4° C. for 30 min. Cells were washed three times with staining buffer and IgG binding detected by addition of 1:200 PE-F(ab')$_2$ fragment of goat anti-human IgG and incubation for 30 min at 4° C. After washing, immunofluorescence staining was analyzed on a FACScan flow cytometer using Cellquest software (Becton Dickinson). Dead cells were excluded from analysis by addition of 1 µg/ml propidium iodide. The results of these studies are summarized in Table 9-11 below.

TABLE 9

Binding of Variants to FcγRIIA and FcγRIIIA Polymorphic Receptors

| IG2 | Res#EU (Kabat) | IgG Complex FCγRIIA-R131 | | | IgG Complex FCγRIIA-H131 | | | IgG Complex FcγRIIIA-F158 | | | IgG Complex FcγRIIIA-V158 | | | IgG Monomer FCγRIIIA-V158 | | |
|---|---|---|---|---|---|---|---|---|---|---|---|---|---|---|---|---|
| | | mean | sd | n | mean | sd | n | mean | sd | n | mean | sd | n | mean | sd | n |
| 11 | T256(269)A | 1.41 | (0.27) | 9 | | | | 1.32 | (0.18) | 9 | 0.97 | (0.03) | 2 | 1.20 | | 1 |
| 254 | T256(269)N | 1.03 | | 1 | | | | 1.13 | | 1 | 0.95 | | 1 | 0.88 | | 1 |
| 14 | D265(278)A | 0.07 | (0.01) | 4 | | | | 0.09 | (0.06) | 4 | 0.01 | | 1 | | | |
| 15 | S267(280)A | 1.64 | (0.18) | 7 | 1.05 | (0.03) | 2 | 1.14 | (0.25) | 7 | | | | | | |
| 189 | S267(280)G | 1.21 | (0.05) | 3 | 0.59 | (0.09) | 3 | 0.09 | (0.02) | 3 | | | | | | |
| 16 | H268(281)A | 1.22 | (0.14) | 12 | 1.09 | (0.01) | 2 | 0.52 | (0.09) | 12 | | | | | | |
| 25 | E283(300)A | 1.24 | (0.23) | 5 | | | | 1.01 | (0.14) | 5 | | | | 0.78 | | 1 |
| 226 | E283(300)Q | 1.12 | | 1 | | | | 1.19 | | 1 | | | | 0.89 | | 1 |
| 227 | E283(300)S | 1.03 | | 1 | | | | 0.85 | | 1 | | | | 0.83 | | 1 |
| 228 | E283(300)N | 1.18 | | 1 | | | | 0.94 | | 1 | | | | 0.63 | | 1 |
| 229 | E283(300)D | 1.14 | | 1 | | | | 0.95 | | 1 | | | | 0.67 | | 1 |
| 30 | K290(307)A | 1.29 | (0.21) | 7 | | | | 1.28 | (0.21) | 7 | 1.12 | (0.05) | 2 | 1.13 | | 1 |
| 73 | K290(307)Q | 1.17 | | 1 | | | | 1.40 | | 1 | 1.02 | | 1 | 1.30 | | 1 |
| 75 | K290(307)S | 1.27 | | 1 | | | | 1.26 | | 1 | 1.05 | | 1 | 1.62 | | 1 |
| 77 | K290(307)E | 1.10 | | 1 | | | | 1.30 | | 1 | 0.98 | | 1 | 1.50 | | 1 |
| 78 | K290(307)R | 1.05 | | 1 | | | | 1.08 | | 1 | 1.07 | | 1 | 1.24 | | 1 |
| 177 | K290(307)G | 1.07 | | 1 | | | | 1.23 | | 1 | 1.11 | | 1 | 2.29 | | 1 |
| 31 | R292(309)A | 0.27 | (0.14) | 9 | | | | 0.90 | (0.18) | 9 | | | | 0.94 | | 1 |
| 80 | R292(309)K | 0.71 | (0.17) | 3 | | | | 1.15 | (0.18) | 3 | | | | 1.64 | | 1 |
| 81 | R292(309)H | 0.21 | (0.09) | 2 | | | | 0.92 | (0.08) | 2 | | | | 1.21 | | 1 |
| 82 | R292(309)Q | 0.47 | (0.12) | 3 | | | | 0.45 | (0.09) | 3 | | | | 0.56 | | 1 |
| 83 | R292(309)N | 0.54 | (0.16) | 3 | | | | 0.88 | (0.02) | 3 | | | | 0.91 | | 1 |
| 144 | E293(310)Q | 0.85 | (0.03) | 2 | | | | 0.99 | (0.04) | 2 | 1.00 | | 1 | 0.97 | | 1 |
| 33 | E294(311)A | 0.87 | (0.19) | 5 | | | | 0.66 | (0.14) | 5 | | | | 0.68 | | 1 |
| 173 | E294(311)Q | 1.01 | | 1 | | | | 0.84 | | 1 | | | | 0.79 | | 1 |
| 174 | E294(311)D | 0.37 | | 1 | | | | 0.14 | | 1 | | | | 0.26 | | 1 |
| 36 | S298(317)A | 0.40 | (0.08) | 12 | | | | 1.30 | (0.18) | 12 | 1.02 | (0.04) | 2 | 1.96 | | 1 |
| 70 | S298(317)G | 0.87 | (0.17) | 4 | | | | 0.46 | (0.09) | 4 | 0.88 | | 1 | 1.88 | | 1 |
| 71 | S298(317)T | 0.41 | (0.21) | 3 | | | | 0.89 | (0.20) | 3 | 0.96 | | 1 | 0.75 | | 1 |
| 72 | S298(317)N | 0.08 | (0.01) | 2 | | | | 0.06 | (0.01) | 2 | 0.66 | | 1 | 0.17 | | 1 |
| 218 | S298(317)V | 0.11 | (0.06) | 3 | | | | 0.33 | (0.19) | 3 | 0.88 | | 1 | 0.39 | | 1 |
| 219 | S298(317)L | 1.14 | (0.12) | 3 | | | | 0.34 | (0.04) | 3 | 0.83 | | 1 | 0.67 | | 1 |
| 40 | V305(324)A | 1.12 | (0.12) | 4 | 1.04 | | 1 | 0.84 | (0.15) | 4 | | | | | | |
| 41 | T307(326)A | 1.19 | (0.37) | 12 | 1.37 | (0.13) | 2 | 1.12 | (0.18) | 12 | | | | | | |
| 45 | N315(334)A | 1.15 | (0.06) | 5 | 1.11 | (0.06) | 2 | 1.07 | (0.21) | 5 | | | | | | |
| 46 | K317(336)A | 1.13 | (0.05) | 4 | 1.04 | | 1 | 1.10 | (0.23) | 4 | | | | | | |
| 48 | K320(339)A | 1.12 | (0.11) | 4 | 1.16 | | 1 | 0.87 | (0.17) | 4 | | | | | | |
| 54 | E333(352)A | 0.92 | (0.12) | 10 | | | | 1.27 | (0.17) | 10 | 1.10 | (0.10) | 2 | 1.29 | | 1 |
| 141 | E333(352)Q | 0.70 | (0.05) | 2 | | | | 1.10 | (0.03) | 2 | 1.05 | | 1 | 1.00 | | 1 |
| 142 | E333(352)N | 0.59 | (0.04) | 2 | | | | 0.56 | (0.10) | 2 | 0.64 | | 1 | 0.56 | | 1 |
| 143 | E333(352)S | | | | | | | 0.94 | | 1 | 0.99 | | 1 | 1.07 | | 1 |
| 152 | E333(352)K | | | | | | | 0.85 | (0.14) | 3 | 0.88 | | 1 | 0.81 | | 1 |
| 153 | E333(352)R | 0.75 | (0.04) | 2 | | | | 0.84 | (0.05) | 2 | 0.93 | | 1 | 0.83 | | 1 |
| 154 | E333(352)D | | | | | | | 1.26 | (0.04) | 3 | 1.00 | | 1 | 1.70 | | 1 |
| 178 | E333(352)G | 0.87 | | 1 | | | | 1.05 | | 1 | | | | 1.23 | | 1 |
| 55 | K334(353)A | 1.01 | (0.15) | 17 | | | | 1.39 | (0.19) | 17 | 1.07 | (0.09) | 3 | 1.60 | (0.01) | 2 |
| 135 | K334(353)R | 1.15 | (0.09) | 5 | | | | 0.68 | (0.07) | 5 | | | | 0.88 | | 1 |
| 136 | K334(353)Q | 1.08 | (0.11) | 7 | | | | 1.31 | (0.26) | 7 | 1.27 | (0.01) | 2 | 1.92 | | 1 |
| 137 | K334(353)N | 1.16 | (0.11) | 7 | | | | 1.15 | (0.16) | 7 | 1.19 | (0.06) | 2 | 1.70 | | 1 |
| 138 | K334(353)S | 1.01 | (0.11) | 3 | | | | 1.19 | (0.08) | 3 | 1.25 | | 1 | 1.82 | | 1 |
| 139 | K334(353)E | 0.74 | (0.15) | 4 | | | | 1.30 | (0.09) | 4 | 1.17 | | 1 | 2.75 | | 1 |
| 140 | K334(353)D | 0.51 | (0.09) | 4 | | | | 1.13 | (0.09) | 4 | 1.07 | | 1 | | | |

TABLE 9-continued

Binding of Variants to FcγRIIA and FcγRIIIA Polymorphic Receptors

| | Res#EU | IgG Complex FCγRIIA-R131 | | | IgG Complex FCγRIIA-H131 | | | IgG Complex FcγRIIIA-F158 | | | IgG Complex FcγRIIIA-V158 | | | IgG Monomer FcγRIIIA-V158 | | |
|---|---|---|---|---|---|---|---|---|---|---|---|---|---|---|---|---|
| IG2 | (Kabat) | mean | sd | n | mean | sd | n | mean | sd | n | mean | sd | n | mean | sd | n |
| 179 | K334(353)G | 0.76 | (0.08) | 5 | | | | 0.88 | (0.22) | 5 | 0.94 | | 1 | 1.28 | | 1 |
| 190 | K334(353)M | 1.06 | | 1 | | | | 1.35 | | 1 | 0.99 | | 1 | 2.08 | | 1 |
| 191 | K334(353)Y | 1.08 | | 1 | | | | 1.31 | | 1 | 0.98 | | 1 | 1.72 | | 1 |
| 192 | K334(353)W | 0.94 | | 1 | | | | 1.07 | | 1 | 0.96 | | 1 | 1.53 | | 1 |
| 193 | K334(353)H | 1.09 | | 1 | | | | 1.26 | | 1 | 0.97 | | 1 | 2.06 | | 1 |
| 220 | K334(353)V | 1.13 | (0.11) | 3 | | | | 1.34 | (0.18) | 3 | 1.00 | | 1 | 2.89 | | 1 |
| 221 | K334(353)L | 1.05 | | 1 | | | | 1.38 | | 1 | 0.96 | | 1 | 3.59 | | 1 |
| 65 | P331(350)A | 1.29 | (0.14) | 3 | | | | 1.03 | (0.19) | 3 | 0.96 | | 1 | 0.78 | | 1 |
| 198 | P331(350)S | 1.00 | | 1 | | | | 0.86 | | 1 | | | | 0.54 | | 1 |
| 199 | P331(350)N | 0.86 | | 1 | | | | 0.23 | | 1 | | | | 0.24 | | 1 |
| 200 | P331(350)E | 1.06 | | 1 | | | | 0.42 | | 1 | | | | 0.36 | | 1 |
| 203 | P331(350)K | 0.94 | | 1 | | | | 0.33 | | 1 | | | | 0.26 | | 1 |
| 96 | S267(280)A H268(281)A | 1.54 | (0.12) | 3 | 1.07 | (0.06) | 2 | 0.84 | | 1 | | | | | | |
| 110 | S298(317)A E333(352)A K334(353)A | 0.35 | (0.13) | 11 | | | | 1.66 | (0.42) | 11 | 1.19 | (0.18) | 3 | | | |
| 271 | E380(405)A L309(328)A | 0.98 | | 1 | | | | 0.92 | | 1 | | | | 1.10 | | 1 |

TABLE 10

Binding of Human IgG1 Variants to Human FcγRIIA-R131 and FcγRIIA-H131 Polymorphic Receptors

| | | | FcγRIIA-R131[c] | | | FcγRIIA-R131[d] | | FcγRIIIA-H131 | | H131/R131 | | |
|---|---|---|---|---|---|---|---|---|---|---|---|---|
| Variant[a] | Class[b] | FcγR | mean | (sd) | N | mean | (sd) | mean | (sd) | mean | (sd) | N |
| Ser267Ala | 4 | ↑II | 1.52 | (0.22) | 11 | 1.53 | (0.06) | 1.10 | (0.12) | 0.71 | (0.07) | 5 |
| Ser267Gly | | ↓III | 1.18 | (0.10) | 4 | | | 0.54 | (0.14) | 0.47 | (0.13) | 5 |
| His268Ala | 5 | ↑II ↓III | 1.21 | (0.14) | 13 | 1.30 | (0.17) | 0.97 | (0.15) | 0.75 | (0.12) | 10 |
| Asp270Ala | 2 | ↑II, III | 0.06 | (0.01) | 5 | 0.04 | (0.02) | 0.45 | (0.11) | 16.6 | (8.5) | 6 |
| Ser298Ala | 7 | ↓II ↑III | 0.40 | (0.15) | 16 | 0.26 | (0.10) | 0.24 | (0.08) | 0.93 | (0.13) | 6 |
| Val305Ala | 10 | ↑FcRn | 1.12 | (0.12) | 4 | 1.00 | (0.14) | 1.06 | (0.10) | 1.08 | (0.10) | 4 |
| Thr307Ala | 4 | ↑II | 1.07 | (0.14) | 11 | 1.28 | (0.13) | 1.18 | (0.06) | 0.94 | (0.09) | 5 |
| Asn315Ala | 4 | ↑II | 1.15 | (0.06) | 5 | 1.11 | (0.18) | 1.10 | (0.16) | 0.99 | (0.05) | 8 |
| Lys317Ala | 10 | ↑FcRn | 1.13 | (0.05) | 4 | 1.10 | (0.13) | 1.08 | (0.08) | 0.99 | (0.07) | 7 |
| Lys320Ala | | no effect | 1.14 | (0.11) | 6 | 1.05 | (0.19) | 1.13 | (0.09) | 1.10 | (0.15) | 7 |
| Ser267Ala His268Ala | | ↑II | 1.41 | (0.00) | 2 | 1.57 | (0.06) | 1.02 | (0.08) | 0.65 | (0.03) | 4 |

[a]Residue numbers are according to the Eu numbering system (Kabat et al. (1991) supra).
[b]Class as noted in Table 6.
[c]Values are from Table 6, 7 or 8.
[d]Values are the ratio of binding of the variant to that of native IgG1 in assays separate from those in column 4 and performed simultaneously with the FcγRIIIA-H131 assays in column 6.

TABLE 11

Binding of Human IgG1 Variants to Human FcγRIIIA-Phe158 and FcγRIIIA-Val158 Polymorphic Receptors

| | | | Phe158[c] | | | Phe158[d] | | Val158[e] | | |
|---|---|---|---|---|---|---|---|---|---|---|
| Variant[a] | Class[b] | FcγR | mean | (sd) | N | mean | (sd) | mean | (sd) | N[f] |
| Asp265Ala | 1 | ↓I, II, III | 0.09 | (0.06) | 4 | 0.05 | (0.02) | 0.02 | (0.01) | 5 |
| | | | | | | 0.12 | (0.08) | 0.05 | (0.02) | 3 |
| Lys290Ala | 3 | ↑II, III | 1.31 | (0.19) | 9 | 1.15 | (0.27) | 1.01 | (0.08) | 4 |
| | | | | | | 1.61 | (0.15) | 0.89 | (0.04) | 3 |
| Ser298Ala | 7 | ↓II ↑III | 1.34 | (0.20) | 16 | 1.49 | (0.27) | 1.07 | (0.07) | 7 |
| | | | | | | 1.85 | (0.05) | 1.18 | (0.09) | 3 |
| Pro331Ala | 4 | ↑II | 1.08 | (0.19) | 3 | 1.00 | (0.23) | 0.97 | (0.02) | 5 |
| | | | | | | 0.94 | (0.07) | 0.88 | (0.09) | 3 |
| Glu333Ala | 9 | ↓II ↑III | 1.27 | (0.17) | 10 | 1.13 | (0.32) | 1.06 | (0.11) | 4 |
| | | | | | | 1.42 | (0.04) | 1.08 | (0.09) | 3 |

TABLE 11-continued

Binding of Human IgG1 Variants to Human FcγRIIIA-Phe158 and FcγRIIIA-Val158 Polymorphic Receptors

| Variant[a] | Class[b] | FcγR | Phe158[c] mean | (sd) | N | Phe158[d] mean | (sd) | Val158[e] mean | (sd) | N[f] |
|---|---|---|---|---|---|---|---|---|---|---|
| Lys334Ala | 9 | ↑III | 1.39 | (0.19) | 17 | 1.39 | (0.22) | 1.10 | (0.07) | 9 |
|  |  |  |  |  |  | 2.46 | (0.08) | 1.26 | (0.21) | 3 |
| Ser298Ala |  | ↓II ↑III | 1.51 | (0.31) | 10 | 2.17 | (0.36) | 1.11 | (0.08) | 5 |
| Glu333Ala |  |  |  |  |  | 3.42 | (0.28) | 1.65 | (0.12) | 3 |
| Lys334Ala |  |  |  |  |  |  |  |  |  |  |

[a]Residue numbers are according to the Eu numbering system (Kabat et al. (1991) supra).
[b]Class as noted in Table 6.
[c]Values are for FcγRIIIA-Phe158 from Table 6.
[d]Values are the ratio of binding of the variant to that of native IgG1 to FcγRIIIA-Phe158 in assays separate from those in column 4 and performed simultaneously with the FcγRIIIA-Val158 assays in column 6. Upper values are for binding in the ELISA format assay; lower values are for binding to CHO cells stable transfected with the α- and γ-chains of the receptor.
[e]Values are the ratio of binding of the variant to that of native IgG1 to FcγRIIIA-V158. Upper values are for binding in the ELISA format assay; lower values are for binding to CHO cells stable transfected with the α- and γ-chains of the receptor.
[f]Number of independent assays for values in columns 5 and 6.

Selected variants were tested for binding to the FcγRIIA-H131 and FcγRIIIA-V158 allotypic receptor forms based on their improved or reduced binding to the allotypic forms used for the assays (i.e. FcγRIIA-Arg131 and FcγRIIIA-Phe158). Tables 9 and 10 show that most of the variants bound equivalently to the FcγRIIA-Arg131 and FcγRIIA-His131 receptors. The exceptions were the Ser267Ala, His268Ala and Ser267Ala/His268Ala variants which displayed binding to FcγRIIA-His131 that was reduced compared to FcγRIIA-Arg131 but still equivalent to native IgG1. The related Ser267Gly variant, however, showed a 50% reduction in binding to the FcγRIIA-His131 receptor compared to native IgG1. In contrast to Ser267Ala and His268Ala, Asp270Ala reduced binding to FcγRIIA-His131 by 50% but completely abrogating binding to FcγRIIA-Arg131. This suggests that Ser267, His268 and Asp270 interact with FcγRIIA in the vicinity of FcγRIIA residue 131.

For FcγRIIIA, the selected variants were assayed in the ELISA-format as well as on stable-transfected CHO cell lines expressing the γ-chains (FcγRIIIA-Phe158 or FcγRIIIA-Val158) with the associated human α-chain. For FcγRIIIA-Phe158, those variants that showed improved binding in the ELISA-format exhibited even more improvement, compared to native IgG1, in the cell-based assay (Table 11). This could be due to the presence of the γ-chain associated with the α-chain enhancing binding of the IgG to FcγRIIIA (Miller et al. *J. Exp. Med.* 183:2227-2233 (1996)). Alternatively, since the cell-based assay utilized monomeric IgG (in contrast to hexameric complexes used in the ELISA-format assay), the cell-based assay may be less subject to an avidity component and thus more sensitive to changes in the binding interface. In contrast, none of the variants exhibited improved binding to the FcγRIIIA-Val158 receptor in the ELISA-format assay, though the Ser298Ala, Lys334Ala and Ser298Ala/Glu333Ala/Lys334Ala variants did bind better than native IgG1 in the cell-based assay.

Human FcγRIIA has two known, naturally occurring allotypes which are determined by the amino acid at position 131. Among the human IgG1 variants tested against both FcγRIIA-Arg131 and FcγRIIA-His131, variants Ser267Ala, Ser267Gly, His268Ala and Asp270Ala could discriminate between the polymorphic forms. This suggests that these IgG1 residues interact with FcγRIIA in the vicinity of FcγRIIA residue 131 and in the IgG1 Fc:FcγRIIIA crystal structure (Sondermann et al. *Nature* 406:267-273 (2000)), Ser267 is adjacent to His131.

Human FcγRIIIA has naturally occurring allotypes at position 48 (Leu, His or Arg) and at position 158 (Val or Phe). The FcγRIIIA-Val158 allotype binds human IgG better than the FcγRIIIA-Phe158 allotype (Koene et al. *Blood* 90: 1109-1114 (1997); and Wu et al. *J. Clin. Invest.* 100: 1059-1070 (1997)) and this difference is reiterated in the ELISA-format, cell-based and ADCC assays in this study. The IgG1 Fc:FcγRIIIA crystal structure offers an explanation for this difference. In the crystal structure, V158 interacts with the IgG1 lower hinge near Leu235-Gly236 and with the FcγRIIIA Trp87 sidechain (which in turn interacts with the important IgG1 Pro329); introduction of the larger Phe158 may alter either or both of these interactions and thereby reduce the binding.

Figure 27C:
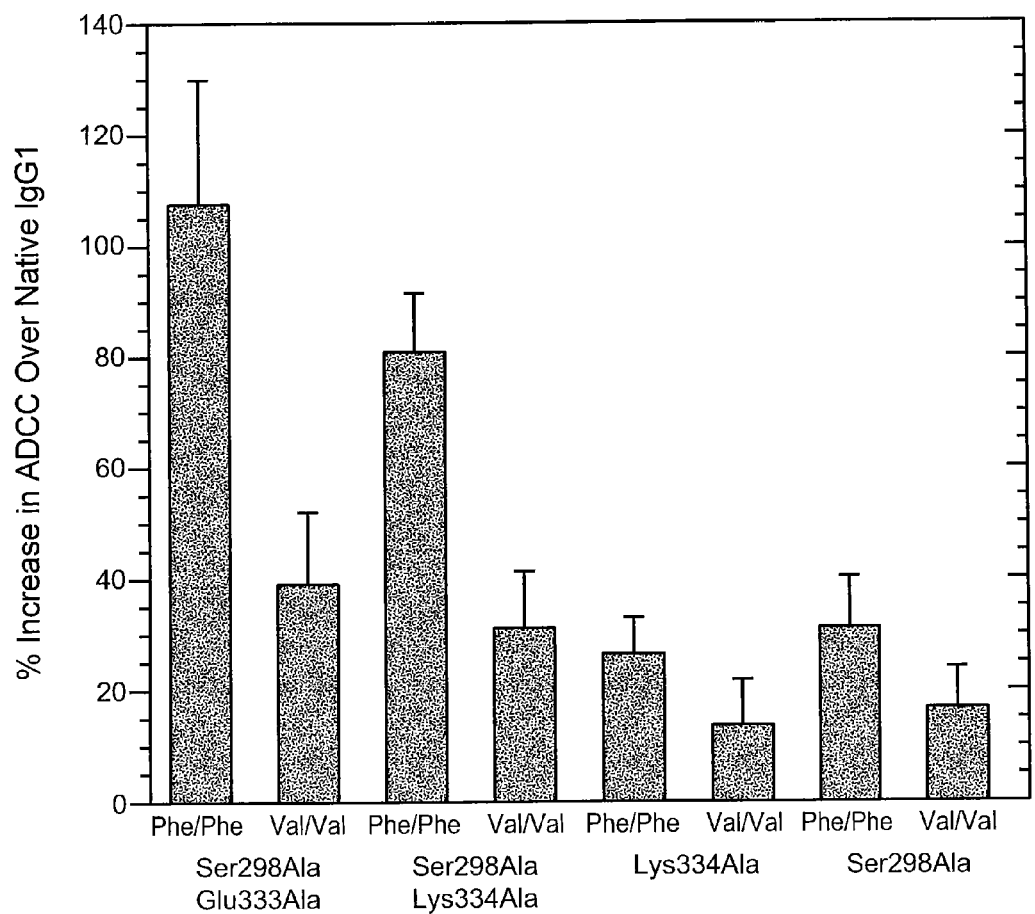

Some of the IgG1 variants exhibited better binding to FcγRIIIA-Phe158 (e.g. Classes 7 and 9) and could be further improved by combining individual variants (Table 8). These same variants showed no or minimal improvement in binding to FcγRIIIA-Val158 in the ELISA-format assay. However, when tested on cells expressing FcγRIIIA-Val158 or in ADCC assays using FcγRIIIA-Val158/Val158 donors, some of these variants did show superior interaction compared to native IgG1 (Table 11, FIG. 27). Comparing the ADCC results of select IgG1 variants with better binding to FcγRIIIA, the variants exhibited a significant improvement in ADCC for both FcγRIIIA-Phe158/Phe158 and FcγRIIIA-Val158/Val158 donors (FIG. 27). Indeed, using the Ser298Ala/Glu333Ala/Lys334Ala variant, the FcγRIIIA-Phe158/Phe158 donor ADCC could be increased over 100% (i.e. >2-fold) compared to native IgG1 (FIG. 27C).

While the influence of FcγRIIA polymorphic forms in various human diseases has been investigated for many years (reviewed in Lehrnbecher et al. *Blood* 94:4220-4232 (1999)), the possible correlation between FcγRIIIA polymorphic forms and human disease has only recently been investigated (Wu et al. *J. Clin. Invest.* 100: 1059-1070 (1997); Lehrnbecher et al. *Blood* 95: 2386-2390 (2000); Nieto et al. *Arthritis & Rheumatism* 43: 735-739 (2000)). Given the possible involvement of FcγR in the mechanism of action of therapeutic antibodies, human IgG1 variants with improved binding capacity to human FcγR, especially variants with better binding to FcγRIIIA and simultaneous abrogation of binding to the inhibitory FcγRIIB, could be used to provide more efficacious therapeutic antibodies. In addition, a recent report on the occurrence of polymorphic FcγR forms in control populations showed that the FcγRIIIA-Phe158 allele is more prevalent than the FcγRIIIA-Val158 allele (Lehrnbecher et al. *Blood* 94: 4220-4232 (1999)). Since the FcγRIIIA-Phe158 receptor binds human IgG1 less well than the FcγRIIIA-Val158 receptor, therapeutic antibodies with variant Fc portions that improve binding to FcγRIIIA-Phe158 at least to the level seen for FcγRIIIA-Val158 (if not more so) could provide increased therapeutic efficacy to the majority of the population.

EXAMPLE 6

Role of IgG Residues Affecting Carbohydrate

To determine whether differences in binding among variants was related to variation in the oligosaccharide at the conserved Asn297-linked glycosylation site, oligosaccharides of various IgG variants were analyzed using matrix-assisted laser desorption/ionization time-of-flight mass spectrometry (MALDI-TOF-MS) as previously described (Papac et al. *Glycobiology* 8: 463-472 (1998)). Following immobilization of approximately 50 μg of IgG to PVDF membranes in 96 well MultiScreen® IP plates (Millipore), proteins were reduced with 50 μL 0.1 M dithiothreitol in 8 M urea, 360 mM Tris, 3.2 mM EDTA, pH 8.6 (RCM buffer). Resultant free sulfhydryl groups were subsequently carboxymethylated by incubation with 0.1 M iodoacetic acid in RCM buffer at 25° C. for 30 min in the dark. Prior to enzymatic release of glycoproteins, membrane-bound proteins were incubated in 1% aqueous polyvinylpyrrolidone 360 (Sigma) solution at 25° C. for 1 hr. Oligosaccharides were released by incubating protein with 32 units of PNGase F (New England Biolabs, Beverly, Mass.) in 25 μL of Tris-acetate buffer, pH 8.4, at 37° C. for 3 hr, followed by acidification by addition of 2.5 μL 1.5 M acetic acid and then incubated for 25° C. for 3 hr. Samples were then purified by cation exchange chromatography using hydrogen form, 100-200 mesh AG50W-X8 resin (Biorad). Released oligosaccharides were analyzed by MALDI-TOF-MS in both positive and negative modes using matrices containing 2,5-dihydroxybenzoic acid (DHB) and 2,4,6-trihydroxyacetophenone (THAP), respectively (Papac et al. *Anal. Chem.* 68: 3215-3223 (1996)). Analysis was performed on a Voyager DE mass spectrometer (PerSeptive Biosystems, Foster City, Calif.) by transferring 0.5 μL of sample to a stainless steel target containing 0.4 μL of the appropriate matrix. Following vacuum dessication, the samples were ionized by irradiation with an N2 laser (337 nm wavelength) and ions were accelerated with a 20 kV voltage. Ion mass assignment was made using oligosaccharide standards (Oxford Glycosciences, Rosedale, N.Y.) in a two-point external calibration. Final spectra were the result of the summation of the individual spectral data from 240 laser ignitions. The results are shown in Table 12 below.

TABLE 12

Percent of Total Oligosaccharide Area by Glycan Type

|  | IgG1 | Glu258 Ala | Asp265 Ala | Tyr296 Phe | Ser298 Ala | Arg301 Ala | Arg301 Met | Val303 Ala | Lys334 Ala |
|---|---|---|---|---|---|---|---|---|---|
| High Mannose ||||||||||
|  | 14.6[a] | 11.1 | 8.0 | 14.8 | 11.3 | 5.3 | 5.4 | 10.2 | 20.9 |
|  | 3.8 | 1.1 | 4.0 |  |  | 0.8 | 2.4 | 0.7 |  |
| Complexes with Terminal Galactose ||||||||||
| 0 | 51.5 | 36.3 | 47.2 | 47.0 | 48.9 | 24.1 | 24.3 | 48.7 | 49.5 |
|  | 0.6 | 0.2 | 6.0 |  |  | 3.7 | 0.9 | 0.2 |  |
| 1 | 23.4 | 34.9 | 25.0 | 23.1 | 28.1 | 23.9 | 27.2 | 28.5 | 17.4 |
|  | 3.2 | 0.9 | 3.5 |  |  | 0.8 | 5.9 | 0.5 |  |
| 2 | 8.5 | 15.8 | 19.5 | 12.5 | 9.6 | 45.3 | 42.0 | 11.4 | 10.8 |
|  | 0.3 | 0.1 | 6.3 |  |  | 2.4 | 5.9 | 0.4 |  |
| 3 | 2.0 | 2.0 | 0.2 | 2.5 | 2.1 | 1.1 | 1.1 | 1.0 | 1.5 |
|  | 0.5 | 0.2 | 0.2 |  |  | 1.0 | 0.3 | 0.1 |  |
| 1-3 | 33.9 | 52.7 | 44.7 | 38.1 | 39.8 | 70.3 | 70.3 | 40.9 | 29.7 |
|  | 4.0 | 1.2 | 10.0 |  |  |  | 4.0 | 1.7 | 1.0 |
| Complexes with Terminal Sialic Acid ||||||||||
|  | 0.0 | 3.0 | 2.4 | 0.0 | 0.0 | 9.7 | 10.9 | 1.3 | 0.0 |
| Complexes with Fucose ||||||||||
| 0 | 4.5 | 1.1 | 1.3 | 3.0 | 1.5 | 0.7 | 1.5 | 1.6 | 6.1 |
|  | 0.6 | 0.1 | 0.2 |  |  | 0.2 | 1.9 | 0.2 |  |
| 1 | 81.1 | 87.9 | 90.7 | 82.1 | 87.2 | 94.0 | 93.4 | 88.1 | 73.1 |
|  | 3.0 | 1.3 | 3.9 |  |  | 1.0 | 1.5 | 0.5 |  |
| Triantennary Complexes ||||||||||
|  | 0.2 | 0.2 | 3.2 | 0.0 | 0.0 | 5.5 | 5.0 | 0.3 | 0.0 |
|  | 0.2 | 0.2 | 0.1 |  |  | 1.2 | 0.8 | 0.3 |  |

[a]Upper values are mean percent and lower values are deviation from mean for two independent analyses on two different lots of IgG.

Previously it was noted that replacing human IgG3 residues which contact the oligosaccharide, e.g. Asp265, Tyr296, Arg301, with Ala resulted in increased galactosylation and sialylation relative to native IgG3 and in reduced binding to both FcγR and C1q (Lund et al. *J. Immunol.* 157: 4963-4969 (1996)). In order to determine if the effect seen for specific Ala substitutions (either deleterious or advantageous) was due to differences in glycosylation, oligosaccharide analysis was performed for selected variants (Table 12). The Asp265Ala, Arg301Ala and Arg301Met variants showed increased galactosylation, a relatively small amount of sialylation, and a small percentage of trianntenary carbohydrate, in agreement with Lund et al., supra. The Arg301Ala and Arg301Met variants also showed an increase in fucose and a decrease in mannose not seen previously. For the Tyr296Phe variant, there were no differences from native IgG1, in contrast to the decrease in galactose and fucose and increase in mannose reported by Lund et al., supra. These differences may be due to the different mammalian cells used to express the antibodies (human kidney 293 cells in this study and Chinese hamster ovary cells in the previous study) or may reflect that Tyr296 was changed to Phe296 in this study whereas it was changed to Ala296 in the Lund et al. study.

The Lys334 sidechain is near the carbohydrate in IgG crystal structures but does not interact with it as intimately as do Asp265, Tyr296 and Arg301. The Lys334Ala variant exhibited a small increase in mannose and small decrease in fucose compared to native IgG1 (Table 12). Ser298 interacts with the carbohydrate only through its Oγ atom, which forms a hydrogen bond to the Asn297 Oγ, and no difference in carbohydrate for the Ser298Ala was evident compared to native IgG1. Neither the Glu258 or Val303 sidechains interact with the carbohydrate, indeed both are located on the opposite face of the CH2 domain from the carbohydrate. However, the Glu258Ala variant showed an increase in galactosylation and a small amount of sialic acid while the Val303Ala variant only showed a small amount of sialic acid. Hence, variation in galactosylation and sialic acid for a given variant (compared to native IgG1) may occur regardless of whether the amino acid sidechain interacts with the carbohydrate.

For the Tyr296Phe, Ser298Ala, Val303Ala and Lys334Ala variants the differences in glycosylation, compared to native IgG1, were minimal and most likely were not the cause of the differences in binding of these variants to the FcγR. For the Glu258Ala, Asp265Ala, Arg301Ala and Arg301Met variants, it is difficult to discern whether reduction or improvement in FcγR binding is due to the change in amino acid sidechain or from differences in glycosylation.

The presence of carbohydrate linked at residue Asn297 is required for binding to FcγR (Lund et al., supra). In addition, the nature of the carbohydrate can influence binding (Umaña et al. *Nature Biotech.* 17: 176-180 (1999); Lifely et al. *Glycobiology* 5:813-822 (1995); Lund et al. *J. Immunol.* 157: 4963-4969 (1996); and Lund et al. *FASEB J.* 9: 115-119 (1995)). In crystal structures of IgG (Fc and intact antibody), Asp265 interacts directly with the Asn297-linked carbohydrate via hydrogen bonds (Deisenhofer, J. *Biochemistry* 20: 2361-2370 (1981); Guddat et al. *Proc. Natl. Acad. Sci. USA* 90: 4271-4275 (1993); Harris et al. *J. Mol. Biol.* 275: 861-872 (1998); and Harris et al. *Biochemistry* 36: 1581-1597 (1997)). Previous studies found that an Asp265Ala change in human IgG3 altered the composition of the Asn297-linked carbohydrate and reduced binding to FcγRI (Lund et al. *J. Immunol.* 157: 4963-4969 (1996); and Lund et al. *FASEB J.* 9: 115-119 (1995)). In human IgG1, Asp265Ala (Class 1) the carbohydrate also differed from that of native IgG1 (Table 12) and binding to FcγRI was reduced. Variants at position 258 and 301 also showed variation from native IgG1 and the other variants (Table 12). The two Arg301 variants exhibited an increase in binding to FcγRIIB, a decrease in binding to FcγRIIIA, and no effect on binding to FcγRI or FcRn (Class 5). Asp265Ala (Class 1) showed decreased binding to all FcγR while Glu258Ala (Class 4) showed increased binding to FcγRII only. Hence, while it is possible that the idiosyncratic carbohydrate on these variants influenced binding rather than the amino acid changes directly affecting interaction with the FcγR, the data do not allow resolution of the two possibilities. For the Tyr296Phe, Ser298Ala, Val303Ala and Lys334Ala variants there were no significant differences in carbohydrate from that of native IgG1 (Table 12). Hence the differences in binding to the various FcγR exhibited by these variants is unlikely to be a result of glycosylation differences.

What is claimed is:

1. Isolated nucleic acid encoding a variant of a parent polypeptide comprising an Fc region, wherein the Fc region mediates antibody-dependent cell-mediated cytotoxicity (ADCC) in the presence of human effector cells more effectively, or binds an Fc gamma receptor III (FcγRIII) with better affinity, than the parent polypeptide and wherein the Fc region comprises an amino acid modification at amino acid position 339 and does not comprise a modification of the lower hinge region wherein the numbering of the residues in the Fc region is that of the EU index as in Kabat.

2. A vector comprising the nucleic acid of claim 1.

3. A host cell containing the vector of claim 2.

4. A method for producing a polypeptide variant comprising culturing the host cell of claim 3 so that the nucleic acid is expressed.

5. The method of claim 4 further comprising recovering the polypeptide variant from the host cell culture.

6. The nucleic acid of claim 1 wherein the parent polypeptide is an antibody or an immunoadhesin.

7. The nucleic acid of claim 6 wherein the parent polypeptide is an antibody.

8. The nucleic acid of claim 1 wherein the parent polypeptide Fc region comprises a human IgG Fc region.

9. The nucleic acid of claim 8 wherein the human IgG Fc region comprises a human IgG1, IgG2, IgG3 or IgG4 Fc region.

10. The nucleic acid method of claim 1 wherein the variant mediates ADCC about 1.5 fold to about 100 fold more effectively than the parent polypeptide.

11. The nucleic acid of claim 1 wherein the variant binds an FcγRIII with better affinity than the parent polypeptide.

12. The nucleic acid of claim 11 wherein the variant further binds an FcγRII with worse affinity than the parent polypeptide.

13. The nucleic acid of claim 1, wherein the amino acid modification is A339T.

* * * * *

SEQUENCE LISTING

<160> NUMBER OF SEQ ID NOS: 11

<210> SEQ ID NO 1
<211> LENGTH: 218
<212> TYPE: PRT
<213> ORGANISM: Artificial Sequence
<220> FEATURE:
<223> OTHER INFORMATION: Sequence is completely synthesized

<400> SEQUENCE: 1

```
Asp Ile Gln Leu Thr Gln Ser Pro Ser Ser Leu Ser Ala Ser Val
 1               5                  10                  15

Gly Asp Arg Val Thr Ile Thr Cys Arg Ala Ser Lys Pro Val Asp
                20                  25                  30

Gly Glu Gly Asp Ser Tyr Leu Asn Trp Tyr Gln Gln Lys Pro Gly
                35                  40                  45

Lys Ala Pro Lys Leu Leu Ile Tyr Ala Ala Ser Tyr Leu Glu Ser
                50                  55                  60

Gly Val Pro Ser Arg Phe Ser Gly Ser Gly Ser Gly Thr Asp Phe
                65                  70                  75

Thr Leu Thr Ile Ser Ser Leu Gln Pro Glu Asp Phe Ala Thr Tyr
                80                  85                  90

Tyr Cys Gln Gln Ser His Glu Asp Pro Tyr Thr Phe Gly Gln Gly
                95                 100                 105
```

```
Thr Lys Val Glu Ile Lys Arg Thr Val Ala Ala Pro Ser Val Phe
            110                 115                 120

Ile Phe Pro Pro Ser Asp Glu Gln Leu Lys Ser Gly Thr Ala Ser
            125                 130                 135

Val Val Cys Leu Leu Asn Asn Phe Tyr Pro Arg Glu Ala Lys Val
            140                 145                 150

Gln Trp Lys Val Asp Asn Ala Leu Gln Ser Gly Asn Ser Gln Glu
            155                 160                 165

Ser Val Thr Glu Gln Asp Ser Lys Asp Ser Thr Tyr Ser Leu Ser
            170                 175                 180

Ser Thr Leu Thr Leu Ser Lys Ala Asp Tyr Glu Lys His Lys Val
            185                 190                 195

Tyr Ala Cys Glu Val Thr His Gln Gly Leu Ser Ser Pro Val Thr
            200                 205                 210

Lys Ser Phe Asn Arg Gly Glu Cys
            215

<210> SEQ ID NO 2
<211> LENGTH: 451
<212> TYPE: PRT
<213> ORGANISM: Artificial Sequence
<220> FEATURE:
<223> OTHER INFORMATION: Sequence is completely synthesized

<400> SEQUENCE: 2

Glu Val Gln Leu Val Glu Ser Gly Gly Gly Leu Val Gln Pro Gly
 1               5                  10                  15

Gly Ser Leu Arg Leu Ser Cys Ala Val Ser Gly Tyr Ser Ile Thr
            20                  25                  30

Ser Gly Tyr Ser Trp Asn Trp Ile Arg Gln Ala Pro Gly Lys Gly
            35                  40                  45

Leu Glu Trp Val Ala Ser Ile Lys Tyr Ser Gly Glu Thr Lys Tyr
            50                  55                  60

Asn Pro Ser Val Lys Gly Arg Ile Thr Ile Ser Arg Asp Asp Ser
            65                  70                  75

Lys Asn Thr Phe Tyr Leu Gln Met Asn Ser Leu Arg Ala Glu Asp
            80                  85                  90

Thr Ala Val Tyr Tyr Cys Ala Arg Gly Ser His Tyr Phe Gly His
            95                  100                 105

Trp His Phe Ala Val Trp Gly Gln Gly Thr Leu Val Thr Val Ser
            110                 115                 120

Ser Ala Ser Thr Lys Gly Pro Ser Val Phe Pro Leu Ala Pro Ser
            125                 130                 135

Ser Lys Ser Thr Ser Gly Gly Thr Ala Ala Leu Gly Cys Leu Val
            140                 145                 150

Lys Asp Tyr Phe Pro Glu Pro Val Thr Val Ser Trp Asn Ser Gly
            155                 160                 165

Ala Leu Thr Ser Gly Val His Thr Phe Pro Ala Val Leu Gln Ser
            170                 175                 180

Ser Gly Leu Tyr Ser Leu Ser Ser Val Val Thr Val Pro Ser Ser
            185                 190                 195

Ser Leu Gly Thr Gln Thr Tyr Ile Cys Asn Val Asn His Lys Pro
            200                 205                 210

Ser Asn Thr Lys Val Asp Lys Lys Val Glu Pro Lys Ser Cys Asp
            215                 220                 225

Lys Thr His Thr Cys Pro Pro Cys Pro Ala Pro Glu Leu Leu Gly
```

```
                        230                 235                 240
Gly Pro Ser Val Phe Leu Phe Pro Pro Lys Pro Lys Asp Thr Leu
                    245                 250                 255
Met Ile Ser Arg Thr Pro Glu Val Thr Cys Val Val Val Asp Val
                260                 265                 270
Ser His Glu Asp Pro Glu Val Lys Phe Asn Trp Tyr Val Asp Gly
            275                 280                 285
Val Glu Val His Asn Ala Lys Thr Lys Pro Arg Glu Glu Gln Tyr
        290                 295                 300
Asn Ser Thr Tyr Arg Val Val Ser Val Leu Thr Val Leu His Gln
    305                 310                 315
Asp Trp Leu Asn Gly Lys Glu Tyr Lys Cys Lys Val Ser Asn Lys
320                 325                 330
Ala Leu Pro Ala Pro Ile Glu Lys Thr Ile Ser Lys Ala Lys Gly
                335                 340                 345
Gln Pro Arg Glu Pro Gln Val Tyr Thr Leu Pro Pro Ser Arg Glu
            350                 355                 360
Glu Met Thr Lys Asn Gln Val Ser Leu Thr Cys Leu Val Lys Gly
        365                 370                 375
Phe Tyr Pro Ser Asp Ile Ala Val Glu Trp Glu Ser Asn Gly Gln
    380                 385                 390
Pro Glu Asn Asn Tyr Lys Thr Thr Pro Pro Val Leu Asp Ser Asp
395                 400                 405
Gly Ser Phe Phe Leu Tyr Ser Lys Leu Thr Val Asp Lys Ser Arg
                410                 415                 420
Trp Gln Gln Gly Asn Val Phe Ser Cys Ser Val Met His Glu Ala
            425                 430                 435
Leu His Asn His Tyr Thr Gln Lys Ser Leu Ser Leu Ser Pro Gly
        440                 445                 450
Lys

<210> SEQ ID NO 3
<211> LENGTH: 218
<212> TYPE: PRT
<213> ORGANISM: homo sapiens

<400> SEQUENCE: 3

Pro Ala Pro Glu Leu Leu Gly Gly Pro Ser Val Phe Leu Phe Pro
  1               5                  10                  15
Pro Lys Pro Lys Asp Thr Leu Met Ile Ser Arg Thr Pro Glu Val
                 20                  25                  30
Thr Cys Val Val Val Asp Val Ser His Glu Asp Pro Glu Val Lys
             35                  40                  45
Phe Asn Trp Tyr Val Asp Gly Val Glu Val His Asn Ala Lys Thr
         50                  55                  60
Lys Pro Arg Glu Glu Gln Tyr Asn Ser Thr Tyr Arg Val Val Ser
     65                  70                  75
Val Leu Thr Val Leu His Gln Asp Trp Leu Asn Gly Lys Glu Tyr
                 80                  85                  90
Lys Cys Lys Val Ser Asn Lys Ala Leu Pro Ala Pro Ile Glu Lys
             95                 100                 105
Thr Ile Ser Lys Ala Lys Gly Gln Pro Arg Glu Pro Gln Val Tyr
            110                 115                 120
Thr Leu Pro Pro Ser Arg Glu Glu Met Thr Lys Asn Gln Val Ser
            125                 130                 135
```

Leu Thr Cys Leu Val Lys Gly Phe Tyr Pro Ser Asp Ile Ala Val
            140                 145                 150

Glu Trp Glu Ser Asn Gly Gln Pro Glu Asn Asn Tyr Lys Thr Thr
            155                 160                 165

Pro Pro Val Leu Asp Ser Asp Gly Ser Phe Phe Leu Tyr Ser Lys
            170                 175                 180

Leu Thr Val Asp Lys Ser Arg Trp Gln Gln Gly Asn Val Phe Ser
            185                 190                 195

Cys Ser Val Met His Glu Ala Leu His Asn His Tyr Thr Gln Lys
            200                 205                 210

Ser Leu Ser Leu Ser Pro Gly Lys
            215

<210> SEQ ID NO 4
<211> LENGTH: 218
<212> TYPE: PRT
<213> ORGANISM: homo sapiens

<400> SEQUENCE: 4

Pro Ala Pro Glu Leu Leu Gly Gly Pro Ser Val Phe Leu Phe Pro
  1               5                  10                  15

Pro Lys Pro Lys Asp Thr Leu Met Ile Ser Arg Thr Pro Glu Val
             20                  25                  30

Thr Cys Val Val Val Asp Val Ser His Glu Asp Pro Glu Val Lys
             35                  40                  45

Phe Asn Trp Tyr Val Asp Gly Val Glu Val His Asn Ala Lys Thr
             50                  55                  60

Lys Pro Arg Glu Glu Gln Tyr Asn Ser Thr Tyr Arg Val Val Ser
             65                  70                  75

Val Leu Thr Val Leu His Gln Asp Trp Leu Asn Gly Lys Glu Tyr
             80                  85                  90

Lys Cys Lys Val Ser Asn Lys Ala Leu Pro Ala Pro Ile Glu Lys
             95                 100                 105

Thr Ile Ser Lys Ala Lys Gly Gln Pro Arg Glu Pro Gln Val Tyr
            110                 115                 120

Thr Leu Pro Pro Ser Arg Asp Glu Leu Thr Lys Asn Gln Val Ser
            125                 130                 135

Leu Thr Cys Leu Val Lys Gly Phe Tyr Pro Ser Asp Ile Ala Val
            140                 145                 150

Glu Trp Glu Ser Asn Gly Gln Pro Glu Asn Asn Tyr Lys Thr Thr
            155                 160                 165

Pro Pro Val Leu Asp Ser Asp Gly Ser Phe Phe Leu Tyr Ser Lys
            170                 175                 180

Leu Thr Val Asp Lys Ser Arg Trp Gln Gln Gly Asn Val Phe Ser
            185                 190                 195

Cys Ser Val Met His Glu Ala Leu His Asn His Tyr Thr Gln Lys
            200                 205                 210

Ser Leu Ser Leu Ser Pro Gly Lys
            215

<210> SEQ ID NO 5
<211> LENGTH: 217
<212> TYPE: PRT
<213> ORGANISM: homo sapiens

<400> SEQUENCE: 5

```
Pro Ala Pro Val Ala Gly Pro Ser Val Phe Leu Phe Pro Pro
 1               5                   10                  15

Lys Pro Lys Asp Thr Leu Met Ile Ser Arg Thr Pro Glu Val Thr
             20                  25                      30

Cys Val Val Asp Val Ser His Glu Asp Pro Glu Val Gln Phe
             35                  40                  45

Asn Trp Tyr Val Asp Gly Val Glu Val His Asn Ala Lys Thr Lys
             50                  55                      60

Pro Arg Glu Glu Gln Phe Asn Ser Thr Phe Arg Val Val Ser Val
             65                  70                      75

Leu Thr Val Val His Gln Asp Trp Leu Asn Gly Lys Glu Tyr Lys
             80                  85                      90

Cys Lys Val Ser Asn Lys Gly Leu Pro Ala Pro Ile Glu Lys Thr
             95                 100                     105

Ile Ser Lys Thr Lys Gly Gln Pro Arg Glu Pro Gln Val Tyr Thr
            110                 115                     120

Leu Pro Pro Ser Arg Glu Glu Met Thr Lys Asn Gln Val Ser Leu
            125                 130                     135

Thr Cys Leu Val Lys Gly Phe Tyr Pro Ser Asp Ile Ala Val Glu
            140                 145                     150

Trp Glu Ser Asn Gly Gln Pro Glu Asn Asn Tyr Lys Thr Thr Pro
            155                 160                     165

Pro Met Leu Asp Ser Asp Gly Ser Phe Phe Leu Tyr Ser Lys Leu
            170                 175                     180

Thr Val Asp Lys Ser Arg Trp Gln Gln Gly Asn Val Phe Ser Cys
            185                 190                     195

Ser Val Met His Glu Ala Leu His Asn His Tyr Thr Gln Lys Ser
            200                 205                     210

Leu Ser Leu Ser Pro Gly Lys
            215

<210> SEQ ID NO 6
<211> LENGTH: 218
<212> TYPE: PRT
<213> ORGANISM: homo sapiens

<400> SEQUENCE: 6

Pro Ala Pro Glu Leu Leu Gly Gly Pro Ser Val Phe Leu Phe Pro
 1               5                  10                  15

Pro Lys Pro Lys Asp Thr Leu Met Ile Ser Arg Thr Pro Glu Val
             20                  25                      30

Thr Cys Val Val Val Asp Val Ser His Glu Asp Pro Glu Val Gln
             35                  40                      45

Phe Lys Trp Tyr Val Asp Gly Val Glu Val His Asn Ala Lys Thr
             50                  55                      60

Lys Pro Arg Glu Glu Gln Phe Asn Ser Thr Phe Arg Val Val Ser
             65                  70                      75

Val Leu Thr Val Leu His Gln Asp Trp Leu Asn Gly Lys Glu Tyr
             80                  85                      90

Lys Cys Lys Val Ser Asn Lys Ala Leu Pro Ala Pro Ile Glu Lys
             95                 100                     105

Thr Ile Ser Lys Thr Lys Gly Gln Pro Arg Glu Pro Gln Val Tyr
            110                 115                     120

Thr Leu Pro Pro Ser Arg Glu Glu Met Thr Lys Asn Gln Val Ser
            125                 130                     135
```

```
Leu Thr Cys Leu Val Lys Gly Phe Tyr Pro Ser Asp Ile Ala Val
                140                 145                 150

Glu Trp Glu Ser Ser Gly Gln Pro Glu Asn Asn Tyr Asn Thr Thr
                155                 160                 165

Pro Pro Met Leu Asp Ser Asp Gly Ser Phe Phe Leu Tyr Ser Lys
                170                 175                 180

Leu Thr Val Asp Lys Ser Arg Trp Gln Gln Gly Asn Ile Phe Ser
                185                 190                 195

Cys Ser Val Met His Glu Ala Leu His Asn Arg Phe Thr Gln Lys
                200                 205                 210

Ser Leu Ser Leu Ser Pro Gly Lys
                215

<210> SEQ ID NO 7
<211> LENGTH: 218
<212> TYPE: PRT
<213> ORGANISM: homo sapiens

<400> SEQUENCE: 7

Pro Ala Pro Glu Phe Leu Gly Gly Pro Ser Val Phe Leu Phe Pro
  1               5                  10                  15

Pro Lys Pro Lys Asp Thr Leu Met Ile Ser Arg Thr Pro Glu Val
                 20                  25                  30

Thr Cys Val Val Val Asp Val Ser Gln Glu Asp Pro Glu Val Gln
                 35                  40                  45

Phe Asn Trp Tyr Val Asp Gly Val Glu Val His Asn Ala Lys Thr
                 50                  55                  60

Lys Pro Arg Glu Glu Gln Phe Asn Ser Thr Tyr Arg Val Val Ser
                 65                  70                  75

Val Leu Thr Val Leu His Gln Asp Trp Leu Asn Gly Lys Glu Tyr
                 80                  85                  90

Lys Cys Lys Val Ser Asn Lys Gly Leu Pro Ser Ser Ile Glu Lys
                 95                 100                 105

Thr Ile Ser Lys Ala Lys Gly Gln Pro Arg Glu Pro Gln Val Tyr
                110                 115                 120

Thr Leu Pro Pro Ser Gln Glu Glu Met Thr Lys Asn Gln Val Ser
                125                 130                 135

Leu Thr Cys Leu Val Lys Gly Phe Tyr Pro Ser Asp Ile Ala Val
                140                 145                 150

Glu Trp Glx Ser Asn Gly Gln Pro Glu Asn Asn Tyr Lys Thr Thr
                155                 160                 165

Pro Pro Val Leu Asp Ser Asp Gly Ser Phe Phe Leu Tyr Ser Arg
                170                 175                 180

Leu Thr Val Asp Lys Ser Arg Trp Gln Glu Gly Asn Val Phe Ser
                185                 190                 195

Cys Ser Val Met His Glu Ala Leu His Asn His Tyr Thr Gln Lys
                200                 205                 210

Ser Leu Ser Leu Ser Leu Gly Lys
                215

<210> SEQ ID NO 8
<211> LENGTH: 215
<212> TYPE: PRT
<213> ORGANISM: Mus musculus

<400> SEQUENCE: 8

Thr Val Pro Glu Val Ser Ser Val Phe Ile Phe Pro Pro Lys Pro
```

```
                1               5                  10                 15
Lys Asp Val Leu Thr Ile Thr Leu Thr Pro Lys Val Thr Cys Val
                               20                 25                 30

Val Val Asp Ile Ser Lys Asp Pro Glu Val Gln Phe Ser Trp
                               35                 40                 45

Phe Val Asp Asp Val Glu Val His Thr Ala Gln Thr Gln Pro Arg
                               50                 55                 60

Glu Glu Gln Phe Asn Ser Thr Phe Arg Ser Val Ser Glu Leu Pro
                               65                 70                 75

Ile Met His Gln Asp Cys Leu Asn Gly Lys Glu Phe Lys Cys Arg
                               80                 85                 90

Val Asn Ser Ala Ala Phe Pro Ala Pro Ile Glu Lys Thr Ile Ser
                               95                 100                105

Lys Thr Lys Gly Arg Pro Lys Ala Pro Gln Val Tyr Thr Ile Pro
                               110                115                120

Pro Pro Lys Glu Gln Met Ala Lys Asp Lys Val Ser Leu Thr Cys
                               125                130                135

Met Ile Thr Asp Phe Phe Pro Glu Asp Ile Thr Val Glu Trp Gln
                               140                145                150

Trp Asn Gly Gln Pro Ala Glu Asn Tyr Lys Asn Thr Gln Pro Ile
                               155                160                165

Met Asp Thr Asp Gly Ser Tyr Phe Val Tyr Ser Lys Leu Asn Val
                               170                175                180

Gln Lys Ser Asn Trp Glu Ala Gly Asn Thr Phe Thr Cys Ser Val
                               185                190                195

Leu His Glu Gly Leu His Asn His His Thr Glu Lys Ser Leu Ser
                               200                205                210

His Ser Pro Gly Lys
                               215

<210> SEQ ID NO 9
<211> LENGTH: 218
<212> TYPE: PRT
<213> ORGANISM: Mus musculus

<400> SEQUENCE: 9

Pro Ala Pro Asn Leu Leu Gly Gly Pro Ser Val Phe Ile Phe Pro
 1               5                  10                 15

Pro Lys Ile Lys Asp Val Leu Met Ile Ser Leu Ser Pro Ile Val
                               20                 25                 30

Thr Cys Val Val Asp Val Ser Glu Asp Asp Pro Asp Val Gln
                               35                 40                 45

Ile Ser Trp Phe Val Asn Asn Val Glu Val His Thr Ala Gln Thr
                               50                 55                 60

Gln Thr His Arg Glu Asp Tyr Asn Ser Thr Leu Arg Val Val Ser
                               65                 70                 75

Ala Leu Pro Ile Gln His Gln Asp Trp Met Ser Gly Lys Glu Phe
                               80                 85                 90

Lys Cys Lys Val Asn Asn Lys Asp Leu Pro Ala Pro Ile Glu Arg
                               95                 100                105

Thr Ile Ser Lys Pro Lys Gly Ser Val Arg Ala Pro Gln Val Tyr
                               110                115                120

Val Leu Pro Pro Glu Glu Glu Met Thr Lys Lys Gln Val Thr
                               125                130                135

Leu Thr Cys Met Val Thr Asp Phe Met Pro Glu Asp Ile Tyr Val
```

```
              140                 145                 150

Glu Trp Thr Asn Asn Gly Lys Thr Glu Leu Asn Tyr Lys Asn Thr
            155                 160                 165

Glu Pro Val Leu Asp Ser Asp Gly Ser Tyr Phe Met Tyr Ser Lys
            170                 175                 180

Leu Arg Val Glu Lys Lys Asn Trp Val Glu Arg Asn Ser Tyr Ser
            185                 190                 195

Cys Ser Val Val His Glu Gly Leu His Asn His His Thr Thr Lys
            200                 205                 210

Ser Phe Ser Arg Thr Pro Gly Lys
            215

<210> SEQ ID NO 10
<211> LENGTH: 218
<212> TYPE: PRT
<213> ORGANISM: Mus musculus

<400> SEQUENCE: 10

Pro Ala Pro Asn Leu Glu Gly Gly Pro Ser Val Phe Ile Phe Pro
  1               5                  10                  15

Pro Asn Ile Lys Asp Val Leu Met Ile Ser Leu Thr Pro Lys Val
             20                  25                  30

Thr Cys Val Val Val Asp Val Ser Glu Asp Asp Pro Asp Val Gln
             35                  40                  45

Ile Ser Trp Phe Val Asn Asn Val Glu Val His Thr Ala Gln Thr
             50                  55                  60

Gln Thr His Arg Glu Asp Tyr Asn Ser Thr Ile Arg Val Val Ser
             65                  70                  75

His Leu Pro Ile Gln His Gln Asp Trp Met Ser Gly Lys Glu Phe
             80                  85                  90

Lys Cys Lys Val Asn Asn Lys Asp Leu Pro Ser Pro Ile Glu Arg
             95                 100                 105

Thr Ile Ser Lys Pro Lys Gly Leu Val Arg Ala Pro Gln Val Tyr
            110                 115                 120

Thr Leu Pro Pro Pro Ala Glu Gln Leu Ser Arg Lys Asp Val Ser
            125                 130                 135

Leu Thr Cys Leu Val Val Gly Phe Asn Pro Gly Asp Ile Ser Val
            140                 145                 150

Glu Trp Thr Ser Asn Gly His Thr Glu Glu Asn Tyr Lys Asp Thr
            155                 160                 165

Ala Pro Val Leu Asp Ser Asp Gly Ser Tyr Phe Ile Tyr Ser Lys
            170                 175                 180

Leu Asn Met Lys Thr Ser Lys Trp Glu Lys Thr Asp Ser Phe Ser
            185                 190                 195

Cys Asn Val Arg His Glu Gly Leu Lys Asn Tyr Tyr Leu Lys Lys
            200                 205                 210

Thr Ile Ser Arg Ser Pro Gly Lys
            215

<210> SEQ ID NO 11
<211> LENGTH: 218
<212> TYPE: PRT
<213> ORGANISM: Mus musculus

<400> SEQUENCE: 11

Pro Pro Gly Asn Ile Leu Gly Gly Pro Ser Val Phe Ile Phe Pro
  1               5                  10                  15
```

-continued

```
Pro Lys Pro Lys Asp Ala Leu Met Ile Ser Leu Thr Pro Lys Val
            20                  25                  30
Thr Cys Val Val Val Asp Val Ser Glu Asp Asp Pro Asp Val His
            35                  40                  45
Val Ser Trp Phe Val Asp Asn Lys Glu Val His Thr Ala Trp Thr
            50                  55                  60
Gln Pro Arg Glu Ala Gln Tyr Asn Ser Thr Phe Arg Val Val Ser
            65                  70                  75
Ala Leu Pro Ile Gln His Gln Asp Trp Met Arg Gly Lys Glu Phe
            80                  85                  90
Lys Cys Lys Val Asn Asn Lys Ala Leu Pro Ala Pro Ile Glu Arg
            95                 100                 105
Thr Ile Ser Lys Pro Lys Gly Arg Ala Gln Thr Pro Gln Val Tyr
           110                 115                 120
Thr Ile Pro Pro Arg Glu Gln Met Ser Lys Lys Lys Val Ser
           125                 130                 135
Leu Thr Cys Leu Val Thr Asn Phe Phe Ser Glu Ala Ile Ser Val
           140                 145                 150
Glu Trp Glu Arg Asn Gly Glu Leu Glu Gln Asp Tyr Lys Asn Thr
           155                 160                 165
Pro Pro Ile Leu Asp Ser Asp Gly Thr Tyr Phe Leu Tyr Ser Lys
           170                 175                 180
Leu Thr Val Asp Thr Asp Ser Trp Leu Gln Gly Glu Ile Phe Thr
           185                 190                 195
Cys Ser Val Val His Glu Ala Leu His Asn His His Thr Gln Lys
           200                 205                 210
Asn Leu Ser Arg Ser Pro Gly Lys
           215
```